(12) United States Patent
Schmitz et al.

(10) Patent No.: US 7,595,398 B2
(45) Date of Patent: Sep. 29, 2009

(54) N-(5-MEMBERED AROMATIC RING)-AMIDO ANTI-VIRAL COMPOUNDS

(75) Inventors: Franz Ulrich Schmitz, Mill Valley, CA (US); Christopher Don Roberts, Belmont, CA (US); Ali Dehghani Mohammad Abadi, Campbell, CA (US); Ronald Conrad Griffith, Escondido, CA (US); Martin Robert Leivers, San Francisco, CA (US); Irina Slobodov, San Mateo, CA (US); Roopa Rai, San Carlos, CA (US)

(73) Assignee: SmithKline Beecham Corporation, Philadelphia, PA (US)

(*) Notice: Subject to any disclaimer, the term of this patent is extended or adjusted under 35 U.S.C. 154(b) by 129 days.

(21) Appl. No.: 11/609,858

(22) Filed: Dec. 12, 2006

(65) Prior Publication Data
US 2007/0265265 A1 Nov. 15, 2007

Related U.S. Application Data

(60) Provisional application No. 60/749,855, filed on Dec. 12, 2005.

(51) Int. Cl.
*C07D 417/12* (2006.01)
*C07D 417/14* (2006.01)
*A61K 31/427* (2006.01)

(52) U.S. Cl. .............. 544/133; 548/148; 548/195; 514/371

(58) Field of Classification Search ........ 514/371; 544/133; 548/148, 195
See application file for complete search history.

(56) References Cited

U.S. PATENT DOCUMENTS

| | | | |
|---|---|---|---|
| 5,189,049 A * | 2/1993 | Frehel et al. | 514/371 |
| 5,738,985 A | 4/1998 | Miles et al. | |
| 6,399,629 B1 * | 6/2002 | Chamberland et al. | 514/313 |
| 6,797,820 B2 * | 9/2004 | Patel et al. | 544/111 |
| 6,852,752 B2 * | 2/2005 | Jacobs et al. | 514/422 |
| 2002/0119962 A1 | 8/2002 | Jacobs et al. | |
| 2005/0069522 A1 | 3/2005 | Colonno et al. | |
| 2006/0276511 A1 | 12/2006 | Serrano-Wu et al. | |
| 2007/0265262 A1 | 11/2007 | Schmitz et al. | |

FOREIGN PATENT DOCUMENTS

| WO | WO 00/26202 A1 | 5/2000 |
|---|---|---|
| WO | WO 02/50071 A1 | 6/2002 |
| WO | WO 02/100851 A2 | 12/2002 |
| WO | WO 03/006443 A2 | 1/2003 |
| WO | WO 2004/014313 A2 | 2/2004 |
| WO | WO 2004/014852 A2 | 2/2004 |
| WO | WO 2006/042954 A1 | 4/2006 |
| WO | WO 2006/061585 A1 | 6/2006 |

OTHER PUBLICATIONS

F. George Njoroge et al. "Challenges in Modern Drug Discovery: A case Study of Boceprevir, an HCV Protease Inhibitor for the Treatment of Hepatitis C Virus Infection" Acc. Chem. Res. 2008, 41(1), 50-59.*
Beaulieu, P.L. et al. "Inhibitors of the HCV NS5B polymerase: new hope for the treatment of hepatitis C infections." *Curr Opin Investig Drugs* 5(8):838-50 (2004).
Ferrari, E. et al. "Characterization of soluble hepatitis C virus RNA-dependent RNA polymerase expressed in *Escherichia coli*." *J Virol* 73(2):1649-54 (1999).
Fried, M.W. et al. "Peginterferon alfa-2a plus ribavirin for chronic hepatitis C virus infection." *N. Engl J Med* 347(13):975-82 (2002).
Griffith et al. "HCV Anti-viral Agents." *Ann Rep Med Chem* 39:223-37 (2004).
Hackbarth et al. "N-alkyl urea hydroxamic acids as a new class of peptide deformylase inhibitors with antibacterial activity." *American Society for Microbiology* Abstract No. XP-002439913 (2002).
Hoofnagle, J.H. "Hepatitis C: the clinical spectrum of disease." *Hepatology* 26(3 Suppl 1):15S-20S (1997).
Hormans, Y. et al. "Isatoribine, an agonist of TLR7, reduces plasma virus concentration in chronic hepatitis C infection." *Hepatology* 42(3):724-31 (2005).
Ishii, K. et al. "Expression of hepatitis C virus NS5B protein: characterization of its RNA polymerase activity and RNA binding." *Hepatology* 29(4):1227-35 (1999).
Lohmann, V. et al. "Selective stimulation of hepatitis C virus and pestivirus NS5B RNA polymerase activity by GTP." *J Biol Chem* 274(16):10807-15 (1999).
Misra, R.N., et al. "N-(cycloalyklamino)acyl-2-aminothiazole inhibitors of cyclin-dependent kinase 2. N-[5- [[[5-(1,1-dimethylethyl)-2-oxazolyl]methyl]thio]-2-thiazolyl]-4-4piperidinecarboxamide (BMS-387032), a highly efficacious and selective antitumor agent" *J. Med. Chem.* XP-002439912 (2004).
Morishi, K. et al. "Mechanisms of hepatitis C virus infection." *Antivir Chem Chemother* 14(6):285-97 (2003).
Ni, Z.J. et al. "Progress and development of small molecule HCV antivirals." *Curr Opin Drug Discov Develop* 7(4):446-59 (2004).
Pettit, G.R., et al. "Antineoplastic agents 365: Dolastatin 10 SAR probes" *Anti-Cancer Drug Design* 13(4),: 243-277 (1998).

(Continued)

*Primary Examiner*—Sharmila Gollamudi Landau
*Assistant Examiner*—Kortney L Klinkel
(74) *Attorney, Agent, or Firm*—R. Steve Thomas

(57) ABSTRACT

Disclosed are compounds having Formula (I) and the compositions and methods thereof for treating or preventing a viral infection mediated at least in part by a virus in the Flaviviridae family of viruses, wherein A, $R^2$, m, R, V, W, T, Z, $R^1$, Y, and p are disclosed herein.

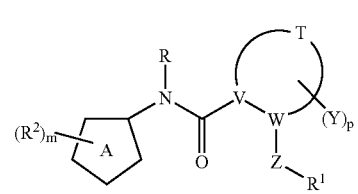

(I)

13 Claims, No Drawings

OTHER PUBLICATIONS

Saunders, J.O. et al. "Inosine Monophosphate Dehydrogenase: Consideration of Structure, Kinetics and Therapeutic Potential." *Ann Rep Med Chem* 25:201-10 (2000).

Simon, R.A., et al. "One-Bead-One-Compound Library of End-Capped Dipeptides and Deconvolution by Microflow NMR." *J. Combin. Chem.* Abstract No. XP-002439911 (2005).

Szabo, E. et al. "Viral hepatitis: new data on hepatitis C infection." *Pathol Oncol Res* 9(4):215-21 (2003).

Thomson, B.J. et al. "Hepatitis C virus infection." *Clin Microbiol Infect* 11(2):86-94 (2005).

Watashi, K. et al. "Cyclophilin B is a functional regulator of hepatitis C virus RNA polymerase." *Mol Cell* 19(1):111-22 (2005).

Yamashita,, T. et al. "RNA-dependent RNA polymerase activity of the soluble recombinant hepatitis C virus NS5B protein truncated at the C-terminal region." *J Biol Chem* 273(25):15479-86 (1998).

\* cited by examiner

N-(5-MEMBERED AROMATIC RING)-AMIDO ANTI-VIRAL COMPOUNDS

CROSS REFERENCE TO RELATED APPLICATION

This application claims the benefit under 35 U.S.C. 119(e) to co-pending provisional application U.S. Ser. No. 60/749,855 filed on Dec. 12, 2005, which is incorporated herein by reference in its entirety.

BACKGROUND OF THE INVENTION

1. Field of the Invention

The invention relates to the field of pharmaceutical chemistry, in particular to compounds, their preparation, compositions, and methods for treating viral infections in patients mediated, at least in part, by a virus in the Flaviviridae family of viruses.

REFERENCE

The following publications are cited in this application as superscript numbers:

1. Szabo, et al., Pathol. Oncol. Res. 2003, 9:215-221.
2. Hoofnagle J H, Hepatology 1997, 26:15S-20S.
3. Thomson B J and Finch R G, Clin Microbial Infect. 2005, 11:86-94.
4. Moriishi K and Matsuura Y, Antivir. Chem. Chemother. 2003, 14:285-297.
5. Fried, et al., N. Engl. J Med 2002, 347:975-982.
6. Ni, Z. J. and Wagman, A. S. Curr. Opin. Drug Discov. Devel. 2004, 7, 446-459.
7. Beaulieu, P. L. and Tsantrizos, Y. S., Curr. Opin. Investig. Drugs 2004, 5, 838-850.
8. Griffith, et al., Ann. Rep. Med. Chem 39, 223-237, 2004.
9. Watashi, et al, Molecular Cell, 19, 111-122, 2005.
10. Horsmans, et al., Hepatology, 42, 724-731, 2005.

All of the above publications are herein incorporated by reference in their entirety to the same extent as if each individual publication was specifically and individually indicated to be incorporated by reference in its entirety.

State of the Art

Chronic infection with HCV is a major health problem associated with liver cirrhosis, hepatocellular carcinoma and liver failure. An estimated 170 million chronic carriers worldwide are at risk of developing liver disease.[1,2] In the United States alone 2.7 million are chronically infected with HCV, and the number of HCV-related deaths in 2000 was estimated between 8,000 and 10,000, a number that is expected to increase significantly over the next years. Infection by HCV is insidious in a high proportion of chronically infected (and infectious) carriers who may not experience clinical symptoms for many years. Liver cirrhosis can ultimately lead to liver failure. Liver failure resulting from chronic HCV infection is now recognized as a leading cause of liver transplantation.

HCV is a member of the Flaviviridae family of RNA viruses that affect animals and humans. The genome is a single ~9.6-kilobase strand of RNA, and consists of one open reading frame that encodes for a polyprotein of ~3000 amino acids flanked by untranslated regions at both 5' and 3' ends (5'- and 3'-UTR). The polyprotein serves as the precursor to at least 10 separate viral proteins critical for replication and assembly of progeny viral particles. The organization of structural and non-structural proteins in the HCV polyprotein is as follows: C-E1-E2-p7-NS2-NS3-NS4a-NS4b-NS5a-NS5b. Because the replicative cycle of HCV does not involve any DNA intermediate and the virus is not integrated into the host genome, HCV infection can theoretically be cured. While the pathology of HCV infection affects mainly the liver, the virus is found in other cell types in the body including peripheral blood lymphocytes.[3,4]

At present, the standard treatment for chronic HCV is interferon alpha (IFN-alpha) in combination with ribavirin and this requires at least six (6) months of treatment. IFN-alpha belongs to a family of naturally occurring small proteins with characteristic biological effects such as antiviral, immunoregulatory and antitumoral activities that are produced and secreted by most animal nucleated cells in response to several diseases, in particular viral infections. IFN-alpha is an important regulator of growth and differentiation affecting cellular communication and immunological control. Treatment of HCV with interferon has frequently been associated with adverse side effects such as fatigue, fever, chills, headache, myalgias, arthralgias, mild alopecia, psychiatric effects and associated disorders, autoimmune phenomena and associated disorders and thyroid dysfunction. Ribavirin, an inhibitor of inosine 5'-monophosphate dehydrogenase (IMPDH), enhances the efficacy of IFN-alpha in the treatment of HCV. Despite the introduction of ribavirin, more than 50% of the patients do not eliminate the virus with the current standard therapy of interferon-alpha (IFN) and ribavirin. By now, standard therapy of chronic hepatitis C has been changed to the combination of pegylated IFN-alpha plus ribavirin. However, a number of patients still have significant side effects, primarily related to ribavirin. Ribavirin causes significant hemolysis in 10-20% of patients treated at currently recommended doses, and the drug is both teratogenic and embryotoxic. Even with recent improvements, a substantial fraction of patients do not respond with a sustained reduction in viral load[5] and there is a clear need for more effective antiviral therapy of HCV infection.

A number of approaches are being pursued to combat the virus. They include, for example, application of antisense oligonucleotides or ribozymes for inhibiting HCV replication. Furthermore, low-molecular weight compounds that directly inhibit HCV proteins and interfere with viral replication are considered as attractive strategies to control CV infection. Among the viral targets, the NS3/4A protease/helicase and the NS5b RNA-dependent RNA polymerase are considered the most promising viral targets for new drugs.[6-8]

Besides targeting viral genes and their transcription and translation products, antiviral activity can also be achieved by targeting host cell proteins that are necessary for viral replication. For example, Watashi et al.[9] show how antiviral activity can be achieved by inhibiting host cell cyclophilins. Alternatively, a potent TLR7 agonist has been shown to reduce HCV plasma levels in humans.[10]

However, none of the compounds described above have progressed beyond clinical trials.[6,8]

Notwithstanding the above, the discovery of new compounds active against one or more members of the Flaviviridae family of viruses would be beneficial particularly in view of the difficulty currently faced in treating diseases mediated, at least in part, by one or more of such viruses.

SUMMARY OF THE INVENTION

This invention is directed to compounds, compositions, and methods for treating viral infections mediated, at least in part, by a virus in the Flaviviridae family of viruses. Specifically, this invention is directed to compounds, stereoisomers, tautomers, or pharmaceutically acceptable salts of Formula (I) and the related compositions and methods wherein:

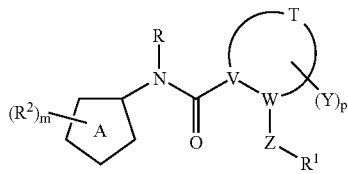

(I)

A is a 5-membered aromatic ring wherein 1 to 3 ring carbon atoms are replaced by N, NH, O, or S, and wherein A may be optionally fused to a 5 to 10 membered aryl, substituted aryl, heteroaryl, substituted heteroaryl, heterocycle, or substituted heterocycle to form a 8 to 13 membered bicyclic or tricyclic ring, and further wherein any ring N or S atom may optionally be oxidized;

each $R^2$ is independently selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, substituted alkylthio, and $R^3$-L- wherein $R^3$ is selected from the group consisting of aryl, substituted aryl, heteroaryl, substituted heteroaryl, heterocyclic, and substituted heterocyclic; and L, defined herein in the $R^3$-L- orientation, is selected from the group consisting of a bond, —O—, —S—, —$CH_2$—, —$CH_2CH_2$—, —$SCH_2$—, —C(O)—, —C(S)—, —NHC(O)—, —C(O)NH—, —$SO_2$—, —$SO_2NH$—, —$SO_2CH_2$—, —$OCH_2$—, —$CH_2CH_2NHC(O)$—, —$CH_2CH_2NHC(O)CH_2$—, —NHN=C($CH_3CH_2OCO$)—, —$NHSO_2$—, =CH—, —NHC(O)$CH_2S$—, —NHC(O)$CH_2C(O)$—, spirocycloalkyl, —C(O)$CH_2S$—, and —C(O)$CH_2O$— provided that when L is =CH—, $R^3$ is heterocyclic or substituted heterocyclic;

m is 0, 1, 2, or 3; provided that when A is a monocyclic ring, m is 1, 2, or 3;

R is selected from the group consisting of hydrogen, alkyl, substituted alkyl, cycloalkyl, and substituted cycloalkyl;

T is a straight chain $C_1$-$C_6$ alkylene or $C_1$-$C_5$ heteroalkylene and forms a 3-8 membered ring with V and W;

V and W are both CH, or one of V or W is CH and the other of V or W is N;

Y is independently selected from the group consisting of halo, oxo, hydroxy, and alkoxy;

p is 0, 1, or 2;

Z is selected from the group consisting of $CH_2$, C(O), C(S), and —$SO_2$—;

$R^1$ is selected from the group consisting of amino, substituted amino, alkyl, arylalkyl, cycloalkyl, substituted cycloalkyl, aryl, substituted aryl, heteroaryl, substituted heteroaryl, alkoxy, aryloxy, arylalkoxy, —$OR^{1a}$, —$CH_2OR^{1a}$, and —$OCH_2R^{1a}$; and $R^{1a}$ is selected from the group consisting of cycloalkyl, substituted cycloalkyl, heterocyclic, substituted heterocyclic, aryl, substituted aryl, heteroaryl, and substituted heteroaryl;

provided that the compound is not 2-(4-phenyl-thiazol-2-ylcarbamoyl)-pyrrolidine-1-carboxylic acid benzyl ester, 2-(4-phenyl-thiazol-2-ylcarbamoyl)-pyrrolidine-1-carboxylic acid phenyl ester, or 4-hydroxy-2-(5-methyl-4-phenyl-thiazol-2-ylcarbamoyl)-pyrrolidine-1-carboxylic acid tert-butyl ester.

DETAILED DESCRIPTION

Throughout this application, the text refers to various embodiments of the present compounds, compositions, and methods. The various embodiments described are meant to provide a variety of illustrative examples and should not be construed as descriptions of alternative species. Rather it should be noted that the descriptions of various embodiments provided herein may be of overlapping scope. The embodiments discussed herein are merely illustrative and are not meant to limit the scope of the present invention.

Definitions

As used herein, the following definitions shall apply unless otherwise indicated.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3$)$_2$CH—), n-butyl ($CH_3CH_2CH_2CH_2$—), isobutyl (($CH_3$)$_2$CHCH$_2$—), sec-butyl (($CH_3$)($CH_3CH_2$)CH—), t-butyl (($CH_3$)$_3$C—), n-pentyl ($CH_3CH_2CH_2CH_2CH_2$—), and neopentyl (($CH_3$)$_3$CCH$_2$—).

"Alkenyl" refers to straight or branched hydrocarbyl groups having from 2 to 6 carbon atoms and preferably 2 to 4 carbon atoms and having at least 1 and preferably from 1 to 2 sites of vinyl (>C=C<) unsaturation. Such groups are exemplified, for example, by vinyl, allyl, and but-3-en-1-yl. Included within this term are the cis and trans isomers or mixtures of these isomers.

"Alkynyl" refers to straight or branched monovalent hydrocarbyl groups having from 2 to 6 carbon atoms and preferably 2 to 3 carbon atoms and having at least 1 and preferably from 1 to 2 sites of acetylenic (—C≡C—) unsaturation. Examples of such alkynyl groups include acetylenyl (—C≡CH), and propargyl (—$CH_2$C≡CH).

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein and with the proviso that any hydroxy substitution is not attached to a vinyl (unsaturated) carbon atom.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein and with the proviso that any hydroxy substitution is not attached to an acetylenic carbon atom.

"Alkylene" refers to divalent saturated aliphatic hydrocarbyl groups preferably having from 1 to 6 and more preferably 1 to 3 carbon atoms that are either straight-chained or branched. This term is exemplified by groups such as methylene (—$CH_2$—), ethylene (—$CH_2CH_2$—), n-propylene (—$CH_2CH_2CH_2$—), iso-propylene (—$CH_2CH(CH_3)$—0 or —$CH(CH_3)CH_2$—), butylene (—$CH_2CH_2CH_2CH_2$—), isobutylene (—$CH_2CH(CH_3)CH_2$—), sec-butylene (—$CH_2CH_2(CH_3)CH$—)and the like. "Straight chain $C_1$-$C_6$ alkylene" refers to unbranched alkylene groups having from 1 to 6 carbons. "Straight chain $C_2$-$C_6$ alkylene" refers to unbranched alkylene groups having from 2 to 6 carbons.

"$C_1$-$C_5$ heteroalkylene" refers to straight chain $C_2$-$C_6$ alkylene groups where one or two —$CH_2$— groups are replaced with —S—, —S(O)—, —$S(O)_2$—, or —O— to give a heteroalkylene having one to five carbons provided that the heteroalkylene does not contain an —O—O—, —S—O—, —O—S—, or —S—S— group wherein the sulfur atom(s) are optionally oxidized to form S(O) or $S(O)_2$.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Acyl includes the "acetyl" group $CH_3C(O)$—.

"Acylamino" refers to the groups —$NR^{47}C(O)$alkyl, —$NR^{47}C(O)$substituted alkyl, —$NR^{47}C(O)$cycloalkyl, —$NR^{47}C(O)$substituted cycloalkyl, —$NR^{47}C(O)$cycloalkenyl, —$NR^{47}C(O)$substituted cycloalkenyl, —$NR^{47}C(O)$alkenyl, —$NR^{47}C(O)$substituted alkenyl, —$NR^{47}C(O)$alkynyl, —$NR^{47}C(O)$substituted alkynyl, —$NR^{47}C(O)$aryl, —$NR^{47}C(O)$substituted aryl, —$NR^{47}C(O)$heteroaryl, —$NR^{47}C(O)$substituted heteroaryl, —$NR^{47}C(O)$heterocyclic, and —$NR^{47}C(O)$substituted heterocyclic wherein $R^{47}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amino" refers to the group —$NH_2$.

"Substituted amino" refers to the group —$NR^{48}R^{49}$ where $R^{48}$ and $R^{49}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, —$SO_2$-alkyl, —$SO_2$-substituted alkyl, —$SO_2$-alkenyl, —$SO_2$-substituted alkenyl, —$SO_2$-cycloalkyl, —$SO_2$-substituted cylcoalkyl, —$SO_2$-cycloalkenyl, —$SO_2$-substituted cylcoalkenyl,—$SO_2$-aryl, —$SO_2$-substituted aryl, —$SO_2$-heteroaryl, —$SO_2$-substituted heteroaryl, —$SO_2$-heterocyclic, and —$SO_2$-substituted heterocyclic and wherein $R^{48}$ and $R^{49}$ are optionally joined, together with the nitrogen bound thereto to form a heterocyclic or substituted heterocyclic group, provided that $R^{48}$ and $R^{49}$ are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. When $R^{48}$ is hydrogen and $R^{49}$ is alkyl, the substituted amino group is sometimes referred to herein as alkylamino. When $R^{48}$ and $R^{49}$ are alkyl, the substituted amino group is sometimes referred to herein as dialkylamino. When referring to a monosubstituted amino, it is meant that either $R^{48}$ or $R^{49}$ is hydrogen but not both. When referring to a disubstituted amino, it is meant that neither $R^{48}$ nor $R^{49}$ are hydrogen.

"Aminocarbonyl" refers to the group —$C(O)NR^{50}R^{51}$ where $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminothiocarbonyl" refers to the group —$C(S)NR^{50}R^{51}$ where $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —$NR^{47}C(O)NR^{50}R^{51}$ where $R^{47}$ is hydrogen or alkyl and $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminothiocarbonylamino" refers to the group —$NR^{47}C(S)NR^{50}R^{51}$ where R is hydrogen or alkyl and $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyloxy" refers to the group —$O$—$C(O)NR^{50}R^{51}$ where $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonyl" refers to the group —$SO_2NR^{50}R^{51}$ where $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonyloxy" refers to the group —$O$—$SO_2NR^{50}R^{51}$ where $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonylamino" refers to the group —$NR^{47}SO_2NR^{50}R^{51}$ where $R^{47}$ is hydrogen or alkyl and $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amidino" refers to the group —C(=NR$^{52}$)NR$^{50}$OR$^{51}$ where R$^{50}$, R$^{51}$, and R$^{52}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{50}$ and R$^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, substituted sulfonyloxy, thioacyl, thiol, alkylthio, and substituted alkylthio, wherein said substituents are as defined herein.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Carbonyl" refers to the divalent group —C(O)— which is equivalent to —C(=O)—.

"Carboxyl" or "carboxy" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)amino" refers to the group —NR$^{47}$C(O)O-alkyl, —NR$^{47}$C(O)O-substituted alkyl, —NR$^{47}$C(O)O-alkenyl, —NR$^{47}$C(O)O-substituted alkenyl, —NR$^{47}$C(O)O-alkynyl, —NR$^{47}$C(O)O-substituted alkynyl, —NR$^{47}$C(O)O-aryl, —NR$^{47}$C(O)O-substituted aryl, —NR$^{47}$C(O)O-cycloalkyl, —NR$^{47}$C(O)O-substituted cycloalkyl, —NR$^{47}$C(O)O-cycloalkenyl, —NR$^{47}$C(O)O-substituted cycloalkenyl, —NR$^{47}$C(O)O-heteroaryl, —NR$^{47}$C(O)O-substituted heteroaryl, —NR$^{47}$C(O)O-heterocyclic, and —NR$^{47}$C(O)O-substituted heterocyclic wherein R$^{47}$ is alkyl or hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, and cyclooctyl.

"Cycloalkenyl" refers to non-aromatic cyclic alkyl groups of from 3 to 10 carbon atoms having single or multiple cyclic rings and having at least one >C=C< ring unsaturation and preferably from 1 to 2 sites of >C=C< ring unsaturation.

"Substituted cycloalkyl" and "substituted cycloalkenyl" refers to a cycloalkyl or cycloalkenyl group having from 1 to 5 or preferably 1 to 3 substituents selected from the group consisting of oxo, thioxo, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO₃H, substituted sulfonyl, substituted sulfonyloxy, thioacyl, thiol, alkylthio, and substituted alkylthio, wherein said substituents are as defined herein.

"Cycloalkyloxy" refers to —O—cycloalkyl.

"Substituted cycloalkyloxy refers to —O-(substituted cycloalkyl).

"Cycloalkylthio" refers to —S-cycloalkyl.

"Substituted cycloalkylthio" refers to —S-(substituted cycloalkyl).

"Cycloalkenyloxy" refers to —O-cycloalkenyl.

"Substituted cycloalkenyloxy refers to —O-(substituted cycloalkenyl).

"Cycloalkenylthio" refers to —S-cycloalkenyl.

"Substituted cycloalkenylthio" refers to —S-(substituted cycloalkenyl).

"Guanidino" refers to the group —NHC(=NH)NH₂.

"Substituted guanidino" refers to —NR$^{53}$C(=NR$^{53}$)N(R$^{53}$)₂ where each R$^{53}$ is independently selected from the group consisting of hydrogen, alkyl, substituted alkyl, aryl, substituted aryl, heteroaryl, substituted heteroaryl, cycloalkyl, substituted cycloalkyl, heterocyclic, and substituted heterocyclic and two R$^{53}$ groups attached to a common guanidino nitrogen atom are optionally joined together with the nitrogen bound thereto to form a heterocyclic or substituted heterocyclic group, provided that at least one R$^{53}$ is not hydrogen, and wherein said substituents are as defined herein.

"Halo" or "halogen" refers to fluoro, chloro, bromo and iodo and preferably is fluoro or chloro.

"Haloalkyl" refers to alkyl groups substituted with 1 to 5, 1 to 3, or 1 to 2 halo groups, wherein alkyl and halo are as defined herein.

"Haloalkoxy" refers to alkoxy groups substituted with 1 to 5, 1 to 3, or 1 to 2 halo groups, wherein alkoxy and halo are as defined herein.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include pyridinyl, pyrrolyl, indolyl, thiophenyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy refers to the group —O-(substituted heteroaryl).

"Heteroarylthio" refers to the group —S-heteroaryl.

"Substituted heteroarylthio" refers to the group —S-(substituted heteroaryl).

"Heterocycle" or "heterocyclic" or "heterocycloalkyl" or "heterocyclyl" refers to a saturated or partially saturated, but not aromatic, group having from 1 to 10 ring carbon atoms and from 1 to 4 ring heteroatoms selected from the group consisting of nitrogen, sulfur, or oxygen. Heterocycle encompasses single ring or multiple condensed rings, including fused bridged and spiro ring systems. In fused ring systems, one or more the rings can be cycloalkyl, aryl, or heteroaryl provided that the point of attachment is through a non-aromatic ring. In one embodiment, the nitrogen and/or sulfur atom(s) of the heterocyclic group are optionally oxidized to provide for the N-oxide, sulfinyl, or sulfonyl moieties.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocycyl.

"Substituted heterocyclyloxy" refers to the group —O-(substituted heterocycyl).

"Heterocyclylthio" refers to the group —S-heterocycyl.

"Substituted heterocyclylthio" refers to the group —S-(substituted heterocycyl).

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Nitro" refers to the group —NO₂.

"Oxo" refers to the atom (=O) or (—O⁻).

"Spirocycloalkyl" and "spiro ring systems" refers to divalent cyclic groups from 3 to 10 carbon atoms having a cycloalkyl ring with a spiro union (the union formed by a single atom which is the only common member of the rings) as exemplified by the following structure:

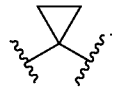

"Sulfonyl" refers to the divalent group —S(O)₂—.

"Substituted sulfonyl" refers to the group —SO₂-alkyl, —SO₂-substituted alkyl, —SO₂-alkenyl, —SO₂-substituted alkenyl, —SO₂-cycloalkyl, —SO₂-substituted cylcoalkyl, —SO₂-cycloalkenyl, —SO₂-substituted cylcoalkenyl, —SO₂-aryl, —SO₂-substituted aryl, —SO₂-heteroaryl, —SO₂-substituted heteroaryl, —SO₂-heterocyclic, —SO₂-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Substituted sulfonyl includes groups such as methyl-SO₂—, phenyl-SO₂—, and 4-methylphenyl-SO₂—.

"Substituted sulfonyloxy" refers to the group —OSO₂-alkyl, —OSO₂-substituted alkyl, —OSO₂-alkenyl, —OSO₂-substituted alkenyl, —OSO₂-cycloalkyl, —OSO₂-substituted cylcoalkyl, —OSO₂-cycloalkenyl, —OSO₂-substituted cylcoalkenyl, —OSO₂-aryl, —OSO₂-substituted aryl, —OSO₂-heteroaryl, —OSO₂-substituted heteroaryl, —OSO₂-heterocyclic, —OSO₂-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Thiol" refers to the group —SH.

"Thiocarbonyl" refers to the divalent group —C(S)— which is equivalent to —C(=S)—.

"Thioxo" refers to the atom (=S).

"Alkylthio" refers to the group —S-alkyl wherein alkyl is as defined herein.

"Substituted alkylthio" refers to the group —S-(substituted alkyl) wherein substituted alkyl is as defined herein.

"Stereoisomer" or "stereoisomers" refer to compounds that differ in the chirality of one or more stereocenters. Stereoisomers include enantiomers and diastereomers.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

"Prodrug" refers to art recognized modifications to one or more functional groups which functional groups are metabolized in vivo to provide a compound of this invention or an active metabolite thereof. Such functional groups are well known in the art including acyl groups for hydroxyl and/or amino substitution, esters of mono-, di- and tri-phosphates wherein one or more of the pendent hydroxyl groups have been converted to an alkoxy, a substituted alkoxy, an aryloxy or a substituted aryloxy group, and the like.

"Patient" refers to mammals and includes humans and non-human mammals.

"Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, and tetraalkylammonium; and when the molecule contains a basic functionality, salts of organic or inorganic acids, such as hydrochloride, hydrobromide, tartrate, mesylate, acetate, maleate, and oxalate [see Stahl and Wermuth, eds., "Handbook of Pharmaceutically Acceptable Salts", (2002), Verlag Helvetica Chimica Acta, Zürich, Switzerland, for an extensive discussion of pharmaceutical salts, their selection, preparation, and use].

"Therapeutically effective amount" is an amount sufficient to treat a specified disorder or disease.

"Treat" or "Treating" or "treatment" of a disease in a patient refers to 1) preventing the disease from occurring in a patient that is predisposed or does not yet display symptoms of the disease; 2) inhibiting the disease or arresting its development; or 3) ameliorating or causing regression of the disease.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group etc.) are not intended for inclusion herein. In such cases, the maximum number of such substitutions is three. For example, serial substitutions of substituted aryl groups with two other substituted aryl groups are limited to -substituted aryl-(substituted aryl)-substituted aryl.

Similarly, it is understood that the above definitions are not intended to include impermissible substitution patterns (e.g., methyl substituted with 5 fluoro groups). Such impermissible substitution patterns are well known to the skilled artisan.

Accordingly, the present invention provides a compound of Formula (I), a stereoisomer, tautomer, or a pharmaceutically acceptable salt thereof

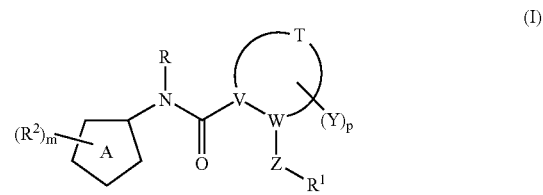

A is a 5-membered aromatic ring wherein 1 to 3 ring carbon atoms are replaced by N, NH, O, or S, and wherein A may be optionally fused to a 5 to 10 membered aryl, substituted aryl, heteroaryl, substituted heteroaryl, heterocycle, or substituted heterocycle to form a 8 to 13 membered bicyclic or tricyclic ring, and further wherein any ring N or S atom may optionally be oxidized;

each $R^2$ is independently selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, substituted alkylthio, and $R^3$-L- wherein $R^3$ is selected from the group consisting of aryl, substituted aryl, heteroaryl, substituted heteroaryl, heterocyclic, and substituted heterocyclic; and L, defined herein in the $R^3$-L- orientation, is selected from the group consisting of a bond, —O—, —S—, —CH$_2$—, —CH$_2$CH$_2$—, —SCH$_2$—, —C(O)—, —C(S)—, —NHC(O)—, —C(O)NH—, —SO$_2$—, —SO$_2$NH—, —SO$_2$CH$_2$—, —OCH$_2$—, —CH$_2$CH$_2$NHC(O)—, —CH$_2$CH$_2$NHC(O)CH$_2$—, —NHN═C(CH₃CH₂OCO)—, —NHSO₂—, ═CH—, —NHC(O)CH₂S—, —NHC(O)CH₂C(O)—, spirocycloalkyl, —C(O)CH₂S—, and —C(O)CH₂O— provided that when L is ═CH—, R³ is heterocyclic or substituted heterocyclic;

m is 0, 1, 2, or 3; provided that when A is a monocyclic ring, m is 1, 2, or 3;

R is selected from the group consisting of hydrogen, alkyl, substituted alkyl, cycloalkyl, and substituted cycloalkyl;

T is a straight chain C₁—C₆ alkylene or C₁-C₅ heteroalkylene and forms a 3-8 membered ring with V and W;

V and W are both CH, or one of V or W is CH and the other of V or W is N;

Y is independently selected from the group consisting of halo, oxo, hydroxy, and alkoxy;

p is 0, 1, or 2;

Z is selected from the group consisting of CH₂, C(O), C(S), and —SO₂—;

R¹ is selected from the group consisting of amino, substituted amino, alkyl, arylalkyl, cycloalkyl, substituted cycloalkyl, aryl, substituted aryl, heteroaryl, substituted heteroaryl, alkoxy, aryloxy, arylalkoxy, —OR¹ᵃ, —CH₂OR¹ᵃ, and —OCH₂R¹ᵃ; and R¹ᵃ is selected from the group consisting of cycloalkyl, substituted cycloalkyl, heterocyclic, substituted heterocyclic, aryl, substituted aryl, heteroaryl, and substituted heteroaryl;

provided that the compound is not 2-(4-phenyl-thiazol-2-ylcarbamoyl)-pyrrolidine-1-carboxylic acid benzyl ester, 2-(4-phenyl-thiazol-2-ylcarbamoyl)-pyrrolidine-1-carboxylic acid phenyl ester, or 4-hydroxy-2-(5-methyl-4-phenyl-thiazol-2-ylcarbamoyl)-pyrrolidine-1-carboxylic acid tert-butyl ester.

In some embodiments, the invention provides compounds of Formula (I) where A is selected from the group consisting of

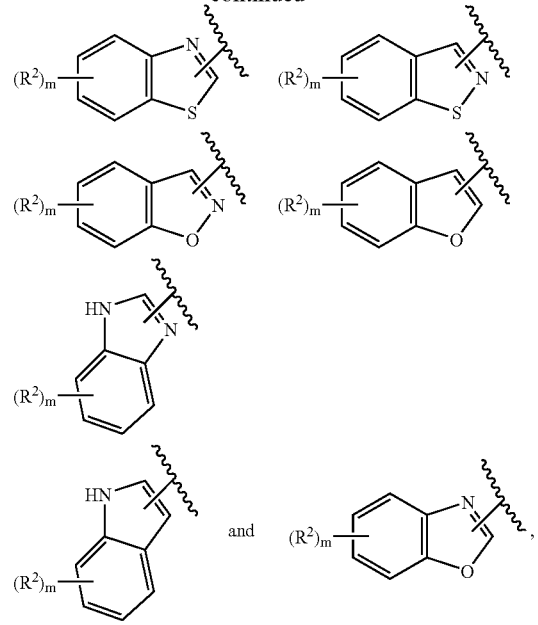

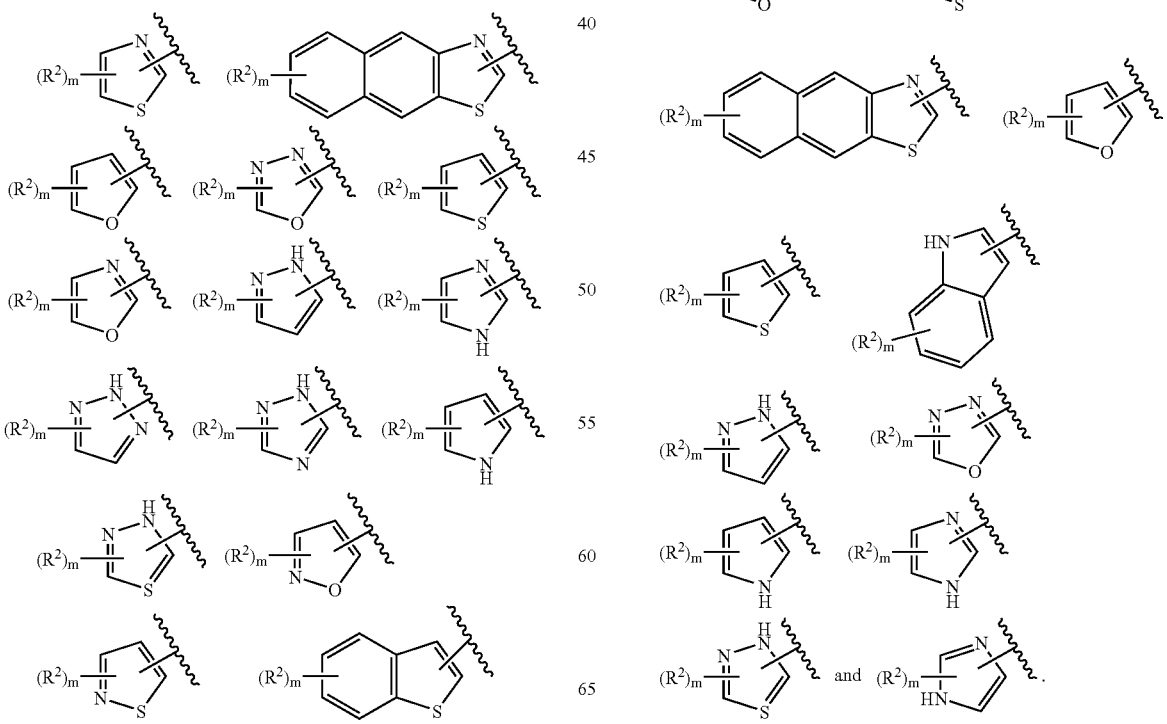

provided that when ring A is fused to a phenyl ring, one or two carbon ring atoms of said phenyl ring are optionally replaced by N and forms a pyridinyl, pyrazinyl, pryridazinyl, or pyrimidinyl ring substituted with —(R²)ₘ and fused to ring A.

In other embodiments, A is selected from the group consisting of

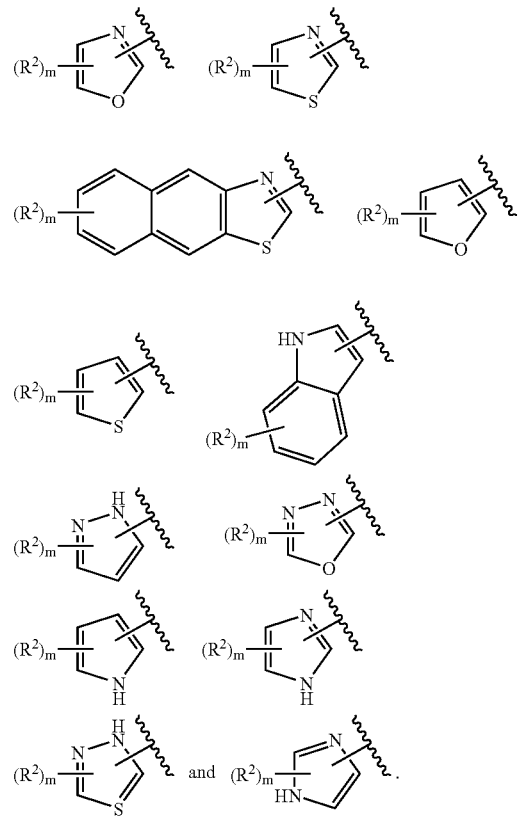

In some embodiments, at least one of $R^2$ is $R^3$-L- wherein $R^3$ is selected from the group consisting of aryl, substituted aryl, heteroaryl, substituted heteroaryl, heterocyclic, and substituted heterocyclic; and L, defined herein in the $R^3$-L- orientation, is selected from the group consisting of a bond, —O—, —S—, —CH$_2$—, —CH$_2$CH$_2$—, —SCH$_2$—, —C(O)—, —C(S)—, —NHC(O)—, —C(O)NH—, —SO$_2$—, —SO$_2$NH—, —SO$_2$CH$_2$—, —OCH$_2$—, —CH$_2$CH$_2$NHC(O)—, —CH$_2$CH$_2$NHC(O)CH$_2$—, —NHN=C(CH$_3$CH$_2$OCO)—, —NHSO$_2$—, =CH—, —NHC(O)CH$_2$S—, —NHC(O)CH$_2$C(O)—, spirocycloalkyl, —C(O)CH$_2$S—, and —C(O)CH$_2$O— provided that when L is =CH—, $R^3$ is heterocyclic or substituted heterocyclic.

In some embodiments, the invention provides compounds of Formula (I) where R is hydrogen.

In some embodiments, the invention provides compounds of Formula (I) where T is selected from the group consisting of —CH$_2$—, —CH$_2$CH$_2$—, —CH$_2$CH$_2$CH$_2$—, —CH$_2$SCH$_2$—, and —CH$_2$CH$_2$CH$_2$CH$_2$—. In some such aspects, R is hydrogen. In some such aspects, $R^1$ is selected from the group consisting of amino, substituted amino, alkyl, arylalkyl, cycloalkyl, substituted cycloalkyl, aryl, substituted aryl, heteroaryl, substituted heteroaryl, alkoxy, aryloxy, and arylalkoxy. In some such aspects, Z is selected from the group consisting of C(O), C(S), and —SO$_2$—.

In some embodiments, the invention provides compounds of Formula (I) where, T is —CH$_2$CH$_2$CH$_2$—.

In some embodiments, the invention provides compounds of Formula (I) where, V is CH and W is N.

In some embodiments, the invention provides compounds of Formula (I) where, wherein p is 0.

In some embodiments, the invention provides compounds of Formula (I) where, wherein Z is C(O).

In some embodiments, the invention provides compounds of Formula (I) where, $R^1$ is arylalkoxy. In some aspects $R^1$ is —OCH$_2$Ph. In some such aspects, $ZR^1$ is —C(O)OCH$_2$Ph.

The present invention further provides a compound having Formula (II) or a stereoisomer, tautomer, or a pharmaceutically acceptable salt thereof,

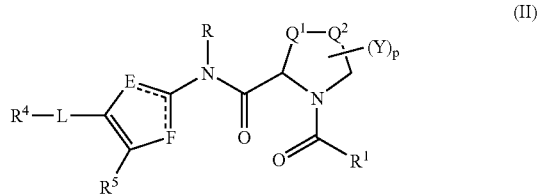

(II)

wherein:
one of E or F is —N= and the other of E or F is —O—, —S—, or —NH—;

$R^4$ is selected from the group consisting of aryl, substituted aryl, heteroaryl, substituted heteroaryl, heterocyclic, and substituted heterocyclic;

L, defined herein in the $R^4$-L- orientation, is selected from the group consisting of a bond, —O—, —S—, —CH$_2$—, —CH$_2$CH$_2$—, —SCH$_2$—, —C(O)—, —C(S)—, —NHC(O)—, —C(O)NH—, —SO$_2$—, —SO$_2$NH—, —SO$_2$CH$_2$—, —OCH$_2$—, —CH$_2$CH$_2$NHC(O)—, —CH$_2$CH$_2$NHC(O)CH$_2$—, —NHN=C(CH$_3$CH$_2$OCO)—, —NHSO$_2$—, =CH—, —NHC(O)CH$_2$S—, —NHC(O)CH$_2$C(O)—, spirocycloalkyl, —C(O)CH$_2$S—, and —C(O)CH$_2$O—;

R is selected from the group consisting of hydrogen, alkyl, substituted alkyl, cycloalkyl, and substituted cycloalkyl;

$R^5$ is selected from the group consisting of hydrogen, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, substituted sulfonyloxy, thioacyl, thiol, alkylthio, and substituted alkylthio;

one of $Q^1$ or $Q^2$ is —O—, —S—, —S(O)—, —S(O)$_2$—, —C(O)—, CHY, or CH$_2$ and the other of $Q^1$ or $Q^2$ is CH$_2$;

Y is independently selected from the group consisting of halo, oxo, hydroxy, and alkoxy;

p is 0, 1, or 2;

$R^1$ is selected from the group consisting of amino, substituted amino, alkyl, arylalkyl, cycloalkyl, substituted cycloalkyl, aryl, substituted aryl, heteroaryl, substituted heteroaryl, alkoxy, aryloxy, arylalkoxy, —OR$^{1a}$, and —OCH$_2$R$^{1a}$; and $R^{1a}$ is selected from the group consisting of cycloalkyl, substituted cycloalkyl, heterocyclic, substituted heterocyclic, aryl, substituted aryl, heteroaryl, and substituted heteroaryl;

provided that the compound is not 2-(4-phenyl-thiazol-2-ylcarbamoyl)-pyrrolidine-1-carboxylic acid benzyl ester, 2-(4-phenyl-thiazol-2-ylcarbamoyl)-pyrrolidine-1-carboxylic acid phenyl ester, or 4-hydroxy-2-(5-methyl-4-phenyl-thiazol-2-ylcarbamoyl)-pyrrolidine-1-carboxylic acid tert-butyl ester.

In some embodiments, the present invention provides a compound of Formula (II) wherein E is —N= and F is —S—.

In some embodiments, the present invention provides a compound of Formula (II) wherein E is —S— and F is —N=.

In some embodiments, the present invention provides a compound of Formula (II) wherein the carbon atom bearing $Q_1$ and N has the S or R stereochemistry.

In some embodiments, the present invention provides a compound of Formula (II) wherein L is a bond, —S—, —CH$_2$CH$_2$—, —SCH$_2$—, —OCH$_2$—, —SO$_2$CH$_2$—, —CH$_2$CH$_2$NHC(O)—, —CH$_2$CH$_2$NHC(O)CH$_2$—, —NHN=C(COOCH$_3$CH$_2$)—, or spirocycloalkyl.

In some embodiments, the present invention provides a compound of Formula (II) wherein $R^4$ is selected from the group consisting of phenyl, benzo[1,3]dioxol-5-yl, benzopyran-3-yl, 1-napthyl, 2-naphthyl, 2-thiazolyl, tetrahydrofuran-5-yl, 1,3,4-oxadiazol-2-yl, thieno[2,3-d]pyrimidin-2-yl, spiro[4.5]decan-4-yl, benzimidazol-2-yl, tetrahydropyran-4-yl, imidazolo[2,1-b]thiazol-5-yl, fluoren-2-yl, tetrahydropyran-4-yl, isoindol-2-yl, 2,7-dioxaspiro[4.4]non-3-yl, and 1,3,4-triazol-2-yl, and wherein each of the aforementioned groups may be substituted or substituted.

In some embodiments, the present invention provides a compound of Formula (II) wherein R⁴ is optionally substituted with (X)$_k$, wherein X is independently selected from the group consisting of acyl, acylamino, amino, substituted amino, oxo, halo, cyano, alkoxy, alkyl, substituted alkyl, nitro, substituted alkoxy, aryl, substituted aryl, substituted aryloxy, cycloalkyl, heterocyclic, substituted heterocyclic, hydroxyl, aminocarbonyl, substituted alkylthio, substituted sulfonyl, aminocarbonyl, aminocarbonylamino, and aminocarbonyloxy, and k is 0, 1, 2, or 3, provided that when R⁴ is aryl or substituted aryl, X is not oxo.

In some embodiments, the present invention provides a compound of Formula (II) wherein X is selected from the group consisting of cyclopropyl-C(O)NH—, phenyl-C(O)NH—, cyclopentyl-C(O)NH—, 4-chlorophenyl-C(O)NH—, 3-chlorophenyl-C(O)NH—, methyl-C(O)NH—, pyridin-3-yl-C(O)NH—, pyridin-4-yl-C(O)NH—, pyrimidin-2-yl-C(O)NH—, pyrimidin-4-yl-C(O)NH—, pyrimidin-5-yl-C(O)NH—, morpholin-4-yl-(alkylene)-C(O)NH—, morpholin-3-yl-(alkylene)-C(O)NH—, morpholin-2-yl-(alkylene)-C(O)NH—, methylamino, 4-methylphenyl-SO₂NH—, amino, ethyl-C(O)NH—, oxo, bromo, methoxy, methyl-SO₂NH—, chloro, phenyl-SO₂NH—, methyl-C(O)NH—, methyl-C(O)—, fluoro, methyl, ethyl, propyl, 4-fluorophenyl, nitro, phenyl, 4-bromobenzyloxy, cyclohexyl, isopropyl, tert-butyl, 4-methylpentyloxymethyl, NH₂C(O)—, hydroxy, cyclohexyl-NHC(O)CH₂S—, allyl, ethoxycarbonylmethylthio, dimethylamino, 3-nitro-phenyl, isobutyl, propoxy, butoxymethyl, butyl-C(O)NH—, methyl-NHC(O)—, ethyl-NHC(O)—, (2-oxo-hexahydro-thieno[3,4-d]imidazol-4-yl)-butyl-C(O)NH—, morpholin-4-yl-(alkylene)—NHC(O)—, morpholin-3-yl-(alkylene)-NHC(O)—, morpholin-2-yl-(alkylene)-NHC(O)—, cyclopropyl-C(O)NH—, cyclohexyl-C(O)NH—, cyclopentyl—NHC(O)—, propyl, isobutyl, carboxy, pentyl-C(O)NH—, pyridin-3-yl-NHC(O)—, pyridin-4-yl-NHC(O)—, pyrimidin-2-yl-NHC(O)—, pyrimidin-4-yl-NHC(O)—, pyrimidin-5-yl-NHC(O)—, phenyl-NHC(O)—, isopropyl-NHC(O)—, and ethyl-NHC(O)—.

In some embodiments, the present invention provides a compound of Formula (II) wherein X is selected from the corresponding X groups in Table 1.

In some embodiments, the present invention provides a compound of Formula (II) wherein R⁵ is hydrogen, alkyl, or halo.

In some embodiments, R is hydrogen and p is 0.

In some embodiments, Q¹ and Q² are CH₂. In some aspects R is hydrogen and p is 0. In some aspects R¹ is selected from the group consisting of amino, substituted amino, alkyl, arylalkyl, cycloalkyl, substituted cycloalkyl, aryl, substituted aryl, heteroaryl, substituted heteroaryl, alkoxy, aryloxy, and arylalkoxy.

In another embodiment, the present invention provides a compound of Formula (IIa) or a stereoisomer, tautomer, or a pharmaceutically acceptable salt thereof,

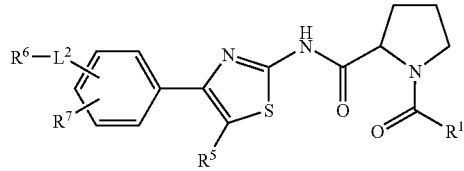

(IIa)

wherein:
L² is —(CH₂)$_n$C(O)NH— or —(CH₂)$_n$NHC(O)—;
n is 0, 1, 2, 3, or 4;
R⁶ is selected from the group consisting of alkyl, substituted alkyl, alkenyl, substituted alkenyl, alkynyl, substitutedalkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic;

R⁷ is selected from the group consisting of hydrogen, amino, substituted amino, halo, cyano, alkoxy, alkyl, substituted alkyl, nitro, substituted alkoxy, aryl, substituted aryl, substituted aryloxy, cycloalkyl, heterocyclic, substituted heterocyclic, hydroxyl, aminocarbonyl, substituted alkylthio, substituted sulfonyl, aminocarbonyl, aminocarbonylamino, and aminocarbonyloxy;

R⁵ is selected from the group consisting of hydrogen, halo, alkyl, and substituted alkyl; and R¹ is selected from the group consisting of amino, substituted amino, alkyl, arylalkyl, cycloalkyl, substituted cycloalkyl, aryl, substituted aryl, heteroaryl, substituted heteroaryl, alkoxy, aryloxy, arylalkoxy, —OR¹³, and —OCH₂R¹ᵃ; and R¹ᵃ is selected from the group consisting of cycloalkyl, substituted cycloalkyl, heterocyclic, substituted heterocyclic, aryl, substituted aryl, heteroaryl, and substituted heteroaryl.

In some embodiments, the present invention provides a compound of Formula (IIa) wherein the pyrrolidine ring has the S or R stereochemistry.

In some embodiments, the present invention provides a compound of Formula (IIa) wherein R⁶L² is attached to the meta position of the phenyl ring.

In some embodiments, the present invention provides a compound of Formula (IIa) wherein R⁶L² is attached to the para position of the phenyl ring.

In some embodiments, the present invention provides a compound of Formula (IIa) wherein R⁵ is hydrogen.

In some embodiments, the present invention provides a compound of Formula (IIa) wherein R⁷ is hydrogen.

In some embodiments, the present invention provides a compound of Formula (IIa) wherein R⁶ is cycloalkyl, substituted cycloalkyl, cycloalkenyl, substituted cycloalkenyl, aryl, substituted aryl, heteroaryl, substituted heteroaryl, heterocyclic, or substituted heterocyclic. In some aspects, R⁶ is selected from the group consisting of cyclopropyl, substituted cyclopropyl, cyclobutyl, substituted cyclobutyl, cyclopentyl, substituted cyclopentyl, cyclohexyl, substituted cyclohexyl, phenyl, substituted phenyl, morpholin-4-yl, morpholin-3-yl, morpholin-2-yl, pyridin-3-yl, substituted pyridin-3-yl, pyridin-4-yl, substituted pyridin-4-yl, pyrimidin-2-yl, substituted pyrimidin-2-yl, pyrimidin-4-yl, substituted pyrimidin-4-yl, pyrimidin-5-yl, and substituted pyrimidin-5-yl.

In some embodiments, the present invention provides a compound of Formula (IIa) wherein R⁶ is selected from the corresponding R⁶ groups in Table 1.

In some embodiments, the present invention provides a compound of Formula (IIa) wherein n is 0. In some aspects, R¹ is selected from the group consisting of amino, substituted amino, alkyl, arylalkyl, cycloalkyl, substituted cycloalkyl, aryl, substituted aryl, heteroaryl, substituted heteroaryl, alkoxy, aryloxy, and arylalkoxy.

In some embodiments, the present invention provides a compound of Formula (IIa) wherein R¹ is arylalkoxy. In some aspects R¹ is —OCH₂Ph.

In some embodiments, R¹ is —OCH₂R¹ᵃ. In some aspects, R¹ᵃ is selected from the group consisting of cyclopropyl, substituted cyclopropyl, cyclobutyl, substituted cyclobutyl, cyclopentyl, substituted cyclopentyl, cyclohexyl, substituted cyclohexyl, phenyl, substituted phenyl, pyridin-3-yl, substituted pyridin-3-yl, pyridin-4-yl, substituted pyridin-4-yl, pyrimidin-2-yl, substituted pyrimidin-2-yl, pyrimidin-4-yl, substituted pyrimidin-4-yl, pyrimidin-5-yl, and substituted pyrimidin-5-yl.

In another embodiment, the present invention provides a compound of Formula (III) or a stereoisomer, tautomer, or a pharmaceutically acceptable salt thereof

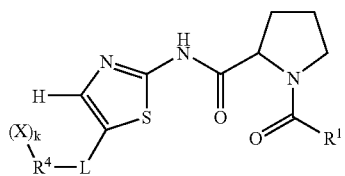

(III)

wherein X, k, R¹, R⁴, and L are previously defined.

In another embodiment, the present invention provides a compound of Formula (IV) or a stereoisomer, tautomer, or a pharmaceutically acceptable salt thereof

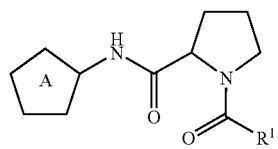

(IV)

wherein R¹ is previously defined and A is substituted or unsubstituted naphtho[2,3-d]thiazol-2-yl.

In another embodiment, the present invention provides a compound of Formula (V) or a stereoisomer, tautomer, or a pharmaceutically acceptable salt thereof,

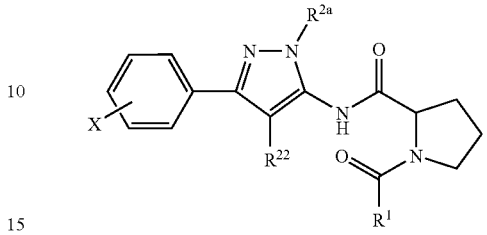

(V)

wherein $R^{2a}$, is selected from the group consisting of hydrogen, alkyl, or aryl; $R^{22}$ is hydrogen or $R^2$, and X, $R^1$, and $R^2$ are previously defined.

In yet other embodiments, the present invention provides a compound, stereoisomer, tautomer, or a pharmaceutically acceptable salt thereof selected from Table 1.

TABLE 1

| Ex. | Structure | Name |
|---|---|---|
| 5001 | 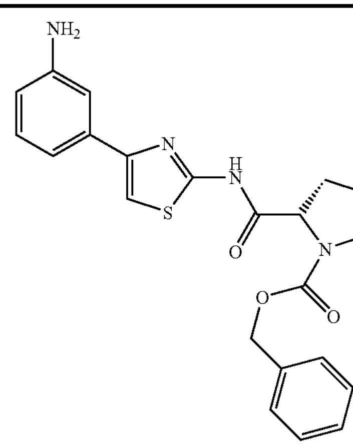 | 2-[4-(3-Amino-phenyl)-thiazol-2-ylcarbamoyl]-pyrrolidine-1-carboxylic acid benzyl ester |
| 5002 | 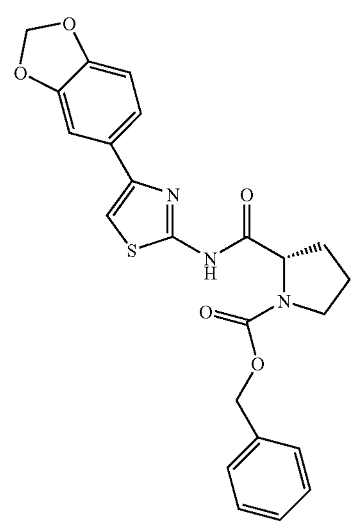 | 2-(4-Benzo[1,3]dioxol-5-yl-thiazol-2-ylcarbamoyl)-pyrrolidine-1-carboxylic acid benzyl ester |

TABLE 1-continued

| Ex. | Structure | Name |
|---|---|---|
| 5003 | 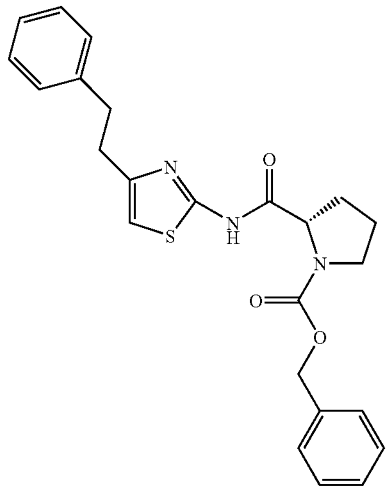 | 2-(4-Phenethyl-thiazol-2-ylcarbamoyl)-pyrrolidine-1-carboxylic acid benzyl ester |
| 5004 | 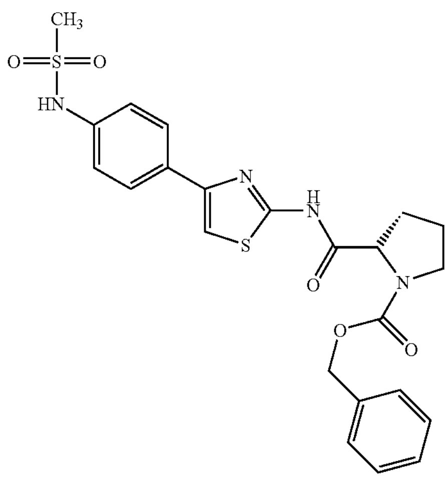 | 2-[4-(4-Methanesulfonylamino-phenyl)-thiazol-2-ylcarbamoyl]-pyrrolidine-1-carboxylic acid benzyl ester |
| 5005 | 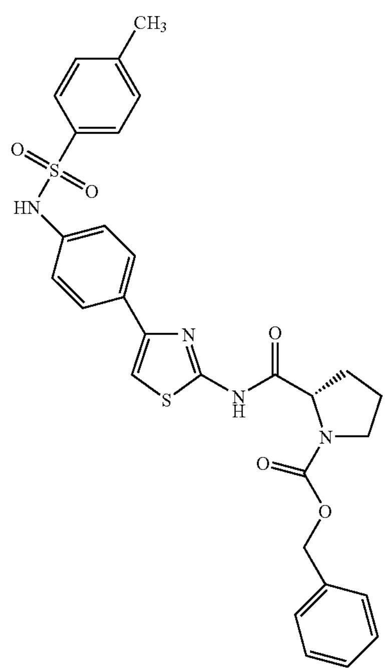 | 2-{4-[4-(Toluene-4-sulfonylamino)-phenyl]-thiazol-2-ylcarbamoyl}-pyrrolidine-1-carboxylic acid benzyl ester |

TABLE 1-continued

| Ex. | Structure | Name |
|---|---|---|
| 5006 | 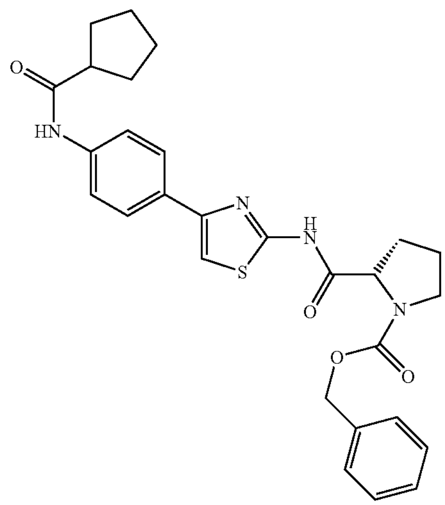 | 2-{4-[4-(Cyclopentanecarbonyl-amino)-phenyl]-thiazol-2-ylcarbamoyl}-pyrrolidine-1-carboxylic acid benzyl ester |
| 5007 | 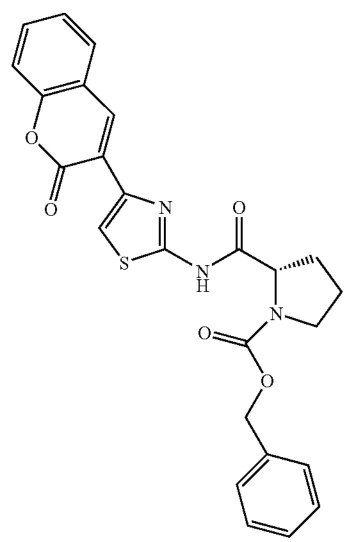 | 2-[4-(2-Oxo-2H-chromen-3-yl)-thiazol-2-ylcarbamoyl]-pyrrolidine-1-carboxylic acid benzyl ester |
| 5008 | 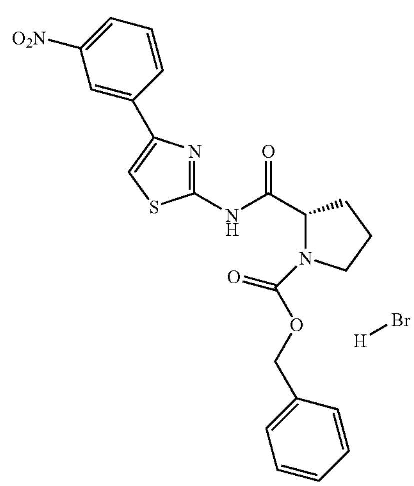 | 2-[4-(3-Nitro-phenyl)-thiazol-2-ylcarbamoyl]-pyrrolidine-1-carboxylic acid benzyl ester; hydrobromide |

TABLE 1-continued

| Ex. | Structure | Name |
|---|---|---|
| 5009 | 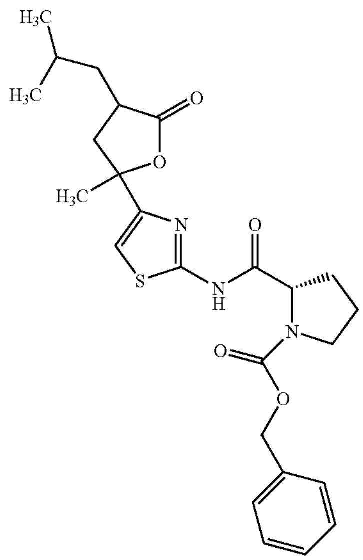 | 2-[4-(4-Isobutyl-2-methyl-5-oxo-tetrahydro-furan-2-yl)-thiazol-2-ylcarbamoyl]-pyrrolidine-1-carboxylic acid benzyl ester |
| 5010 | 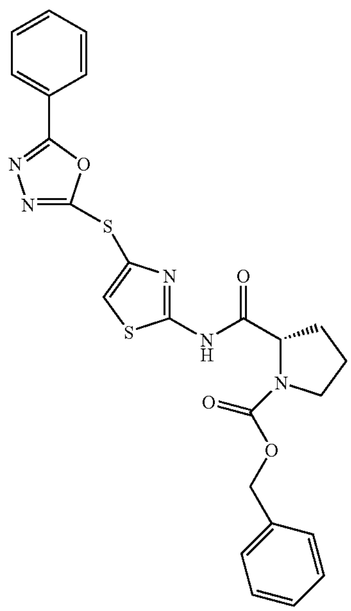 | 2-[4-(5-Phenyl-[1,3,4]oxadiazol-2-ylsulfanyl)-thiazol-2-ylcarbamoyl]-pyrrolidine-1-carboxylic acid benzyl ester |
| 5011 | 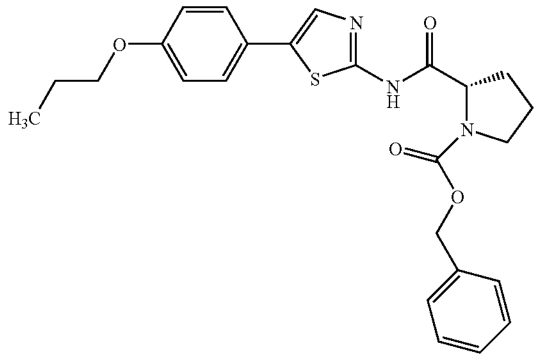 | 2-[5-(4-Propoxy-phenyl)-thiazol-2-ylcarbamoyl]-pyrrolidine-1-carboxylic acid benzyl ester |

TABLE 1-continued
| Ex. | Structure | Name |
|---|---|---|
| 5012 | 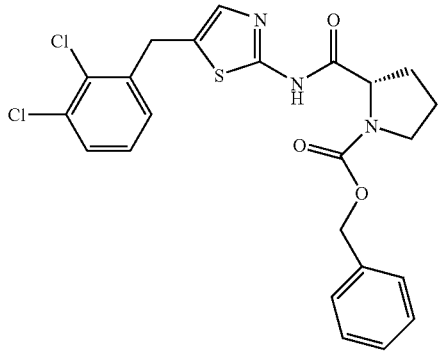 | 2-[5-(2,3-Dichloro-benzyl)-thiazol-2-ylcarbamoyl]-pyrrolidine-1-carboxylic acid benzyl ester |
| 5013 | 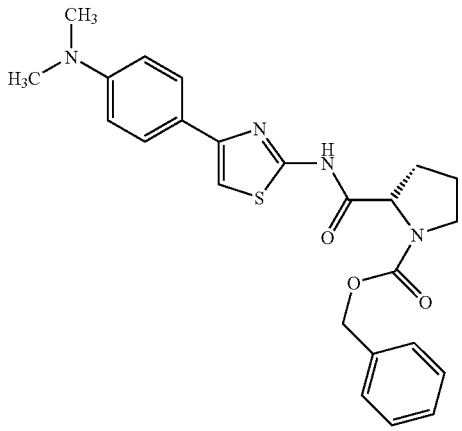 | 2-[4-(4-Dimethylamino-phenyl)-thiazol-2-ylcarbamoyl]-pyrrolidine-1-carboxylic acid benzyl ester |
| 5014 | 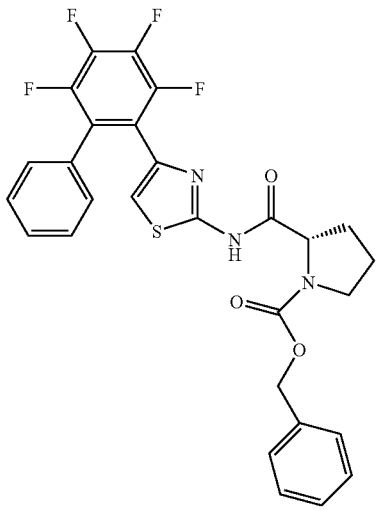 | 2-[4-(3,4,5,6-Tetrafluoro-biphenyl-2-yl)-thiazol-2-ylcarbamoyl]-pyrrolidine-1-carboxylic acid benzyl ester |

TABLE 1-continued

| Ex. | Structure | Name |
|---|---|---|
| 5015 | 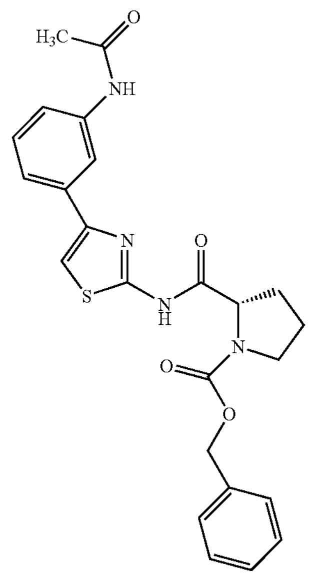 | 2-[4-(3-Acetylamino-phenyl)-thiazol-2-ylcarbamoyl]-pyrrolidine-1-carboxylic acid benzyl ester |
| 5016 | 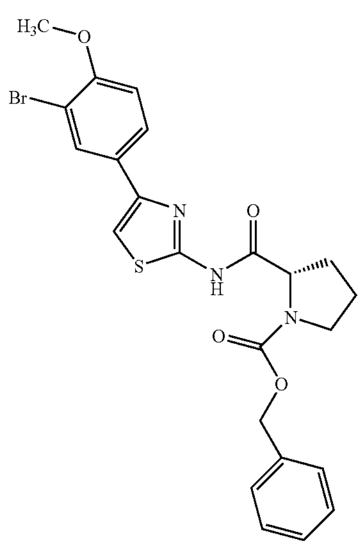 | 2-[4-(3-Bromo-4-methoxy-phenyl)-thiazol-2-ylcarbamoyl]-pyrrolidine-1-carboxylic acid benzyl ester |

TABLE 1-continued

| Ex. | Structure | Name |
|---|---|---|
| 5017 | 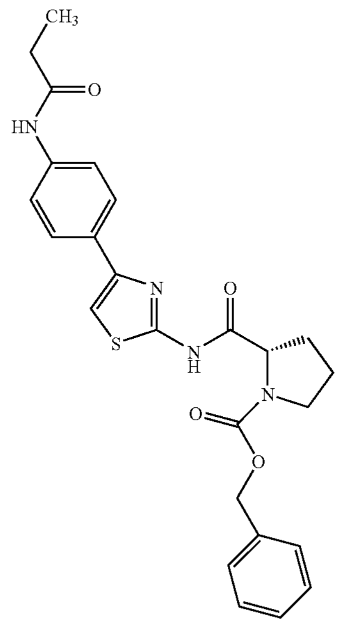 | 2-[4-(4-Propionylamino-phenyl)-thiazol-2-ylcarbamoyl]-pyrrolidine-1-carboxylic acid benzyl ester |
| 5018 | 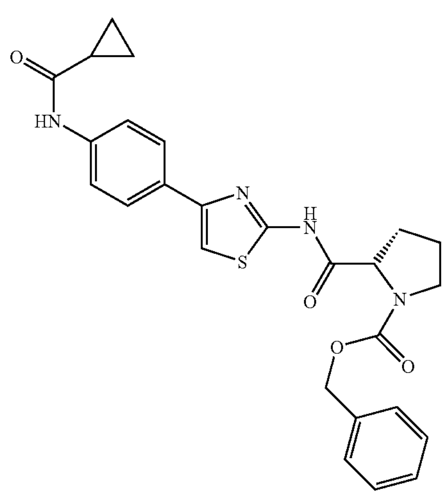 | 2-{4-[4-(Cyclopropanecarbonyl-amino)-phenyl]-thiazol-2-ylcarbamoyl}-pyrrolidine-1-carboxylic acid benzyl ester |

TABLE 1-continued

| Ex. | Structure | Name |
|---|---|---|
| 5019 | 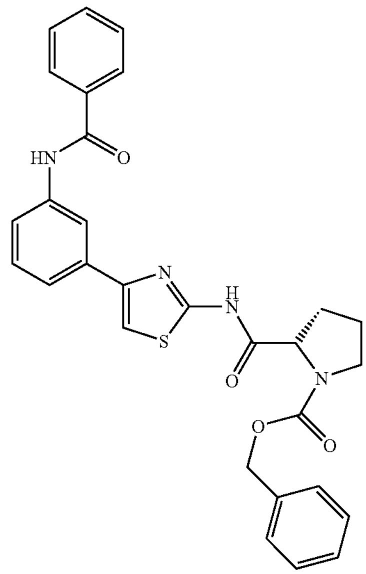 | 2-[4-(3-Benzoylamino-phenyl)-thiazol-2-ylcarbamoyl]-pyrrolidine-1-carboxylic acid benzyl ester |
| 5020 | 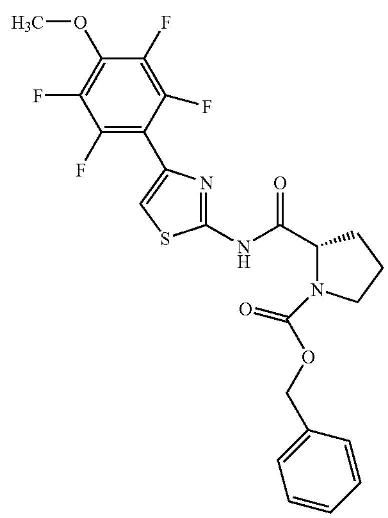 | 2-[4-(2,3,5,6-Tetrafluoro-4-methoxy-phenyl)-thiazol-2-ylcarbamoyl]-pyrrolidine-1-carboxylic acid benzyl ester |
| 5021 | 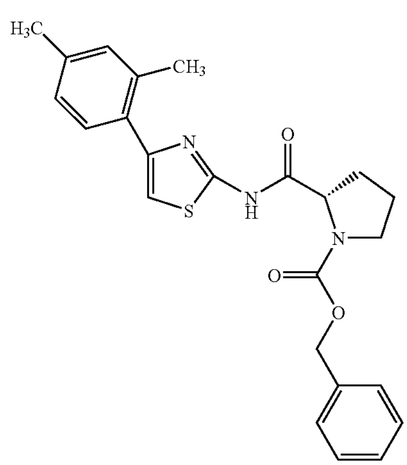 | 2-[4-(2,4-Dimethyl-phenyl)-thiazol-2-ylcarbamoyl]-pyrrolidine-1-carboxylic acid benzyl ester |

/ 
| Ex. | Structure | Name |
|---|---|---|
| 5022 | 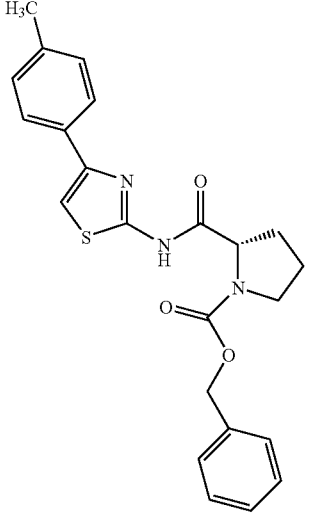 | 2-(4-p-Tolyl-thiazol-2-ylcarbamoyl)-pyrrolidine-1-carboxylic acid benzyl ester |
| 5023 | 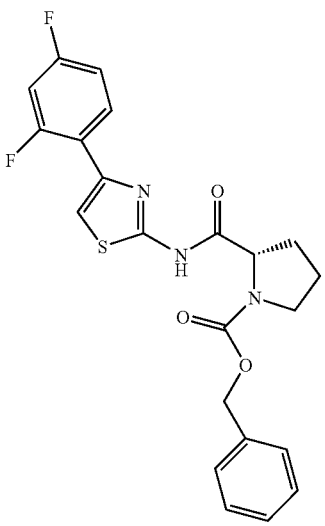 | 2-[4-(2,4-Difluoro-phenyl)-thiazol-2-ylcarbamoyl]-pyrrolidine-1-carboxylic acid benzyl ester |

TABLE 1-continued
| Ex. | Structure | Name |
|---|---|---|
| 5024 | 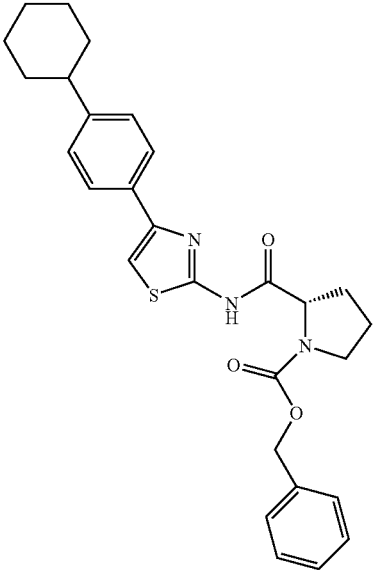 | 2-[4-(4-Cyclohexyl-phenyl)-thiazol-2-ylcarbamoyl]-pyrrolidine-1-carboxylic acid benzyl ester |
| 5025 | 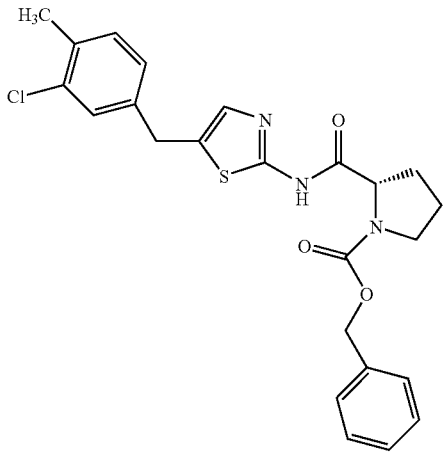 | 2-[5-(3-Chloro-4-methyl-benzyl)-thiazol-2-ylcarbamoyl]-pyrrolidine-1-carboxylic acid benzyl ester |

TABLE 1-continued

| Ex. | Structure | Name |
|---|---|---|
| 5026 | 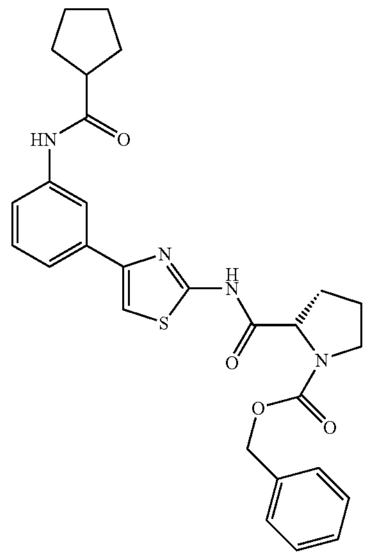 | 2-{4-[3-(Cyclopentanecarbonyl-amino)-phenyl]-thiazol-2-ylcarbamoyl}-pyrrolidine-1-carboxylic acid benzyl ester |
| 5027 | 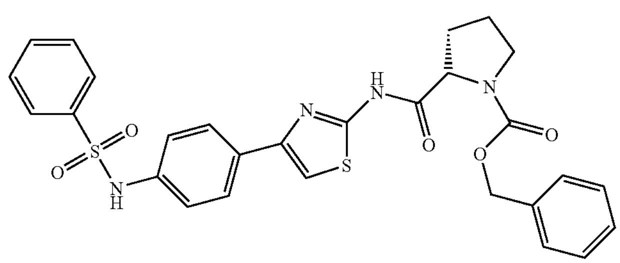 | 2-[4-(4-Benzenesulfonylamino-phenyl)-thiazol-2-ylcarbamoyl]-pyrrolidine-1-carboxylic acid benzyl ester |
| 5028 | 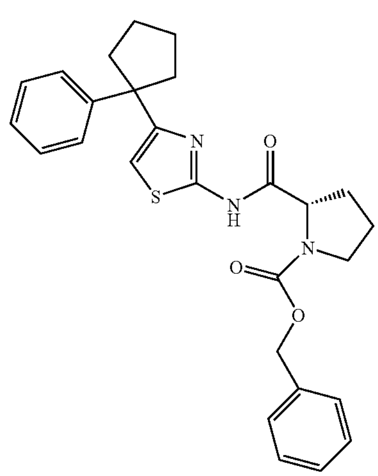 | 2-[4-(1-Phenyl-cyclopentyl)-thiazol-2-ylcarbamoyl]-pyrrolidine-1-carboxylic acid benzyl ester |

TABLE 1-continued

| Ex. | Structure | Name |
|---|---|---|
| 5029 | 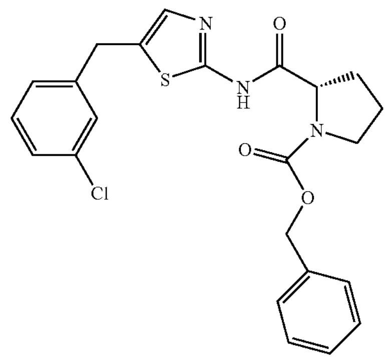 | 2-[5-(3-Chloro-benzyl)-thiazol-2-ylcarbamoyl]-pyrrolidine-1-carboxylic acid benzyl ester |
| 5030 | 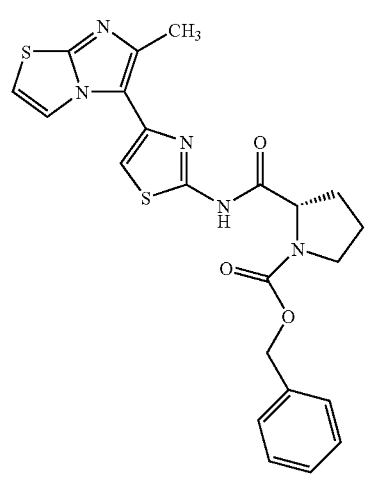 | 2-[4-(6-Methyl-imidazo[2,1-b]thiazol-5-yl)-thiazol-2-ylcarbamoyl]-pyrrolidine-1-carboxylic acid benzyl ester |
| 5031 | 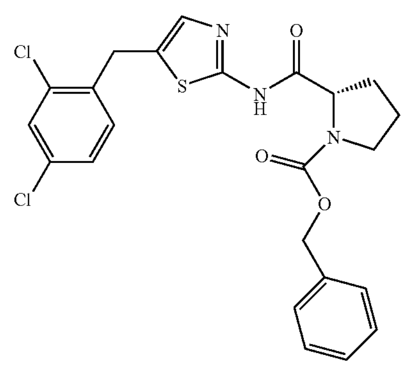 | 2-[5-(2,4-Dichloro-benzyl)-thiazol-2-ylcarbamoyl]-pyrrolidine-1-carboxylic acid benzyl ester |

TABLE 1-continued
| Ex. | Structure | Name |
|---|---|---|
| 5032 | 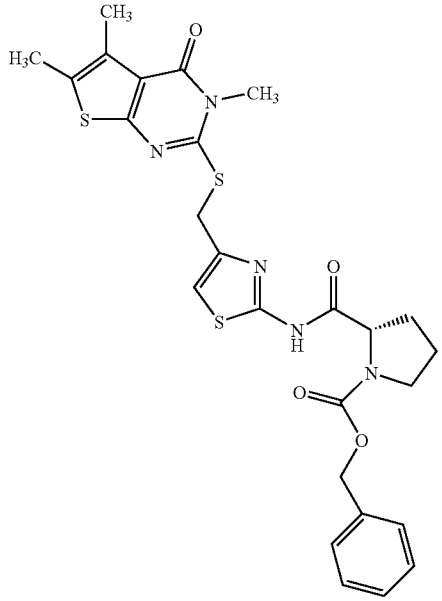 | 2-[4-(3,5,6-Trimethyl-4-oxo-3,4-dihydro-thieno[2,3-d]pyrimidin-2-ylsulfanylmethyl)-thiazol-2-ylcarbamoyl]-pyrrolidine-1-carboxylic acid benzyl ester |
| 5033 | 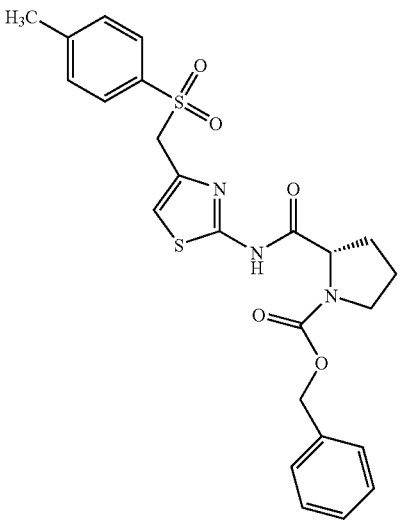 | 2-[4-(Toluene-4-sulfonylmethyl)-thiazol-2-ylcarbamoyl]-pyrrolidine-1-carboxylic acid benzyl ester |

TABLE 1-continued
| Ex. | Structure | Name |
|---|---|---|
| 5034 | 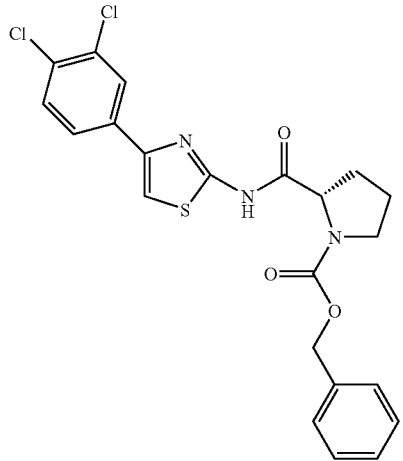 | 2-[4-(3,4-Dichloro-phenyl)-thiazol-2-ylcarbamoyl]-pyrrolidine-1-carboxylic acid benzyl ester |
| 5035 | 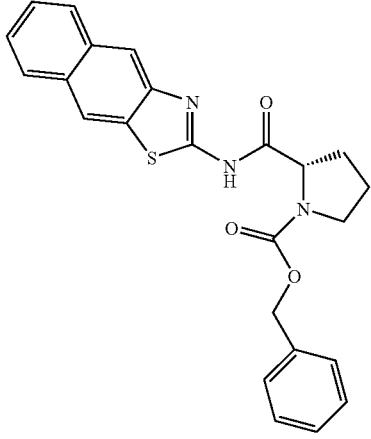 | 2-(Naphtho[2,3-d]thiazol-2-ylcarbamoyl)-pyrrolidine-1-carboxylic acid benzyl ester |
| 5036 | 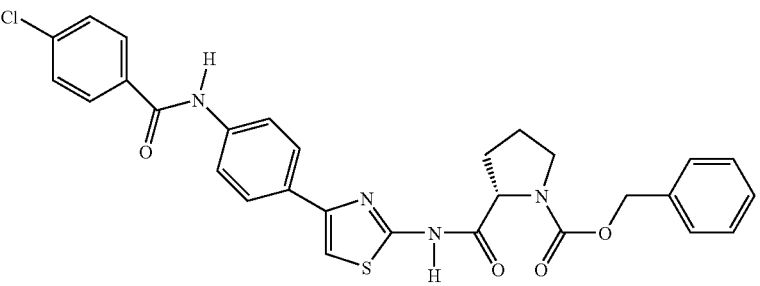 | 2-{4-[4-(4-Chloro-benzoylamino)-phenyl]-thiazol-2-ylcarbamoyl}-pyrrolidine-1-carboxylic acid benzyl ester |

TABLE 1-continued

| Ex. | Structure | Name |
|---|---|---|
| 5037 | 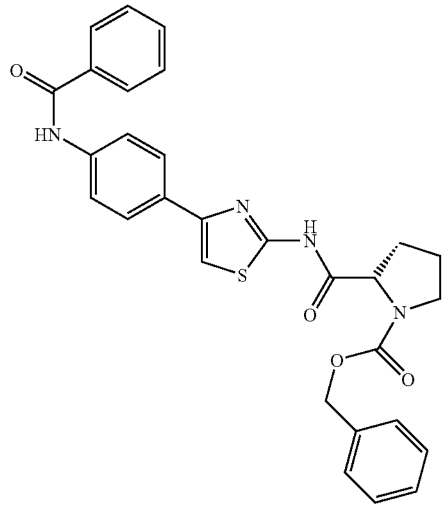 | 2-[4-(4-Benzoylamino-phenyl)-thiazol-2-ylcarbamoyl]-pyrrolidine-1-carboxylic acid benzyl ester |
| 5038 | 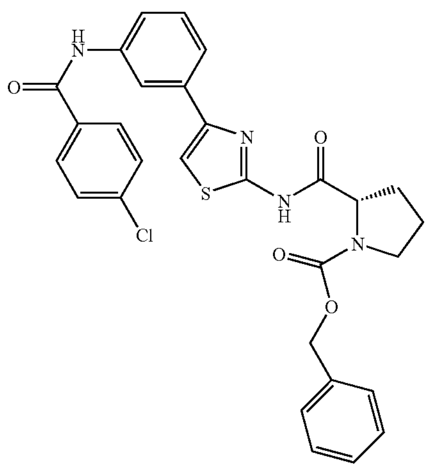 | 2-{4-[3-(4-Chloro-benzoylamino)-phenyl]-thiazol-2-ylcarbamoyl}-pyrrolidine-1-carboxylic acid benzyl ester |
| 5039 | 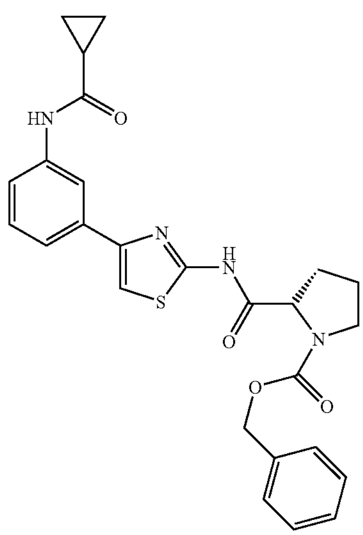 | 2-{4-[3-(Cyclopropanecarbonyl-amino)-phenyl]-thiazol-2-ylcarbamoyl}-pyrrolidine-1-carboxylic acid benzyl ester |

TABLE 1-continued
| Ex. | Structure | Name |
|---|---|---|
| 5040 | 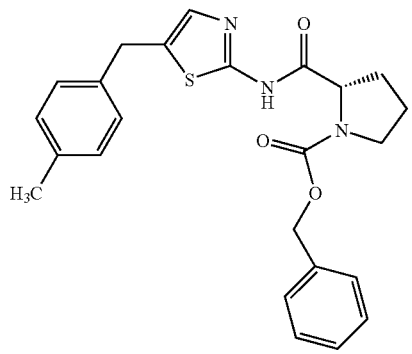 | 2-[5-(4-Methyl-benzyl)-thiazol-2-ylcarbamoyl]-pyrrolidine-1-carboxylic acid benzyl ester |
| 5041 | 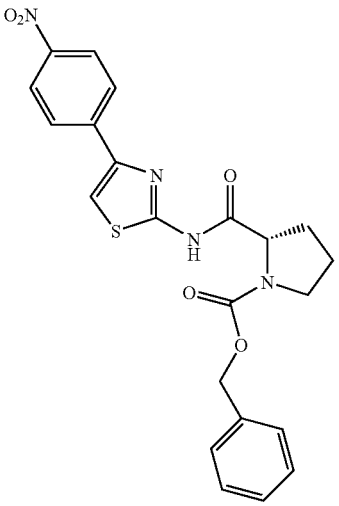 | 2-[4-(4-Nitro-phenyl)-thiazol-2-ylcarbamoyl]-pyrrolidine-1-carboxylic acid benzyl ester |
| 5042 | 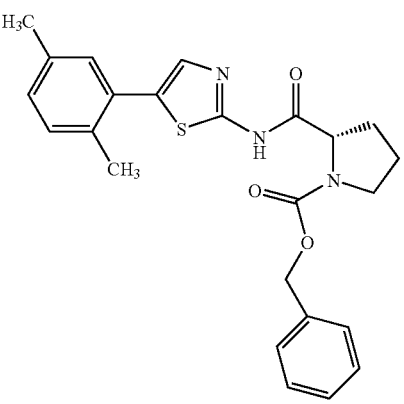 | 2-[5-(2,5-Dimethyl-phenyl)-thiazol-2-ylcarbamoyl]-pyrrolidine-1-carboxylic acid benzyl ester |

TABLE 1-continued
| Ex. | Structure | Name |
|---|---|---|
| 5043 | 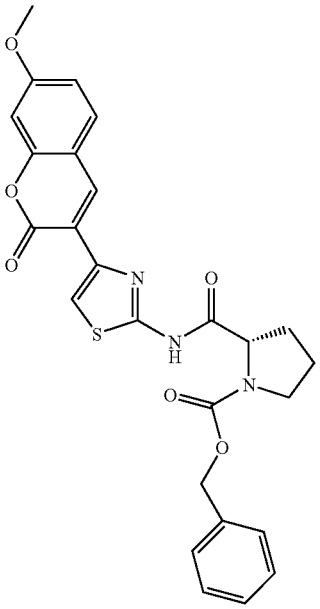 | 2-[4-(7-Methoxy-2-oxo-2H-chromen-3-yl)-thiazol-2-ylcarbamoyl]-pyrrolidine-1-carboxylic acid benzyl ester |
| 5044 | 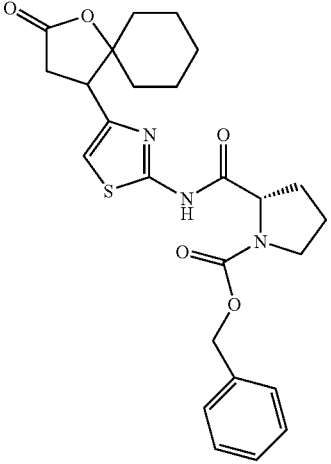 | 2-[4-(2-Oxo-1-oxa-spiro[4.5]dec-4-yl)-thiazol-2-ylcarbamoyl]-pyrrolidine-1-carboxylic acid benzyl ester |

TABLE 1-continued

| Ex. | Structure | Name |
|---|---|---|
| 5045 | 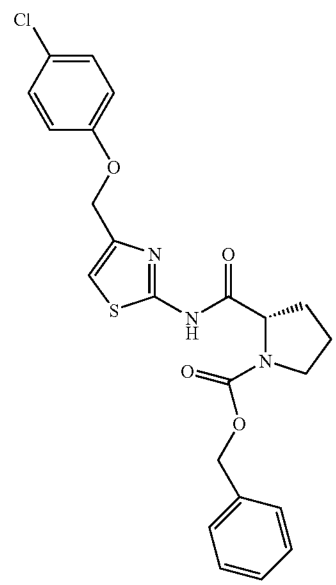 | 2-[4-(4-Chloro-phenoxymethyl)-thiazol-2-ylcarbamoyl]-pyrrolidine-1-carboxylic acid benzyl ester |
| 5046 | 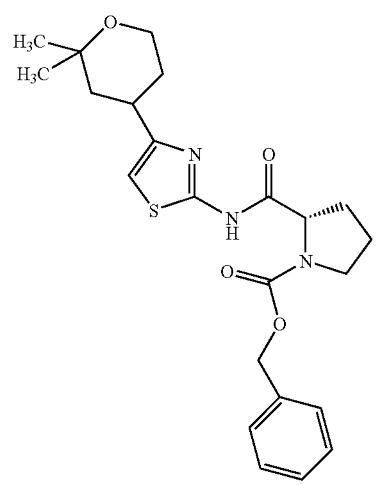 | 2-[4-(2,2-Dimethyl-tetrahydro-pyran-4-yl)-thiazol-2-ylcarbamoyl]-pyrrolidine-1-carboxylic acid benzyl ester |
| 5047 | 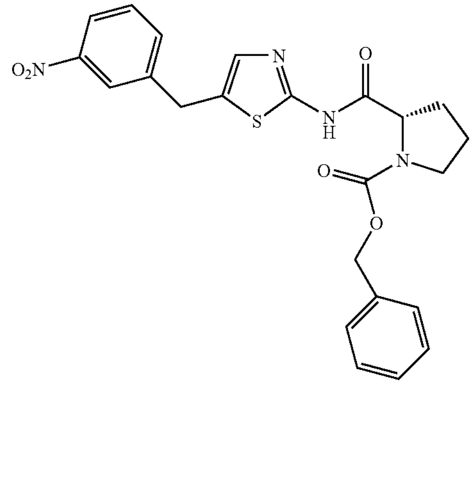 | 2-[5-(3-Nitrobenzyl)-thiazol-2-ylcarbamoyl]-pyrrolidine-1-carboxylic acid benzyl ester |

TABLE 1-continued

| Ex. | Structure | Name |
|---|---|---|
| 5048 | 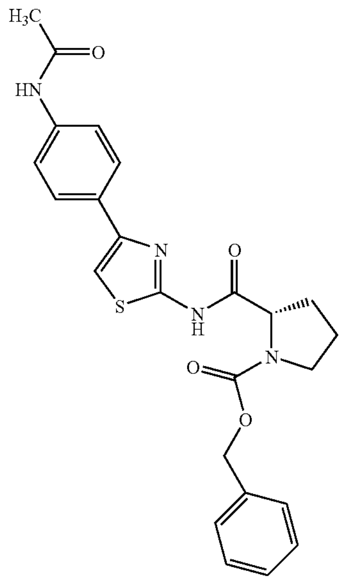 | 2-[4-(4-Acetylamino-phenyl)-thiazol-2-ylcarbamoyl]-pyrrolidine-1-carboxylic acid benzyl ester |
| 5049 | 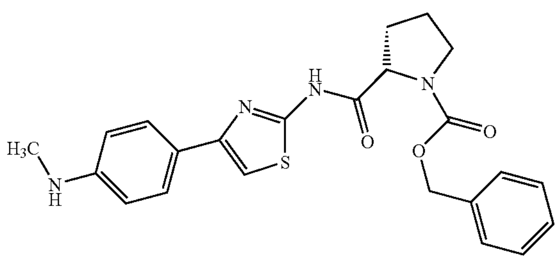 | 2-[4-(4-Methylamino-phenyl)-thiazol-2-ylcarbamoyl]-pyrrolidine-1-carboxylic acid benzyl ester |
| 5050 | 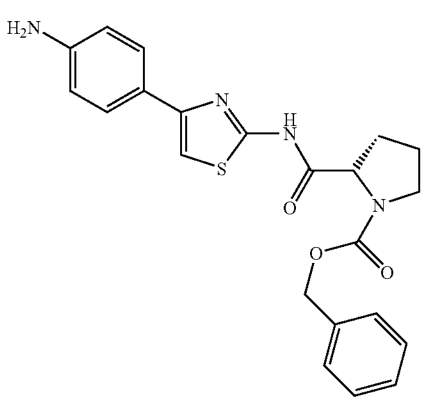 | 2-[4-(4-Amino-phenyl)-thiazol-2-ylcarbamoyl]-pyrrolidine-1-carboxylic acid benzyl ester |

TABLE 1-continued
| Ex. | Structure | Name |
|---|---|---|
| 5051 | 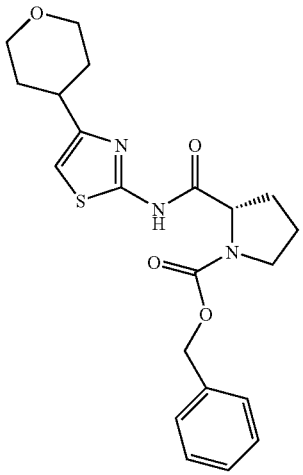 | 2-[4-(Tetrahydro-pyran-4-yl)-thiazol-2-ylcarbamoyl]-pyrrolidine-1-carboxylic acid benzyl ester |
| 5052 | 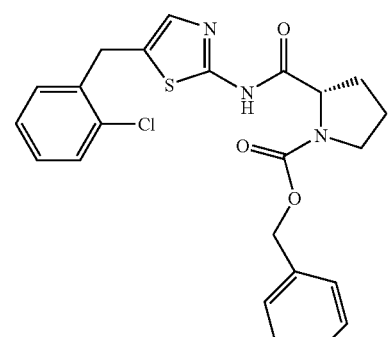 | 2-[5-(2-Chloro-benzyl)-thiazol-2-ylcarbamoyl]-pyrrolidine-1-carboxylic acid benzyl ester |

TABLE 1-continued
| Ex. | Structure | Name |
|---|---|---|
| 5053 | 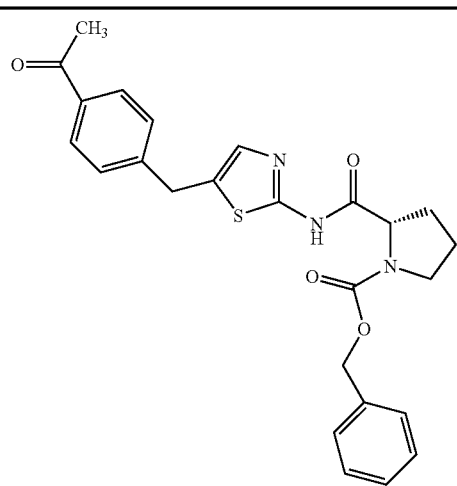 | 2-[5-(4-Acetyl-benzyl)-thiazol-2-ylcarbamoyl]-pyrrolidine-1-carboxylic acid benzyl ester |
| 5054 | 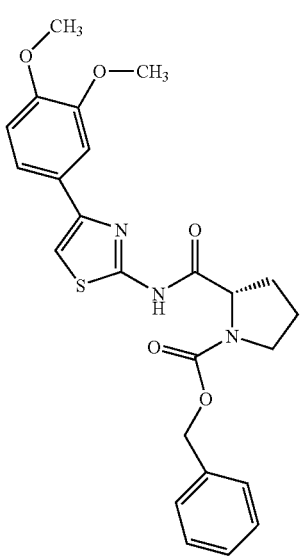 | 2-[4-(3,4-Dimethoxy-phenyl)-thiazol-2-ylcarbamoyl]-pyrrolidine-1-carboxylic acid benzyl ester |

TABLE 1-continued
| Ex. | Structure | Name |
|---|---|---|
| 5055 | 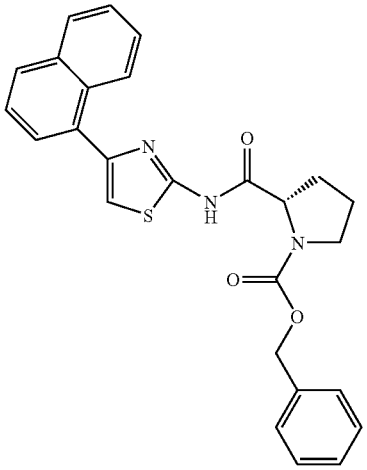 | 2-(4-Naphthalen-1-yl-thiazol-2-ylcarbamoyl)-pyrrolidine-1-carboxylic acid benzyl ester |
| 5056 | 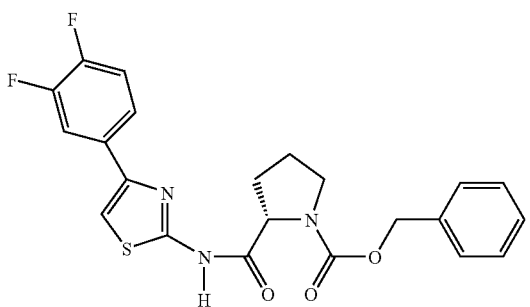 | 2-[4-(3,4-Difluoro-phenyl)-thiazol-2-ylcarbamoyl]-pyrrolidine-1-carboxylic acid benzyl ester |
| 5057 | 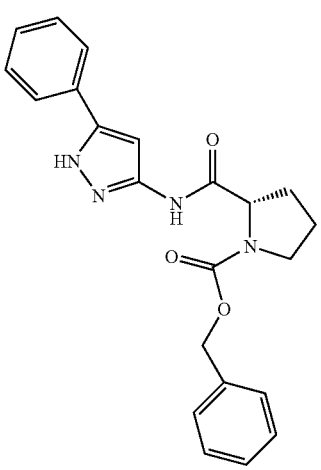 | 2-(5-Phenyl-1H-pyrazol-3-ylcarbamoyl)-pyrrolidine-1-carboxylic acid benzyl ester |

TABLE 1-continued

| Ex. | Structure | Name |
|---|---|---|
| 5058 | 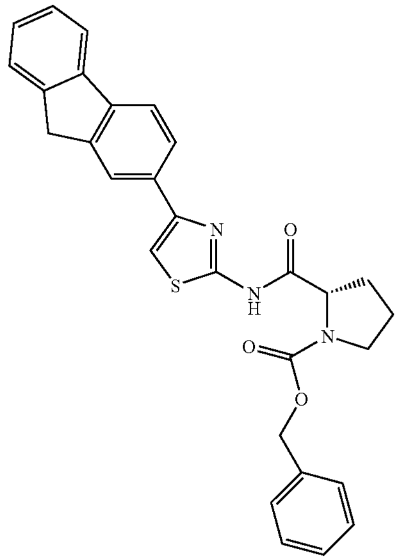 | 2-[4-(9H-Fluoren-2-yl)-thiazol-2-ylcarbamoyl]-pyrrolidine-1-carboxylic acid benzyl ester |
| 5059 | 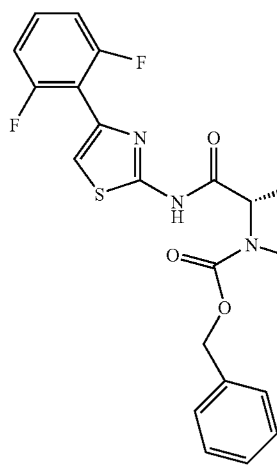 | 2-[4-(2,6-Difluoro-phenyl)-thiazol-2-ylcarbamoyl]-pyrrolidine-1-carboxylic acid benzyl ester |
| 5060 | 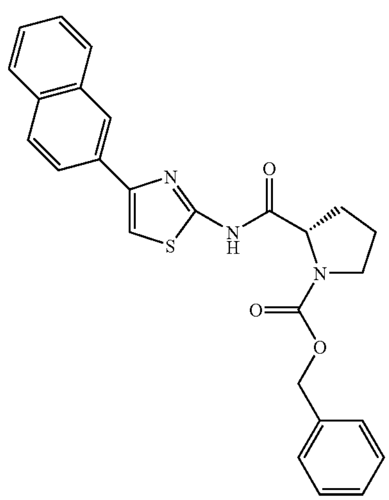 | 2-(4-Naphthalen-2-yl-thiazol-2-ylcarbamoyl)-pyrrolidine-1-carboxylic acid benzyl ester |

TABLE 1-continued

| Ex. | Structure | Name |
|---|---|---|
| 5061 | 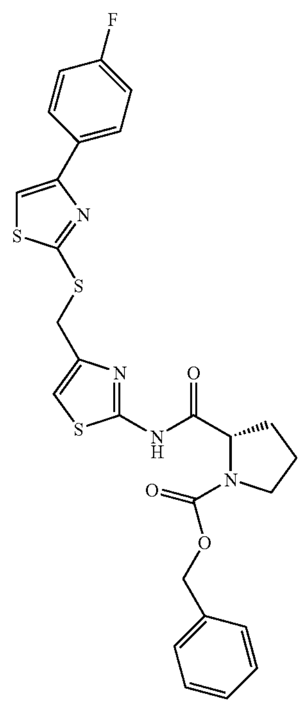 | 2-{4-[4-(4-Fluoro-phenyl)-thiazol-2-ylsulfanylmethyl]-thiazol-2-ylcarbamoyl}-pyrrolidine-1-carboxylic acid benzyl ester |
| 5062 | 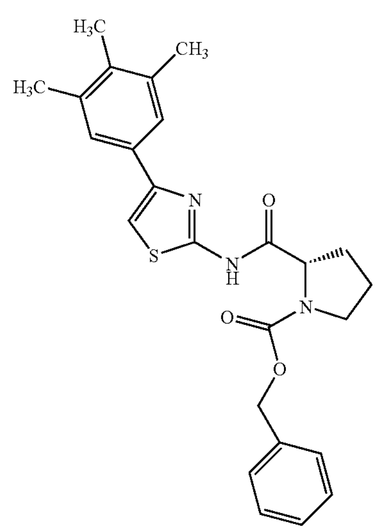 | 2-[4-(3,4,5-Trimethyl-phenyl)-thiazol-2-ylcarbamoyl]-pyrrolidine-1-carboxylic acid benzyl ester |

TABLE 1-continued
| Ex. | Structure | Name |
| --- | --- | --- |
| 5063 | 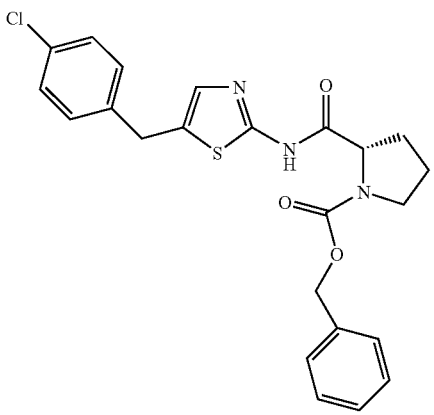 | 2-[5-(4-Chloro-benzyl)-thiazol-2-ylcarbamoyl]-pyrrolidine-1-carboxylic acid benzyl ester |
| 5064 | 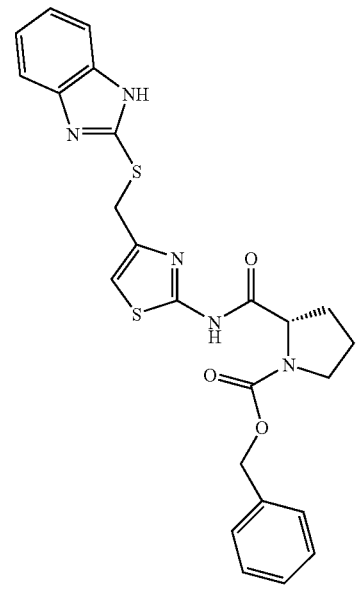 | 2-[4-(1H-Benzoimidazol-2-ylsulfanylmethyl)-thiazol-2-ylcarbamoyl]-pyrrolidine-1-carboxylic acid benzyl ester |
| 5065 | 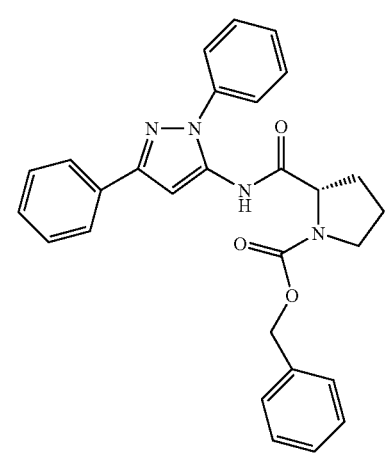 | 2-(2,5-Diphenyl-2H-pyrazol-3-ylcarbamoyl)-pyrrolidine-1-carboxylic acid benzyl ester |

TABLE 1-continued

| Ex. | Structure | Name |
|---|---|---|
| 5066 | 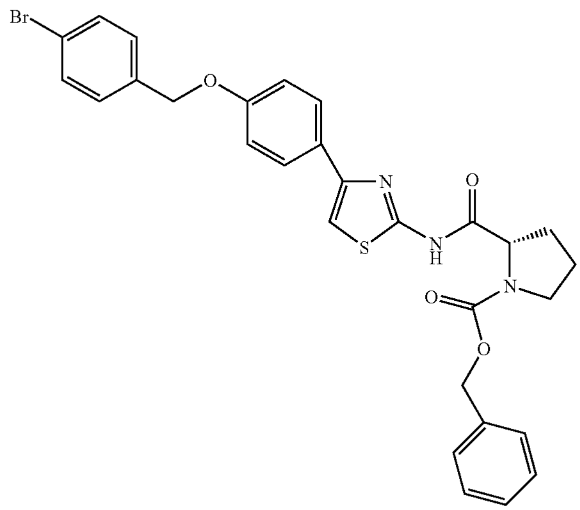 | 2-{4-[4-(4-Bromo-benzyloxy)-phenyl]-thiazol-2-ylcarbamoyl}-pyrrolidine-1-carboxylic acid benzyl ester |
| 5067 | 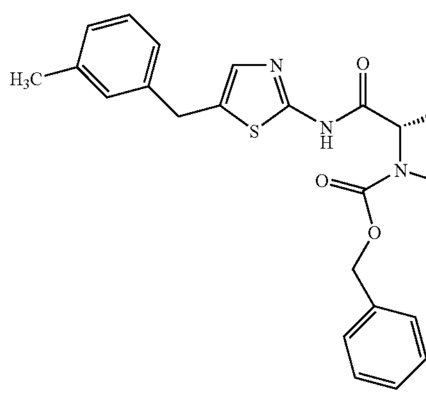 | 2-[5-(3-Methyl-benzyl)-thiazol-2-ylcarbamoyl]-pyrrolidine-1-carboxylic acid benzyl ester |
| 5068 | 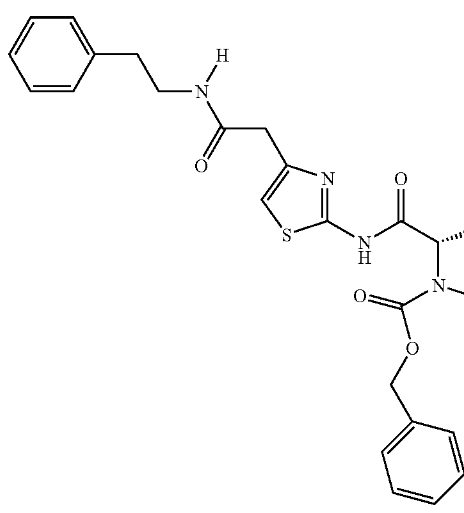 | 2-[4-(Phenethylcarbamoyl-methyl)-thiazol-2-ylcarbamoyl]-pyrrolidine-1-carboxylic acid benzyl ester |

TABLE 1-continued

| Ex. | Structure | Name |
|---|---|---|
| 5069 | 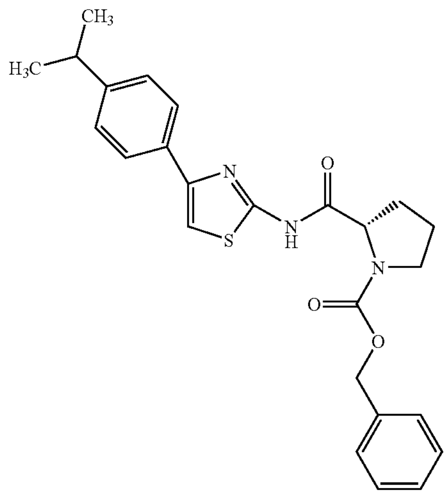 | 2-[4-(4-Isopropyl-phenyl)-thiazol-2-ylcarbamoyl]-pyrrolidine-1-carboxylic acid benzyl ester |
| 5070 | 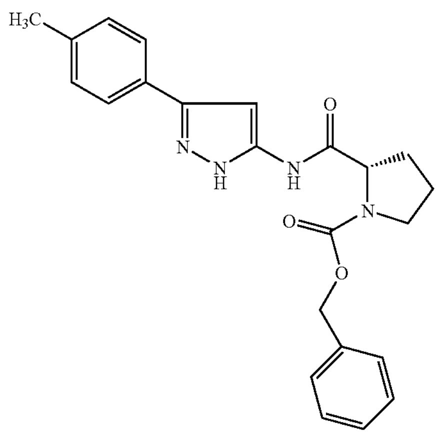 | 2-(5-p-Tolyl-2H-pyrazol-3-ylcarbamoyl)-pyrrolidine-1-carboxylic acid benzyl ester |
| 5071 | 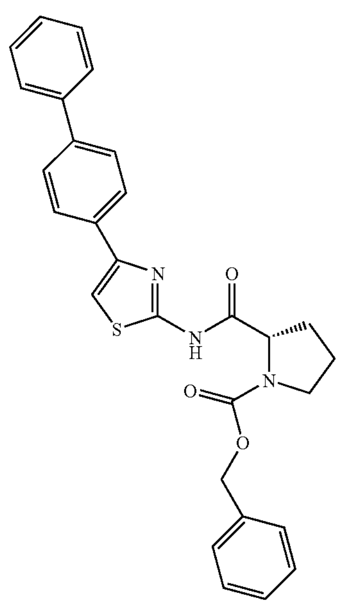 | 2-(4-Biphenyl-4-yl-thiazol-2-ylcarbamoyl)-pyrrolidine-1-carboxylic acid benzyl ester |

TABLE 1-continued
| Ex. | Structure | Name |
|---|---|---|
| 5072 | 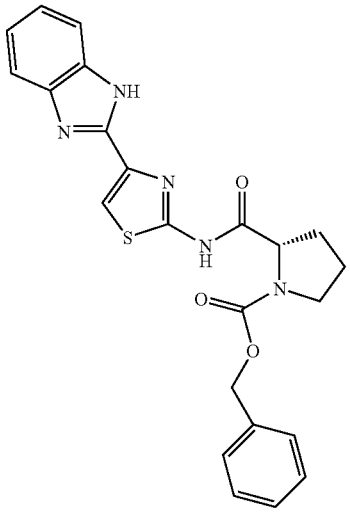 | 2-[4-(1H-Benzoimidazol-2-yl)-thiazol-2-ylcarbamoyl]-pyrrolidine-1-carboxylic acid benzyl ester |
| 5073 | 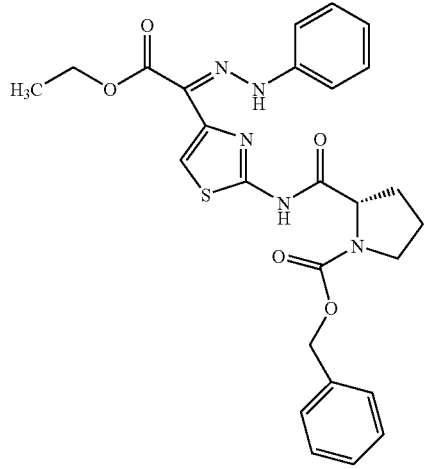 | 2-{4-[Ethoxycarbonyl-(phenyl-hydrazono)-methyl]-thiazol-2-ylcarbamoyl}-pyrrolidine-1-carboxylic acid benzyl ester |
| 5074 | 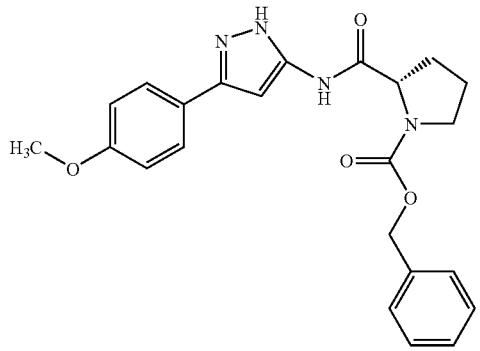 | 2-[5-(4-Methoxy-phenyl)-2H-pyrazol-3-ylcarbamoyl]-pyrrolidine-1-carboxylic acid benzyl ester |

TABLE 1-continued
| Ex. | Structure | Name |
|---|---|---|
| 5075 | 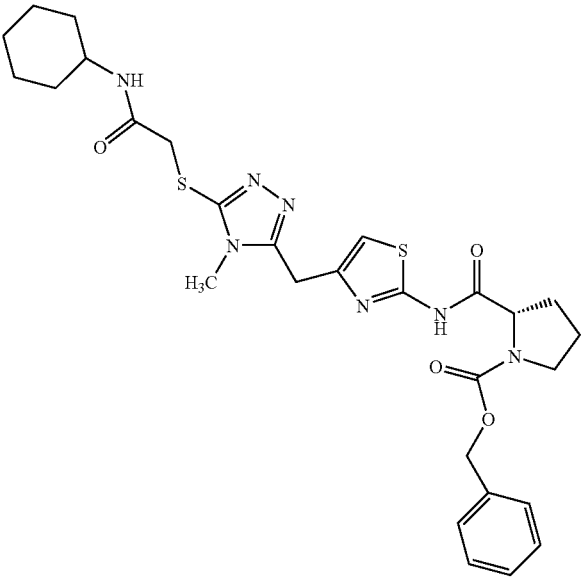 | 2-[4-(5-Cyclohexylcarbamoylmethyl sulfanyl-4-methyl-4H-[1,2,4]triazol-3-ylmethyl)-thiazol-2-ylcarbamoyl]-pyrrolidine-1-carboxylic acid benzyl ester |
| 5076 | 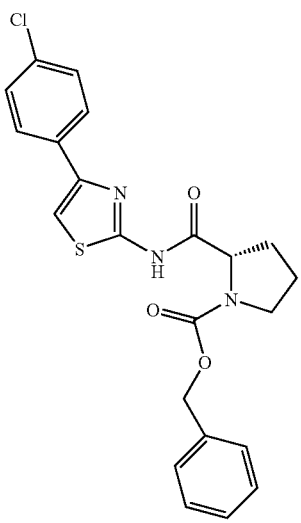 | 2-[4-(4-Chloro-phenyl)-thiazol-2-ylcarbamoyl]-pyrrolidine-1-carboxylic acid benzyl ester |

TABLE 1-continued

| Ex. | Structure | Name |
|---|---|---|
| 5077 | 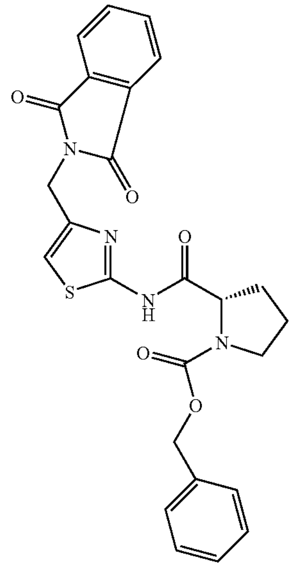 | 2-[4-(1,3-Dioxo-1,3-dihydro-isoindol-2-ylmethyl)-thiazol-2-ylcarbamoyl]-pyrrolidine-1-carboxylic acid benzyl ester |
| 5078 | 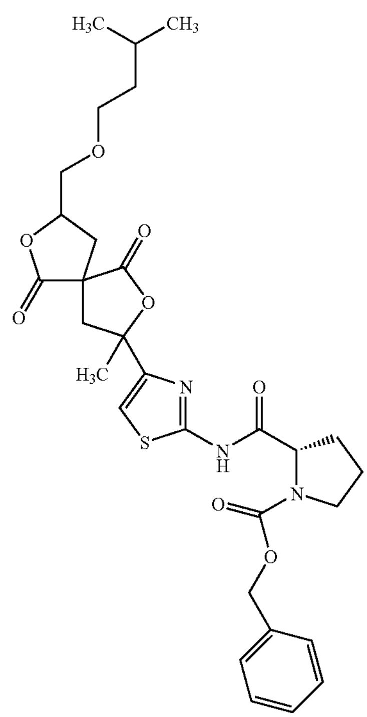 | 2-{4-[3-Methyl-8-(3-methyl-butoxymethyl)-1,6-dioxo-2,7-dioxa-spiro[4.4]non-3-yl]-thiazol-2-ylcarbamoyl}-pyrrolidine-1-carboxylic acid benzyl ester |

| Ex. | Structure | Name |
|---|---|---|
| 5079 | 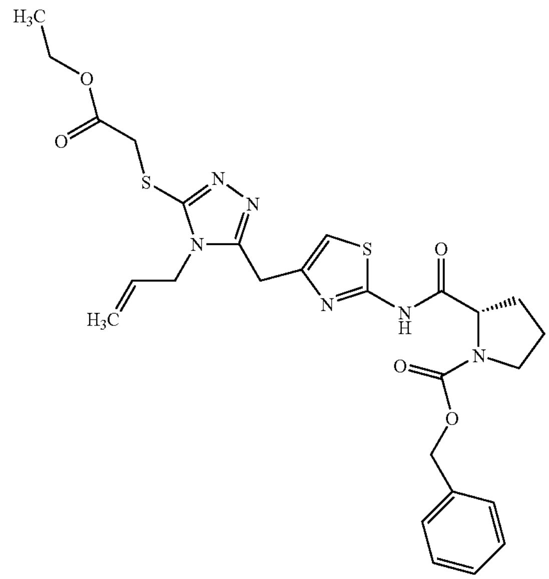 | 2-[4-(4-Allyl-5-ethoxycarbonylmethylsulfanyl-4H-[1,2,4]triazol-3-ylmethyl)-thiazol-2-ylcarbamoyl]-pyrrolidine-1-carboxylic acid benzyl ester |
| 5080 | 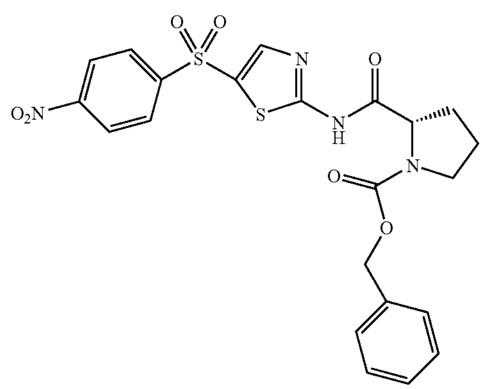 | 2-[5-(4-Nitro-benzenesulfonyl)-thiazol-2-ylcarbamoyl]-pyrrolidine-1-carboxylic acid benzyl ester |
| 5081 | 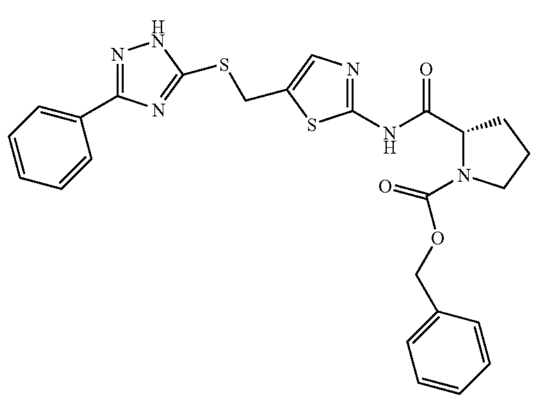 | 2-[5-(5-Phenyl-2H-[1,2,4]triazol-3-ylsulfanylmethyl)-thiazol-2-ylcarbamoyl]-pyrrolidine-1-carboxylic acid benzyl ester |

TABLE 1-continued

| Ex. | Structure | Name |
|---|---|---|
| 5082 | 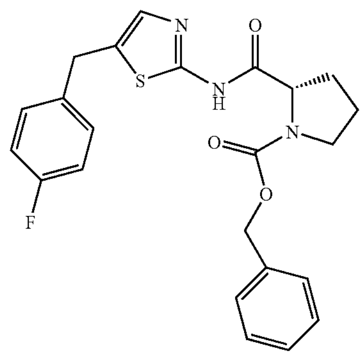 | 2-[5-(4-Fluoro-benzyl)-thiazol-2-ylcarbamoyl]-pyrrolidine-1-carboxylic acid benzyl ester |
| 5083 | 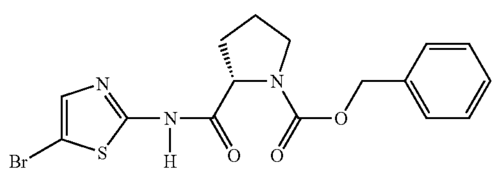 | 2-(5-Bromo-thiazol-2-ylcarbamoyl)-pyrrolidine-1-carboxylic acid benzyl ester |
| 5084 | 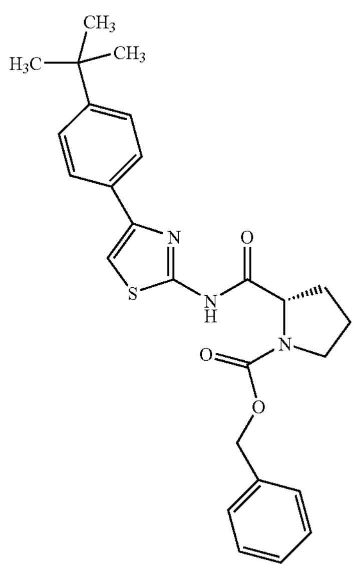 | 2-[4-(4-tert-Butyl-phenyl)-thiazol-2-ylcarbamoyl]-pyrrolidine-1-carboxylic acid benzyl ester |

TABLE 1-continued

| Ex. | Structure | Name |
|---|---|---|
| 5085 | 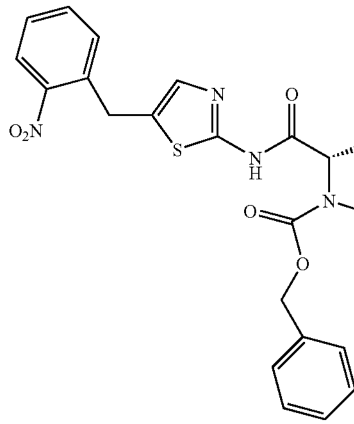 | 2-[5-(2-Nitro-benzyl)-thiazol-2-ylcarbamoyl]-pyrrolidine-1-carboxylic acid benzyl ester |
| 5086 | 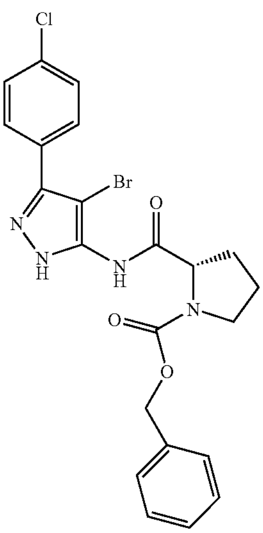 | 2-[4-Bromo-5-(4-chloro-phenyl)-2H-pyrazol-3-ylcarbamoyl]-pyrrolidine-1-carboxylic acid benzyl ester |
| 5087 | 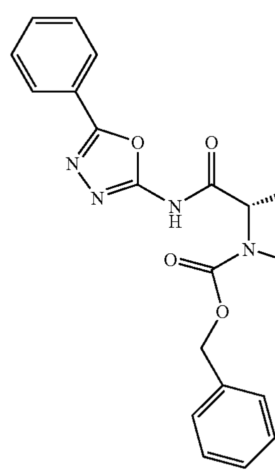 | 2-(5-Phenyl-[1,3,4]oxadiazol-2-ylcarbamoyl)-pyrrolidine-1-carboxylic acid benzyl ester |

TABLE 1-continued

| Ex. | Structure | Name |
|---|---|---|
| 5088 | 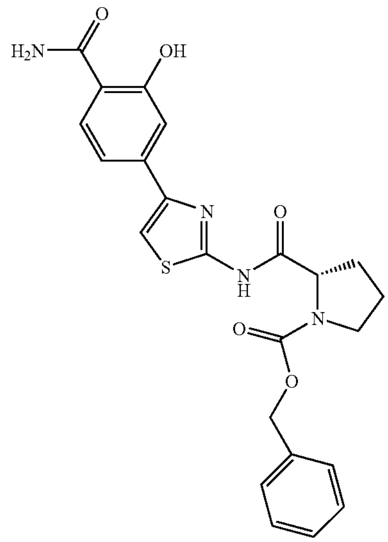 | 2-[4-(4-Carbamoyl-3-hydroxy-phenyl)-thiazol-2-ylcarbamoyl]-pyrrolidine-1-carboxylic acid benzyl ester |
| 5089 | 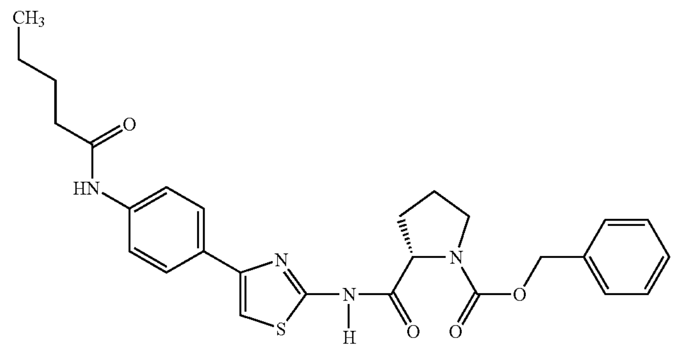 | 2-[4-(4-Pentanoylamino-phenyl)-thiazol-2-ylcarbamoyl]-pyrrolidine-1-carboxylic acid benzyl ester |
| 5090 | 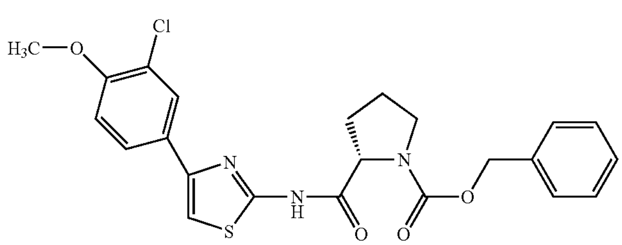 | 2-[4-(3-Chloro-4-methoxy-phenyl)-thiazol-2-ylcarbamoyl]-pyrrolidine-1-carboxylic acid benzyl ester |
| 5091 | 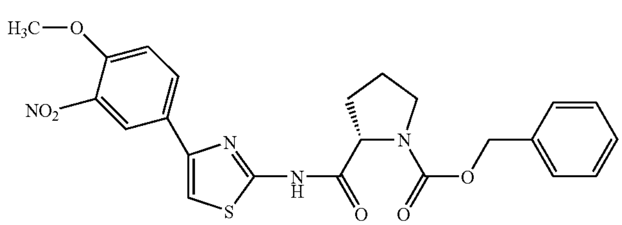 | 2-[4-(4-Methoxy-3-nitro-phenyl)-thiazol-2-ylcarbamoyl]-pyrrolidine-1-carboxylic acid benzyl ester |

TABLE 1-continued

| Ex. | Structure | Name |
|---|---|---|
| 5092 | 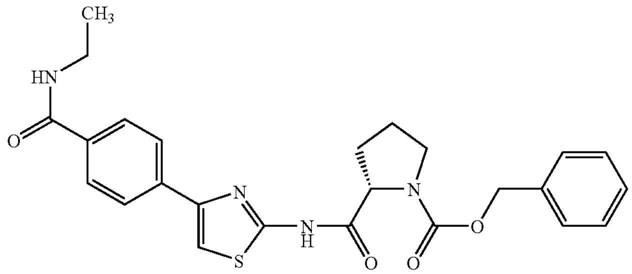 | 2-[4-(4-Ethylcarbamoyl-phenyl)-thiazol-2-ylcarbamoyl]-pyrrolidine-1-carboxylic acid benzyl ester |
| 5093 | 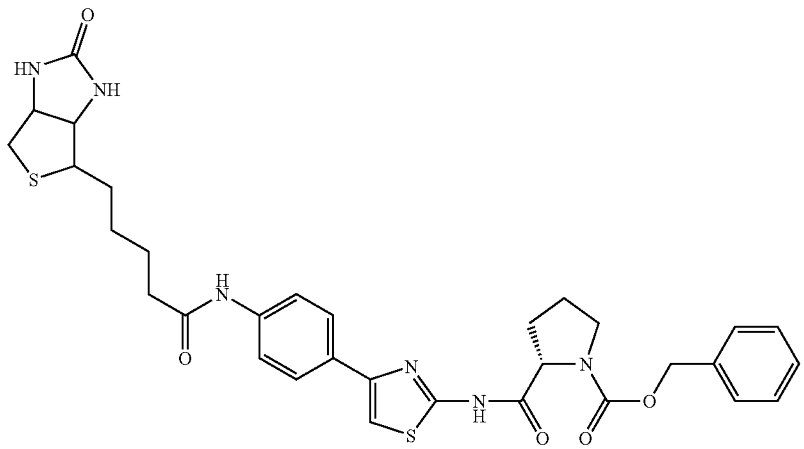 | 2-(4-{4-[5-(2-Oxo-hexahydro-thieno[3,4-d]imidazol-4-yl)-pentanoylamino]-phenyl}-thiazol-2-ylcarbamoyl)-pyrrolidine-1-carboxylic acid benzyl ester |
| 5094 | 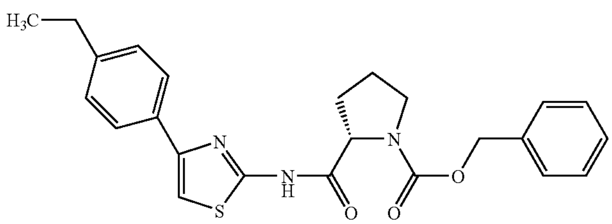 | 2-[4-(4-Ethyl-phenyl)-thiazol-2-ylcarbamoyl]-pyrrolidine-1-carboxylic acid benzyl ester |
| 5095 | 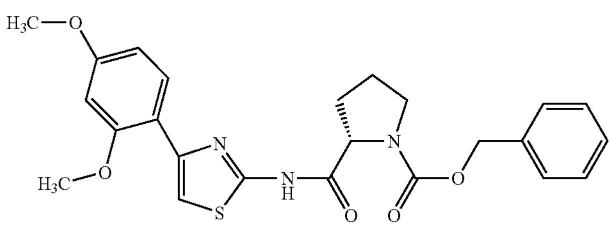 | 2-[4-(2,4-Dimethoxy-phenyl)-thiazol-2-ylcarbamoyl]-pyrrolidine-1-carboxylic acid benzyl ester |
| 5096 | 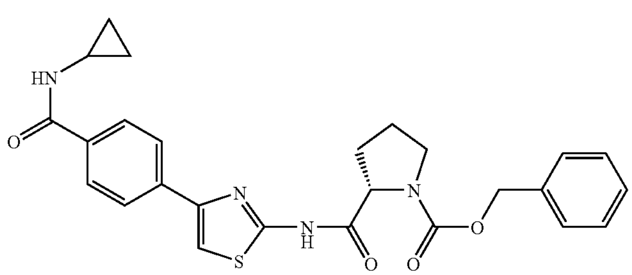 | 2-[4-(4-Cyclopropylcarbamoyl-phenyl)-thiazol-2-ylcarbamoyl]-pyrrolidine-1-carboxylic acid benzyl ester |

TABLE 1-continued

| Ex. | Structure | Name |
|---|---|---|
| 5097 | 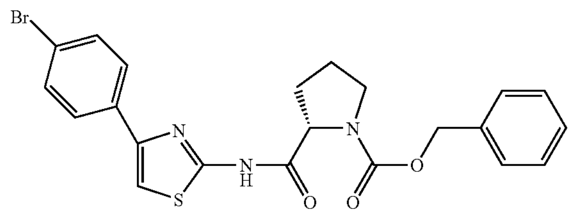 | 2-[4-(4-Bromo-phenyl)-thiazol-2-ylcarbamoyl]-pyrrolidine-1-carboxylic acid benzyl ester |
| 5098 | 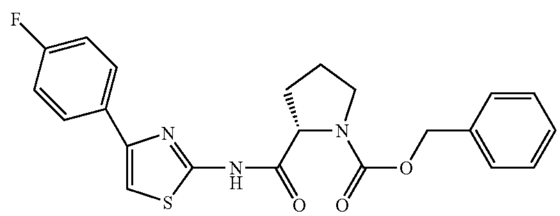 | 2-[4-(4-Fluoro-phenyl)-thiazol-2-ylcarbamoyl]-pyrrolidine-1-carboxylic acid benzyl ester |
| 5099 | 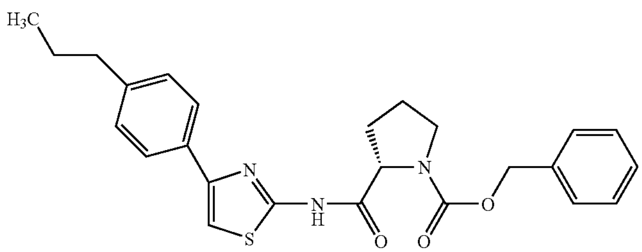 | 2-[4-(4-Propyl-phenyl)-thiazol-2-ylcarbamoyl]-pyrrolidine-1-carboxylic acid benzyl ester |
| 5100 | 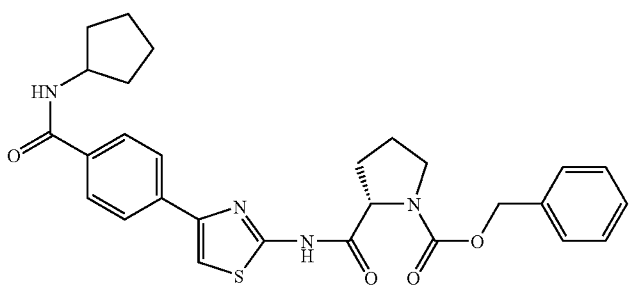 | 2-[4-(4-Cyclopentylcarbamoyl-phenyl)-thiazol-2-ylcarbamoyl]-pyrrolidine-1-carboxylic acid benzyl ester |
| 5101 | 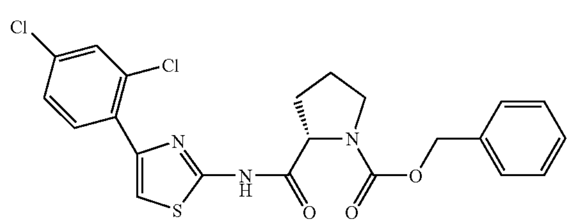 | 2-[4-(2,4-Dichloro-phenyl)-thiazol-2-ylcarbamoyl]-pyrrolidine-1-carboxylic acid benzyl ester |
| 5102 | 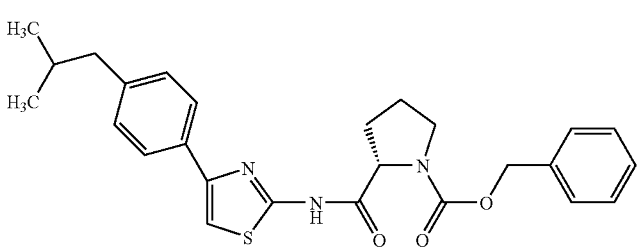 | 2-[4-(4-Isobutyl-phenyl)-thiazol-2-ylcarbamoyl]-pyrrolidine-1-carboxylic acid benzyl ester |

TABLE 1-continued

| Ex. | Structure | Name |
|---|---|---|
| 5103 | 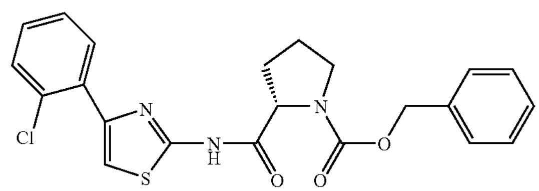 | 2-[4-(2-Chloro-phenyl)-thiazol-2-ylcarbamoyl]-pyrrolidine-1-carboxylic acid benzyl ester |
| 5104 | 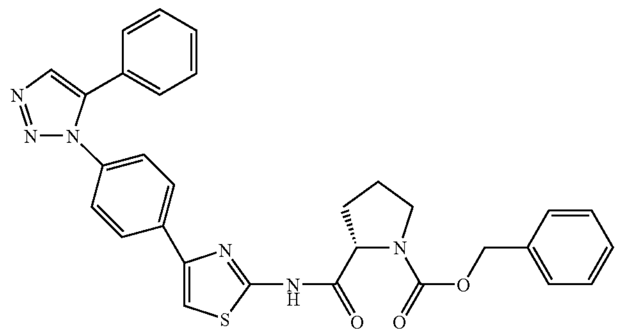 | 2-{4-[4-(5-Phenyl-[1,2,3]triazol-1-yl)-phenyl]-thiazol-2-ylcarbamoyl}-pyrrolidine-1-carboxylic acid benzyl ester |
| 5105 | 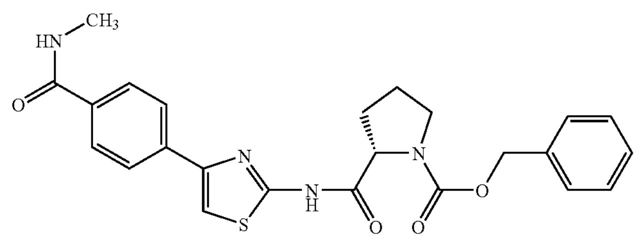 | 2-[4-(4-Methylcarbamoyl-phenyl)-thiazol-2-ylcarbamoyl]-pyrrolidine-1-carboxylic acid benzyl ester |
| 5106 | 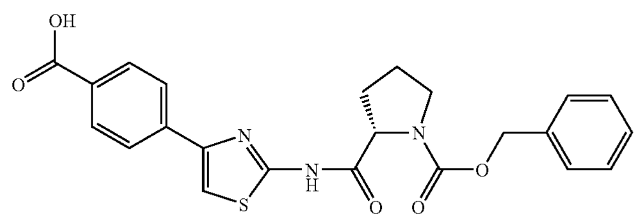 | 2-[4-(4-Carboxy-phenyl)-thiazol-2-ylcarbamoyl]-pyrrolidine-1-carboxylic acid benzyl ester |
| 5107 | 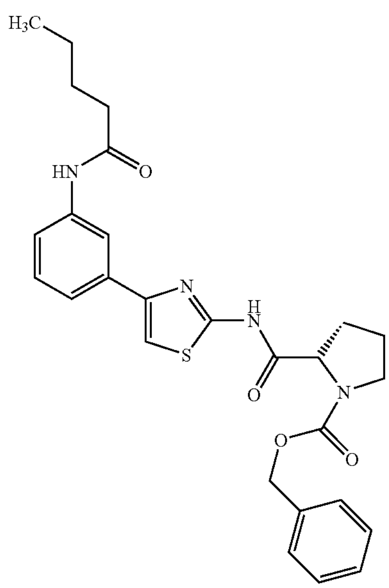 | 2-[4-(3-Pentanoylamino-phenyl)-thiazol-2-ylcarbamoyl]-pyrrolidine-1-carboxylic acid benzyl ester |

| Ex. | Structure | Name |
|---|---|---|
| 5108 | 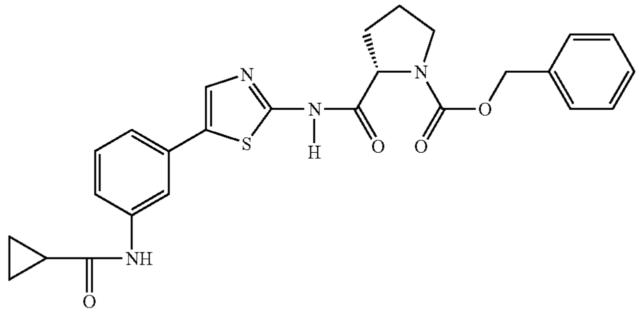 | 2-{5-[3-(Cyclopropanecarbonyl-amino)-phenyl]-thiazol-2-ylcarbamoyl}-pyrrolidine-1-carboxylic acid benzyl ester |
| 5109 | 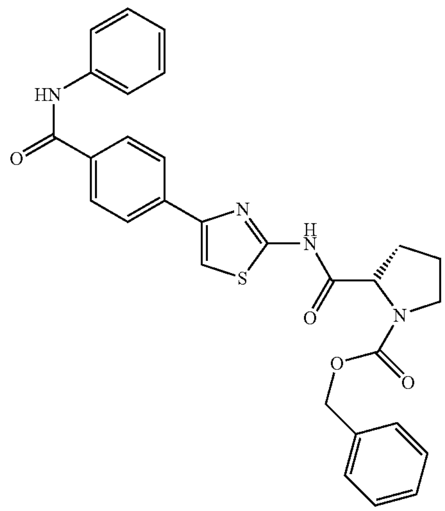 | 2-[4-(4-Phenylcarbamoyl-phenyl)-thiazol-2-ylcarbamoyl]-pyrrolidine-1-carboxylic acid benzyl ester |
| 5110 | 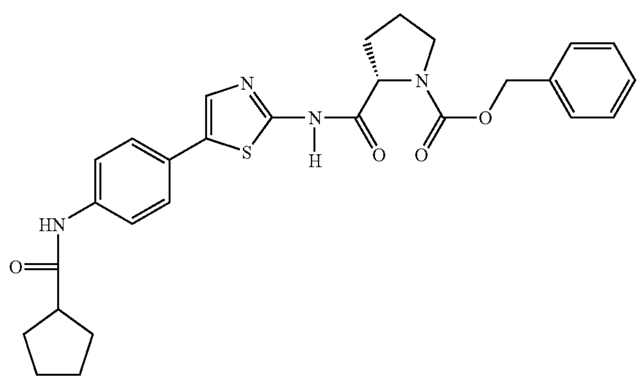 | 2-{5-[4-(Cyclopentanecarbonyl-amino)-phenyl]-thiazol-2-ylcarbamoyl}-pyrrolidine-1-carboxylic acid benzyl ester |
| 5111 | 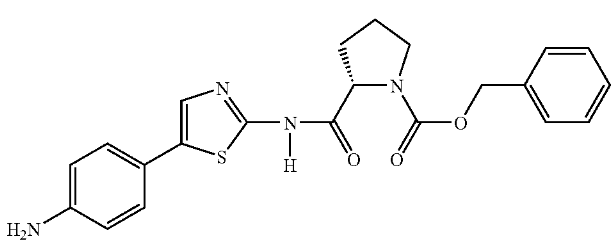 | 2-[5-(4-Amino-phenyl)-thiazol-2-ylcarbamoyl]-pyrrolidine-1-carboxylic acid benzyl ester |

TABLE 1-continued

| Ex. | Structure | Name |
|---|---|---|
| 5112 | 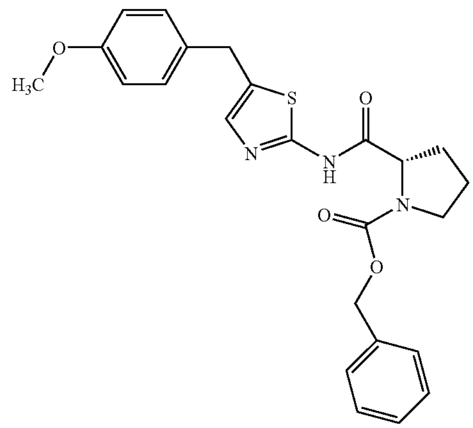 | 2-[5-(4-Methoxy-benzyl)-thiazol-2-ylcarbamoyl]-pyrrolidine-1-carboxylic acid benzyl ester |
| 5113 | 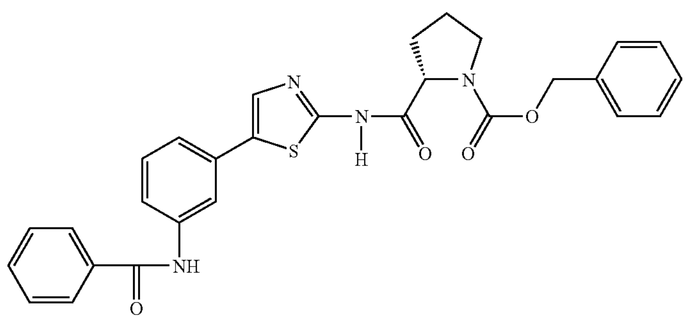 | 2-[5-(3-Benzoylamino-phenyl)-thiazol-2-ylcarbamoyl]-pyrrolidine-1-carboxylic acid benzyl ester |
| 5114 | 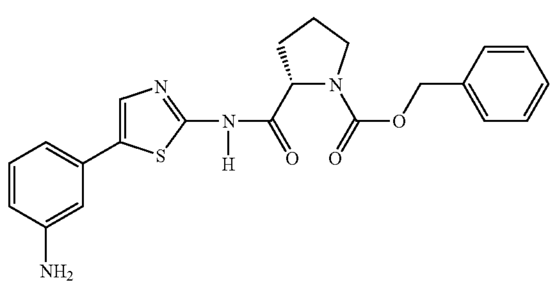 | 2-[5-(3-Amino-phenyl)-thiazol-2-ylcarbamoyl]-pyrrolidine-1-carboxylic acid benzyl ester |
| 5116 | 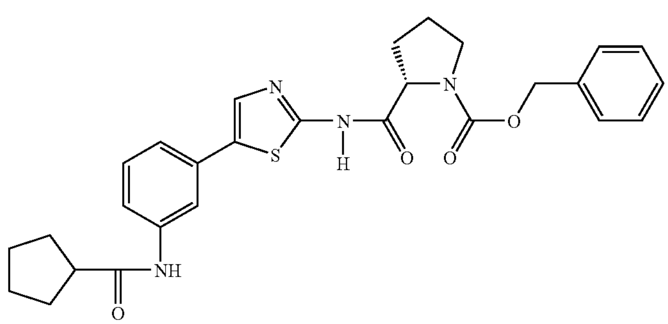 | 2-{5-[3-(Cyclopentanecarbonyl-amino)-phenyl]-thiazol-2-ylcarbamoyl}-pyrrolidine-1-carboxylic acid benzyl ester |

TABLE 1-continued

| Ex. | Structure | Name |
|---|---|---|
| 5117 | 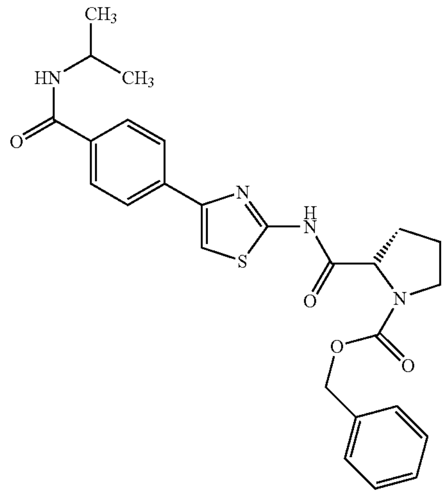 | 2-[4-(4-Isopropylcarbamoyl-phenyl)-thiazol-2-ylcarbamoyl]-pyrrolidine-1-carboxylic acid benzyl ester |
| 5201 | 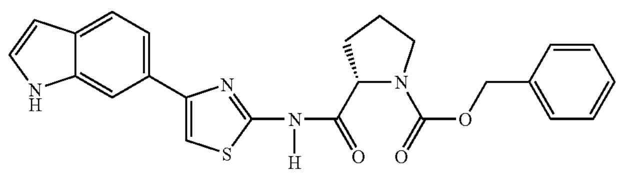 | 2-[4-(1H-Indol-6-yl)-thiazol-2-ylcarbamoyl]-pyrrolidine-1-carboxylic acid benzyl ester |
| 5202 | 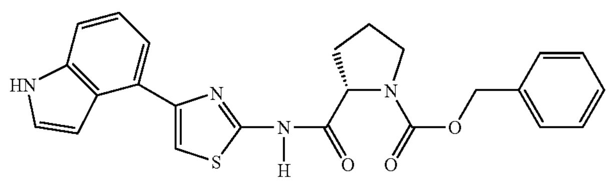 | 2-[4-(1H-Indol-4-yl)-thiazol-2-ylcarbamoyl]-pyrrolidine-1-carboxylic acid benzyl ester |
| 5203 | 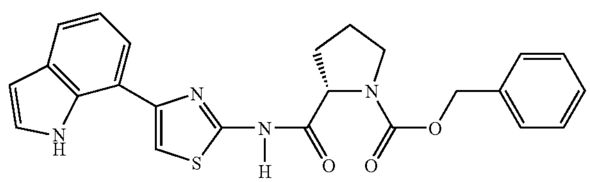 | 2-[4-(1H-Indol-7-yl)-thiazol-2-ylcarbamoyl]-pyrrolidine-1-carboxylic acid benzyl ester |
| 5204 | 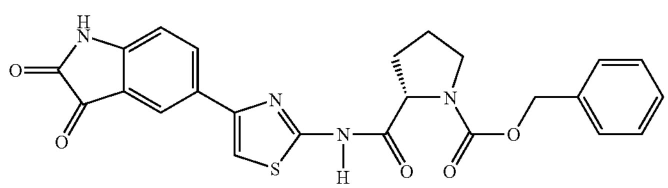 | 2-[4-(2,3-Dioxo-2,3-dihydro-1H-indol-5-yl)-thiazol-2-ylcarbamoyl]-pyrrolidine-1-carboxylic acid benzyl ester |
| 5205 | 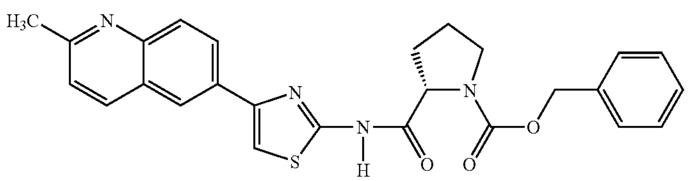 | 2-[4-(2-Methyl-quinolin-6-yl)-thiazol-2-ylcarbamoyl]-pyrrolidine-1-carboxylic acid benzyl ester |

TABLE 1-continued

| Ex. | Structure | Name |
|---|---|---|
| 5206 | 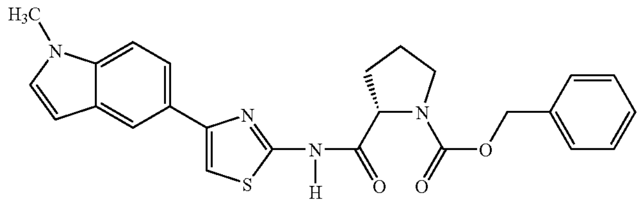 | 2-[4-(1-Methyl-1H-indol-5-yl)-thiazol-2-ylcarbamoyl]-pyrrolidine-1-carboxylic acid benzyl ester |
| 5207 | 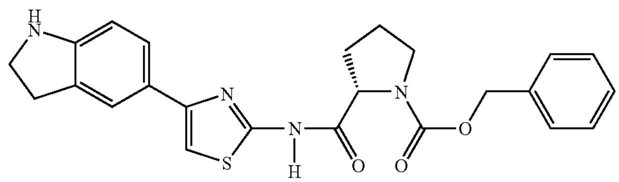 | 2-[4-(2,3-Dihydro-1H-indol-5-yl)-thiazol-2-ylcarbamoyl]-pyrrolidine-1-carboxylic acid benzyl ester |
| 5208 | 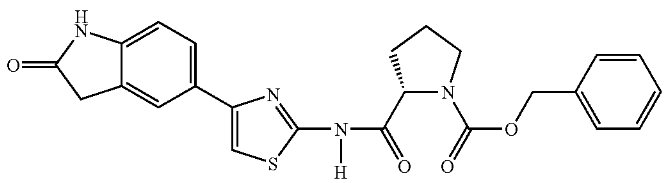 | 2-[4-(2-Oxo-2,3-dihydro-1H-indol-5-yl)-thiazol-2-ylcarbamoyl]-pyrrolidine-1-carboxylic acid benzyl ester |
| 5209 | 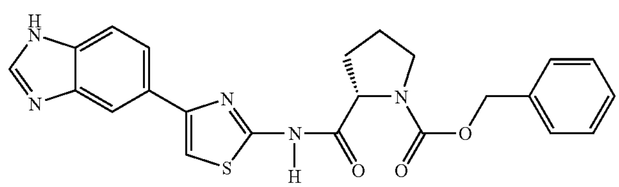 | 2-[4-(1H-Benzoimidazol-5-yl)-thiazol-2-ylcarbamoyl]-pyrrolidine-1-carboxylic acid benzyl ester |
| 5210 | 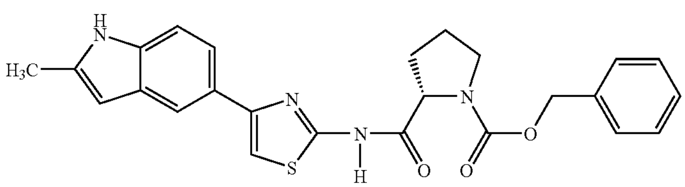 | 2-[4-(2-Methyl-1H-indol-5-yl)-thiazol-2-ylcarbamoyl]-pyrrolidine-1-carboxylic acid benzyl ester |
| 5211 | 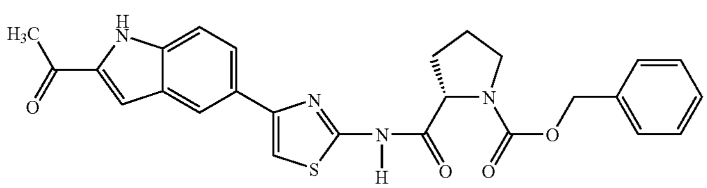 | 2-[4-(2-Acetyl-1H-indol-5-yl)-thiazol-2-ylcarbamoyl]-pyrrolidine-1-carboxylic acid benzyl ester |
| 5212 | 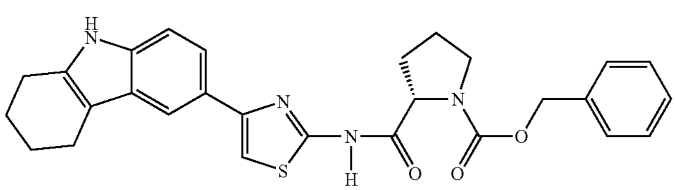 | 2-[4-(6,7,8,9-Tetrahydro-5H-carbazol-3-yl)-thiazol-2-ylcarbamoyl]-pyrrolidine-1-carboxylic acid benzyl ester |

TABLE 1-continued

| Ex. | Structure | Name |
|---|---|---|
| 5213 | 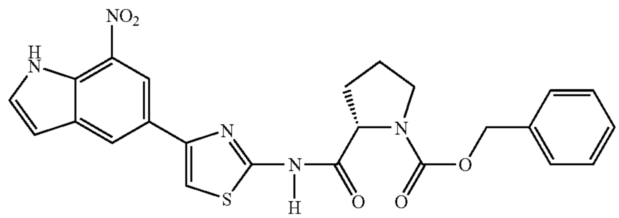 | 2-[4-(7-nitro-1H-indol-5-yl)-thiazol-2-ylcarbamoyl]-pyrrolidine-1-carboxylic acid benzyl ester |
| 5214 | 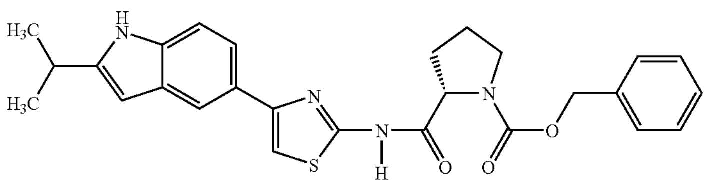 | 2-[4-(2-Isopropyl-1H-indol-5-yl)-thiazol-2-ylcarbamoyl]-pyrrolidine-1-carboxylic acid benzyl ester |
| 5215 | 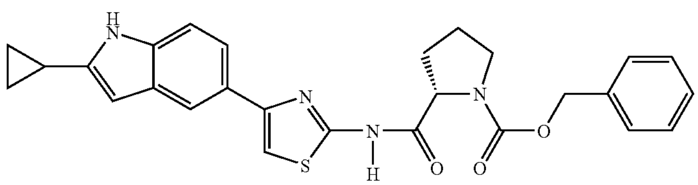 | 2-[4-(2-Cyclopropyl-1H-indol-5-yl)-thiazol-2-ylcarbamoyl]-pyrrolidine-1-carboxylic acid benzyl ester |
| 5216 | 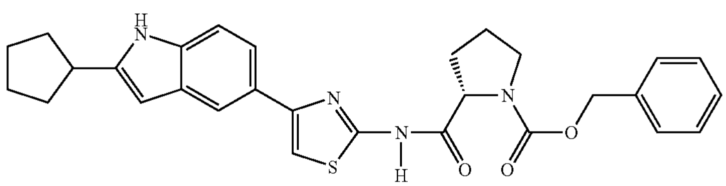 | 2-[4-(2-Cyclopentyl-1H-indol-5-yl)-thiazol-2-ylcarbamoyl]-pyrrolidine-1-carboxylic acid benzyl ester |
| 5217 | 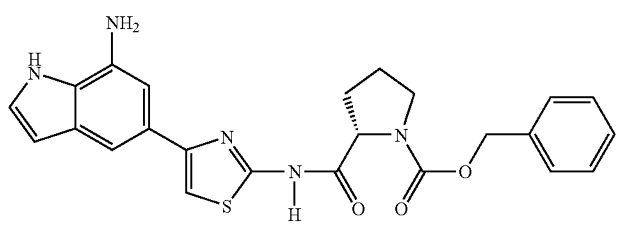 | 2-[4-(7-Amino-1H-indol-5-yl)-thiazol-2-ylcarbamoyl]-pyrrolidine-1-carboxylic acid benzyl ester |
| 5218 | 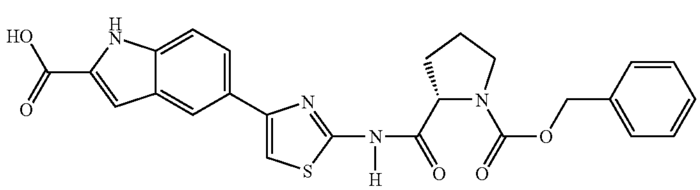 | 5-{2-[(1-Benzyloxycarbonyl-pyrrolidine-2-carbonyl)-amino]-thiazol-4-yl}-1H-indole-2-carboxylic acid |
| 5219 | 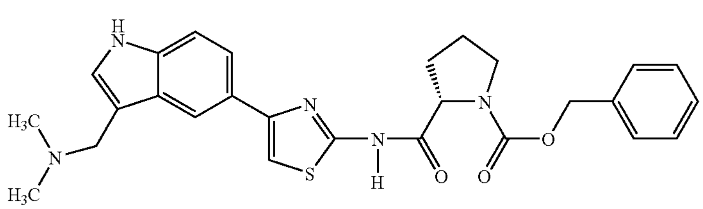 | 2-[4-(3-Dimethylaminomethyl-1H-indol-5-yl)-thiazol-2-ylcarbamoyl]-pyrrolidine-1-carboxylic acid benzyl ester |

TABLE 1-continued

| Ex. | Structure | Name |
|---|---|---|
| 5220 | 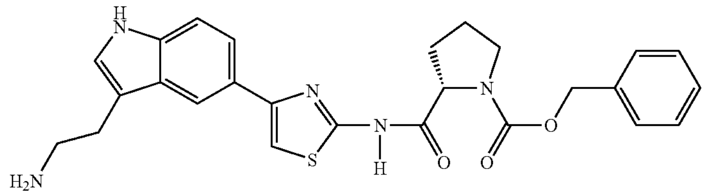 | 2-{4-[3-(2-Amino-ethyl)-1H-indol-5-yl]-thiazol-2-ylcarbamoyl}-pyrrolidine-1-carboxylic acid benzyl ester |
| 5221 | 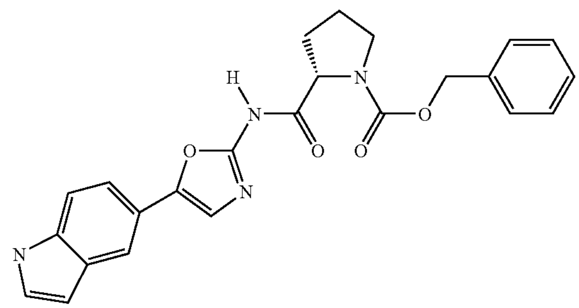 | 2-[5-(1H-Indol-5-yl)-oxazol-2-ylcarbamoyl]-pyrrolidine-1-carboxylic acid benzyl ester |
| 5222 | 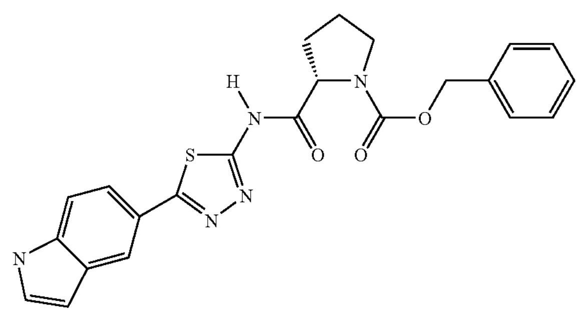 | 2-[5-(1H-Indol-5-yl)-[1,3,4]thiadiazol-2-ylcarbamoyl]-pyrrolidine-1-carboxylic acid benzyl ester |
| 5223 | 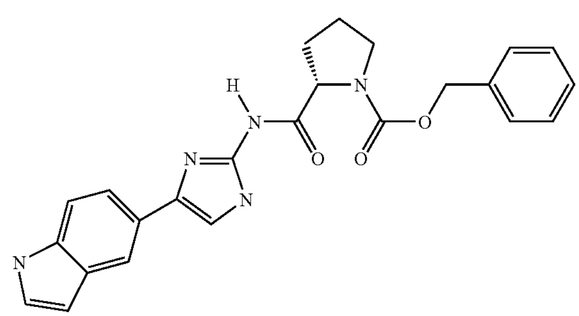 | 2-[4-(1H-Indol-5-yl)-1H-imidazol-2-ylcarbamoyl]-pyrrolidine-1-carboxylic acid benzyl ester |

TABLE 1-continued

| Ex. | Structure | Name |
|---|---|---|
| 5301 | 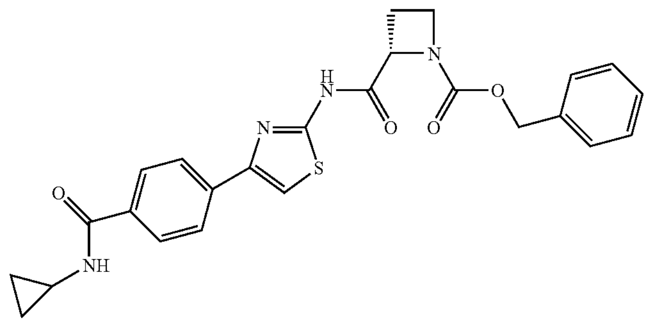 | 2-[4-(4-Cyclopropylcarbamoyl-phenyl)-thiazol-2-ylcarbamoyl]-azetidine-1-carboxylic acid benzyl ester |
| 5302 | 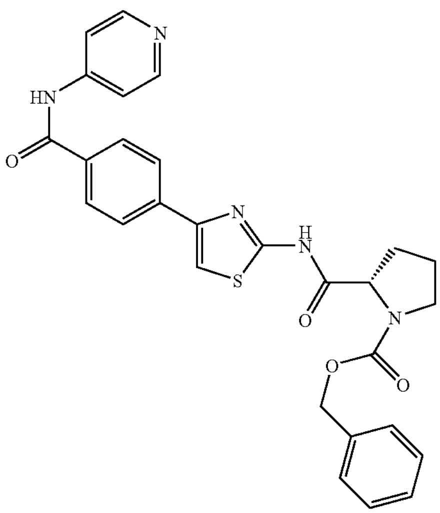 | 2-{4-[4-(Pyridin-4-ylcarbamoyl)-phenyl]-thiazol-2-ylcarbamoyl}-pyrrolidine-1-carboxylic acid benzyl ester |
| 5303 | 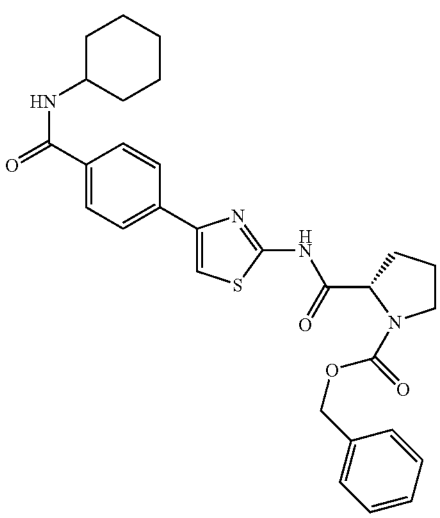 | 2-[4-(4-Cyclohexylcarbamoyl-phenyl)-thiazol-2-ylcarbamoyl]-pyrrolidine-1-carboxylic acid benzyl ester |
| 5304 | 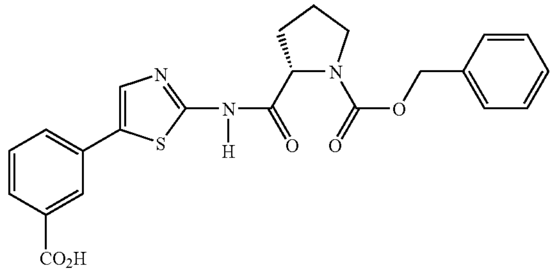 | 2-[5-(3-Carboxy-phenyl)-thiazol-2-ylcarbamoyl]-pyrrolidine-1-carboxylic acid benzyl ester |

TABLE 1-continued

| Ex. | Structure | Name |
|---|---|---|
| 5305 | 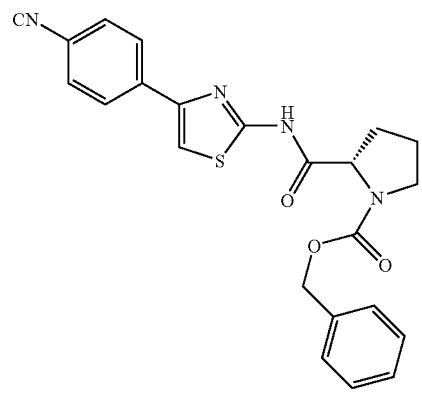 | 2-[4-(4-Cyanophenyl)-thiazol-2-ylcarbamoyl]-pyrrolidine-1-carboxylic acid benzyl ester |
| 5306 | 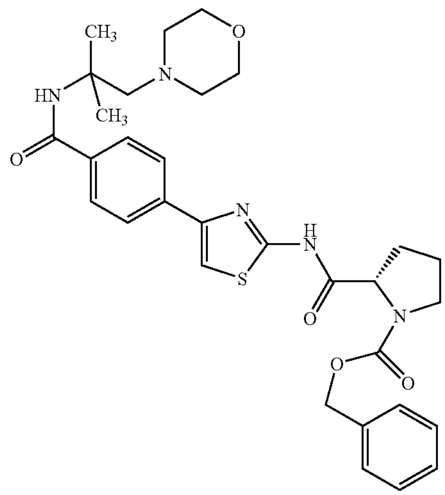 | 2-{4-[4-(1,1-Dimethyl-2-morpholin-4-yl-ethylcarbamoyl)-phenyl]-thiazol-2-ylcarbamoyl}-pyrrolidine-1-carboxylic acid benzyl ester |
| 5307 | 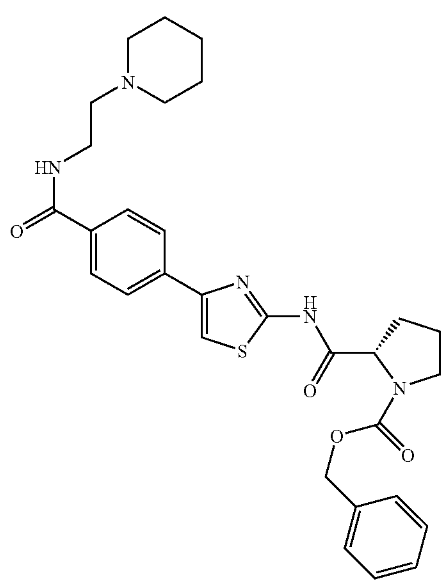 | 2-{4-[4-(2-Piperidin-1-yl-ethylcarbamoyl)-phenyl]-thiazol-2-ylcarbamoyl}-pyrrolidine-1-carboxylic acid benzyl ester |

TABLE 1-continued

| Ex. | Structure | Name |
|---|---|---|
| 5308 | 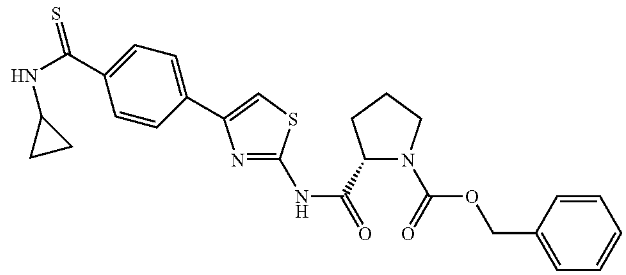 | 2-[4-(4-Cyclopropylthiocarbamoyl-phenyl)-thiazol-2-ylcarbamoyl]-pyrrolidine-1-carboxylic acid benzyl ester |
| 5309 | 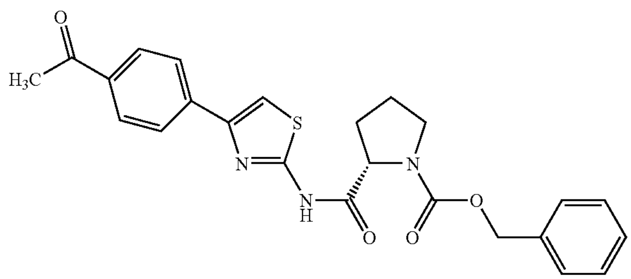 | 2-[4-(4-Acetyl-phenyl)-thiazol-2-ylcarbamoyl]-pyrrolidine-1-carboxylic acid benzyl ester |
| 5310 | 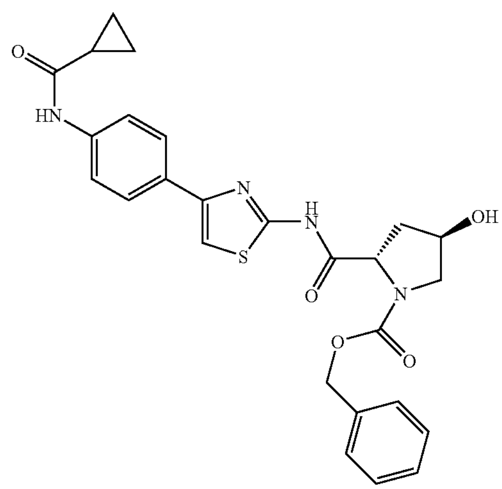 | 2-{4-[4-(Cyclopropanecarbonyl-amino)-phenyl]-thiazol-2-ylcarbamoyl}-4-hydroxy-pyrrolidine-1-carboxylic acid benzyl ester |
| 5311 | 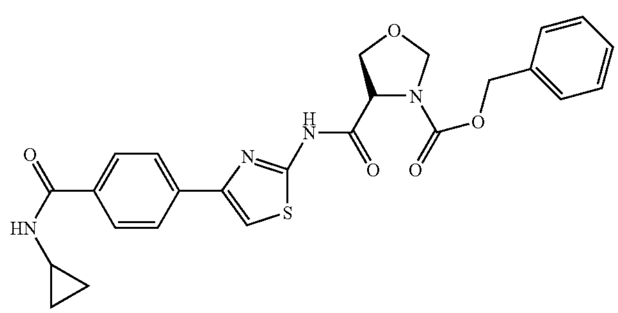 | 4-[4-(4-Cyclopropylcarbamoyl-phenyl)-thiazol-2-ylcarbamoyl]-oxazolidine-3-carboxylic acid benzyl ester |

TABLE 1-continued
| Ex. | Structure | Name |
|---|---|---|
| 5312 | 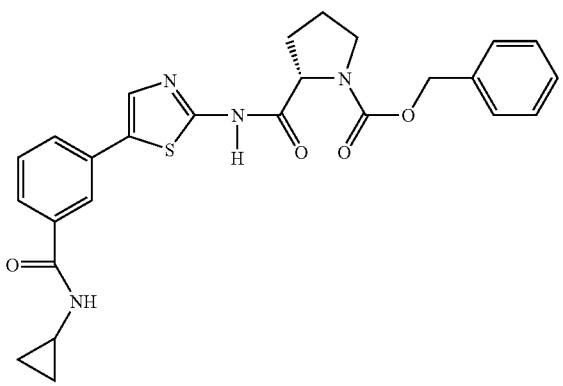 | 2-[5-(3-Cyclopropylcarbamoyl-phenyl)-thiazol-2-ylcarbamoyl]-pyrrolidine-1-carboxylic acid benzyl ester |
| 5313 | 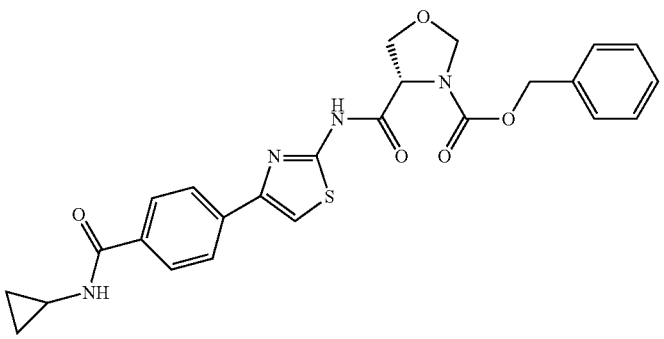 | 4-[4-(4-Cyclopropylcarbamoyl-phenyl)-thiazol-2-ylcarbamoyl]-oxazolidine-3-carboxylic acid benzyl ester |
| 5314 | 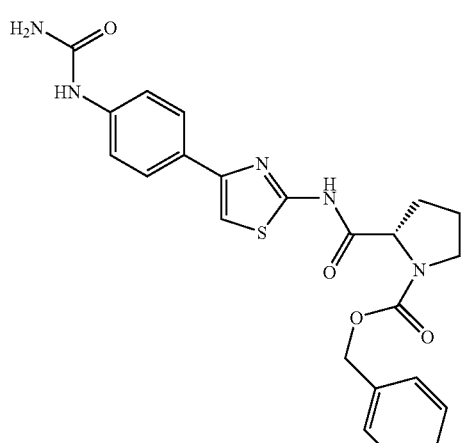 | 2-[4-(4-Ureido-phenyl)-thiazol-2-ylcarbamoyl]-pyrrolidine-1-carboxylic acid benzyl ester |

TABLE 1-continued

| Ex. | Structure | Name |
|---|---|---|
| 5315 | 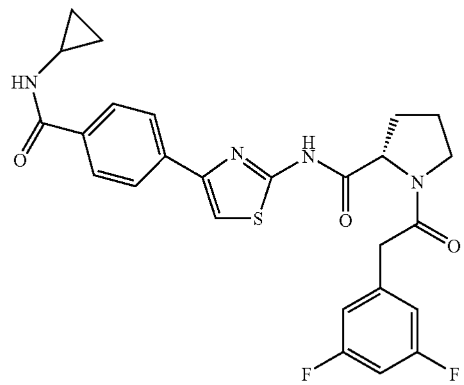 | 1-[2-(3,5-Difluoro-phenyl)-acetyl]-pyrrolidine-2-carboxylic acid [4-(4-cyclopropylcarbamoyl-phenyl)-thiazol-2-yl]-amide |
| 5316 | 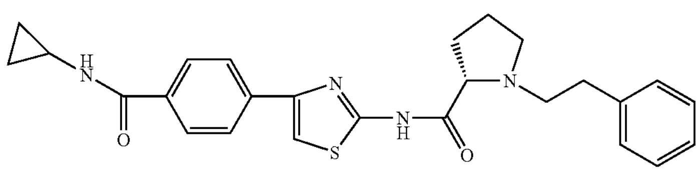 | 1-Phenethyl-pyrrolidine-2-carboxylic acid [4-(4-cyclopropylcarbamoyl-phenyl)-thiazol-2-yl]-amide |
| 5317 | 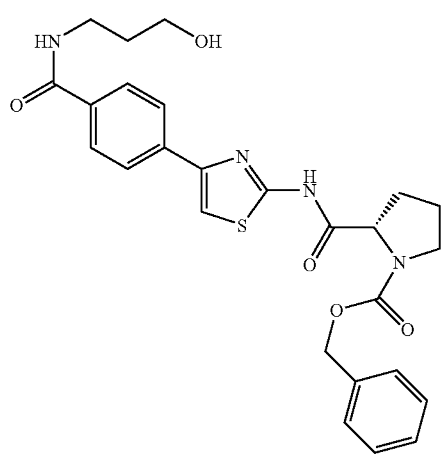 | 2-{4-[4-(3-Hydroxy-propylcarbamoyl)-phenyl]-thiazol-2-ylcarbamoyl}-pyrrolidine-1-carboxylic acid benzyl ester |

TABLE 1-continued

| Ex. | Structure | Name |
|---|---|---|
| 5318 | 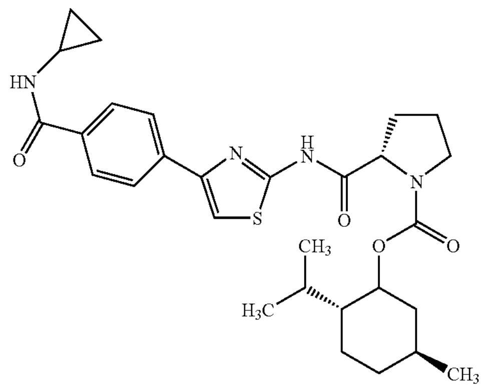 | 2-[4-(4-Cyclopropylcarbamoyl-phenyl)-thiazol-2-ylcarbamoyl]-pyrrolidine-1-carboxylic acid 2-isopropyl-5-methyl-cyclohexyl ester |
| 5319 | 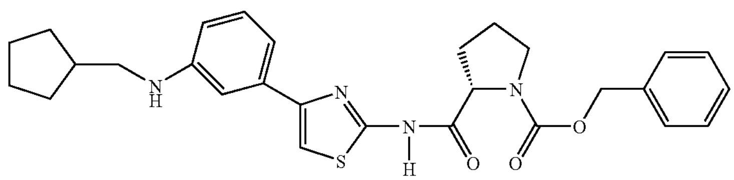 | 2-{4-[3-(Cyclopentylmethyl-amino)-phenyl]-thiazol-2-ylcarbamoyl}-pyrrolidine-1-carboxylic acid benzyl ester |
| 5320 | 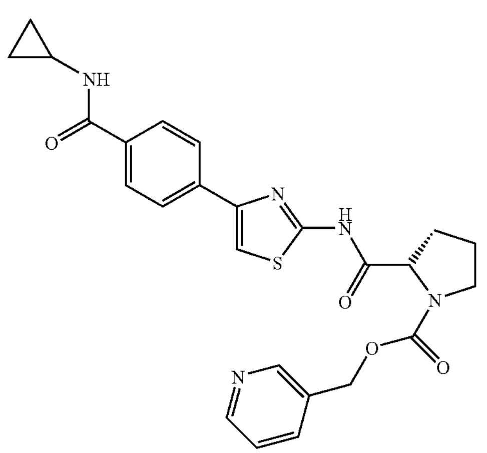 | 2-[4-(4-Cyclopropylcarbamoyl-phenyl)-thiazol-2-ylcarbamoyl]-pyrrolidine-1-carboxylic acid pyridin-3-ylmethyl ester |

TABLE 1-continued

| Ex. | Structure | Name |
|---|---|---|
| 5321 | 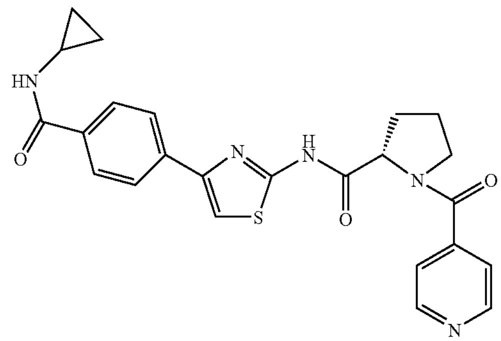 | 1-(Pyridine-4-carbonyl)-pyrrolidine-2-carboxylic acid [4-(4-cyclopropylcarbamoyl-phenyl)-thiazol-2-yl]-amide |
| 5322 | 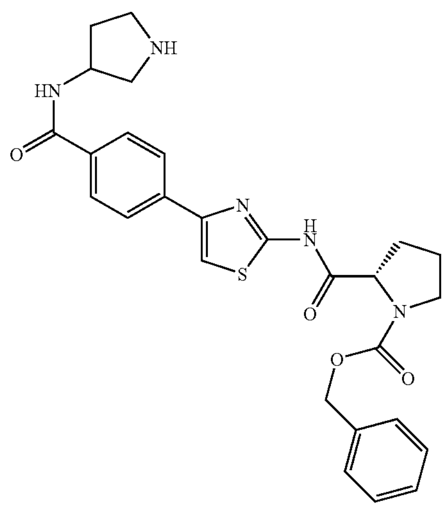 | 2-{4-[4-(Pyrrolidin-3-ylcarbamoyl)-phenyl]-thiazol-2-ylcarbamoyl}-pyrrolidine-1-carboxylic acid benzyl ester |
| 5323 | 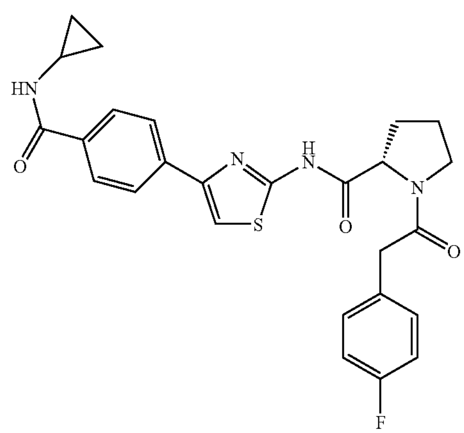 | 1-[2-(4-Fluoro-phenyl)-acetyl]-pyrrolidine-2-carboxylic acid [4-(4-cyclopropylcarbamoyl-phenyl)-thiazol-2-yl]-amide |

TABLE 1-continued

| Ex. | Structure | Name |
|---|---|---|
| 5324 | 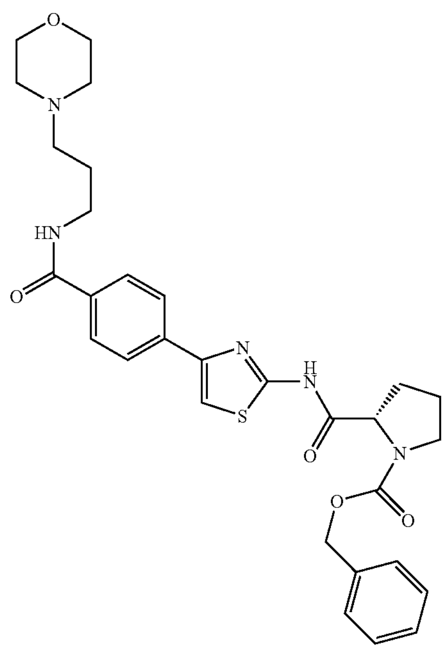 | 2-{4-[4-(3-Morpholin-4-yl-propylcarbamoyl)-phenyl]-thiazol-2-ylcarbamoyl}-pyrrolidine-1-carboxylic acid benzyl ester |
| 5325 | 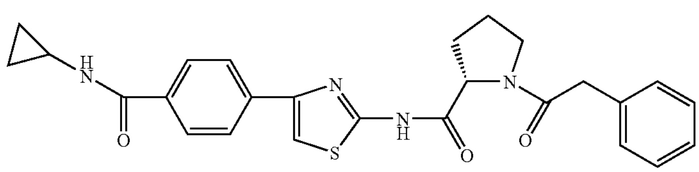 | 1-Phenylacetyl-pyrrolidine-2-carboxylic acid [4-(4-cyclopropylcarbamoyl-phenyl)-thiazol-2-yl]-amide |
| 5326 | 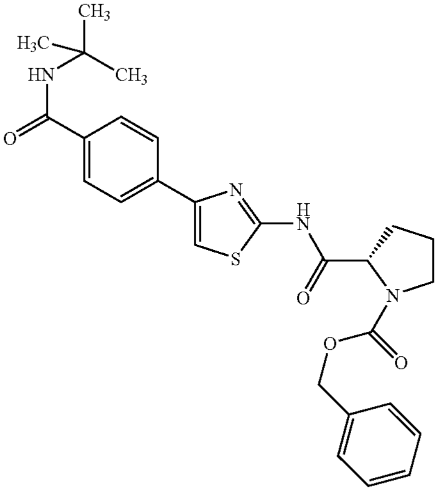 | 2-[4-(4-tert-Butylcarbamoyl-phenyl)-thiazol-2-ylcarbamoyl]-pyrrolidine-1-carboxylic acid benzyl ester |

| Ex. | Structure | Name |
|---|---|---|
| 5327 | 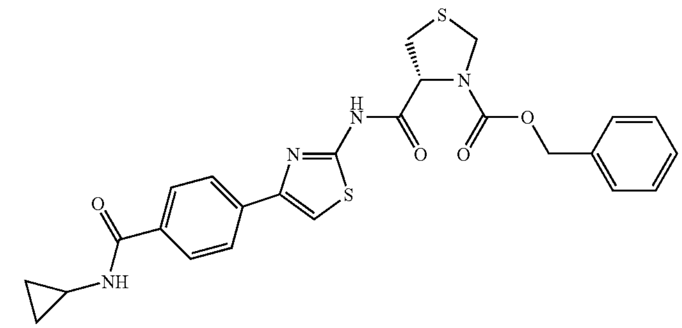 | 4-[4-(4-Cyclopropylcarbamoyl-phenyl)-thiazol-2-ylcarbamoyl]-thiazolidine-3-carboxylic acid benzyl ester |
| 5328 | 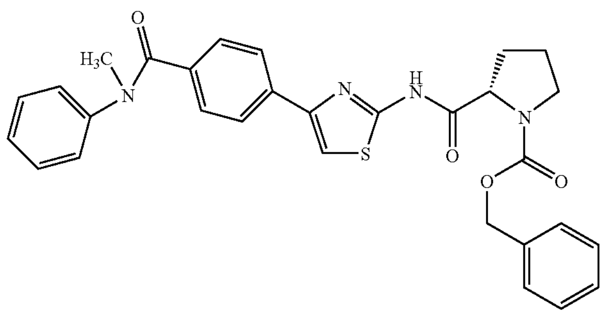 | 2-{4-[4-(Methyl-phenyl-carbamoyl)-phenyl]-thiazol-2-ylcarbamoyl}-pyrrolidine-1-carboxylic acid benzyl ester |
| 5329 | 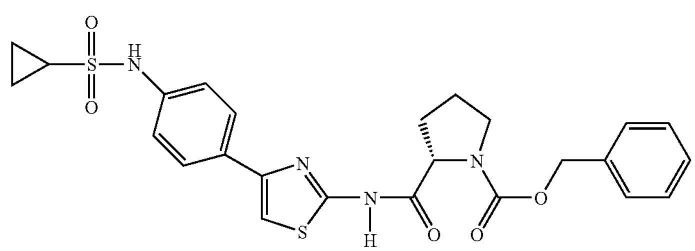 | 2-[4-(4-Cyclopropanesulfonylamino-phenyl)-thiazol-2-ylcarbamoyl]-pyrrolidine-1-carboxylic acid benzyl ester |
| 5330 | 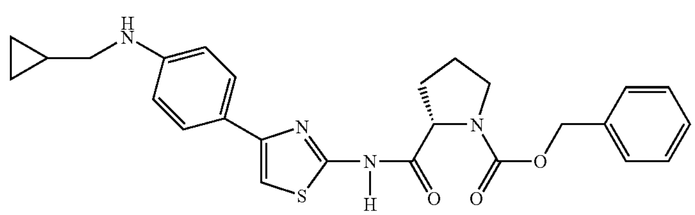 | 2-{4-[4-(Cyclopropylmethyl-amino)-phenyl]-thiazol-2-ylcarbamoyl}-pyrrolidine-1-carboxylic acid benzyl ester |
| 5331 | 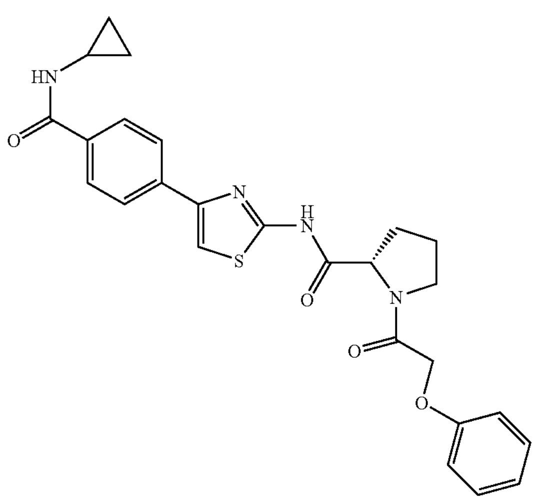 | 1-(2-Phenoxy-acetyl)-pyrrolidine-2-carboxylic acid [4-(4-cyclopropylcarbamoyl-phenyl)-thiazol-2-yl]-amide |

TABLE 1-continued

| Ex. | Structure | Name |
|---|---|---|
| 5332 | 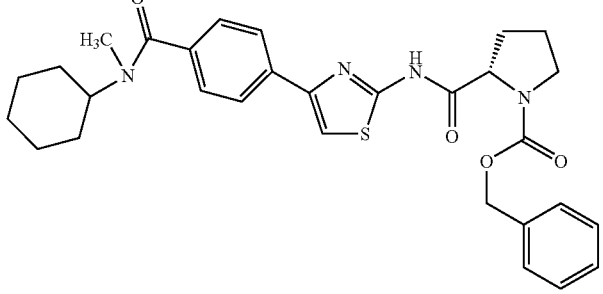 | 2-{4-[4-(Cyclohexyl-methyl-carbamoyl)-phenyl]-thiazol-2-ylcarbamoyl}-pyrrolidine-1-carboxylic acid benzyl ester |
| 5333 | 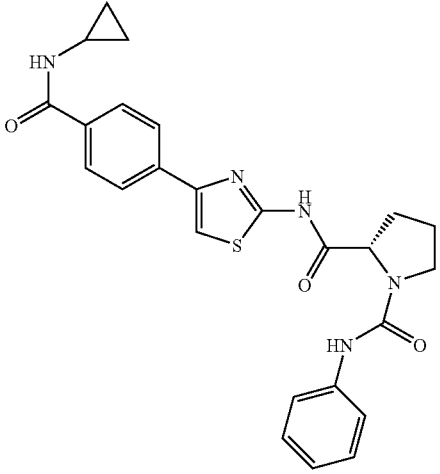 | Pyrrolidine-1,2-dicarboxylic acid 2-{[4-(4-cyclopropylcarbamoyl-phenyl)-thiazol-2-yl]-amide} 1-phenylamide |
| 5334 | 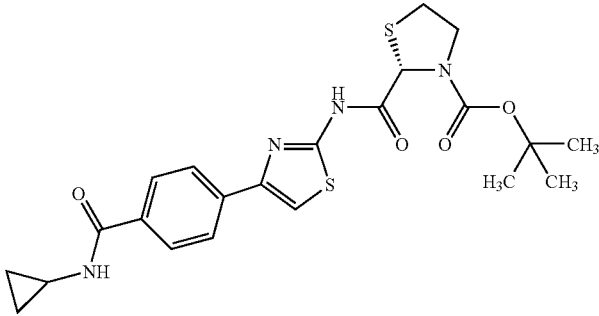 | 2-[4-(4-Cyclopropylcarbamoyl-phenyl)-thiazol-2-ylcarbamoyl]-thiazolidine-3-carboxylic acid tert-butyl ester |
| 5335 | 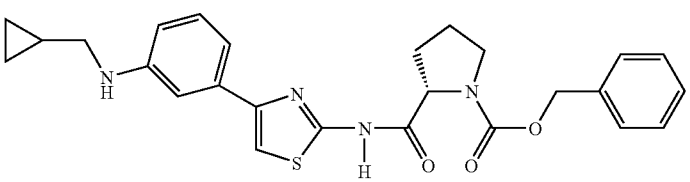 | 2-{4-[3-(Cyclopropylmethyl-amino)-phenyl]-thiazol-2-ylcarbamoyl}-pyrrolidine-1-carboxylic acid benzyl ester |

TABLE 1-continued
| Ex. | Structure | Name |
|---|---|---|
| 5336 | 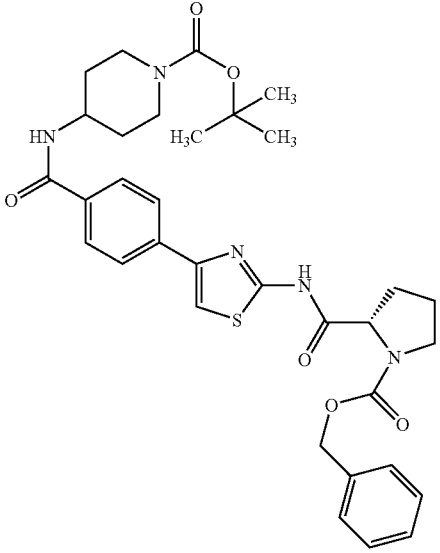 | 4-(4-{2-[(1-Benzyloxycarbonyl-pyrrolidine-2-carbonyl)-amino]-thiazol-4-yl}-benzoylamino)-piperidine-1-carboxylic acid tert-butyl ester |
| 5337 | 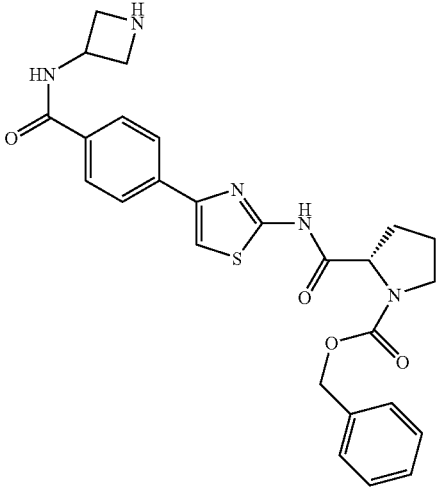 | 2-{4-[4-(Azetidin-3-ylcarbamoyl)-phenyl]-thiazol-2-ylcarbamoyl}-pyrrolidine-1-carboxylic acid benzyl ester |
| 5338 | 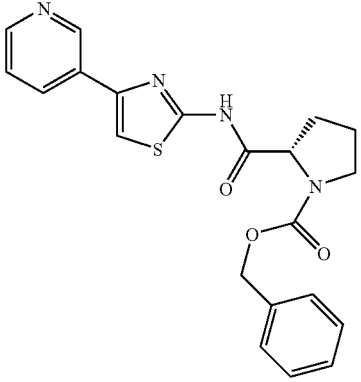 | 2-(4-Pyridin-3-yl-thiazol-2-ylcarbamoyl)-pyrrolidine-1-carboxylic acid benzyl ester |

TABLE 1-continued

| Ex. | Structure | Name |
|---|---|---|
| 5339 | 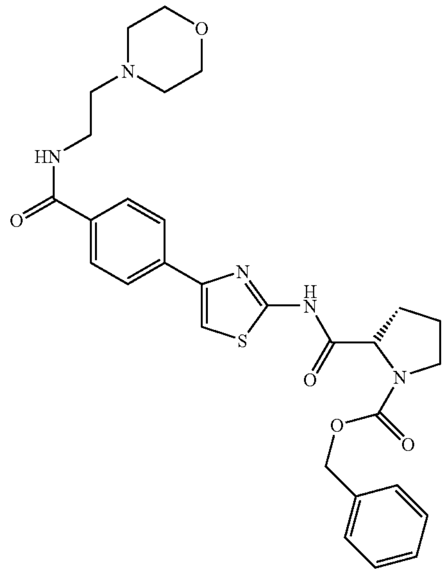 | 2-{4-[4-(2-Morpholin-4-yl-ethylcarbamoyl)-phenyl]-thiazol-2-ylcarbamoyl}-pyrrolidine-1-carboxylic acid benzyl ester |
| 5340 | 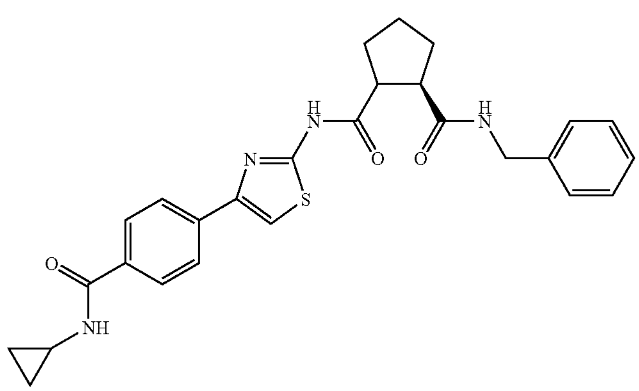 | Cyclopentane-1,2-dicarboxylic acid 1-benzylamide 2-{[4-(4-cyclopropylcarbamoyl-phenyl)-thiazol-2-yl]-amide} |

| Ex. | Structure | Name |
|---|---|---|
| 5341 | 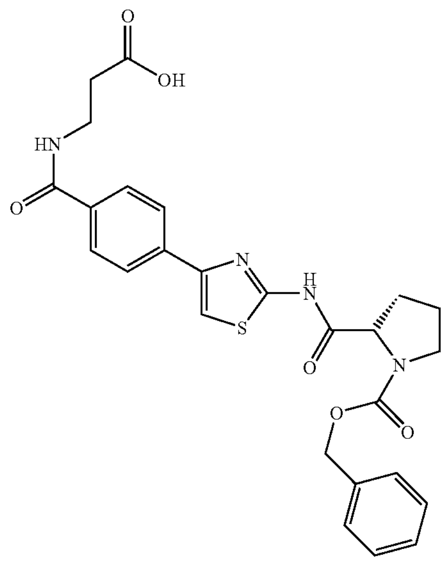 | 2-{4-[4-(2-Carboxy-ethylcarbamoyl)-phenyl]-thiazol-2-ylcarbamoyl}-pyrrolidine-1-carboxylic acid benzyl ester |
| 5342 | 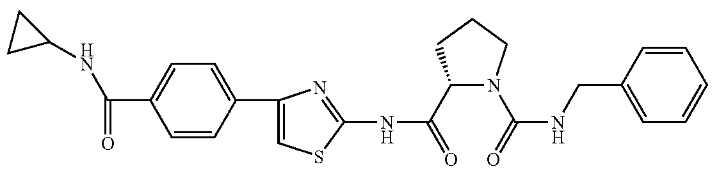 | Pyrrolidine-1,2-dicarboxylic acid 1-benzylamide 2-{[4-(4-cyclopropylcarbamoyl-phenyl)-thiazol-2-yl]-amide} |
| 5343 | 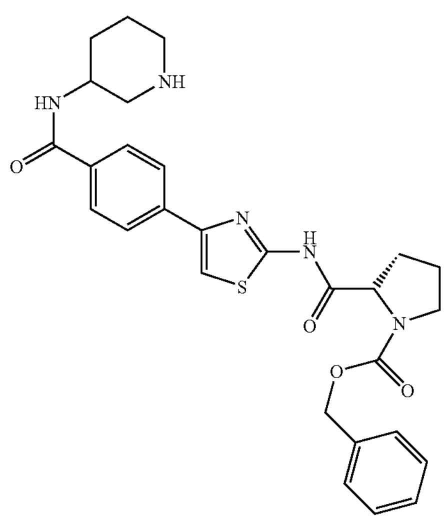 | 2-{4-[4-(Piperidin-3-ylcarbamoyl)-phenyl]-thiazol-2-ylcarbamoyl}-pyrrolidine-1-carboxylic acid benzyl ester |

TABLE 1-continued
| Ex. | Structure | Name |
|---|---|---|
| 5344 | 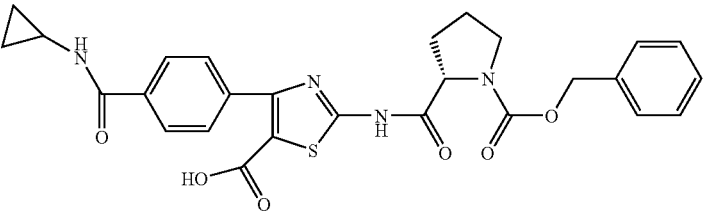 | 2-[(1-Benzyloxycarbonyl-pyrrolidine-2-carbonyl)-amino]-4-(4-cyclopropylcarbamoyl-phenyl)-thiazole-5-carboxylic acid |
| 5345 | 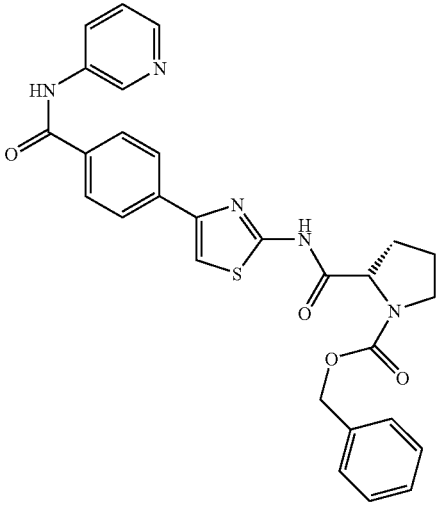 | 2-{4-[4-(Pyridin-3-ylcarbamoyl)-phenyl]-thiazol-2-ylcarbamoyl}-pyrrolidine-1-carboxylic acid benzyl ester |
| 5346 | 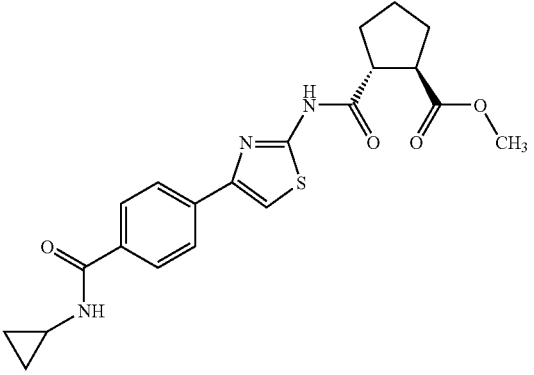 | 2-[4-(4-Cyclopropylcarbamoyl-phenyl)-thiazol-2-ylcarbamoyl]-cyclopentanecarboxylic acid methyl ester |

TABLE 1-continued

| Ex. | Structure | Name |
|---|---|---|
| 5347 | 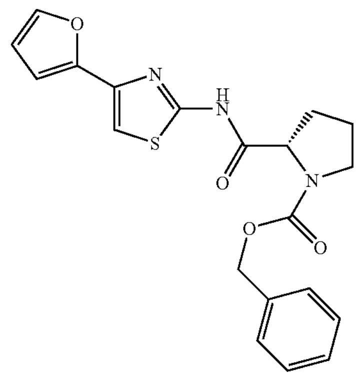 | 2-(4-Furan-2-yl-thiazol-2-ylcarbamoyl)-pyrrolidine-1-carboxylic acid benzyl ester |
| 5348 | 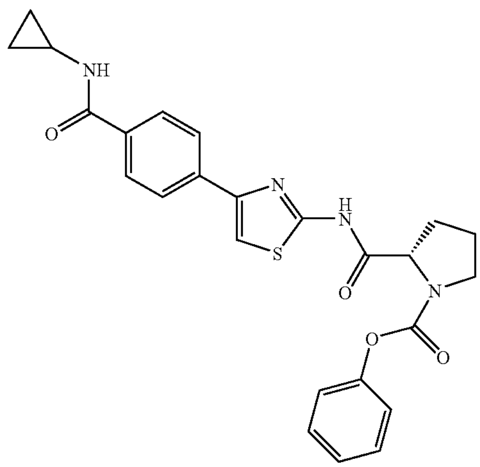 | 2-[4-(4-Cyclopropylcarbamoyl-phenyl)-thiazol-2-ylcarbamoyl]-pyrrolidine-1-carboxylic acid phenyl ester |
| 5349 | 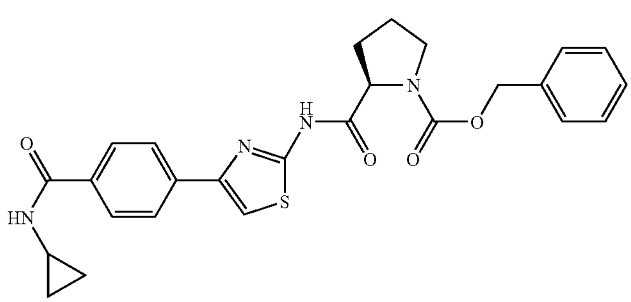 | 2-[4-(4-Cyclopropylcarbamoyl-phenyl)-thiazol-2-ylcarbamoyl]-pyrrolidine-1-carboxylic acid benzyl ester |
| 5350 | 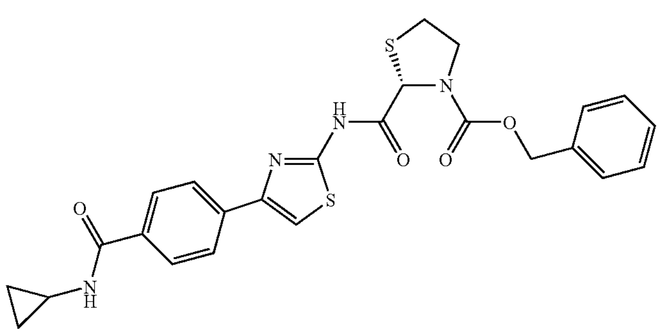 | 2-[4-(4-Cyclopropylcarbamoyl-phenyl)-thiazol-2-ylcarbamoyl]-thiazolidine-3-carboxylic acid benzyl ester |

TABLE 1-continued

| Ex. | Structure | Name |
|---|---|---|
| 5351 | 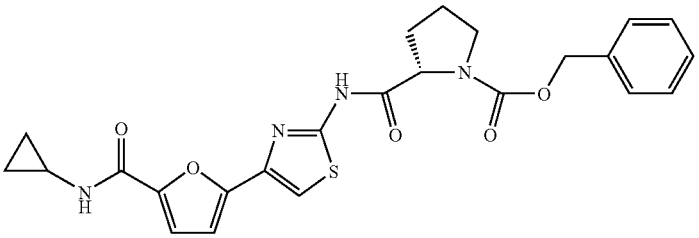 | 2-[4-(5-Cyclopropylcarbamoyl-furan-2-yl)-thiazol-2-ylcarbamoyl]-pyrrolidine-1-carboxylic acid benzyl ester |
| 5352 | 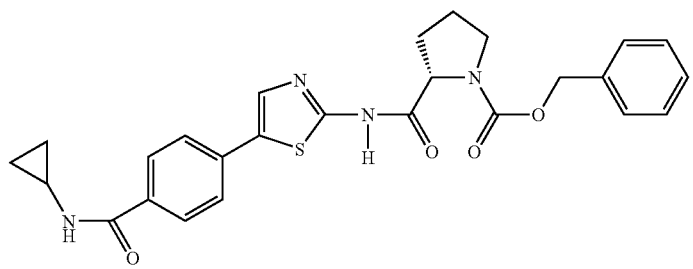 | 2-[5-(4-Cyclopropylcarbamoyl-phenyl)-thiazol-2-ylcarbamoyl]-pyrrolidine-1-carboxylic acid benzyl ester |
| 5353 | 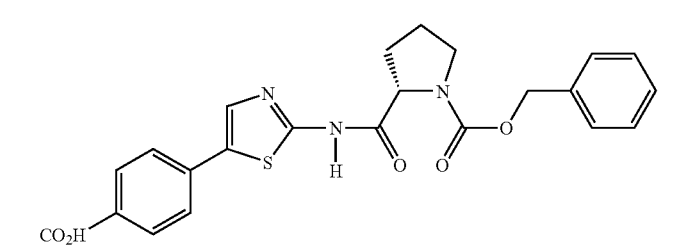 | 2-[5-(4-Carboxy-phenyl)-thiazol-2-ylcarbamoyl]-pyrrolidine-1-carboxylic acid benzyl ester |
| 5354 | 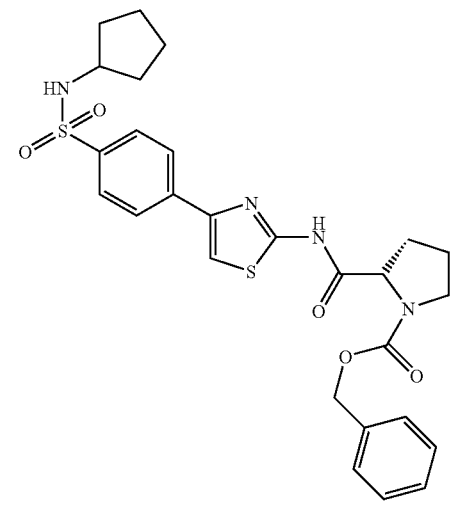 | 2-[4-(4-Cyclopentylsulfamoyl-phenyl)-thiazol-2-ylcarbamoyl]-pyrrolidine-1-carboxylic acid benzyl ester |
| 5355 | 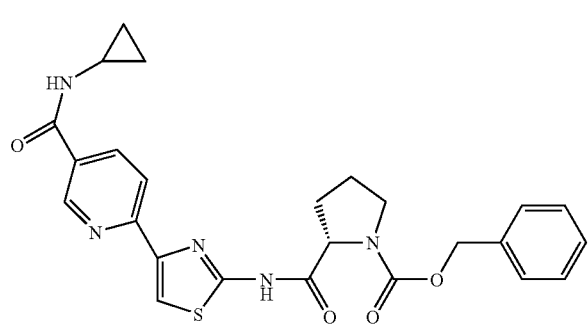 | 2-[4-(5-Cyclopropylcarbamoyl-pyridin-2-yl)-thiazol-2-ylcarbamoyl]-pyrrolidine-1-carboxylic acid benzyl ester |

TABLE 1-continued

| Ex. | Structure | Name |
|---|---|---|
| 5356 | 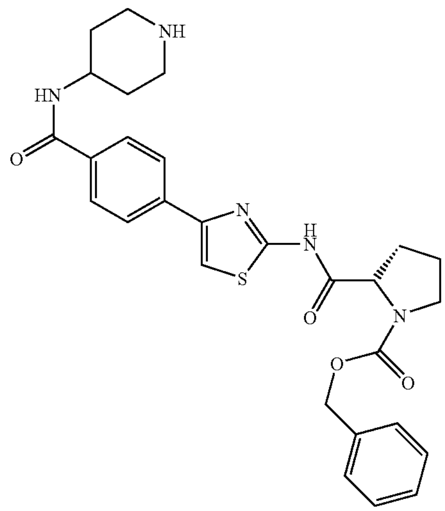 | 2-{4-[4-(Piperidin-4-ylcarbamoyl)-phenyl]-thiazol-2-ylcarbamoyl}-pyrrolidine-1-carboxylic acid benzyl ester |
| 5357 | 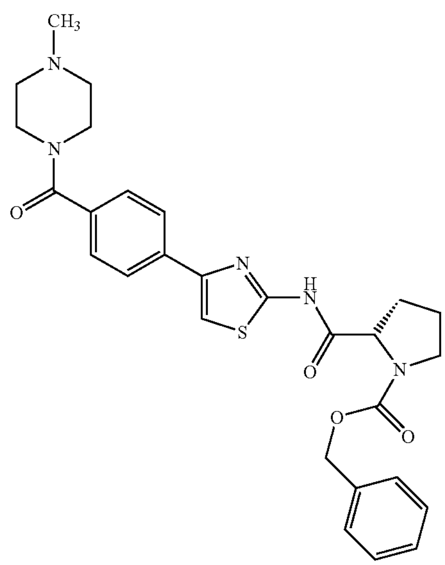 | 2-{4-[4-(4-Methyl-piperazine-1-carbonyl)-phenyl]-thiazol-2-ylcarbamoyl}-pyrrolidine-1-carboxylic acid benzyl ester |
| 5358 | 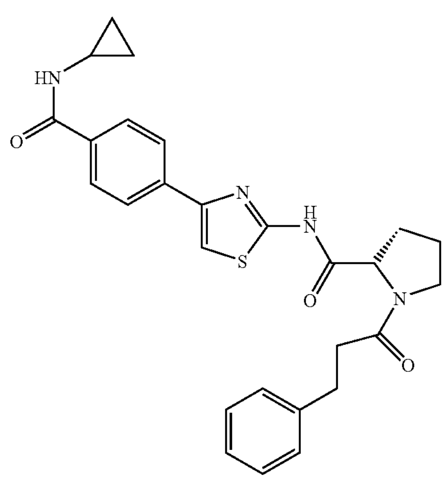 | 1-(3-Phenyl-propionyl)-pyrrolidine-2-carboxylic acid [4-(4-cyclopropylcarbamoyl-phenyl)-thiazol-2-yl]-amide |

TABLE 1-continued

| Ex. | Structure | Name |
|---|---|---|
| 5359 | 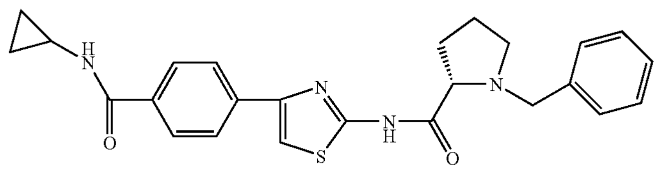 | 1-Benzyl-pyrrolidine-2-carboxylic acid [4-(4-cyclopropylcarbamoyl-phenyl)-thiazol-2-yl]-amide |
| 5360 | 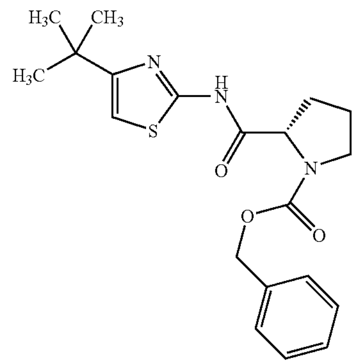 | 2-(4-tert-Butyl-thiazol-2-ylcarbamoyl)-pyrrolidine-1-carboxylic acid benzyl ester |
| 5361 | 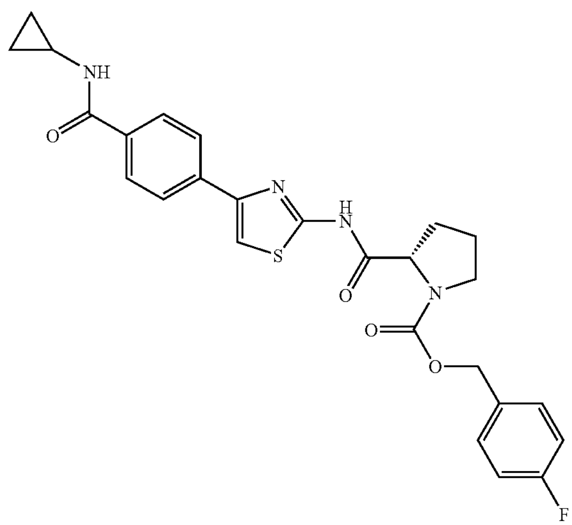 | 2-[4-(4-Cyclopropylcarbamoyl-phenyl)-thiazol-2-ylcarbamoyl]-pyrrolidine-1-carboxylic acid 4-fluoro-benzyl ester |
| 5362 | 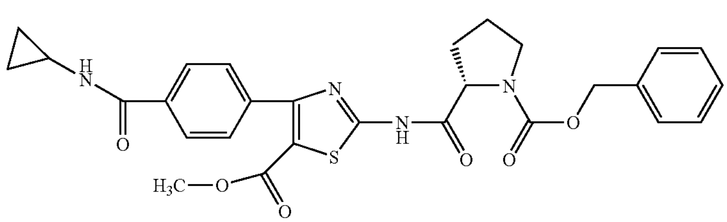 | 2-[(1-Benzyloxycarbonyl-pyrrolidine-2-carbonyl)-amino]-4-(4-cyclopropylcarbamoyl-phenyl)-thiazole-5-carboxylic acid methyl ester |

TABLE 1-continued

| Ex. | Structure | Name |
|---|---|---|
| 5363 | 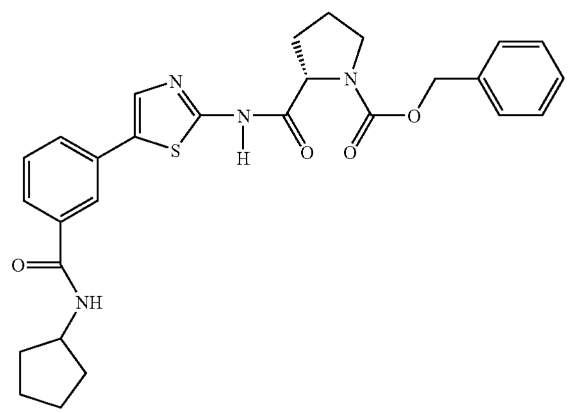 | 2-[5-(3-Cyclopentylcarbamoyl-phenyl)-thiazol-2-ylcarbamoyl]-pyrrolidine-1-carboxylic acid benzyl ester |
| 5364 | 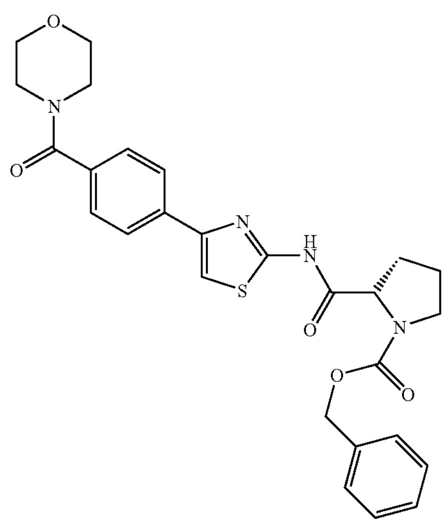 | 2-{4-[4-(Morpholine-4-carbonyl)-phenyl]-thiazol-2-ylcarbamoyl}-pyrrolidine-1-carboxylic acid benzyl ester |
| 5365 | 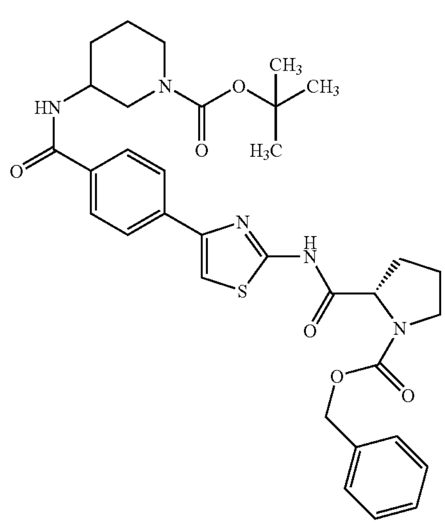 | 3-(4-{2-[(1-Benzyloxycarbonyl-pyrrolidine-2-carbonyl)-amino]-thiazol-4-yl}-benzoylamino)-piperidine-1-carboxylic acid tert-butyl ester |

TABLE 1-continued

| Ex. | Structure | Name |
|---|---|---|
| 5366 | 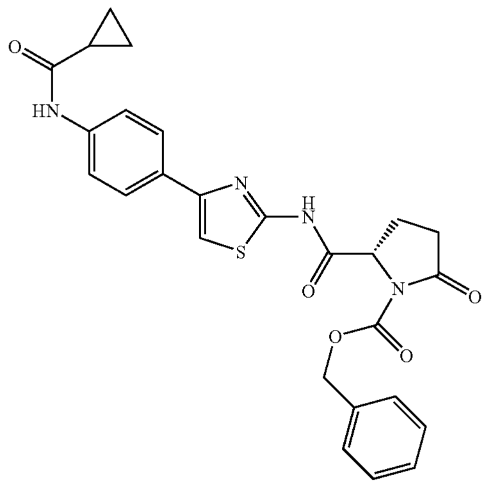 | 2-{4-[4-(Cyclopropanecarbonyl-amino)-phenyl]-thiazol-2-ylcarbamoyl}-5-oxo-pyrrolidine-1-carboxylic acid benzyl ester |
| 5367 | 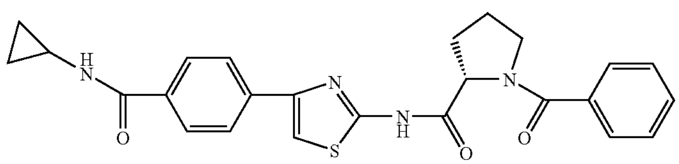 | 1-Benzoyl-pyrrolidine-2-carboxylic acid [4-(4-cyclopropylcarbamoyl-phenyl)-thiazol-2-yl]-amide |
| 5368 | 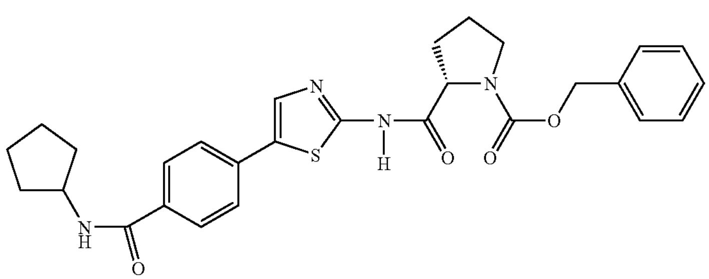 | 2-[5-(4-Cyclopentylcarbamoyl-phenyl)-thiazol-2-ylcarbamoyl]-pyrrolidine-1-carboxylic acid benzyl ester |

TABLE 1-continued

| Ex. | Structure | Name |
|---|---|---|
| 5369 | 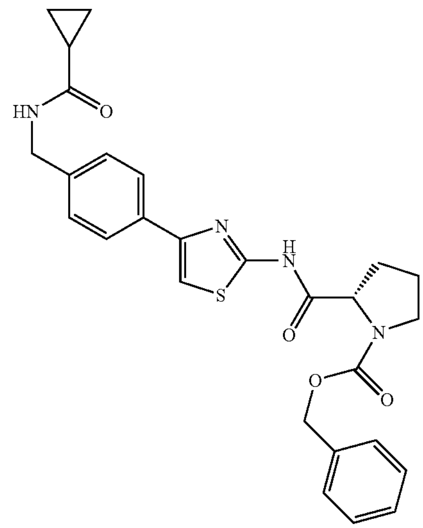 | 2-(4-{4-[(Cyclopropanecarbonyl-amino)-methyl]-phenyl}-thiazol-2-ylcarbamoyl)-pyrrolidine-1-carboxylic acid benzyl ester |
| 5370 | 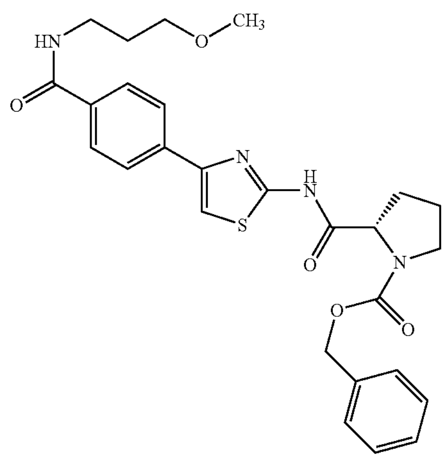 | 2-{4-[4-(3-Methoxy-propylcarbamoyl)-phenyl]-thiazol-2-ylcarbamoyl}-pyrrolidine-1-carboxylic acid benzyl ester |
| 5371 | 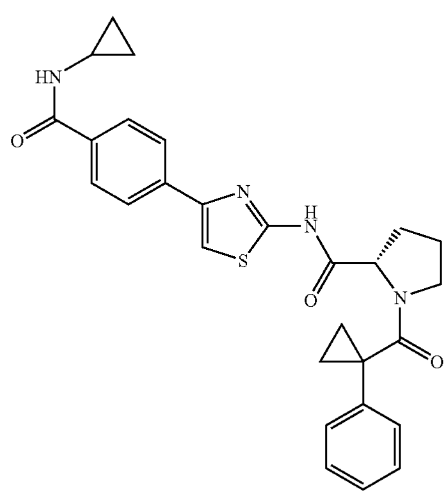 | 1-(1-Phenyl-cyclopropanecarbonyl)-pyrrolidine-2-carboxylic acid [4-(4-cyclopropylcarbamoyl-phenyl)-thiazol-2-yl]-amide |

TABLE 1-continued

| Ex. | Structure | Name |
|---|---|---|
| 5372 | 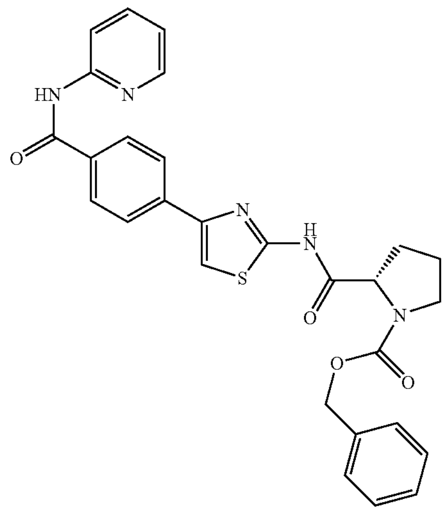 | 2-{4-[4-(Pyridin-2-ylcarbamoyl)-phenyl]-thiazol-2-ylcarbamoyl}-pyrrolidine-1-carboxylic acid benzyl ester |
| 5373 | 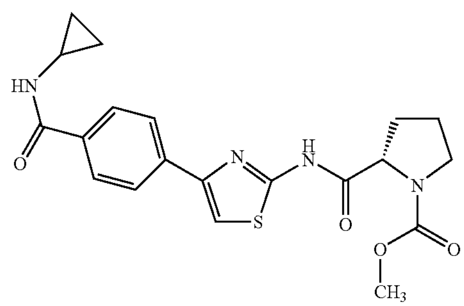 | 2-[4-(4-Cyclopropylcarbamoyl-phenyl)-thiazol-2-ylcarbamoyl]-pyrrolidine-1-carboxylic acid methyl ester |
| 5374 | 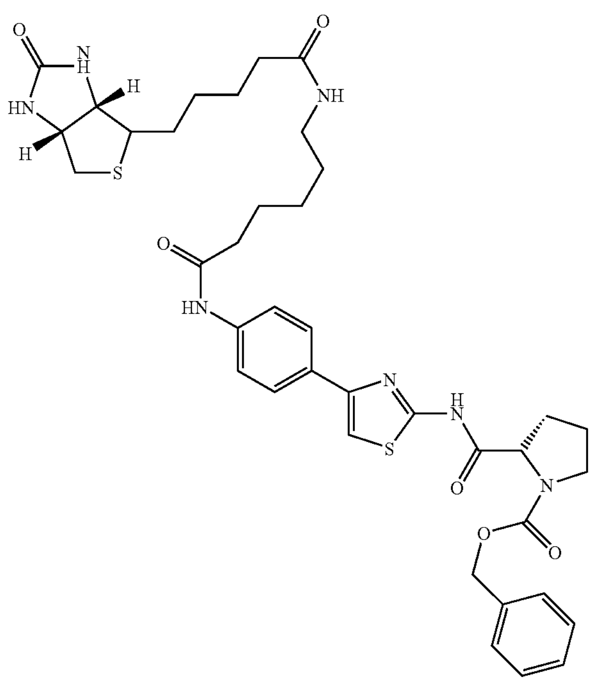 | 2-[4-(4-{6-[5-(2-Oxo-hexahydro-thieno[3,4-d]imidazol-6-yl)-pentanoylamino]-hexanoylamino}-phenyl)-thiazol-2-ylcarbamoyl]-pyrrolidine-1-carboxylic acid benzyl ester |

TABLE 1-continued
| Ex. | Structure | Name |
|---|---|---|
| 5375 | 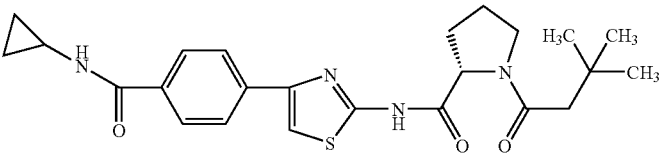 | 2-[4-(4-Cyclopropylcarbamoyl-phenyl)-thiazol-2-ylcarbamoyl]-pyrrolidine-1-carboxylic acid tert-butyl ester |
| 5376 | 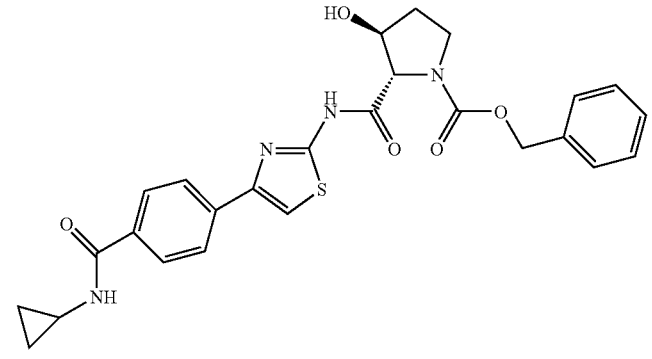 | 2-[4-(4-Cyclopropylcarbamoyl-phenyl)-thiazol-2-ylcarbamoyl]-3-hydroxy-pyrrolidine-1-carboxylic acid benzyl ester |
| 5377 | 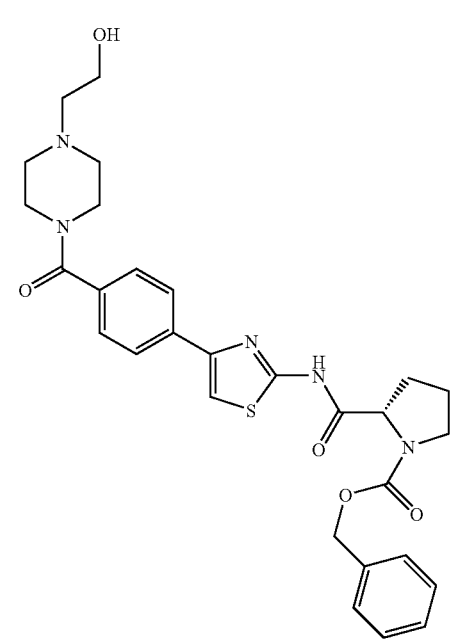 | 2-(4-{4-[4-(2-Hydroxy-ethyl)-piperazine-1-carbonyl]-phenyl}-thiazol-2-ylcarbamoyl)-pyrrolidine-1-carboxylic acid benzyl ester |

TABLE 1-continued
| Ex. | Structure | Name |
|---|---|---|
| 5378 | 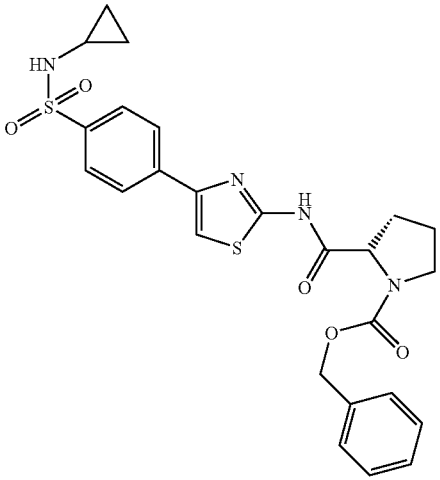 | 2-[4-(4-Cyclopropylsulfamoyl-phenyl)-thiazol-2-ylcarbamoyl]-pyrrolidine-1-carboxylic acid benzyl ester |
| 5379 | 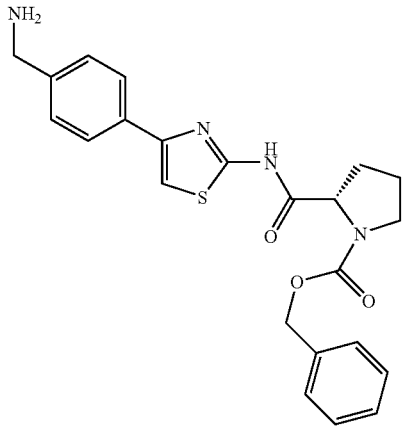 | 2-[4-(4-Aminomethyl-phenyl)-thiazol-2-ylcarbamoyl]-pyrrolidine-1-carboxylic acid benzyl ester |
| 5380 | 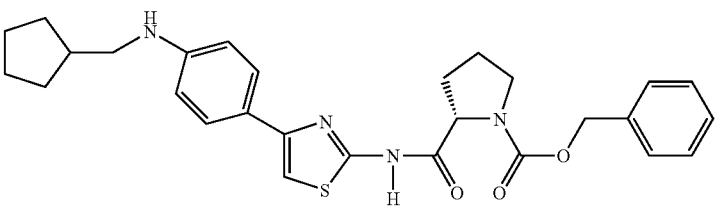 | 2-{4-[4-(Cyclopentylmethyl-amino)-phenyl]-thiazol-2-ylcarbamoyl}-pyrrolidine-1-carboxylic acid benzyl ester |

TABLE 1-continued

| Ex. | Structure | Name |
|---|---|---|
| 5381 | 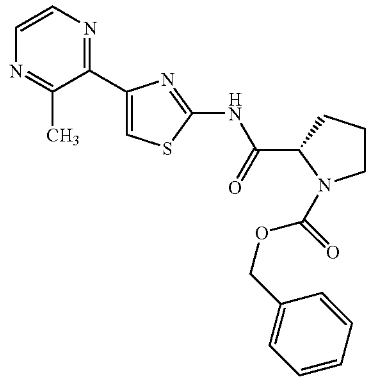 | 2-[4-(3-Methyl-pyrazin-2-yl)-thiazol-2-ylcarbamoyl]-pyrrolidine-1-carboxylic acid benzyl ester |
| 5382 | 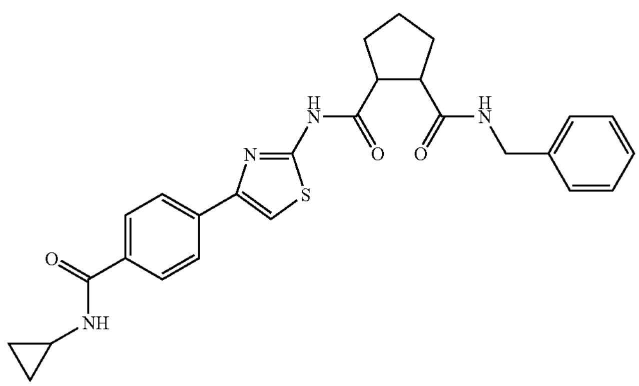 | Cyclopentane-1,2-dicarboxylic acid 1-benzylamide 2-{[4-(4-cyclopropylcarbamoyl-phenyl)-thiazol-2-yl]-amide} |
| 5383 | 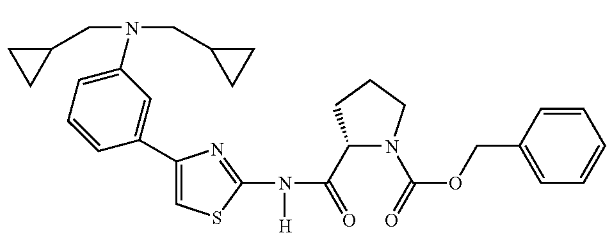 | 2-{4-[3-(Bis-cyclopropylmethyl-amino)-phenyl]-thiazol-2-ylcarbamoyl}-pyrrolidine-1-carboxylic acid benzyl ester |

TABLE 1-continued

| Ex. | Structure | Name |
|---|---|---|
| 5384 | 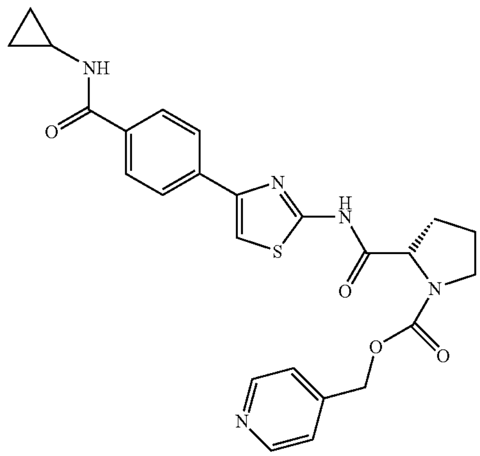 | 2-[4-(4-Cyclopropylcarbamoyl-phenyl)-thiazol-2-ylcarbamoyl]-pyrrolidine-1-carboxylic acid pyridin-4-ylmethyl ester |

In another embodiment, the present invention provides a pharmaceutical composition comprising a pharmaceutically acceptable carrier and a therapeutically effective amount of a compound of Formula (I)-(V) or a stereoisomer, tautomer, or a pharmaceutically acceptable salt thereof for treating or preventing in a patient a viral infection mediated at least in part by a virus in the Flaviviridae family of viruses.

In some embodiments, the composition is for treating or preventing HCV.

In other embodiments, the composition comprises a compound from Table 1 or a stereoisomer, tautomer, or a pharmaceutically acceptable salt thereof.

In one embodiment, the present invention provides a method for treating or preventing a viral infection in a patient mediated at least in part by a virus in the Flaviviridae family of viruses which method comprises administering to the patient a compound of Formula (I)-(V) or a stereoisomer, tautomer, or a pharmaceutically acceptable salt thereof.

In one embodiment, the present invention provides use of a compound or a stereoisomer, tautomer, or a pharmaceutically acceptable salt thereof as described herein in the manufacture of a medicament for treating a viral infection in a patient, wherein the viral infection is mediated at least in part by a virus in the Flaviviridae family of viruses.

In some aspects, the viral infection is a hepatitis C mediated viral infection.

In other aspects, the administration of a therapeutically effective amount of the compounds of the invention are used in combination with one or more agents active against hepatitis C virus.

In some embodiments, the agent active against hepatitis C virus is an inhibitor of HCV proteases, HCV polymerase, HCV helicase, HCV NS4B protein, HCV entry, HCV assembly, HCV egress, HCV NS5A protein, or inosine 5'-monophosphate dehydrogenase.

In other embodiments, agent active against hepatitis C virus is interferon.

In still other embodiments of the method of treatment or prevention, the compound is selected from the group consisting of a compound from Table 1 or a stereoisomer, tautomer, or a pharmaceutically acceptable salt thereof.

Administration and Pharmaceutical Composition

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors. The drug can be administered more than once a day, preferably once or twice a day. All of these factors are within the skill of the attending clinician.

Therapeutically effective amounts of compounds of Formula (I)-(V) may range from approximately 0.05 to 50 mg per kilogram body weight of the recipient per day; preferably about 0.1-25 mg/kg/day, more preferably from about 0.5 to 10 mg/kg/day. Thus, for administration to a 70 kg person, the dosage range would most preferably be about 35-700 mg per day.

In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen that can be adjusted according to the degree of affliction. Compositions can take the form of tablets, pills, capsules, semisolids, powders, sustained release formulations, solutions, suspensions, elixirs, aerosols, or any other appropriate compositions. Another preferred manner for administering compounds of this invention is inhalation. This is an effective method for delivering a therapeutic agent directly to the respiratory tract (see U.S. Pat. No. 5,607,915).

The choice of formulation depends on various factors such as the mode of drug administration and bioavailability of the drug substance. For delivery via inhalation the compound can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract.

MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory airstream during breathing by the device. In order to achieve a free flowing powder, the therapeutic agent is formulated with an excipient such as lactose. A measured amount of the therapeutic agent is stored in a capsule form and is dispensed with each actuation.

Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of Formula (I)-(V) in combination with at least one pharmaceutically acceptable excipient. Acceptable excipients are non-toxic, aid administration, and do not adversely affect the therapeutic benefit of the compound of Formula (I)-(V). Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The amount of the compound in a formulation can vary within the full range employed by those skilled in the art. Typically, the formulation will contain, on a weight percent (wt %) basis, from about 0.01-99.99 wt % of a compound of Formula (I)-(V) based on the total formulation, with the balance being one or more suitable pharmaceutical excipients. Preferably, the compound is present at a level of about 1-80 wt %. Representative pharmaceutical formulations containing a compound of Formula (I)-(V) are described below.

Additionally, the present invention is directed to a pharmaceutical composition comprising a therapeutically effective amount of a compound of the present invention in combination with a therapeutically effective amount of another active agent against RNA-dependent RNA virus and, in particular, against HCV. Agents active against HCV include, but are not limited to, ribavirin, levovirin, viramidine, thymosin alpha-1, an inhibitor of HCV NS3 serine protease, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes, but is not limited to, recombinant interferon-α2a (such as Roferon interferon available from Hoffman-LaRoche, Nutley, N.J.), interferon-α2b (such as Intron-A interferon available from Schering Corp., Kenilworth, N.J., USA), a consensus interferon, and a purified interferon-α product. For a discussion of ribavirin and its activity against HCV, see J. O. Saunders and S. A. Raybuck, "Inosine Monophosphate Dehydrogenase: Consideration of Structure, Kinetics and Therapeutic Potential," *Ann. Rep. Med. Chem.*, 35:201-210 (2000).

The agents active against hepatitis C virus also include agents that inhibit HCV proteases, HCV polymerase, HCV helicase, HCV NS4B protein, HCV entry, HCV assembly, HCV egress, HCV NS5A protein, and inosine 5'-monophosphate dehydrogenase. Other agents include nucleoside analogs for the treatment of an HCV infection. Still other compounds include those disclosed in WO 2004/014313 and WO 2004/014852 and in the references cited therein. The patent applications WO 2004/014313 and WO 2004/014852 are hereby incorporated by references in their entirety.

Specific antiviral agents include Omega IFN (BioMedicines Inc.), BILN-2061 (Boehringer Ingelheim), Summetrel (Endo Pharmaceuticals Holdings Inc.), Roferon A (F. Hoffman-La Roche), Pegasys (F. Hoffman-La Roche), Pegasys/Ribaravin (F. Hoffman-La Roche), CellCept (F. Hoffman-La Roche), Wellferon (GlaxoSmithKline), Albuferon-α (Human Genome Sciences Inc.), Levovirin (ICN Pharmaceuticals), IDN-6556 (Idun Pharmaceuticals), IP-501 (Indevus Pharmaceuticals), Actimmune (InterMune Inc.), Infergen A (InterMune Inc.), ISIS 14803 (ISIS Pharamceuticals Inc.), JTK-003 (Japan Tobacco Inc.), Pegasys/Ceplene (Maxim Pharmaceuticals), Ceplene (Maxim Pharmaceuticals), Civacir (Nabi Biopharmaceuticals Inc.), Intron A/Zadaxin (RegeneRx), Levovirin (Ribapharm Inc.), Viramidine(Ribapharm Inc.), Heptazyme (Ribozyme Pharmaceuticals), Intron A (Schering-Plough), PEG-Intron (Schering-Plough), Rebetron (Schering-Plough), Ribavirin (Schering-Plough), PEG-Intron/Ribavirin (Schering-Plough), Zadazim (SciClone), Rebif (Serono), IFN-β/EMZ701 (Transition Therapeutics), T67 (Tularik Inc.), VX-497 (Vertex Pharmaceuticals Inc.), VX-950/LY-570310 (Vertex Pharmaceuticals Inc.), Omniferon (Viragen Inc.), XTL-002 (XTL Biopharmaceuticals), SCH 503034 (Schering-Plough), isatoribine and its prodrugs ANA971 and ANA975 (Anadys), R1479 (Roche Biosciences), Valopicitabine (Idenix), NIM811 (Novartis), and Actilon (Coley Pharmaceuticals).

In some embodiments, the compositions and methods of the present invention contain a compound of Formula (I) and interferon. In some aspects, the interferon is selected from the group consisting of interferon alpha 2B, pegylated interferon alpha, consensus interferon, interferon alpha 2A, and lymphoblastiod interferon tau.

In other embodiments the compositions and methods of the present invention contain a compound of Formula (I) and a compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'monophospate dehydrogenase inhibitor, amantadine, and rimantadine.

General Synthetic Methods

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Third Edition, Wiley, N.Y., 1999, and references cited therein.

Furthermore, the compounds of this invention contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's *Reagents for Organic Synthesis*, Volumes 1-15 (John Wiley and Sons, 1991), Rodd's *Chemistry of Carbon Compounds*, Volumes 1-5 and Supplementals (Elsevier Science Publishers, 1989), *Organic Reactions*, Volumes 1-40 (John Wiley and Sons, 1991), March's *Advanced Organic Chemistry*, (John Wiley and Sons, 4th Edition), and Larock's *Comprehensive Organic Transformations* (VCH Publishers Inc., 1989).

The various starting materials, intermediates, and compounds of the invention may be isolated and purified where appropriate using conventional techniques such as precipitation, filtration, crystallization, evaporation, distillation, and chromatography. Characterization of these compounds may be performed using conventional methods such as by melting point, mass spectrum, and various other spectroscopic analyses.

Accordingly, in one embodiment the present invention provides a method for synthesizing a compound, stereoisomer, tautomer, or a pharmaceutically acceptable salt of Formula (I)

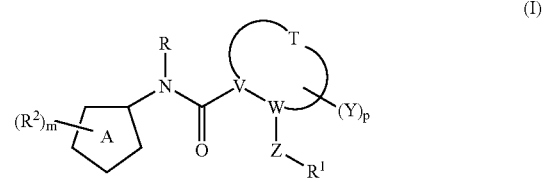

(I)

wherein the method comprises reacting an amine having the formula

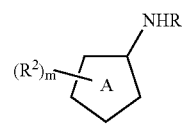

with an acid having the formula

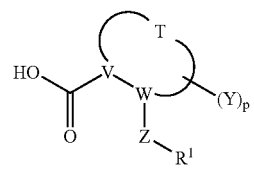

in the presence of an amide coupling reagent wherein A, R, $R^1$, $R^2$, T, V, W, Z, Y, m, and p are as defined for Formula (I); provided that the compound is not 2-(4-phenyl-thiazol-2-ylcarbamoyl)-pyrrolidine-1-carboxylic acid benzyl ester, 2-(4-phenyl-thiazol-2-ylcarbamoyl)-pyrrolidine-1-carboxylic acid phenyl ester, or 4-hydroxy-2-(5-methyl-4-phenyl-thiazol-2-ylcarbamoyl)-pyrrolidine-1-carboxylic acid tert-butyl ester.

A variety of amide coupling reagents may be used to from the amide bond, including the use of carbodiimides such as N—N'-dicyclohexylcarbodiimide (DCC), N—N'-diisopropylcarbodiimide (DIPCDI), and 1-ethyl-3-(3'-dimethylaminopropyl)carbodiimide (EDCI). The carbodiimides may be used in conjunction with additives such as benzotriazoles 7-aza-1-hydroxybenzotriazole (HOAt), 1-hydroxybenzotriazole (HOBt), and 6-chloro-1-hydroxybenzotriazole (Cl—HOBt).

Amide coupling reagents also include aminimum and phosphonium based reagents. Aminium salts include N-[(dimethylamino)-1H-1,2,3-triazolo[4,5-b]pyridine-1-ylmethylene]-N-methylmethanaminium hexafluorophosphate N-oxide (HATU), N-[(1H-benzotriazol-1-yl)(dimethylamino)methylene]-N-methylmethanaminium hexafluorophosphate N-oxide (HBTU), N-[(1H-6-chlorobenzotriazol-1-yl)(dimethylamino)methylene]-N-methylmethanaminium hexafluorophosphate N-oxide (HCTU), N-[(1H-benzotriazol-1-yl)(dimethylamino)methylene]-N-methylmethanaminium tetrafluoroborate N-oxide (TBTU), and N-[(1H-6-chlorobenzotriazol-1-yl)(dimethylamino)methylene]-N-methylmethanaminium tetrafluoroborate N-oxide (TCTU). Phosphonium salts include 7-azabenzotriazol-1-yl-N-oxytris(pyrrolidino)phosphonium hexafluorophosphate (PyAOP) and benzotriazol-1-yl-N-oxy-tris(pyrrolidino) phosphonium hexafluorophosphate (PyBOP).

The amide formation step may be conducted in a polar solvent such as dimethylformamide (DMF) and may also include an organic base such as diisopropylethylamine (DIEA).

Scheme 1 shows the synthesis of the compounds of the invention where A is a 4-substituted thiazol-2-yl group, R, is hydrogen, V, W, and T together form a (S)-pyrrolidine ring, p is 0, and Z-R$^1$ together form a benzyloxycarbonyl group. Bromide 1.1 is reacted with thiourea to form amine 1.2. The amine is next coupled to N-benzyloxycarbonyl protected L-proline (Z-Pro-OH) using standard peptide coupling procedures to form the amide 1.3.

Scheme 1

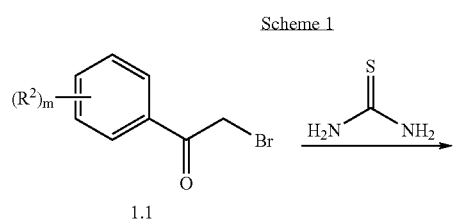

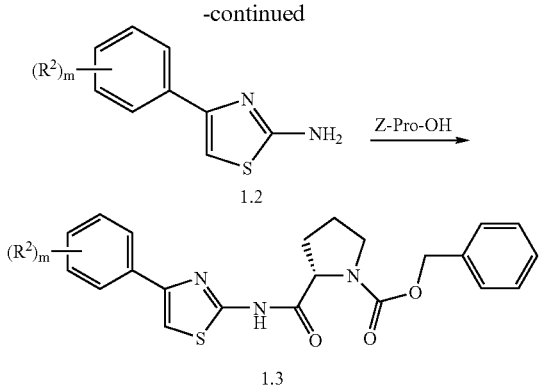

Scheme 2 shows the synthesis of the compounds of the invention where R$^2$ is an acyamino or substituted amino group. Starting material 2.1 is synthesized as in Scheme 1 and is reduced to amine 2.2. The reduction can be carried out by treating 2.1 with a reagent such as SnCl$_2$ in refluxing ethanol/ethyl acetate to form amine 1.2. The amine is next acylated with the appropriate acyl reagent such as RC(O)Cl to form the amide 2.3. Alternatively, amine 2.2 can be reacted with an appropriate electrophile to form substituted amine 2.4.

Scheme 2

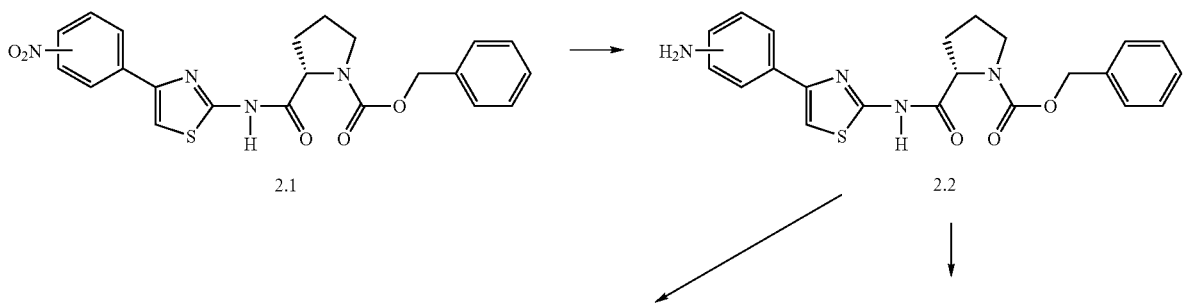

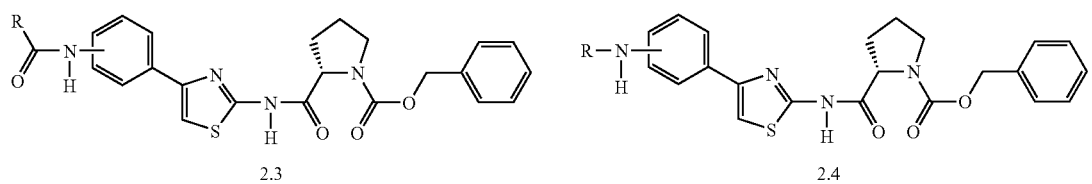

Scheme 3 shows the synthesis of the compounds of the invention where A is a 5-substituted thiazol-2-yl group, V, W, and T together form a (S)-pyrrolidine ring, p is 0, and Z-R¹ together form a benzyloxycarbonyl group. Amine 3.1 is reacted with N-benzyloxycarbonyl protected L-proline (Z-Pro-OH) to form bromide 3.2. The bromide is next coupled to an aryl boronic acid under Suzuki reaction conditions to form thiazole 3.3. Functionalization of the amino group as described in Scheme 2 gives the substituted amines 3.4 and 3.5.

| | |
|---|---|
| F.W. = | Formula weight |
| g = | gram |
| HATU = | N-[(dimethylamino)-1H-1,2,3-triazolo[4,5-b]pyridine-1-ylmethylene]-N-methylmethanaminium hexafluorophosphate N-oxide |
| HPLC = | high pressure liquid chromatography |
| KOAc = | potassium acetate |

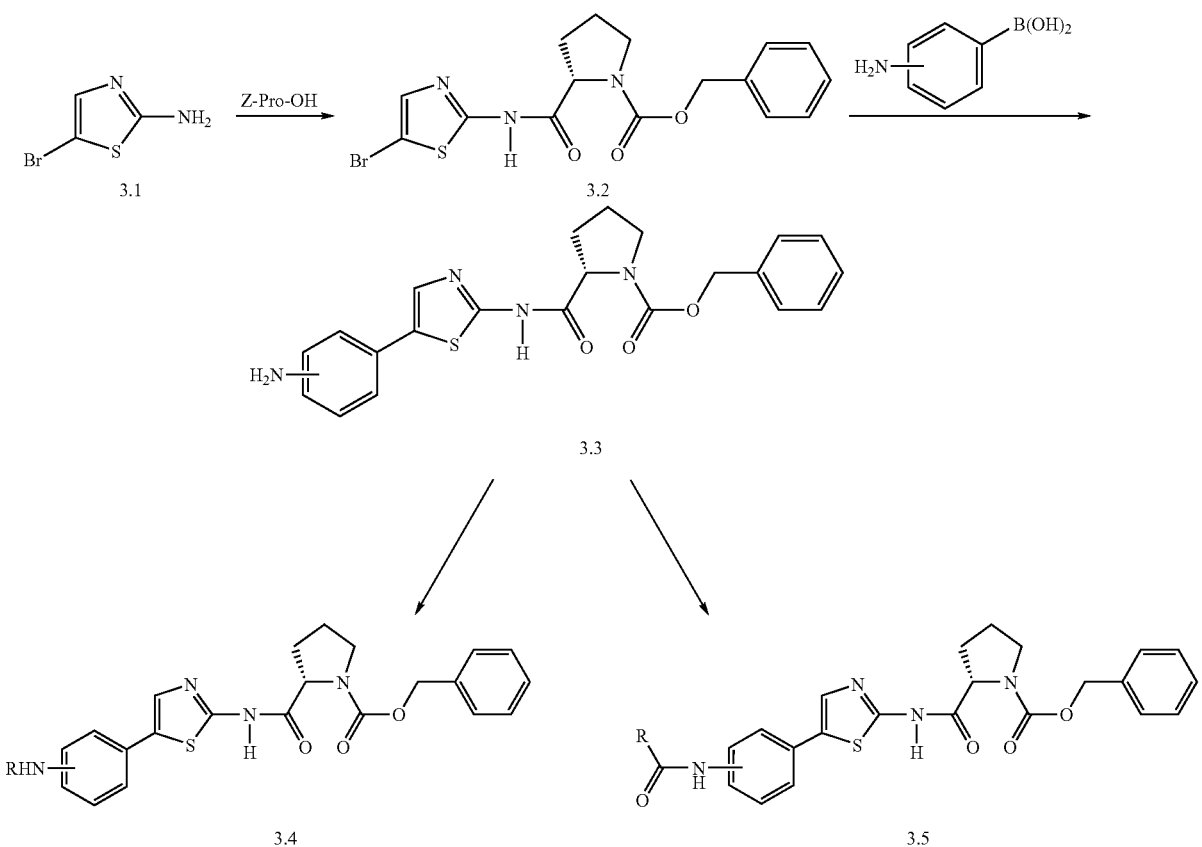

The foregoing and other aspects of the present invention may be better understood in connection with the following representative examples.

EXAMPLES

The examples below as well as throughout the application, the following abbreviations have the following meanings. If not defined, the terms have their generally accepted meanings.

| | |
|---|---|
| atm = | atmospheres |
| cm = | centimeter |
| DIEA = | diisopropylethylamine |
| DMF = | dimethylformamide |
| DMSO = | dimethylsulfoxide |
| eq. = | Equivalents |

| | |
|---|---|
| L = | liter |
| MeCN = | acetonitrile |
| mg = | milligram |
| mL = | milliliter |
| mmol = | millimole |
| MS = | mass spectrum |
| TEA = | triethylamine |
| TFA = | trifluoroacetic acid |
| THF = | tetrahydrofuran |
| TLC = | thin layer chromatography |
| v/v = | volume/volume |
| µL = | microliter |

General Procedure A

A mixture of (S)-Pyrrolidine-1,2-dicarboxylic acid 1-benzyl ester (F.W.=249.27, 0.4 g, 1.6 mmol), HATU (F.W.=380.25, 0.61 g, 1.6 mmol), and DIEA (0.4 mL, 0.05 mmol) in DMF (16 mL) was stirred at room temperature for 1 h to provide a 0.10 mM solution. To each of the following amines was added 1 mL of this solution (0.10 mM) and the reaction mixtures were stirred at room temperature overnight. The resulting mixtures were diluted with DMF (5 mL) and water (0.5mL) then purified by reverse phase HPLC to furnish the corresponding products.

General Procedure B

A mixture of (S)-Pyrrolidine-1,2-dicarboxylic acid 1-benzyl ester (F.W.=249.27, 0.35 g, 1.4 mmol), HATU (F.W.=380.25, 0.53 g, 1.4 mmol), and DIEA (0.4 mL, 0.05 mmol) in DMF (20 mL) was stirred at room temperature for 1 h to provide a 0.070 mM solution. To each of the amines described in the following Examples was added 1 mL of this solution (0.070 mM) and the reaction mixtures were stirred at room temperature overnight. The resulting mixtures were diluted with DMF (5 mL) and water (0.5mL) then purified by reverse phase HPLC to furnish the corresponding products.

General Procedure C

A mixture of (S)-Pyrrolidine-1,2-dicarboxylic acid 1-benzyl ester (F.W.=249.27, 0.15 g, 0.6 mmol), HATU (F.W.=380.25, 0.209 g, 0.55 mmol), and DIEA (0.1 mL, 0.76 mmol) in DMF (5 mL) was stirred at room temperature for 1 h. This mixture had to be prepared each time for the reactions of the amines described in the following Examples. The individual mixtures were stirred at room temperature for 20 h., then filtered and separated by reverse phase HPLC (20-100% of buffer B; buffer A: water containing 0.1% TFA; buffer B: MeCN containing 0.1% TFA). The combined fraction was evaporated to dryness to furnish the desired products.

General Procedure D

2-[4-(4-amino-phenyl)-thiazol-2-ylcarbamoyl]-pyrrolidine-1-carboxylic acid benzyl ester (compound 5050, 38 mg, 0.092 mmol) was dissolved in 3.5 mL of methylene chloride. To this solution was added triethylamine (12.8 µL, 0.092 mmol). To this solution at 0° C., were added sulfonyl chlorides (1 equivalent) described in the following Examples. Reaction mixtures were brought to room temperature and stirred until completion. Reaction mixtures were quenched using water and evaporated. The residues were redissolved in 5 mL of DMF and water (0.5 mL) and purified using reverse phase HPLC to furnish the corresponding products.

General Procedure E

2-[4-(4-amino-phenyl)-thiazol-2-ylcarbamoyl]-pyrrolidine-1-carboxylic acid benzyl ester (Compound 5001, 39 mg, 0.092 mmol) was dissolved in 3 mL of dry methylene chloride. To this solution was added triethylamine (12.8 µL, 0.092 mmol). This solution was brought to 0° C. and 1 equivalent of the appropriate acyl chloride was added. Reaction mixtures were stirred at 0° C. for 20 minutes, quenched using water, and evaporated. The resulting mixtures were diluted with DMF (5 mL) and water (0.5 mL) and purified using reverse phase HPLC to furnish the corresponding products.

General Procedure F

2-[4-(2-Chloro-phenyl)-thiazol-2-ylcarbamoyl]-pyrrolidine-1-carboxylic acid benzyl ester (Compound 5106, 0.55 mmol, 0.25 g) and HATU (0.55 mmol, 0.21 g) were combined in 16 mL of DMF. To this solution wad added DIEA (0.6 mmol, 0.13 mL). This solution was stirred at room temperature for 2 hours. 4 mL of this solution was then added to the amines described in the following examples. The resulting mixture was stirred at room temperature overnight and purified using reverse phase HPLC to yield the desired product.

General Procedure G

A mixture of Z-Pro-OH (0.96 g, 3.84 mmol), HATU (1.46 g, 3.84 mmol), and DIEA (0.094 mL, 5.4 mmol) in DMF (30 mL) was stirred at room temperature for 1 hour. 1 or 2 mL of this solution was added to the amines described in the following Examples and reaction mixtures stirred at room temperature overnight. The resulting mixtures were diluted with DMF (5 mL) and water (0.5 mL) and purified using reverse phase HPLC to furnish the corresponding products.

General Procedure H

2-[4-(4-amino-phenyl)-thiazol-2-ylcarbamoyl]-pyrrolidine-1-carboxylic acid benzyl ester (Compound 5050, 39 mg, 0.092 mmol) was dissolved in 3 mL of dry methylene chloride. To this solution was added triethylamine (12.8 µL, 0.092 mmol). This solution was brought to 0° C. and 1 equivalent of the appropriate acyl chloride described in the following Examples was added. Reaction mixtures were stirred at 0° C. for 20 minutes, quenched using water, and evaporated. The resulting mixtures were diluted with DMF (5 mL) and water (0.5 mL) and purified using reverse phase HPLC to furnish the corresponding products.

General Procedure J

A mixture of 2-(5-bromo-thiazol-2-ylcarbamoyl)-pyrrolidine-1-carboxylic acid benzyl ester (Example 83, 0.350 g, 0.85 mmol), aryl boronic acid (1.1 eq), $Pd[P(Ph)_3]_4$ (8 mg), and $NaHCO_3$ (sat. aq., 1.1 mL) in MeOH (12 mL) was degassed and heated to 70° C. overnight. The resulting mixture was filtered, concentrated, and purified by reverse phase HPLC (20-100% of buffer B; buffer A: water containing 0.1% TFA; buffer B: MeCN containing 0.1 TFA). The combined fraction was evaporated to dryness to furnish the desired product.

General Procedure K

A mixture of (S)-2-[5-(3-amino-phenyl)-thiazol-2-ylcarbamoyl]-pyrrolidine-1-carboxylic acid benzyl ester (Compound 5114, Example 114, 0.05 g, 0.12 mmol) with different acyl chlorides and TEA (0.018 mL) in dichloromethane (3 mL) was stirred at 0° C. for 20 min. then was quenched with water. The mixture was concentrated in vacuo and the resulting residue was dissolved in DMF (5 mL) and water (0.5 mL) then purified by reverse phase prep. LC/MS to furnish the corresponding desired product.

General Procedure 3A 4-(2-Amino-thiazol-4-yl)-benzoic acid

Thiourea (0.47 g, 6.2 mmol) and NaOAc (1.5 g, 6.2 mmol) were combined in 35 mL of ethanol. To this suspension was added 4-(2-bromo-acetyl)-benzoic acid (1.5 g, 6.2 mmol). The reaction mixture was stirred at room temperature overnight. It was evaporated to dryness and used in the next step without any further purification. MS: 221.0 (M+H$^+$)

2-[4-(4-carboxy-phenyl)-thiazol-2-ylcarbamoyl]-pyrrolidine-1-carboxylic acid benzyl ester Z-ProOH (0.56 g, 2.2 mmol) and HATU (2.2 mmol, 0.83 g) were combined in 35 mL of DMF. To this solution was added DIEA (2.4 mmol, 0.42 mL). This solution was stirred at room temperature for 1 hr. 4-(2-Amino-thiazol-4-yl)-benzoic acid (2.2 mmol, 0.5 g) was then added to the solution. The reaction mixture was stirred at 70° C. overnight. It was brought to room temperature and then evaporated to dryness. The crude was purified using reverse phase HPLC. MS: 452.1 (M+H$^+$)

2-[4-(4-N-substituted-carbamoyl-phenyl)-thiazol-2-ylcarbamoyl]-pyrrolidine-1-carboxylic acid benzyl ester 2-[4-(2-carboxy-phenyl)-thiazol-2-ylcarbamoyl]-pyrrolidine-1-carboxylic acid benzyl ester (0.55 mmol, 0.25 g) and HATU (0.55 mmol, 0.21 g) were combined in 16 mL of DMF. To this solution wad added DIEA (0.6 mmol, 0.13 mL). This solution was stirred at room temperature for 2 hours. 4 mL of this solution was then added to each of the amines. These reaction mixtures were stirred at room temperature overnight. They were diluted with DMF up to 10 mL and purified using reverse phase HPLC.

General Procedure 3B

Pyrrolidine-2-carboxylic acid [4-(4-cyclopropyl-carbamoyl-phenyl)-thiazol-2-yl]-amide (General Procedure 3I, 100 mg, 0.28 mmol), was suspended in 6 mL of dry DCM. To this suspension was added triethylamine (0.05 ml, 0.36 mmol). This suspension was cooled to 0° C. and the appropriate acyl chloride or chloroformate (1.1 equiv) was added. Reaction mixtures were stirred at 0° C. for 30 minutes and then quenched using H$_2$O. Organic layer was isolated and dried to yield the desired products.

General Procedure 3C

A carboxylic acid (0.2 mmol) was dissolved in DMF (5 mL) and treated with HATU (1.1 eq. 83.6 mg) and DIEA (2.2 eq, 76 µL) and stirred for 15 minutes. Then 1-[4-(2-Amino-thiazol-4-yl)-phenyl]-ethanone (1 eq, 51.8 mg) was added and the mixture stirred at ambient temperature overnight. The reaction was cooled, filtered and the solvents removed. The resulting mixture was redissolved in 5 ml of 90% DMF, 10% water with 0.1% TFA and purified by reverse phase HPLC to give the product.

General Procedure 3D

A mixture of (S)-2-[4-(4-Amino-phenyl)-thiazol-2-ylcarbamoyl]-pyrrolidine-1-carboxylic acid benzyl ester (Compound 5050, Example 50, 0.050 g, 0.12 mmol), glacial acetic acid (0.04 mL, 0.71 mmol), NaBH$_3$CN (0.021 g, 0.33 mmol), and an aldehyde in MeOH (3 mL) was stirred at room temperature overnight. The mixture was concentrated in vacuo to give the crude product. Purification of the crude product by reverse phase HPLC (CH$_3$CN/H$_2$O) furnished the corresponding products.

General Procedure 3E

A mixture of 2-(5-Bromo-thiazol-2-ylcarbamoyl)-pyrrolidine-1-carboxylic acid benzyl ester (Compound 5083, Example 83, 0.150 g, 0.37 mmol), aryl boronic acids (2 eq), Pd[P(Ph$_3$]$_4$ (60 mg), in MeOH (9 mL), NaHCO$_3$ (sat. aq., 2 mL) was degassed and heated to reflux overnight. The resulting mixture was filtered, concentrated, and purified by reverse phase HPLC (20-100% of buffer B; buffer A: water containing 0.1% TFA; buffer B: MeCN containing 0.1 TFA). The combined fraction was evaporated to dryness to furnish the corresponding intermediates.

The intermediates were mixed with aqueous NaOH (1 M, 2 mL, 2 mmol) in THF/H$_2$O/MeOH (2:2:1, 5 mL) and stirred at room temperature for 3 h. The reaction mixtures were neutralized with 1 N HCl, concentrated in vacuo and dried to give the desired products.

General Procedure 3F

A mixture of (S)-2-[5-(4-Carboxy-phenyl)-thiazol-2-ylcarbamoyl]-pyrrolidine-1-carboxylic acid benzyl ester, HATU, and DIEA (0.04 mL, 0.05 mmol) in DMF (2.0 mL) was stirred at room temperature for 1 h. The amine was added and the reaction mixture was stirred at room temperature for 20 h. The resulting mixture was diluted with DMF (5 mL) and water (0.5 mL) then purified by reverse phase HPLC to furnish the corresponding product.

General Procedure 3G

A mixture of (S)-2-[5-(3-Carboxy-phenyl)-thiazol-2-ylcarbamoyl]-pyrrolidine-1-carboxylic acid benzyl ester (Compound 5304, Example 304, 0.02 g, 0.04 mmol), HATU (0.033 g, 0.09 mmol)), and DIEA (0.04 mL, 0.05 mmol) in DMF (2.0 mL) was stirred at room temperature for 1 h. The amine was added and the reaction mixture was stirred at room temperature for 20 h. The resulting mixture was purified by reverse phase prep. HPLC to furnish the product.

General Procedure 3H

A mixture of (S)-2-[4-(3-Amino-phenyl)-thiazol-2-ylcarbamoyl]-pyrrolidine-1-carboxylic acid benzyl ester (Compound 5001, Example 1, 0.030 g, 0.07 mmol), glacial acetic acid (0.03 mL, mmol), NaBH$_3$CN (0.014 g, mmol), and an aldehyde in MeOH (2 mL) was stirred at room temperature overnight. The mixture was concentrated in vacuo to give the crude product. Purification of the crude product by reverse phase HPLC (CH$_3$CN/H$_2$O) furnished the products.

General Procedure 3I

(S)-Pyrrolidine-2-carboxylic acid [4-(4-cyclopropyl-carbamoyl-phenyl)-thiazol-2-yl]-amide A mixture of (S)-2-[4-(4-Cyclopropylcarbamoyl-phenyl)-thiazol-2-ylcarbamoyl]-pyrrolidine-1-carboxylic acid tertbutyl ester (compound 5375, Example 375, 0.13 g, 0.29 mmol) and TFA (5 mL) in dichloromethane (5 mL) was stirred at room temperature for 2 h. The mixture was concentrated and dried to give the product which was converted to the hydrochloride salt. $^1$H NMR(DMSO-d$_6$) δ(ppm) 12.95 (s, 1H), 10.0-9.98 (m, 1H), 8.89-8.85 (m, 1H), 8.48-8.47 (d, 1H), 7.96-7.82 (m, 5H), 4.51-4.48 (m, 1H), 3.38-3.25 (m, 2H), 2.97-2.83 (m, 1H), 2.44-2.37 (m, 1H), 2.06-1.92 (m, 3H), 0.73-0.56 (m, 4H); MS: 392.91 (M+H$^+$).

To a mixture of (S)-pyrrolidine-2-carboxylic acid [4-(4-cyclopropylcarbamoyl-phenyl)-thiazol-2-yl]-amide (0.04 g, 0.09 mmol) and TEA (0.007 mL) in dichloromethane (3 mL) was added acyl chlorides. The mixture was allowed to warm to room temperature and was stirred for 1 h then concentrated in vacuo to give the corresponding crude products. Purification of the crude products by silica gel (MeOH/DCM) furnished the desired products.

General Procedure 3J

A mixture of (S)-Pyrrolidine-2-carboxylic acid [4-(4-cyclopropylcarbamoyl-phenyl)-thiazol-2-yl]-amide (General Procedure 3I, 0.040 g, 0.09 mmol), glacial acetic acid (0.04 mL, 0.71 mmol), NaBH$_3$CN (0.015 g, 0.23 mmol), and an aldehyde in MeOH (3 mL) was stirred at room temperature overnight. The mixture was concentrated in vacuo to give the crude product. Purification of the crude products by reverse phase HPLC (CH$_3$CN/H$_2$O) furnished the corresponding products.

Example 1

2-[4-(3-Amino-phenyl)-thiazol-2-ylcarbamoyl]-pyrrolidine-1-carboxylic acid benzyl ester (Compound 5001)

Thiourea (0.31 g, 4.1 mmol) and sodium acetate (0.44 g, 5.3 mmol) were combined in 30 mL of dry ethanol. To this suspension was added 2-bromo-1-(3-nitro-phenyl)-ethanone (1.0 g, 4.1 mmol). Reaction mixture was stirred at room temperature overnight. Reaction mixture was evaporated to dryness to yield 4-(3-nitro-phenyl)-thiazol-2-ylamine, which was used in the next step without any further purification. MS: 222.0 (M+H$^+$).

Z-Pro-OH (1.5 g, 6.15 mmol) and HATU (2.3 g, 6.15 mmol) were combined in 30 mL of dry DMF. To this solution was added DIEA (1.5 mL, 8.8 mmol). This solution was stirred at room temperature for 1 hour. To this solution was added 4-(3-nitro-phenyl)-thiazol-2-ylamine (0.9, 4.1 mmol). Reaction mixture was stirred at room temperature overnight. The crude material was purified using reverse phase HPLC to yield 2-[4-(3-Nitro-phenyl)-thiazol-2-ylcarbamoyl]-pyrrolidine-1-carboxylic acid benzyl ester. MS: 453.1 (M+H$^+$).

500 mg (1.1 mmol) of 2-[4-(3-Nitro-phenyl)-thiazol-2-ylcarbamoyl]-pyrrolidine-1-carboxylic acid benzyl ester was dissolved in 30 mL of 1:1 mixture of EtOH/EtOAc. To this solution was added SnCl$_2$ (0.87 g, 3.9 mmol). Reaction mixture was heated under reflux for 5 hours. After 5 hours reaction mixture was cooled to room temperature and evaporated. It was redissolved in EtOAc (150 mL) and washed using sat. K$_2$CO$_3$. Organic phase was isolated, washed using brine and water and evaporated to dryness to give Compound 5001. MS: 422.1 (M+H$^+$).

Example 2

2-(4-Benzo-5-yl-thiazol-2-ylcarbamoyl)-pyrrolidine-1-carboxylic acid benzyl ester (Compound 5002)

Using General Procedure G from 10 mg of 4-Benzo[1,2]dioxol-5-yl-thiazol-2-ylamine in 1 mL of solution. MS: 452.0 (M+H$^+$).

Example 3

2-(4-Phenyl-thiazol-2-ylcarbamoyl)-pyrrolidine-1-carboxylic acid benzyl ester (Compound 5003)

Using General Procedure G from 30 mg of 4-phenethyl-thiazol-2-ylamine in 2 mL of solution. MS: 436.1 (M+H$^+$).

Example 4

2-[4-(4-Methanesulfonylamino-phenyl)-thiazol-2-ylcarbamoyl]-pyrrolidine-1-carboxylic acid benzyl ester (Compound 5004)

Using General Procedure D from 7.1 μL methane sulfonyl chloride. MS: 579.1 (M+H$^+$).

Example 5

2-{4-[4-(Toluene-4-sulfonylamino)-phenyl]-thiazol-2-ylcarbamoyl}-pyrrolidine-1-carboxylic acid benzyl ester (Compound 5005)

Using General Procedure G from 10 mg of N-[4-(2-Amino-thiazol-4-yl)-phenyl]-4-methyl-benzenesulfonamide in 1 mL of solution. MS: 577.1 (M+H$^+$).

Example 6

2-[4-[4-Cyclopentanecarbonyl-amino)-phenyl]-thiazol-2-ylcarbamoyl}-pyrrolidine-1-carboxylic acid benzyl ester (Compound 5006)

Using General Procedure H from 9.5 μL of cyclopentane carbonyl chloride. MS: 519.2 (M+H$^+$).

Example 7

2-[4-(2-Oxo-2H-chromen-3-yl)-thiazol-2-ylcarbamoyl]-pyrrolidine-1-carboxylic acid benzyl ester (Compound 5007)

Using General Procedure G from 10 mg of 3-(2-amino-thiazol-4-yl)-chromen-2-one in 1 mL of solution. MS: 476.0 (M+H$^+$).

Example 8

2-[4-(3-nitro-phenyl)-thiazol-2-ylcarbamoyl]-pyrrolidine-1-carboxylic acid benzyl ester (Compound 5008)

Using General Procedure G from 10 mg of 4-(3-nitro-phenyl)-thiazol-2-ylamine in 1 mL of solution. MS: 454.1 (M+H$^+$).

Example 9

2-[4-(4-Isobutyl-2-methyl-5-oxo-tetrahydro-furan-2-yl)-thiazol-2-ylcarbamoyl]-pyrrolidine-1-carboxylic acid benzyl ester (Compound 5009)

Using General Procedure G from 10 mg of 5-(2-Amino-thiazol-4-yl)-3-isobutyl-5-methyl-dihydro-furan-2-one in 1 mL of solution. MS: 486.3 (M+H$^+$).

Example 10

2-[4-(5-Phenyl-[1,3,4]-oxadiazol-2-ylsulfanyl)-thiazol-2-ylcarbamoyl]-pyrrolidine-1-carboxylic acid benzyl ester (Compound 5010)

Using General Procedure G from 10 mg of 4-(5-phenyl-[1,3,4]oxadiazol-2-ylsulfanyl)-thiazol-2-ylamine in 1 mL of solution. MS: 522.7 (M+H$^+$).

Example 11

2-[5-(4-Propoxy-phenyl)-thiazol-2-ylcarbamoyl]-pyrrolidine-1-carboxylic acid benzyl ester (Compound 5011)

Using General Procedure G from 10 mg of 4-(4-Propoxyphenyl)-thiazol-2-ylamine in 1 mL of solution. MS: 466.2 (M+H$^+$).

Example 12

2-[5-(2,3-Dichloro-benzyl)-thiazol-2-ylcarbamoyl]-pyrrolidine-1-carboxylic acid benzyl ester (Compound 5012)

Using General Procedure G from 10 mg of 5-(2,3-dichlorobenzyl)-thiazol-2-ylamine in 1 mL of solution. MS: 490.0 (M+H$^+$).

Example 13

2-[4-(4-Dimethylamino-phenyl)-thiazol-2-ylcarbamoyl]-pyrrolidine-1-carboxylic acid benzyl ester (Compound 5013)

2-[4-(4-amino-phenyl)-thiazol-2-ylcarbamoyl]-pyrrolidine-1-carboxylic acid benzyl ester (Compound 5050, 75 mg, 0.18 mmol) was dissolved in 5 mL of THF. To this solution was added DIEA (62.7 µL, 0.36 mmol), followed by iodomethane (22.5 µL, 0.36 mmol). Reaction mixture was heated at 50° C. overnight. Reaction mixture was evaporated to dryness. It was redissolved in 5 mL of DMF and purified using reverse phase HPLC to furnish the desired product. MS: 451.1 (M+H$^+$).

Example 14

2-[4-(3,4,5,6-Tetrafluoro-biphenyl-2-yl)-thiazol-2-ylcarbamoyl]-pyrrolidine-1-carboxylic acid benzyl ester (Compound 5014)

Using General Procedure G from 20 mg of 4-(3,4,5,6-tetrafluoro-biphenyl-2-yl)-thiazol-2-ylamine in 1 mL of solution. MS: 556.1 (M+H$^+$).

Example 15

2-[4-(3-Acetylamino-phenyl)-thiazol-2-ylcarbamoyl]-pyrrolidine-1-carboxylic acid benzyl ester (Compound 5015)

Using General Procedure G from 10 mg of N-[3-(2-Amino-thiazol-4-yl)-phenyl]-acetamide in 1 mL of solution. MS: 465.1 (M+H$^+$).

Example 16

2-[4-(3-Bromo-4-methoxy-phenyl)-thiazol-2-ylcarbamoyl]-pyrrolidine-1-carboxylic acid benzyl ester (Compound 5016)

Using General Procedure B from 10 mg of 4-(3-Bromo-4-methoxy-phenyl)-thiazol-2-ylamine. MS: 516.1(M+H$^+$).

Example 17

2-{4-(4-Propionylamino-phenyl)-thiazol-2-ylcarbamoyl]-pyrrolidine-1-carboxylic acid benzyl ester (Compound 5017)

Using General Procedure G from 10 mg of N-(2-aminothiazol-4-yl)-propionamide in 1 mL of solution. MS: 479.1 (M+H$^+$).

Example 18

2-[4-[4-Cyclopropanecarbonyl-amino)-phenyl]-thiazol-2-ylcarbamoyl}-pyrrolidine-1-carboxylic acid benzyl ester (Compound 5018)

Using General Procedure H from 8.6 µL of cyclopropane carbonyl chloride. MS: 491.1 (M+H$^+$)

Example 19

2-[4-(3-Benzoylamino-phenyl)-thiazol-2-ylcarbamoyl]-pyrrolidine-1-carboxylic acid benzyl ester (Compound 5019)

Using General Procedure E from 10 µL of benzoyl chloride. MS: 527.1 (M+H$^+$).

Example 20

2-[4-(2,3,5,6-Tetrafluoro-4-methoxy-phenyl)-thiazol-2-ylcarbamoyl]-pyroolidine-1-carboxylic acid benzyl ester (Compound 5020)

Using General Procedure G from 10 mg of 4-(2,3,5,6-tetrafluoro-4-methoxy-phenyl)-thiazol-2-ylamine in 1 mL of solution. MS: 510.0 (M+H$^+$).

Example 21

2-[4-(2,4-Dimethyl-phenyl)-thiazol-2-ylcarbamoyl]-pyrrolidine-1-carboxylic acid benzyl ester (Compound 5021)

Using General Procedure G from 30 mg of 4-(2,4-Dimethyl-phenyl)-thiazol-2-ylamine in 2 mL of solution. MS: 436.1 (M+H$^+$).

Example 22

2-[4-p-Tolyl-thiazol-2-ylcarbamoyl)-pyrrolidine-1-carboxylic acid benzyl ester (Compound 5022)

Using General Procedure G from 30 mg of 4-p-tolyl-thiazol-2-ylamine in 2 mL of solution. MS: 422.1 (M+H$^+$).

Example 23

2-[4-(1H-Indol-5-yl)-phenylcarbamoyl]-pyrrolidine-1-carboxylic acid benzyl ester (Compound 5023)

Using General Procedure G from m 30 mg of 4-(2,4-Difluoro-phenyl)-thiazol-2-ylamine in 2 mL of solution. MS: 444.0 (M+H$^+$).

Example 24

2-[4-(4-Cyclohexyl-phenyl)-thiazol-2-ylcarbamoyl]-pyrrolidine-1-carboxylic acid benzyl ester (Compound 5024)

Using General Procedure G from 10 mg of 4-(4-cyclohexyl-phenyl)-thiazol-2-ylamine in 1 mL of solution. MS: 490.1 (M+H$^+$).

Example 25

2-[5-(3-Chloro-4-methyl-benzyl)-thiazol-2-ylcarbamoyl]-pyrrolidine-1-carboxylic acid benzyl ester (Compound 5025)

Using General Procedure G from 10 mg of 5-(3-chloro-4-methyl-benzyl)-thiazol-2-ylamine in 1 mL of solution. MS: 470.1 (M+H$^+$).

Example 26

2-{4-[3-(Cyclopentamecarbonyl-amino)-phenyl]-thiazol-2-ylcarbamoyl]-pyrrolidine-1-carboxylic acid benzyl ester (Compound 5026)

Using General Procedure E from 9.5 µL of cyclopentane carbonyl chloride. MS: 519.2 (M+H$^+$).

Example 27

2-[4-(4-Benzenesulfonylamino-phenyl)-thiazol-2-ylcarbamoyl]-pyrrolidine-1-carboxylic acid benzyl ester (Compound 5027)

Using General Procedure D from 7.1 µL benzene sulfonyl chloride. MS: 563.1 (M+H$^+$).

Example 28

2-[4-(1-Phenyl-cyclopentyl)-thiazol-2-ylcarbamoyl]-pyrrolidine-1-carboxylic acid benzyl ester (Compound 5028)

Using General Procedure G from 10 mg of 4-(1-phenyl-cyclopentyl)-thiazol-2-ylamine in 1 mL of solution. MS: 476.1 (M+H$^+$).

Example 29

2-[5-(3-Chloro-benzyl)-thiazol-2-ylcarbamoyl]-pyrrolidine-1-carboxylic acid benzyl ester (Compound 5029)

Using General Procedure G from 10 mg of 5-(3-Chloro-benzyl)-thiazol-2-ylamine in 1 mL of solution. MS: 456.0 (M+H$^+$).

Example 30

2-[4-(6-Methyl-imidazo[2,1-b]thiazol-5-yl)-thiazol-2-ylcarbamoyl]-pyrrolidine-1-carboxylic acid benzyl ester (Compound 5030)

Using General Procedure G from 10 mg of 4-(6-Methyl-imidazo[2,1-b]thiazol-5-yl)-thiazol-2-ylamine in 1 mL of solution. MS: 468.1 (M+H$^+$).

Example 31

2-[5-(2,4-Dichloro-benzyl)-thiazol-2-ylcarbamoyl]-pyrrolidine-1-carboxylic acid benzyl ester (Compound 5031)

From 10 mg of 5-(2,4-Dichloro-benzyl)-thiazol-2-ylamine in 1 mL of solution. MS: 490.0 (M+H$^+$).

Example 32

2-[4-(3,5,6-Trimethyl-4-oxo-3,4-dihydro-thieno[2,3-d]pyrimidin-2-ylsulfanylmethyl)-thiazol-2-ylcarbamoyl]-pyrrolidine-1-carboxylic acid benzyl ester (Compound 5032)

Using General Procedure G from 10 mg of 2-(2-Amino-thiazol-4-ylmethylsulfanyl)-3,5,6-trimethyl-4a, 7a-dihydro-3H-thieno[2,3-d]pyrimidin-4-one in 1 mL of solution. MS: 570.1 (M+H$^+$).

Example 33

2-[4-(Toluene-4-sulfonylmethyl)-thiazol-2-ylcarbamoyl]-pyrrolidine-1-carboxylic acid benzyl ester (Compound 5033)

Using General Procedure G from 10 mg of 4-(toluene-4-sulfonylmethyl)-thiazol-2-ylamine in 1 mL of solution. MS: 500.1 (M+H$^+$).

Example 34

2-[4-(3,4-Dichloro-phenyl)-thiazol-2-ylcarbamoyl]-pyrrolidine-1-carboxylic acid benzyl ester (Compound 5034)

Using General Procedure G from 30 mg of 4-(3,4-dichloro-phenyl)-thiazol-2-ylamine in 2 mL of solution. MS: 476.0 (M+H$^+$).

Example 35

2-(Naphtho[2,3-d]thiazol-2-ylcarbamoyl)-pyrrolidine-1-carboxylic acid benzyl ester (Compound 5035)

Using General Procedure B from 10 mg of Naphtho[2,3-d]thiazol-2-ylamine. MS: 432.1 (M+H$^+$).

Example 36

2-{4-[4-(4-Chloro-benzoylamino)-phenyl]-thiazol-2-ylcarbamoyl}-pyrrolidine-1-carboxylic acid benzyl ester (Compound 5036)

A mixture of 4-Chlorobenzoic acid (0.017 g, 0.11 mmol), HATU (0.042 g, 0.11 mmol), and DIEA 0.09 mL, 0.67 mmol) in DMF (2 mL) was stirred at room temperature for 1 h. (S)-2-[4-(4-Amino-phenyl)-thiazol-2-ylcarbamoyl]-pyrrolidine-1-carboxylic acid benzyl ester (FW=422.5096 , 0.029 g, 0.054 mmol) was added. The reaction mixture was stirred at room temperature for 20 h. The mixture was filtered to afford the crude product. The mixture was filtered and separated by reverse phase HPLC (20-100% of buffer B; buffer A: water containing 0.1% TFA; buffer B: MeCN containing 0.1 TFA). The combined fraction was evaporated to dryness to furnish the desired product. MS: 562.1(M+H$^+$).

Example 37

2-[4-(4-Benzoylamino-phenyl)-thiazol-2-ylcarbamoyl]-pyrrolidine-1-carboxylic acid benzyl ester (Compound 5037)

Using General Procedure H from 10 µL of benzoyl chloride. MS: 527.1 (M+H$^+$).

Example 38

2-{4-[3-(4-Chloro-benzoylamino)-phenyl]-thiazol-2-ylcarbamoyl}-pyrrolidine-1-carboxylic acid benzyl ester (Compound 5038)

Using General Procedure G from 10 mg of N-(2-amino-thiazol-4-yl)-4-chloro-benzamide in 1 mL of solution. MS: 561.1 (M+H$^+$).

Example 39

2-{4-[3-(Cyclopropanecarbonyl-amino)-phenyl]-thiazol-2-ylcarbamoyl]-pyrrolidine-1-carboxylic acid benzyl ester (Compound 50039)

Using General Procedure E from 8.6 µL of cyclopropane carbonyl chloride. MS: 491.1 (M+H$^+$).

Example 40

2-[5-(4-Methyl-benzyl)-thiazol-2-ylcarbamoyl]-pyrrolidine-1-carboxylic acid benzyl ester (Compound 5040)

Using General Procedure G from 10 mg of 5-(4-Methyl-benzyl)-thiazol-2-ylamine in 1 mL of solution. MS: 436.1 (M+H$^+$).

Example 41

2-[4-(4-Nitro-phenyl)-thiazol-2-ylcarbamoyl]-pyrrolidine-1-carboxylic acid benzyl ester (Compound 5041)

Using General Procedure G from 10 mg of 4-(4-Nitro-phenyl)-thiazol-2-ylamine in 1 mL of solution. MS: 453.1 (M+H$^+$).

Example 42

2-[5-(2,5-Dimethyl-phenyl)-thiazol-2-ylcarbamoyl]-pyrrolidine-1-carboxylic acid benxyl ester (Compound 5042)

Using General Procedure G from 10 mg of 5-(2,5-Dimethyl-phenyl)-thiazol-2-ylamine in 1 mL of solution. MS: 436.1 (M+H$^+$).

Example 43

2-[4-(7-Methoxy-2-oxo-2H-chromen-3-yl)-thiazol-2-ylcarbamoyl]-pyrrolidine-1-carboxylic acid benzyl ester (Compound 5043)

Using General Procedure G from 10 mg of 3-(2-amino-thiazol-4-yl)-7-methoxy-chromen-2-one in 1 mL of solution. MS: 506.1 (M+H$^+$).

Example 44

2-[4-(2-Oxo-1-oxa-spiro[4.5]dec-4-yl)-thiazol-2-ylcarbamoyl]-pyrrolidine-1-carboxylic acid benzyl ester (Compound 5044)

Using General Procedure G from 10 mg of 4-(2-Amino-thiazol-4-yl)-1-oxa-spiro[4.5]decan-2-one in 1 mL of solution. MS: 484.1 (M+H$^+$).

Example 45

2-[4-(4-Chloro-phenoxymethyl)-thiazol-2-ylcarbamoyl]-pyrrolidine-1-carboxylic acid benzyl ester (Compound 5045)

Using General Procedure G from 10 mg of 5-(3-Chloro-4-methyl-benzyl)-thiazol-2-ylamine in 1 mL of solution. MS: 472.0 (M+H$^+$).

Example 46

2-[4-(2,2-Dimethyl-tetrahydro-pyran-4-yl)-thiazol-2-ylcarbamoyl]-pyrrolidine-1-carboxylic acid benzyl ester (Compound 5046)

Using General Procedure G from 10 mg of 4-(2,2-Dimethyl-tetrahydro-pyran-4-yl)-thiazol-2-ylamine in 1 mL of solution. MS: 444.2 (M+H$^+$).

Example 47

2-[5-(3-Nitrobenzyl)-thiazol-2-ylcarbamoyl]-pyrrolidine-1-carboxylic acid benzyl ester (Compound 5067)

Using General Procedure B from 10 mg of 5-(3-Nitrobenzyl)-thiazol-2-ylamine. MS: 467.1 (M+H$^+$).

Example 48

2-[4-(4-Acetylamino-phenyl)-thiazol-2-ylcarbamoyl]-pyrrolidine-1-carboxylic acid benzyl ester (Compound 5048)

Using General Procedure G from 10 mg of N-[4-(2-Amino-thiazol-4-yl)-phenyl]-acetamide in 1 mL of solution. MS: 465.1 (M+H$^+$).

Example 49

2-[4-(4-Methylamino-phenyl)-thiazol-2-ylcarbamoyl]-pyrrolidine-1-carboxylic acid benzyl ester (Compound 5049)

2-[4-(4-amino-phenyl)-thiazol-2-ylcarbamoyl]-pyrrolidine-1-carboxylic acid benzyl ester (Compound 5050, 38 mg, 0.092 mmol) was dissolved in 3.5 mL of methylene chloride. To this solution was added triethylamine (12.8 μL, 0.092 mmol) followed by 6 μL (0.092 mmol) of methyl iodide. This solution was heated under reflux for 1 hour. It was evaporated and redissolved in 5 mL of DMF. The crude was purified using reverse phase HPLC to furnish the desired product. MS: 437.1 (M+H$^+$).

Example 50

2-[4-(4-Amino-phenyl)-thiazol-2-ylcarbamoyl]-pyrrolidine-1-carboxylic acid benzyl ester (Compound 5050)

1.0 g (13.2 mmol) of thiourea, sodium acetate (2.2 g 26.4 mmol), and 25 mL of dry ethanol were combined in a 25 mL round bottom flask. To this suspension was added nitrobenzene bromoacetate (4.2 g, 1.72 mmol). Reaction mixture was heated under reflux overnight. This suspension was cooled to room temperature. The solid was collected by suction filtration and washed using water. The resulting solid was dried to yield 4-(4-nitro-phenyl)-thiazol-2-ylamine. MS: 222.1 (M+H$^+$).

Z-Pro-OH (1.46 g, 5.85 mmol) and HATU (2.2 g, 5.85 mmol) were combined in 30 mL of dry DMF. To this solution was added DIEA(1.5 mL, 8.8 mmol). This solution was stirred at room temperature for 1 hour. To this solution was added 4-(4-nitro-phenyl)-thiazol-2-ylamine (1.0 g, 4.5 mmol). Reaction mixture was stirred at room temperature overnight. The crude material was purified using HPLC to yield 2-[4-(4-Nitro-phenyl)-thiazol-2-ylcarbamoyl]-pyrrolidine-1-carboxylic acid benzyl ester. MS: 453.1 (M+H$^+$).

400 mg (0.88 mmol) of 2-[4-(4-Nitro-phenyl)-thiazol-2-ylcarbamoyl]-pyrrolidine-1-carboxylic acid benzyl ester was dissolved in 30 mL of 1:1 mixture of EtOH/EtOAc. To this solution was added SnCl$_2$ (0.7 g, 3.1 mmol). Reaction mixture was heated under reflux for 5 hours. After 5 hours reaction mixture was cooled to room temperature and evaporated. It was redissolved in EtOAc (150 mL) and washed using sat. K$_2$CO$_3$. Organic phase was isolated, washed using brine and water and evaporated to dryness to give Compound 5050. MS: 422.1 (M+H$^+$).

Example 51

2-[4-(Tetrahydro-pyran-4-yl)-thiazol-2-ylcarbamoyl]-pyrrolidine-1-carboxylic acid benzyl eater (Compound 5051)

Using General Procedure G from 10 mg of 4-(Tetrahydro-pyran-4-yl)-thiazol-2-ylamine in 1 mL of solution. MS: 416.1 (M+H$^+$).

Example 52

2-[5-(2-Chloro-benzyl)-thiazol-2-ylcarbamoyl]-pyrrolidine-1-carboxylic acid benzyl ester (Compound 5052)

Using General Procedure G from 10 mg of 5-(2-Chloro-benzyl)-thiazol-2-ylamine in 1 mL of solution. MS: 456.0 (M+H$^+$).

Example 53

2-[5-(4-Acetyl-benzyl)-thiazol-2-ylcarbamoyl]-pyrrolidine-1-carboxylic acid benzyl ester (Compound 5053)

Using General Procedure G from 10 mg of 1-[4-(2-Amino-thiazol-5-ylmethyl)-phenyl]-ethanone in 1 mL of solution. MS: 464.1 (M+H$^+$).

Example 54

2-[4-(3,4-Dimethoxy-phenyl)-thiazol-2-ylcarbamoyl]-pyrrolidine-1-carboxylic acid benzyl ester (Compound 5054)

Using General Procedure G from 10 mg of 4-(3,4-dimethoxy-phenyl)-thiazol-2-ylamine in 1 mL of solution. MS: 468.1 (M+H$^+$).

Example 55

2-(4-Napthalen-1-yl-thiazol-2-ylcarbamoyl)-pyrrolidine-1-carboxylic acid benzyl ester (Compound 5055)

Using General Procedure G from 30 mg of 4-Napthalen-1-yl-thiazol-2-ylamine in 2 mL of solution. MS: 458.1 (M+H$^+$).

Example 56

2-[4-(3,4-Difluoro-phenyl)-thiazol-2-ylcarbamoyl]-pyrrolidine-1-carboxylic acid benzyl ester (Compound 5056)

Using General Procedure C from 0.106 g (0.5 mmol) of 4-(3,4-Difluoro-phenyl)-thiazol-2-ylamine. MS: 444.1 (M+H$^+$).

Example 57

2-(5-Phenyl-1H-pyrazol-3-ylcarbamoyl)-pyrrolidine-1-carboxylic benzyl ester (Compound 5057)

Using General Procedure G from 30 mg of 5-phenyl-1H-pyrazol-3-ylamine in 2 mL of solution. MS: 391.1 (M+H$^+$).

Example 58

2-[4-(9H-Fluoren-2-yl)-thiazol-2-ylcarbamoyl]-pyrrolidine-1-carboxylic acid benzyl ester (Compound 5058)

Using General Procedure G from 10 mg of 4-(9H-Fluoren-2-yl)-thiazol-ylamine in 1 mL of solution. MS: 496.1 (M+H$^+$)

Example 59

2-[[4-(2,6-Difluoro-phenyl)-thiazol-2-ylcarbamoyl-pyrrolidine-1-carboxylic acid benzyl ester (Compound 5059)

Using General Procedure G from 10 mg of 4-(2,6-Difluoro-phenyl)-thiazol-2-ylamine in 1 mL of solution. MS: 444.0 (M+H$^+$).

Example 60

2-(4-Napthalen-2-yl-thiazol-2-ylcarbamoyl)-pyrrolidine-1-carboxylic acid benzyl ester (Compound 5060)

Using General Procedure G from 30 mg of 4-Napthalen-2yl-thiazol-2-ylamine in 2 mL of solution. MS: 458.1 (M+H$^+$).

Example 61

2-{4-[4-(4-Fluoro-phenyl)-thiazol-2-ylsulfanylmethyl]-thioazol-2-ylcarbamoyl}-pyrrolidine-1-carboxylic acid benzyl ester (Compound 5061)

Using General Procedure G from 10 mg of 4-[4-(4-fluoro-phenyl)-thiazol-2-ylsulfanylethyl]-thiazol-2-ylamine in 1 mL of solution. MS: 555.7 (M+H$^+$).

Example 62

2-[4-(3,4,5-Trimethyl-phenyl)-thiazol-2-ylcarbamoyl-pyrrolidine-1-carboxylic acid benzyl ester (Compound 5062)

Using General Procedure G from m 10 mg of 4-(3,4,5-trimethyl-phenyl)-thiazol-2-ylamine in 1 mL of solution. MS: 450.1 (M+H$^+$).

Example 63

2-[5-(4-Chloro-benzyl)-thiazol-2-ylcarbamoyl]-pyrrolidine-1-carboxylic acid benzyl ester (Compound 5063)

Using General Procedure B from 10 mg of 5-(4-Chloro-benzyl)-thiazol-2-ylamine. MS: 456.1(M+H$^+$).

Example 64

2-[4-(1H-Benzoimidazol-2-ylsulfanylmethyl)thiazol-2-ylcarbanoyl]-pyrrolidine-carboxylic acid benzyl ester (Compound 5064)

Using General Procedure G from 10 mg of 4-(1H-Benzoimidazol-2-ylsulfanylmethyl)-thiazol-2-ylamine in 1 mL of solution. MS: 494.2 (M+H$^+$).

Example 65

2-(2,5-Diphenyl-2H-pyrazol-3-ylcarbamoyl)-pyrrolidine-1-carboxylic acid benzyl ester (Compound 5065)

Using General Procedure G from 10 mg of 2,5-diphenyl-2H-pyrazol-3-ylamine in 1 mL of solution. MS: 467.1 (M+H$^+$).

Example 66

2-{4-[4-(4-Bromo-benzyloxy)-phenyl]-thiazol-2-ylcarbamoyl}-pyrrolidine-1-carboxylic acid benzyl ester (Compound 5066)

Using General Procedure G from 10 mg of 4-[4-(4-Bromo-phenoxy)-phenyl]-thiazol-2-ylamine in 1 mL of solution. MS: 592.0 (M+H$^+$).

Example 67

2-[5-(3-Methyl-benzyl)-thiazol-2-ylcarbamoyl]-pyrrolidine-1-carboxylic acid benzyl ester (Compound 5067)

Using General Procedure B from 10 mg of 5-(3-Methyl-benzyl)-thiazol-2-ylamine. MS: 436.1(M+H$^+$).

Example 68

2-[4-(Phenethylcarbamoyl-methyl)-thiazol-2-ylcarbamoyl]-pyrrolidine-1-carboxylic acid benzyl ester (Compound 5068)

Using General Procedure B from 10 mg of 2-(2-Aminothiazol-4-yl)-N-phenethyl-acetamide. MS: 493.1(M+H$^+$).

Example 69

2-[4-(4-isopropyl-phenyl)-thiazol-2-ylcarbanoyl]-pyrrolidine-1-carboxylic acid benzyl ester (Compound #5069)

Using General Procedure G from 30 mg of 4-(4-isopropyl-phenyl)-thiazol-2-ylamine in 2 mL of solution. MS: 450.1 (M+H$^+$).

Example 70

2-(5-p-Tolyl)-2H-Pyrazol-3-ylcarbamoyl)-pyrrolidine-2-carboxylic acid benzyl ester (Compound 5070)

Using General Procedure G from 30 mg of 2-p-tolyl-5H-imidazol-4-ylamine 9n 2 mL of solution. MS: 405.1 (M+H$^+$)

Example 71

2-(4-Biphenyl-4-yl-thiazol-2-ylcarbamoyl-pyrrolidine-1-carboxylic acid benzyl ester (Compound 5071)

Using General Procedure G from 10 mg of 4-biphenyl-4-yl-thiazol-2-ylamine in 1 mL of solution. MS: 484.1 (M+H$^+$).

Example 72

2-[4-(1H-Benzoimidazol-2-yl)-thiazol-2-ylcarbamoyl]-pyrrolidine-1-carboxylic acid benzyl ester (Compound 5072)

Using General Procedure G from 10 mg of 4-(1H-Benzoimidazol-2-yl)-thiazol-2-ylamine in 1 mL of solution. MS: 448.1 (M+H$^+$).

Example 73

2-{4-[Ethoxycarbonyl-(phenyl-hydrazone)-methyl]-thiazol-2-ylcarbamoyl}-pyrrolidine-1-carboxylic acid benzyl ester (Compound 5073)

Using General Procedure G from 10 mg of (2-amino-thiazol-4-yl)-phenyl-hydrazono)-acetic acid ethyl ester in 1 mL of solution. MS: 522.1 (M+H$^+$).

Example 74

2-[5-(4-Methoxy-phenyl)-2H-pyrazol-3-ylcarbamoyl]-pyrrolidine-1-carboxylic acid benzyl ester (Compound 5074)

Using General Procedure G from 30 mg of 5-(4-Methoxy-phenyl)-2H-pyrazol-3-ylamine in 2 mL of solution. MS: 421.1 (M+H$^+$).

Example 75

2-[4-(5-cyclohexylcarbamoylmethylsulfanyl-4-methyl-4H[1,2,4]triazol-3-ylmethyl)-thiazol-2-ylcarbamoyl]-pyrrolidine-1-carboxylic acid benzyl ester (Compound 5075)

Using General Procedure G from 10 mg of 2-[5-(2-amino-thiazol-4-ylmethyl)-4-methyl-4H-[1,2,4]triazol-3-ylsulfanyl]-N-cyclohexyl-acetamide in 1 mL of solution. MS: 598.1 (M+H$^+$).

Example 76

2-[4-(4-chloro-phenyl)-thiazol-2-ylcarbanoyl]-pyrrolidine-1-carboxylic acid benzyl ester (Compound 5076)

Using General Procedure G from 30 mg of 4-(4-chlorophenyl)-thiazol-2-ylamine in 2 mL of solution. MS: 442.0 (M+H$^+$).

Example 77

2-[4-(1,3-dioxo-1,3-dihydro-isoindol-2-ylmethyl)-thiazol-2-ylcarbamoyl]-pyrrolidine-1-carboxylic acid benzyl ester (Compound 5077)

Using General Procedure G from 10 mg of 2-(2-amino-thiazol-4-ylmethyl)-isoindol-1,3-dione in 1 mL of solution. MS: 491.1 (M+H$^+$)

Example 78

2-{4-[3-Methyl-8-(3-methyl-butoxymethyl)-1,6-dioxo-2,7-dioxa-spiro[4.4]non-3-yl]-thiazol-2-ylcarbamoyl}-pyrrolidine-1-carboxylic acid benzyl ester (Compound 5078)

Using General Procedure G from 10 mg of 3-(2-amino-thiazol-4-yl)-3-methyl-8-(3-methyl-butoxymethyl)-2,7-dioxa-spiro[4.4]nonane-1,6-dione in 1 mL of solution. MS: 600.2 (M+H$^+$).

Example 79

2-[4-(4-Allyl-5-ethoxycarbonyl methylsulfanyl-4H-[1,2,4]triazol-3-ylmethyl)-thiazol-2-ylcarbamoyl]-pyrrolidine-1-carboxylic acid benzyl ester (Compound 5079)

Using General Procedure G from 10 mg of [4-allyl-5-(2-amino-thiazol-4-ylmethyl)-4H-[1,2,4]triazol-3-ylsulfanyl]-acetic acid ethyl ester in 1 mL of solution. MS: 571.1 (M+H$^+$).

Example 80

2-[5-(4-Nitro-benzenesulfonyl)-thiazol-2-ylcarbamoyl]-pyrrolidine-1-carboxylic acid benzyl ester (Compound 5080)

Using General Procedure G from 30 mg of 5-(4-nitro-benzenesulfonyl)-2-ylamine in 2 mL of solution. MS: 517.0 (M+H$^+$).

Example 81

2-[5-(5-Phenyl-2H-[1,2,4]triazol-3-ylsulfanylmethyl0-thiazol-2-ylcarbamoyl]-pyrrolidine-1-carboxylic acid benzyl ester (Compound 5081)

Using General Procedure G from 10 mg of 5-(5-phenyl-2H-[1,2,4]-triazol-3-ylsulfanylmethyl)-thiazol-2-ylamine in 1 mL of solution. MS: 521.1 (M+H$^+$).

Example 82

2-[5-(4-Fluoro-benzyl)-thiazol-2-ylcarbamoyl]-pyrrolidine-1-carboxylic acid benzyl ester (Compound 5082)

Using General Procedure G from 10 mg of 5-(4-fluoro-benzyl)-thiazol-2-ylamine in 1 mL of solution. MS: 440.1 (M+H$^+$).

Example 83

2-(5-Bromo-thiazol-2-ylcarbamoyl)-pyrrolidine-1-carboxylic acid benzyl ester (Compound 5083)

A mixture of (S)-Pyrrolidine-1,2-dicarboxylic acid 1-benzyl ester (1.44 g, 5.78 mmol), HATU (2.2 g, 5.78 mmol), and DIEA (1.5 mL, 11.6 mmol)in DMF (30 mL) was stirred at room temperature for 1 h. The 2-Amino-5-bromo-thiazole hydrobromide salt (FW=259.95, 1.0 g, 3.85 mmol) was added. The reaction mixture was stirred at room temperature for 20 h. The mixture was filtered to afford the crude product. The mixture was filtered and separated by reverse phase HPLC (20-100% of buffer B; buffer A: water containing 0.1% TFA; buffer B: MeCN containing 0.1 TFA). The combined fraction was evaporated to dryness to furnish the desired product. MS: 504.1 (M+H$^+$).

Example 84

2-[4-(4-tert-Butyl-phenyl)-thiazol-2-ylcarbamoyl]-pyrrolidine-1-carboxylic acid benzyl ester (Compound 5084)

Using General Procedure G from 30 mg of 4-(4-tert-butyl-phenyl)-thiazol-2-ylamine in 2 mL of solution. MS: 464.1 (M+H$^+$).

Example 85

2-[5-(2-Nitro-benzyl)-thiazol-2-ylcarbamoyl]-pyrrolidine-1-carboxylic acid benzyl ester (Compound 5085)

Using General Procedure G from 10 mg of 5-(2-nitro-benzyl)-thiazol-2-ylamine in 1 mL of solution. MS: 467.1 (M+H$^+$).

Example 86

2-[4-Bromo-5-(4-chloro-phenyl)-2H-pyrazol-3-yl-carbamoyl]-pyrrolidine-1-carboxylic acid benzyl ester (Compound 5086)

Using General procedure B from 10 mg of 4-Bromo-5-(4-chloro-phenyl)-2H-pyrazol-3-ylamine. MS: 503.1(M+H$^+$).

Example 87

2-(5-Phenyl-[1,3,4]oxadiazol-2-ylcarbamoyl-pyrrolidine-1-carboxylic acid benzyl ester (Compound 5087)

Using General Procedure G from 10 mg of 5-phenyl-[1,3,4]oxadiazol-2-ylamine in 1 mL of solution. MS: 393.1 (M+H$^+$).

Example 88

2-[4-(4-Carbamoyl-3-hydroxy-phenyl)-thiazol-2-ylcarbamoyl]-pyrrolidine-1-carboxylic acid benzyl ester (Compound 5088)

Using General Procedure G from 10 mg of 4-(2-amino-thiazol-4-yl)-2-hydroxy-benzamide in 1 mL of solution. MS: 467.1 (M+H$^+$).

Example 89

2-[4-(4-Pentanoylamino-phenyl)-thiazol-2-ylcarbamoyl]-pyrrolidine-1-carboxylic acid benzyl ester (Compound 5089)

80 mg (0.19 mmol)) of Compound 5050 was dissolved in 5 mL of dry methylene chloride. To this solution at 0° C. was added triethylamine (0.19 mmol, 25 µL) followed by pentanoyl chloride (0.19 mmol, 22 µL). Reaction mixture was stirred at 0° C. for 15 minutes. Reaction mixture was quenched using water and evaporated. It was redissolved in 5 mL of DMF and purified using reverse phase HPLC. MS: 507.2 (M+H$^+$).

Example 90

2-[4-(3-Chloro-4-methoxy-phenyl)-thiazol-2-ylcarbamoyl]-pyrrolidine-1-carboxylic acid benzyl ester (Compound 5090)

Using General Procedure A from 10 mg of 4-(3-Chloro-4-methoxy-phenyl)-thiazol-2-ylamine. MS: 472.1(M+H$^+$).

Example 91

2-[4-(4-Methoxy-3-nitro-phenyl)-thiazol-2-ylcarbamoyl]-pyrrolidine-1-carboxylic acid benzyl ester (Compound 5091)

Using General Procedure A from 10 mg of 4-(3-Nitro-4-methoxy-phenyl)-thiazol-2-ylamine. MS: 483.1(M+H$^+$).

Example 92

2-[4-(4-ethylcarbamoyl-phenyl)-thiazol-2-ylcarbamoyl]-pyrrolidine-1-carboxylic acid benzyl ester (Compound 5092)

Using General Procedure F from 0.14 µL of ethylamine. MS: 479.1 (M+H$^+$).

Example 93

2-(4-{4-[5-(2-Oxo-hexahydro-thieno[3,4-d]imidazol-4-yl)-pentanoylamino]-phenyl}-thiazol-2-ylcarbamoyl)-pyrrolidine-1-carboxylic acid benzyl ester (Compound 5093)

70 mg (0.28 mmol) of biotin was dissolved in 5 mL of dry DMF. To this solution were added DIEA (0.34 mmol, 0.06 mL) and HATU (0.28 mmol, 0.1 g). This solution was stirred at room temperature for 2 hours. 80 mg (0.189 mmol) of Compound 5050 was then added to the reaction mixture and stirred at room temperature overnight. Reaction mixture was evaporated to dryness and redissolved in 5 mL of DMF and purified using reverse phase HPLC. MS: 649.2 (M+H$^+$).

Example 94

2-[4-(4-Ethyl-phenyl)-thiazol-2-ylcarbamoyl]-pyrrolidine-1-carboxylic acid benzyl ester (Compound 5094)

Using General Procedure A from 10 mg of 4-(4-Ethyl-phenyl)-thiazol-2-ylamine. MS: 436.1(M+H$^+$).

Example 95

2-[4-(2,4-Dimethoxy-phenyl)-thiazol-2-ylcarbamoyl]-pyrrolidine-1-carboxylic acid benzyl ester (Compound 5095)

Using General Procedure A from 10 mg of 4-(2,4-Dimethoxy-phenyl)-thiazol-2-ylamine. MS: 468.1(M+H$^+$).

Example 96

2-[4-(4-Cyclopropylcarbamoyl-phenyl)-thiazol-2-ylcarbamoyl]-pyrrolidine-1-carboxylic acid benzyl ester (Compound 5096)

Using General Procedure F from 10 µL of cyclopropyl amine. MS: 491.2 (M+H$^+$).

Example 97

2-[4-(4-Bromo-phenyl)-thiazol-2-ylcarbamoyl]-pyrrolidine-1-carboxylic acid benzyl ester (Compound 5097)

Using General Procedure A from 10 mg of 4-(4-Bromo-phenyl)-thiazol-2-ylamine. MS: 486.1(M+H$^+$).

Example 98

2-[4-(4-Fluoro-phenyl)-thiazol-2-ylcarbamoyl]-pyrrolidine-1-carboxylic acid benzyl ester (Compound 5098)

Using General Procedure A from 10 mg of 4-(4-Fluoro-phenyl)-thiazol-2-ylamine. MS: 426.1 (M+H$^+$).

Example 99

2-[4-(4-Propyl-phenyl)-thiazol-2-ylcarbamoyl]-pyrrolidine-1-carboxylic acid benzyl ester (Compound 5099)

Using General Procedure A from 10 mg of 4-(4-Propyl-phenyl)-thiazol-2-ylamine. MS: 450.1(M+H$^+$).

Example 100

2-[4-(4-Cyclopentylcarbamoyl-phenyl)-thiazol-2-ylcarbamoyl]-pyrrolidine-1-carboxylic acid benzyl ester (Compound 5100)

Using General Procedure F from 10 µL of cyclopropyl amine. MS: 519.2 (M+H$^+$).

Example 101

2-[4-(2,4-Dichloro-phenyl)-thiazol-2-ylcarbamoyl]-pyrrolidine-1-carboxylic acid benzyl ester (Compound 5101)

Using General Procedure A from 10 mg of 4-(2,4-Dichloro-phenyl)-thiazol-2-ylamine. MS: 476.1(M+H$^+$).

Example 102

2-[4-(4-Isobutyl-phenyl)-thiazol-2-ylcarbamoyl]-pyrrolidine-1-carboxylic acid benzyl ester (Compound 5102)

Using General Procedure A from 10 mg of 4-(4-Isobutyl-phenyl)-thiazol-2-ylamine. MS: 476.1 (M+H$^+$).

Example 103

2-[4-(2-Chloro-phenyl)-thiazol-2-ylcarbamoyl]-pyrrolidine-1-carboxylic acid benzyl ester (Compound 5103)

Using General Procedure A from 10 mg of 4-(2-Chloro-phenyl)-thiazol-2-ylamine. MS: 442.1 (M+H$^+$).

Example 104

2-{4-[4-(5-Phenyl-[1,2,3]triazol-1-yl)-phenyl]-thiazol-2-ylcarbamoyl}-pyrrolidine-1-carboxylic acid benzyl ester (Compound 5104)

Using General Procedure A from 10 mg of 4-[4-(5-Phenyl-[1,2,3]triazol-1-yl)-phenyl]-thiazol-2-ylamine. MS: 551.1 (M+H$^+$).

Example 105

2-[4-(4-Methylcarbamoyl-phenyl)-thiazol-2-ylcarbamoyl]-pyrrolidine-1-carboxylic acid benzyl ester (Compound 5105)

Using General Procedure F from 0.14 µL of methylamine. MS: 465.1 (M+H$^+$).

Example 106

2-[4-(2-Chloro-phenyl)-thiazol-2-ylcarbamoyl]-pyrrolidine-1-carboxylic acid benzyl ester (Compound 5106)

0.47 g (6.2 mmol) of thiourea and NaOAc (1.5 g, 6.2 mmol) were combined in 35 mL of ethanol. To this suspension was added 4-(2-bromo-acetyl)-benzoic acid (1.5 g, 6.2 mmol). Reaction mixture was stirred at room temperature overnight. It was evaporated to dryness to yield 4-(2-amino-thiazol-4-yl)-benzoic acid which was used in the next step without any further purification. MS: 221.0 (M+H$^+$).

0.56 g (2.2 mmol) of Z-Pro-OH and HATU (2.2 mmol, 0.83 g) were combined in 35 mL of DMF. To this solution was added DIEA (2.4 mmol, 0.42 mL). This solution was stirred at room temperature for 1 hour. 4-(2-amino-thiazol-4-yl)-benzoic acid (2.2 mmol, 0.5 g) was then added to the solution. Reaction mixture was stirred at 70° C. overnight. It was brought to room temperature and then evaporated to dryness. The crude was purified using reverse phase HPLC to yield the title compound. MS: 452.1 (M+H$^+$).

Example 108

(S)-2-{5-[3-(Cyclopropanecarbonyl-amino)-phenyl]-thiazol-2-ylcarbamoyl}-pyrrolidine-1-carboxylic acid benzyl ester From cyclopropanecarbonyl chloride (0.012 mL) using general procedure K; MS: 491.1 (M+H$^+$)

Example 109

2-[4-(4-phenylcarbamoyl-[phenyl)-thiazol-2-ylcarbamoyl]-pyrrolidine-1-carboxylic acid benzyl ester (Compound 5109)

From 15 µL of phenylamine following General Procedure 3A. MS: 527.2 (M+H$^+$); H$^1$ NMR (DMSO-d6): δ(ppm) 12.49 (d, 1H), 10.23 (s, 1H), 8.02 (s, 4H), 7.80 (m, 3H), 7.38 (m, 3H), 7.11 (m, 3H), 5.02 (m, 2H), 4.56 (m, 1H), 3.51 (m, 2H), 2.29 (m, 1H), 1.91 (m, 4H).

Example 110

(S)-2-{5-[4-(Cyclopentanecarbonyl-amino)-phenyl]-thiazol-2-ylcarbamoyl}-pyrrolidine-1-carboxylic acid benzyl ester (Compound 5110)

A mixture of (S)-2-[5-(4-Amino-phenyl)-thiazol-2-ylcarbamoyl]-pyrrolidine-1-carboxylic acid benzyl ester (Compound 5111, Example 111, 0.05 g, 0.12 mmol), Cyclopentanecarbonyl chloride (0.015 mL), and TEA (0.018 mL) in dichloromethane (3 mL) was stirred at 0° C. for 20 min. then was quenched with water. The mixture was concentrated in vacuo and the resulting residue was dissolved in DMF (5 mL) and water (0.5 mL) then purified by reverse phase prep. LC/MS to furnish the desired product; MS: 519.1 (M+H$^+$).

Example 111

(S)-2-[5-(4-Amino-phenyl)-thiazol-2-ylcarbamoyl]-pyrrolidine-1-carboxylic acid benzyl ester (Compound 5111)

From 4-(4,4,5,5-Tetramethyl-[1,3,2]dioxaborolan-2-yl)-phenylamine (0.21 g, 0.96 mmol) using general procedure J; MS: 423.1 (M+H$^+$).

Example 112

2-[5-(4-methoxy-benzyl)-thiazol-2-ylcarbamoyl]-pyrrolidine-1-carboxylic acid benzyl ester (Compound 5112)

A mixture of Z-Pro-OH (0.96 g, 3.84 mmol), HATU (1.46 g, 3.84 mmol), and DIEA (0.094 mL, 5.4 mmol) in DMF (30 mL) was stirred at room temperature for 1 hour. 1 mL of this solution was added to 10 mg of 5-(4-Methoxy-benzyl)-thiazol-2-ylamine and reaction mixture stirred at room temperature overnight. The resulting mixture was diluted with DMF (5 mL) and water (0.5 mL) and purified using reverse phase HPLC to furnish the corresponding product. MS: 452.1 (M+H$^+$)

Example 113

(S)-2-[5-(3-Benzoylamino-phenyl)-thiazol-2-ylcarbamoyl]-pyrrolidine-1-carboxylic acid benzyl ester (Compound 5113)

From benzoyl chloride (0.016 mL) using general procedure K; MS: 527.1 (M+H$^+$).

Example 114

(S)-2-[5-(3-Amino-phenyl)-thiazol-2-ylcarbamoyl]-pyrrolidine-1-carboxylic acid benzyl ester (Compound 5114)

From 3-aminophenylboronic acid (0.29 g, 0.96 mmol) using general procedure J; MS: 423.1 (M+H$^+$).

Example 116

(S)-2-{5-[3-(Cyclopentanecarbonyl-amino)-phenyl]-thiazol-2-ylcarbamoyl}-pyrrolidine-1-carboxylic acid benzyl ester (Compound 5116)

From cyclopentanecarbonyl chloride (0.015 mL) using general procedure K; MS: 519.1 (M+H$^+$).

Example 117

2-[4-(4-Isopropylcarbamoyl-[phenyl)-thiazol-2-ylcarbamoyl]-pyrrolidine-1-carboxylic acid benzyl ester (Compound 5117)

From 15 μL of isopropylamine following General Procedure 3A. MS: 493.2 (M+H$^+$); H$^1$ NMR (DMSO-d$_6$): δ(ppm) 12.42 9d, 1H), 8.21 (d, 1H), 7.92 (m, 4H), 7.78 (d, 1H), 7.38 (m, 2H), 7.21 (dd, 2H), 5.01 (m, 2H), 4.51 (m, 1H), 4.09 (m, 1H), 3.48 (m, 2H), 2.21 (m, 1H), 1.91 (m, 4H), 1.08 (m, 6H).

Example 301

(S)-2-[4-(4-Cyclopropylcarbamoyl-phenyl)-thiazol-2-ylcarbamoyl]-azetidine-1-carboxylic acid benzyl ester (Compound 5301)

(S)-Azetidine-1,2-dicarboxylic acid 1-benzyl ester (S)-Azetidine-2-carboxylic acid (250.4 mg, 2.5 mmol) was dissolved in DMF (15 mL) and distilled water (6 mL). The solution was cooled to 0° C., and DIEA (645 μL, 3.7 mmol) was added followed by benzyl chloroformate (530 μL, 3.7 mmol). The reaction was stirred at 0° C. and allowed to warm to ambient temperature overnight. The reaction was filtered and purified by reverse phase HPLC to give the desired product.

(S)-2-[4-(4-Cyclopropylcarbamoyl-phenyl)-thiazol-2-ylcarbamoyl]-azetidine-1-carboxylic acid benzyl ester (Compound 5301)

(S)-Azetidine-1,2-dicarboxylic acid 1-benzyl ester (45.7 mg, 0.19 mmol) was dissolved in DMF (1.5 mL). Triethylamine (53 μL, 0.38 mmol) and pentafluorophenyl trifluoroacetate (33 μL, 0.19 mmol) were added, and the reaction was stirred at ambient temperature for 30 minutes. Then 4-(2-Amino-thiazol-4-yl)-N-cyclopropyl-benzamide trifluoroacetic acid salt (62.9 mg, 0. 17 mmol) was added. The reaction was stirred at ambient temperature overnight and then heated to 70° C. for 4 hours. The reaction was cooled, filtered, and purified by reverse phase HPLC to give the desired product. Yield 7.2 mg. MS: 477.1 (M+H$^+$); H$^1$ NMR (DMSO-d$_6$): δ(ppm) 0.50-0.85 (m, 4H), 2.10-2.30 (m, 1H), 2.48-2.62 (m, 1H), 2.78-2.90 (m, 1H), 3.80-4.07 (m, 2H), 4.80-5.13 (m, 3H), 7.07-7.42 (m, 4H), 7.78-7.99 (m, 5H), 8.40-8.47 (m, 1H), 12.40-12.58 (m, 1H).

Example 302

2-{4-[4-(Pyridin-4-yl-ethylcarbamoyl)-phenyl]-thiazol-2-ylcarbamoyl}-pyrrolidine-1-carboxylic acid benzyl ester (Compound 5302)

From 50 mg of pyridine-4-ylamine following General Procedure 3A. MS: 528.1 (M+H$^+$); H$^1$ NMR (DMSO-d$_6$): δ(ppm) (TFA salt) 12.49 (s, 1H), 11.70 (s, 1H), 8.71 (d, 2H), 8.28 (d, 2H), 8.10 (s, 4H), 7.94 (d, 2H), 7.30 (s, 2H), 7.09 (dd, 2H), 5.00 (m, 2H), 4.29 (m, 1H), 3.60 (m, 2H), 2.24 (m, 2H), 1.91 (m, 4H)

Example 303

2-[4-(4-Cyclohexylcarbamoyl-phenyl)-thiazol-2-ylcarbamoyl]-pyrrolidine-1-carboxylic acid benzyl ester (Compound 5303)

From 50 mg of cyclohexylamine following General Procedure 3A. MS: 564.2 (M+H$^+$); H$^1$ NMR (DMSO-d$_6$): δ(ppm) 12.46 (br s, 1H), 8.22 (br s, 1H), 7.91 (m, 5H), 7.32 (s, 2H), 7.10 (dd, 2H), 5.02 (m, 2H), 4.45 (m, 1H), 2.27 (m, 1H), 1.65-1.80 (m, 8H), 1.25 (m, 6H)

Example 304

(S)-2-[5-(3-Carboxy-phenyl)-thiazol-2-ylcarbamoyl]-pyrrolidine-1-carboxylic acid benzyl ester (Compound 5304)

Following General Procedure 3E, (S)-2-[5-(3-Methoxycarbonyl-phenyl)-thiazol-2-ylcarbamoyl]-pyrrolidine-1-carboxylic acid benzyl ester), MS: 465.1 (M+H$^+$), was obtained from 3-phenylboronic acid methyl ester (0.13 g, 0.73 mmol). Then the title compound was obtained from 0.10 g of (S)-2-[5-(3-Methoxycarbonyl-phenyl)-thiazol-2-ylcarbamoyl]-pyrrolidine-1-carboxylic acid benzyl ester.

$^1$HNMR (DMSO-d$_6$) δ(ppm)12.50 (s, 1H), 8.13-7.89 (m, 4H), 7.63-7.15 (m, 6H), 5.16-4.95 (m, 2H), 4.59-4.54 (m, 1H), 2.34-2.31 (m, 1H), 1.98-1.93 (m, 3H), 1.29-1.20 (m, 1H); MS: 452.1 (M+H$^+$).

Example 305

2-[4-(4-Cyano-phenyl)-thiazol-2-ylcarbamoyl]-pyrrolidine-1-carboxylic acid benzyl ester (Compound 5305)

4-(2-Amino-thiazol-4-yl)-benzonitrile 4-(2-Bromo-acetyl)-benzonitrile (2.9 g, 12.9 mmol) was combined with 1.0 g (12.9 mmol) of thiourea. This mixture was suspended in 60 mL of EtOH. To this suspension was added NaOAc (1.4 g, 16.8 mmol). This suspension was stirred at room temperature for 30 minutes. The solvent was evaporated under reduced pressure to yield the desired product.

2-[4-(4-Cyano-phenyl)-thiazol-2-ylcarbamoyl]-pyrrolidine-1-carboxylic acid benzyl ester (Compound 5305)

Synthesized from 4-(2-Amino-thiazol-4-yl)-benzonitrile using General Procedure 3A. MS: 433.1(M+H$^+$); H$^1$ NMR (MeOH-d$_4$): δ(ppm) 12.42 (s, 1H), 8.08 (dd, 2H), 7.89 (dd, 3H), 7.37 (d, 2H), 7.08 (m, 2H), 5.01 (m, 2H), 4.50 (m, 1H), 3.44 (m, 1H), 2.23 (m, 1H), 1.84 (m, 4H).

Example 306

2-{4-[4-(1,1-Dimethyl-2-morpholin-4-yl-ethylcarbamoyl)-phenyl]-thiazol-2-ylcarbamoyl}-pyrrolidine-1-carboxylic acid benzyl ester (Compound 5306)

From 50 mg of 1,1-Dimethyl-2-morpholin-4-yl-ethylamine following General Procedure 3A. MS: 592.7(M+H$^+$); H$^1$ NMR (MeOH-d$_4$): δ(ppm) 7.96 9M, 4H), 7.55 (m, 1H), 7.34 (m, 2H), 7.13 (br s, 1H), 7.03 (br s, 2H), 5.03 (m, 2H), 4.51 (m, 1H), 3.97 (m, 4H), 3.58 (m, 4H), 2.33 (m, 1H), 2.01 (m, 2H), 1.56 (s, 6H), 1.76 (s, 2H), 1.38 (m, 4H).

Example 307

2-{4-[4-(2-piperidin-1-yl-ethylcarbamoyl)-phenyl]-thiazol-2-ylcarbamoyl}-pyrrolidine-1-carboxylic acid benzyl ester (Compound 5307)

From 50 mg of 2-piperadin-1-yl-ethylamine following General Procedure 3A. MS: 562.2 (M+H$^+$); H$^1$ NMR (DMSO-d$_6$): δ(ppm) (TFA salt) 12.49 (br s, 1H), 8.22 (br s, 1H), 8.78 (br s, 1H), 7.91 (m, 5H), 7.10 (m, 4H), 5.02 (m, 2H), 4.42 (m, 1H), 3.6-3.4 (br s, 1H), 2.99 (m, 2H), 2.22 (m, 1H), 1.90-1.70 (m, 12H), 1.35 m (4H)

Example 308

(S)-2-[4-(4-Cyclopropylthiocarbamoyl-phenyl)-thiazol-2-ylcarbamoyl]-pyrrolidine-1-carboxylic acid benzyl ester (Compound 5308)

4-(2-Amino-thiazol-4-yl)-benzoic acid

A solution of 4-acetyl-benzoic acid (10 g, 61 mmol), in HOAc (400 mL) at 55° C. was treated with bromine (1 eq., 3.12 mL) dropwise over 10 minutes. After 90 minutes the reaction was cooled, the acetic acid was removed, ethyl acetate (50 mL) was added and then removed to get rid of the remainder of the acetic acid. The crude bromo ketone was then dissolved in ethanol (200 mL) with NaOAc (12 g) and thiourea (1 eq. 4.4 g) was added. The suspension was stirred at room temperature for 15 hours. The solvents were removed and the solids washed with water (3×100 mL) then ether:ethanol (4:1, 3×100 mL) and dried to give the product as a tan solid. MS: 221.2 (M+H$^+$).

4-(2-Amino-thiazol-4-yl)-N-cyclopropyl-benzamide 4-(2-Amino-thiazol-4-yl)-benzoic acid (4.4 g, 20 mmol) was dissolved in DMF (100 mL) and treated with HATU (1.1 eq. 8.4 g) and DIEA (2.1 eq, 7.5 mL) and stirred for 15 minutes. Then cyclopropyl amine (1.1 eq, 1.5 mL) was added and the mixture stirred at ambient temperature for 1 hr. The reaction was diluted with 100 mL of water, extracted with EtOAc (3×100 mL) dried with brine (100 mL) and then Na$_2$SO$_4$ and the solvents removed. The resulting solid was triturated with ether to give the product >95% purity by HPLC. MS: 260.3 (M+H).

4-(2-Amino-thiazol-4-yl)-N-cyclopropyl-thiobenzamide

A solution of 4-(2-Amino-thiazol-4-yl)-N-cyclopropyl-benzamide (265 mg, 1 mmol), in THF (5 mL), was treated with Lawesson's reagent (0.75 eq) and heated to 70° C. overnight in a sealed vial. The reaction was cooled, filtered and the solvents removed. The resulting mixture was redissolved in 5 ml of 90% DMF, 10% water with 0.1% TFA and purified by reverse phase HPLC to give the product. MS: 275.4 (M+H$^+$).

(S)-2-[4-(4-Cyclopropylthiocarbamoyl-phenyl)-thiazol-2-ylcarbamoyl]-pyrrolidine-1-carboxylic acid benzyl ester (compound 5308).

Z-protected (S)-proline (36 mg) was dissolved in DMF (15 mL) and treated with HATU (1.1 eq. 50 mg) and DIEA (2.1 eq, 55 IL) and stirred for 15 minutes. Then 4-(2-Amino-thiazol-4-yl)-N-cyclopropyl-thiobenzamide (1 eq, 40 mg) was added and the mixture stirred at ambient temperature overnight. The reaction was cooled, filtered and the solvents removed. The resulting mixture was redissolved in 5 ml of 90% DMF, 10% water with 0.1% TFA and purified by reverse phase HPLC to give the product. Yield 44.2 mg. MS: 507.6 (M+H). H$^1$-NMR (DMSO-d$_6$): δ(ppm) 12.4 (m, 1H), 10.1 (m, 1H), 7.9 (m, 2H), 7.7 (m, 2H), 7.3 (m, 2H), 7.2-7.0 (m, 2H), 5.2-4.8 (m, 2H), 4.5 (m, 1H), 3.4 (m, 3H), 2.2 (m, 1H), 1.91 (m, 4H), 0.8 (m, 4H).

Example 309

(S)-2-[4-(4-Acetyl-phenyl)-thiazol-2-ylcarbamoyl]-pyrrolidine-1-carboxylic acid benzyl ester (Compound 5309)

1-[4-(2-Amino-thiazol-4-yl)-phenyl]-ethanone

A solution of 1-(4-Acetyl-phenyl)-ethanone (8.1 g, 5 mmol), in HOAc (50 mL) at 60° C. was treated with bromine (1 eq., 0.26 mL) dropwise over 10 minutes. After 5 more minutes the reaction was cooled, the acetic acid was removed, ethyl acetate (50 mL) was added and then removed to get drive off the remainder of the acetic acid. The crude bromo ketone was then dissolved in ethanol (30 mL) with NaOAc (1.1 g) and thiourea (1 eq., 375 mg) was added. The suspension was stirred at room temperature for 15 hours. The solvents were removed and the resulting mixture was redissolved in 5 ml of 90% DMF, 10% water with 0.1% TFA and purified by reverse phase HPLC to give the product. MS: 219.1 (M+H$^-$).

(S)-2-[4-(4-Acetyl-phenyl)-thiazol-2-ylcarbamoyl]-pyrrolidine-1-carboxylic acid benzyl ester (compound 5309)

Z-protected (S)-proline (200 mg) was dissolved in DMF (15 mL) and treated with HATU (1.1 eq. 316 mg) and DIEA (2.1 eq, 315 µL) and stirred for 15 minutes. Then 1-[4-(2-Amino-thiazol-4-yl)-phenyl]-ethanone (1 eq, 200 mg) was added and the mixture stirred at ambient temperature overnight. The reaction was cooled, filtered and the solvents removed. The resulting mixture was redissolved in 5 ml of 90% DMF, 10% water with 0.1% TFA and purified by reverse phase HPLC to give the product. Yield 25 mg. MS: 450.3 (M+H). H$^1$-NMR (DMSO-d$_6$): δ(ppm) 12.5 (m, 1H), 8.0 (s, 4H), 7.8 (m, 1H), 7.2-7.0 (m, 5H), 5.2-4.8 (m, 2H), 4.5 (m, 1H), 3.4 (m, 2H), 2.6 (s, 3H), 2.2 (m, 1H), 1.9 (m, 3H).

Example 310

(2S,4R)-2-[4-(4-Cyclopropylcarbamoyl-phenyl)-thiazol-2-ylcarbamoyl]-4-hydroxy-pyrrolidine-1-carboxylic acid benzyl ester (compound 5310)

From (2S,4R)-4-hydroxy-pyrrolidine-1,2-dicarboxylic acid 1-benzyl ester using General Procedure 3C. Yield 5.4 mg. MS: 507.3 (M+H). H$^1$-NMR (DMSO-d$_6$): δ(ppm) 12.5 (m, 1H), 8.4 (m, 1H), 7.9-7.7 (m, 5H), 7.4-7.0 (m, 6H), 5.1-5.0 (m, 2H), 4.58 (m, 4.6), 4.3 (m, 1H), 3.5 (m, 1H), 2.2 (m, 1H), 1.9 (m, 1H), 0.7-0.5 (m, 4H).

Example 311

(R)-4-[4-(4-Cyclopropylcarbamoyl-phenyl)-thiazol-2-ylcarbamoyl]-oxazolidine-3-carboxylic acid benzyl ester (Compound 5311)

From (R)-oxazolidine-3,4-dicarboxylic acid 3-benzyl ester using General Procedure 3C. Yield 8.4 mg. MS: 493.3 (M+H). H$^1$-NMR (DMSO-d$_6$): δ(ppm) 8.4 (m, 1H), 7.9-7.8 (m, 5H), 7.3-7.1 (m, 5H), 5.2-5.0 (m, 4H), 4.3 (m, 1H), 4.1 (m, 1H), 2.8 (m, 1H), 2.4 (s, 2H), 1.2-1.1 (m, 2H), 0.7-0.5 (m, 4H).

Example 312

(S)-2-[5-(3-Cyclopropylcarbamoyl-phenyl)-thiazol-2-ylcarbamoyl]-pyrrolidine-1-carboxylic acid benzyl ester (Compound 5312)

From 0.03 mL (0.36 mmol) of cyclopropylamine using General Procedure 3G. $^1$HNMR (DMSO-d$_6$) δ (ppm) 12.42-12.39 (d, 1H), 8.53 (s, 1H), 7.98-7.11 (m, 9H), 5.07-4.89 (m, 2H), 4.50 (m, 1H), 3.85 (m, 2H), 2.25 (m, 1H), 1.90 (m, 2H), 1.14 (s, 1H), 0.72-0.60 (m,4H); MS: 491.1 (M+H$^+$).

Example 313

(S)-4-[4-(4-Cyclopropylcarbamoyl-phenyl)-thiazol-2-ylcarbamoyl]-oxazolidine-3-carboxylic acid benzyl ester (Compound 5313)

(S)-Oxazolidine-3,4-dicarboxylic acid 3-benzyl ester (51.3 mg, 0.20 mmol) was dissolved in DMF (1.5 mL). Triethylamine (56 µL, 0.40 mmol) and pentafluorophenyl trifluoroacetate (35 µL, 0.20 mmol) were added, and the reaction was allowed to stir at ambient temperature for 25 minutes. Then 4-(2-Amino-thiazol-4-yl)-N-cyclopropyl-benzamide trifluoroacetic acid salt (148.8 mg, 0.40 mmol) was added, and the reaction was stirred at ambient temperature overnight. The reaction was filtered and purified by reverse phase HPLC to give the desired product. Yield 10.2 mg. MS: 493.1 (M+H$^+$); H$^1$ NMR (DMSO-d$_6$): δ(ppm) 0.52-0.74 (m, 4H), 4.05-4.37 (m, 2H), 4.58-4.69 (m, 1H), 4.90-5.17 (m, 4H), 7.00-7.45 (m, 4H), 7.72-7.98 (m, 5H), 8.37-8.48 (m, 1H), 12.48-12.51 (s, 1H).

Example 314

2-[4-(4-Ureido-phenyl)-thiazol-2-yl carbamoyl]-pyrrolidine-1-carboxylic acid benzyl ester (Compound 5314)

2-[4-(4-Amino-phenyl)-thiazol-2-ylcarbamoyl]-pyrrolidine-1-carboxylic acid benzyl ester (Compound 5050, Example 50, 40 mg, 0.095 mmol) was dissolved in 4 ml of 1:1 dioxane/TMS isocyanate. Reaction mixture was heated at 70° C. for 7 hours. It was then evaporated to dryness. The crude was redissolved in 10 ml of DMF and purified on reverse phase HPLC. MS: 466.1 (M+H$^+$); H$^1$ NMR (DMSO-d$_6$): δ(ppm) 12.39 (d, 1H), 7.72 (d, 2H), 7.42 (d, 3H), 7.35 (s, 2H), 7.10 (dd, 2H), 5.88 (br s, 2H), 5.02 (m, 2H), 4.50 (m, 1H), 2.25 (m, 2H), 1.90 (m, 4H).

Example 315

1-[2-(3,5-Difluoro-phenyl)-acetyl]-pyrrolidine-2-carboxylic acid [4-(4-cyclopropylcarbamoyl-phenyl)-thiazol-2-yl]-amide (Compound 5315)

From 53.4 mg of (3,5-Difluoro-phenyl)-acetyl chloride following General Procedure 3B. MS: 511.1 (M+H$^+$); H$^1$ NMR (DMSO-d$_6$): δ(ppm) 12.38 (s, 1H), 8.42 (s, 1H), 7.91 (m, 4H), 6.97 (m, 3H), 4.57 (m, 1H), 3.63 (m, 4H), 2.88 (m, 1H), 2.19 (m, 1H), 1.97 (m, 4H), 0.61 (m, 4H).

Example 316

(S)-1-Phenethyl-pyrrolidine-2-carboxylic acid [4-(4-cyclopropylcarbamoyl-phenyl)-thiazol-2-yl]-amide (Compound 5316)

From 0.014 mL of phenylacetaldehyde using General Procedure 3J. $^1$HNMR (DMSO-d$_6$) δ(ppm) 13.07 (s, 1H), 10.09 (s, 1H), 8.47-8.46 (d,1H), 7.97-7.86 (m, 5H), 7.34-7.23 (m, 5H), 4.55-4.49 (m, 1H), 3.45-3.34 (m, 2H), 3.03-2.82 (m, 3H), 2.66-2.60 (m, 1H), 2.12-1.96 (m, 3H), 0.73-0.68 (m,4H); MS: 461.2 (M+H$^+$).

Example 317

2-{4-[4-(3-Hydroxy-propylcarbamoyl)-phenyl]-thiazol-2-ylcarbamoyl}-pyrrolidine-1-carboxylic acid benzyl ester (Compound 5317)

From 10.3 mg (0.14 mmol) of 3-amino-1-propan-1-ol following General Procedure 3A. MS: 509.2 (M+H$^+$); H$^1$ NMR (DMSO-d$_6$): δ(ppm) 12.47 (d, 2H), 8.45 (m, 1H), 7.84 (m, 4H), 7.35 (d, 2H), 7.11 (dd, 2H), 5.01 (m, 2H), 4.54 (m, 2H), 3.85, (br s, 1H), 3.46 (t, 2H), 3.32 (m, 2H), 2.25 (m, 2H), 1.89 (m, 4H), 1.68 (m, 2H).

Example 318

2-[4-(4-Cyclopropylcarbamoyl-phenyl)-thiazol-2-ylcarbamoyl]-pyrrolidine-1-carboxylic acid 2-isopropyl-5-methyl-cyclohexyl ester (Compound 5318)

From 64.5 mg of (1R)-(−)-methyl chloroformate following General Procedure 3B. MS: 539.1(M+H$^+$); H$^1$ NMR (DMSO-d$_6$): δ(ppm) 12.01 (br s, 1H), 8.02 (br s, 1H), 7.51 (m, 4H), 3.99 (m, 2H), 3.00 (m, 2H), 2.50 (m, 2H), 2.12 (s, 1H), 1.83 (m, 2H), 1.47 (m, 4H), 1.70-0.72 (m, 6H), 0.41 (s, 3H), 0.33 (m, 10H).

Example 319

(S)-2-{4-[3-(Cyclopentylmethyl-amino)-phenyl]-thiazol-2-ylcarbamoyl}-pyrrolidine-1-carboxylic acid benzylester (Compound 5319)

From 0.06 mL (0.8 mmol) of cyclopentylaldehyde using General Procedure 3G. $^1$HNMR (DMSO-d$_6$) δ (ppm) 12.51-12.49 (d, 1H), 7.69-7.11 (m, 10H), 5.18-4.99 (m, 4H), 4.60-4.54 (m, 1H), 3.62-3.49 (m, 3H), 2.34-2.21 (m, 2H), 1.98-1.29 (m, 13H), 1.17-1.13 (m, 2H); MS: 505.2 (M+H$^-$).

Example 320

2-[4-(4-Cyclopropylcarbamoyl-phenyl)-thiazol-2-ylcarbamoyl]-pyrrolidine-1-carboxylic acid pyridine-3-ylmethyl ester (Compound 5320)

From 400 mg of pyridine-3-yl methanol following procedure for Example 384. MS: 492.1 (M+H$^+$); H$^1$ NMR (DMSO-d$_6$): δ(ppm) 12.52 (d, 1H), 8.8-7.8 (m, 10H), 5.20 (m, 2H), 4.50 (m, 1H), 3.50 (m, 2H), 2.84 (m, 2H), 2.27 (m, 1H), 1.89 (m, 4H), 0.62 (m, 4H).

Example 321

1-(Pyridine-4-carbonyl)-pyrrolidine-2-carboxylic acid [4-(4-cyclopropylcarbamoyl-phenyl)-thizol-2-yl]-amide (Compound 5321)

From 50 mg of isonicotinoyl chloride (hydrochloride) following General Procedure 3B. MS: 462.1 (M+H$^+$); H$^1$ NMR (DMSO-d$_6$): δ(ppm) 12.56 (s, 1H), 8.70 (dd, 2H), 8.51 (dd, 2H), 7.90 (m, 4H), 7.69 (br s, 1H), 4.70 (m, 1H), 3.64 (m, 2H), 2.25 (m, 1H), 1.98 (m, 2H), 1.19 (m, 1H), 0.60 (m, 4H).

Example 322

2-{4-[4-(Pyrrolidin-3-ylcarbamoyl)-phenyl]-thiazol-2-ylcarbamoyl}-pyrrolidine-1-carboxylic acid benzyl ester (Compound 5322)

From 52.1 mg of 3-amino-pyrrolidine-1-carboxylic acid tert-butyl ester using procedure for synthesis of Compound 5337 (Example 337) MS: 520.2(M+H$^+$); H$^1$ NMR (HCl salt) (DMSO-d$_6$): δ(ppm) 12.5 (s, 1H), 9.6 (d, 1H), 9.6 (d, 1H), 8.9 (d, 1H), 8.0 (s, 4H), 7.8 (d, 1H), 7.3 (d, 2H), 7.1 (dd, 3H), 5.1 (m, 2H), 3.3 (m, 7H), 4.5 (m, 2H), 5.1 (m, 2H), 3.3 (m, 7H), 2.1 (m, 6H).

Example 323

1-[2-(4-Fluoro-phenyl)-acetyl]-pyrrolidine-2-carboxylic acid [4-(4-cyclopropylcarbamoyl-phenyl)-thiazol-2-yl]-amide (Compound 5323)

From 48.3 mg of (4-fluoro-phenyl)-acetyl chloride following General Procedure 3B. MS: 493.1 (M+H$^+$); H$^1$ NMR (DMSO-d$_6$): δ(ppm) 12.40 (s, 1H), 8.22 (s, 1H), 7.79 (dd, 2H), 7.70 (s, 1H), 7.19 (dt, 5H), 4.50 (m, 1H), 3.7-3.3 (m, 4H), 2.83 (m, 1H), 2.13 (m, 1H), 1.91 (m, 4H).

Example 324

2-{4-{4-(3-Morpholin-4-yl-propylcarbamoyl)-phenyl]-thiazol-2-ylcarbamoyl}-pyrrolidine-1-carboxylic acid benzyl ester (Compound 5324)

From 50 mg of 3-morpholin-4-yl-propylamine following General Procedure 3A. MS: 578.2(M+H$^+$); H$^1$ NMR (DMSO-d$_6$): δ(ppm) (HCl salt) 12.48 (s, 1H), 10.12 (br s, 1H), 8.57 (s, 1H), 7.92 (m, 4H), 7.37 (s, 2H), 7.11 (dd, 3H), 5.01 (m, 2H), 4.52 (m, 1H), 3.96 (m, 8H), 3.08 (m, 6H), 2.28 (m, 1H), 1.96 (m, 6H).

Example 325

(S)-1-Phenylacetyl-pyrrolidine-2-carboxylic acid [4-(4-cyclopropylcarbamoyl-phenyl)-thiazol-2-yl]-amide (Compound 5325)

From 0.02 mL phenylacetylchloride using General Procedure 3I. $^1$HNMR (DMSO-d$_6$) δ(ppm) 12.35 (s, 1H), 8.43-8.42 (d, 1H), 7.95-7.70 (m,6H), 7.45-7.43 (d, 1H), 7.31-7.15 (m, 5H), 4.57-4.52 (m, 1H), 3.69-3.57 (m, 4H), 3.16-3.14 (m, 2H), 2.95-2.83 (m, 3 H), 2.19-1.86 (m, 5H), 0.69-0.58 (m,4H); MS: 475.1(M+H$^+$).

Example 326

2-[4-(4-tert-Butylcarbamoyl-phenyl)-thiazol-2-ylcarbamoyl]-pyrrolidine-1-carboxylic acid benzyl ester (Compound 5326)

From 50 mg of tert-butylamine following General Procedure 3A. MS: 507.2 (M+H$^+$); H$^1$ NMR (DMSO-d$_6$): δ(ppm) 12.44 (s, 1H), 7.95 (m, 6H), 7.73 (s, 1H), 7.08 (dd, 2H), 5.01 (m, 2H), 4.49 (m, 1H), 3.48 (m, 2H), 2.25 (m, 1H), 1.94 (m, 4H).1.38 (s, 9H).

Example 327

(R)-4-[4-(4-Cyclopropylcarbamoyl-phenyl)-thiazol-2-ylcarbamoyl]-thiazolidine-3-carboxylic acid benzyl ester (Compound 5327)

(R)-Thiazolidine-3,4-dicarboxylic acid 3-benzyl ester (R)-Thiazolidine-4-carboxylic acid (309.9 mg, 2.33 mmol) was dissolved in DMF (10 mL) and distilled water (10 mL). The solution was cooled to 0° C., and DIEA (0.590 mL, 3.39 mmol) was added followed by benzyl chloroformate (0.485 mL, 3.40 mmol). The reaction was stirred at 0° C. and allowed to warm to ambient temperature overnight. The reaction was filtered and purified by reverse phase HPLC to give the desired product.

(R)-4-[4-(4-Cyclopropylcarbamoyl-phenyl)-thiazol-2-ylcarbamoyl]-thiazolidine-3-carboxylic acid benzyl ester (Compound 5327)

(R)-Thiazolidine-3,4-dicarboxylic acid 3-benzyl ester (52.5 mg, 0.20 mmol) was dissolved in DMF (2 mL). DIEA (68.5 μL, 0.39 mmol) was added followed by HATU (74.8 mg, 0.20 mmol). The reaction was stirred at ambient temperature for 15 minutes. Then 4-(2-Amino-thiazol-4-yl)-N-cyclopropyl-benzamide (51.1 mg, 0.20 mmol) was added, and the reaction was stirred at ambient temperature overnight. The reaction was filtered and purified by reverse phase HPLC to give the desired product. Yield 18.5 mg. MS: 509.1 (M+H$^+$); H$^1$ NMR (DMSO-d$_6$): δ(ppm) 0.54-0.75 (m, 4H), 2.78-2.90 (m, 1H), 4.51-4.59 (m, 1H), 4.62-4.70 (m, 1H), 4.83-5.18 (m, 3H), 7.07-7.43 (m, 5H), 7.77-7.99 (m, 5H), 8.39-8.47 (m, 1H), 12.55-12.64 (s, 1H).

Example 328

2-{4-[4-(Methyl-phenyl-carbamoyl)-phenyl]-thiazol-2-ylcarbamoyl}-pyrrolidine-1-carboxylic acid benzyl ester (Compound 5328)

From 50 mg of methyl-phenyl amine following General Procedure 3A. MS: 541.2 (M+H$^+$); H$^1$ NMR (DMSO-d$_6$): δ(ppm) 12.41 (s, 1H), 7.69 (d, 4H), 7.50-7.0 (m, 11H), 5.02 (m, 2H0, 4.49 (m, 1H), 3.60 (m, 1H), 3.11 (m, 1H), 2.52 (s, 3H), 2.28 (m, 1H), 1.91 (m, 4H).

Example 329

(S)-2-[4-(4-Cyclopropanesulfonylamino-phenyl)-thiazol-2-ylcarbamoyl]-pyrrolidine1-carboxylic acid benzylester (Compound 5329)

To a stirred mixture of (S)-2-[4-(4-Amino-phenyl)-thiazol-2-ylcarbamoyl]-pyrrolidine-1-carboxylic acid benzyl ester (Compound 5050, Example 50, 0.06 g, 0.14 mmol) in DCM (2.0 mL) at 0° C. was added TEA (0.0.025 mL) followed by addition of cyclopropanesulfonyl chloride (0.016 mL). The reaction mixture was stirred at room temperature for 1 h then was concentrated in vacuo to give the crude product. Purification of the crude product by reverse phase HPLC furnished the desired product. $^1$HNMR (DMSO-d$_6$) δ(ppm) 7.87-7.83 (m, 2H), 7.37-7.07 (m, 7H), 5.17-5.13 (m, 2H), 4.89-4.87 (m, 3H), 4.52-4.47 (m, 1H), 3.69-3.54 (m, 2H), 2.60-2.56 (m, 1H), 2.38-2.35 (m, 1H), 2.08-1.96 (m, 3 H), 1.07-0.95 (m, 4H); MS: 527.1 (M+H$^+$).

Example 330

(S)-2-{4-[4-(Cyclopropylmethyl-amino)-phenyl]-thiazol-2-ylcarbamoyl}-pyrrolidine-1-carboxylic acid benzylester (Compound 5330)

From 0.01 mL of cyclopropylaldehyde using General Procedure 3D. $^1$HNMR (DMSO-d$_6$) δ(ppm) 12.34-12.31 (d, 1H), 7.65-7.62 (d, 2H), 7.36-7.08 (m, 6H), 6.64 (bs, 2 H), 5.09-4.89 (m, 2H), 4.53-4.47 (m, 1H), 3.52-3.34 (m, 7H), 3.16 (s, 1H), 2.96-2945 (d, 2 H), 2.27 (m, 1H), 1.91-1.83 (m, 3H), 1.12-1.07 (m, 4H), 0.47-0.48 (d, 2H), 0.24-0.23 (d, 2 H); MS: 477.2 (M+H$^+$).

Example 331

1-(2-Phenoxy-acetyl)-pyrrolodine-2-carboxylic acid [4-(4-cyclopropylcarbamoyl-phenyl)-thiazol-2-yl]-amide (Compound 5331)

From 51.2 mg of phenoxy-acetyl chloride following General Procedure 3B. MS: 491.7 (M+H$^+$); H$^1$ NMR (DMSO-d$_6$): δ(ppm) 12.38 (s, 1H), 8.49 (s, 1H), 7.92 (m, 4H), 7.09 (m, 2H), 6.91 (m, 3H), 4.72 (m, 2H), 3.64 (m, 2H), 2.85 (m, 2H), 1.95 (m, 1H), 2.03 (m, 4H), 0.58 (m, 4H).

Example 332

2-{4-[4-(Cyclohexyl-methyl-carbamoyl)-phenyl]-thiazol-2-ylcarbamoyl}-pyrrolidine-1-carboxylic acid benzyl ester (Compound 5332)

From 50 mg of cyclohexyl-methyl-amine following General Procedure 3A. MS: 547.2 (M+H$^+$); H$^1$ NMR (DMSO-d$_6$): δ(ppm) 12.47 (d, 1H), 7.89 (m, 4H), 7.53-7.02 (m, 6H), 5.01 (m, 2H), 4.46 (m, 2H), 3.64 (br s, 1H), 2.81 (m, 4H), 2.38 (m, 5H), 1.91-0.94 (m, 4H).

Example 333

Pyrrolidine-1,2-dicarboxylic acid 2-{[4-(4-cyclopropylcarbamoyl-phenyl)-thiazol-2-yl]-amide}1-phenylamide (Compound 5333)

Pyrrolidine-2-carboxylic acid [4-(4-cyclopropyl carbamoyl-phenyl)-thiazol-2-yl]-amide (General Procedure 31, 100 mg, 0.28 mmol) was suspended in 4 mL of toluene. To this suspension was added triethylamine (0.05 ml, 0.36 mmol) followed by phenyl isocyanate (83.3 mg, 0.7 mmol). Reaction mixture was heated at 70° C. overnight, providing the crude product. The crude was evaporated under reduced pressure, redissolved in 10 mL of DMF, filtered and purified by reverse phase HPLC. MS: 476.7(M+H$^+$); H$^1$ NMR (DMSO-d$_6$): δ(ppm) 12.39 (br s, 1H), 8.61 (br s, 1H), 7.91 (dd, 1H), 7.42-6.91 (m, 9H), 4.64 (m, 1H), 3.45 (m, 4H), 2.42 (m, 1H), 2.36 (m, 1H), 2.01 (m, 4H), 0.60 (m, 4H).

Example 334

(S)-2-[4-(4-Cyclopropylcarbamoyl-phenyl)-thiazol-2-ylcarbamoyl]-thiazolidine-3-carboxylic acid tert-butyl ester (Compound 5334)

(S)-Thiazolidine-2,3-dicarboxylic acid 3-tert-butyl ester (49.4 mg, 0.21 mmol) was dissolved in DMF (2 mL). DIEA (74 µL, 0.42 mmol) was added followed by HATU (80.7 mg, 0.21 mmol). The reaction was stirred at ambient temperature for 15 minutes. Then 4-(2-Amino-thiazol-4-yl)-N-cyclopropyl-benzamide (54.6 mg, 0.21 mmol) was added. The reaction was stirred at ambient temperature overnight and then heated to 50° C. for 7 hours. The reaction was cooled, filtered, and purified by reverse phase HPLC to give the desired product. Yield 30.5 mg. MS: 475.1 (M+H$^+$); H$^1$ NMR (DMSO-d$_6$): δ(ppm) 0.54-0.75 (m, 4H), 1.22-1.47 (m, 9H), 2.79-2.90 (m, 1H), 3.05-3.25 (m, 2H), 3.55-3.75 (m, 1H), 5.33-5.50 (m, 2H), 7.78-7.98 (m, 5H), 8.40-8.48 (d, 1H), 12.50-12.59 (s, 1H).

Example 335

(S)-2-{4-[3-(Cyclopropylmethyl-amino)-phenyl]-thiazol-2-ylcarbamoyl}-pyrrolidine-1carboxylic acid benzyl ester (Compound 5335)

From 0.06 mL (0.8 mmol) of cyclopropylaldehyde using General Procedure 3H. $^1$HNMR (DMSO-d$_6$) δ(ppm) 12.55-12.53 (m, 1H), 7.81-7.13 (m, 10H), 5.16-4.35 (m, 3H), 3.59-3.45 (m, 2H), 3.23-3.21 (m, 2H), 2.34-2.31 (m, 1H), 1.98-1.90 (m, 3H), 1.17-1.13 (m, 2H), 0.62-0.59 (d, 2H), 0.41-0.39 (d, 2H); MS: 477.2 (M+H$^+$).

Example 336

4-(4-{2-[(1-Benzyloxycarbonyl-pyrrolidine-2-carbonyl)-amino]-thiazol-4-yl}-benzoylamino)-piperidine-1-carboxylic acid tert-butyl ester (Compound 5336)

125 mg (0.28 mmol) of 2-[4-(2-carboxy-phenyl)-thiazol-2-ylcarbamoyl]-pyrrolidine-1-carboxylic acid benzyl ester (IS2277-52) was dissolved in 4 mL of DMF. To this solution was added HATU (160.9 mg, 0.42 mmol) and DIEA (0.05 mL, 0.36 mmol). This solution was stirred at room temperature for 1 hour. To this solution was added 56.1 mg (0.28 mmol) of 3-amino-piperidine-1-carboxylic acid tert-butyl ester. Reaction mixture was stirred overnight at room temperature, and then purified using reverse phase HPLC. MS: 634.2 (M+H$^+$); H$^1$ NMR (meOH-d$_4$): δ(ppm) 8.02 (m, 2H), 7.89 (m, 2H), 7.58 (m, 1H), 7.39 (m, 3H), 7.19 (m, 1H), 7.07 (m, 2H), 5.03 (m, 2H), 45.2 (m, 1H), 4.11 (m, 3H), 3.61 (m, 4H), 3.19 (m, 1H), 2.97 (m, 2H), 2.41 (m, 1H), 2.28 (m, 1H), 2.01 (m, 4H), 1.48 (s, 9H).

Example 337

2-{4-[4-(Azetidin-3-ylcarbamoyl)-phenyl]-thiazol-2-ylcarbamoyl}-pyrrolidine-1-carboxylic acid benzyl ester (Compound 5337)

2-[4-(2-Carboxy-phenyl)-thiazol-2-ylcarbamoyl]-pyrrolidine-1-carboxylic acid benzyl ester (IS2277-52, 125 mg, 0.28 mmol) was dissolved in 4 mL of DMF. To this solution was added HATU (160.9 mg, 0.42 mmol) and DIEA (0.05 mL, 0.36 mmol). This solution was stirred at room temperature for 1 hour. To this solution was added 48.2 mg (0.28 mmol) of 3-amino-azetidine-1-carboxylic acid tert-butyl ester. Reaction mixture was stirred at room temperature overnight to yield crude 2-{4-[4-(1-tert-butoxycarbonyl-azetidin-3-ylcarbamoyl)-phenyl]-thiazol-2-ylcarbamoyl}-pyrrolodine-1-carboxylic acid benzyl ester, which was then purified using reverse phase HPLC. The purified material was dissolved in 4 mL of 1:1 solution of CH$_2$Cl$_2$/TFA and stirred for 1.5 hours at room temperature. Reaction mixture was evaporated under reduced pressure to give pure desired product. MS: 506.1 (M+H$^+$); H$^1$ NMR (DMSO-d$_6$): δ(ppm) 12.50 (br s, 1H), 8.47 (br s, 1H), 7.91 (m, 5H), 7.10 (m, 4H), 5.31 (br s, 1H), 5.02 (m, 2H), 4.51 (m, 1H), 4.08 (m, 3H), 2.47 (m, 3H), 2.23 (m, 1H), 1.90 (m, 4H), 1.94 (m, 2H).

Example 338

2-(4-Pyridin-3-yl-thiazol-2-ylcarbamoyl)-pyrrolidine-1-carboxylic acid benzyl ester (Compound 5338)

Pyrrolidine-1-carboxylic acid benzyl ester, (224 mg, 0.9 mmol) was combined with 376 mg (1.0 mmol) of HATU. This mixture was dissolved in 15 ml of DMF. To this solution was added DIEA (1.8 mmol, 0.3 mL). This solution was stirred at room temperature for 1.5 hours. To this solution was then added 4-pyridin-3-yl-thiazol-2-ylamine (100 mg, 0.56 mg). Reaction mixture was stirred at room temperature overnight and then purified using reverse phase HPLC. MS: 409.1 (M+H$^+$); H$^1$ NMR (DMSO-d$_6$): δ(ppm) (HCl salt) 12.62 (s, 1H), 9.28 (s, 1H), 8.78 (s, 1H), 8.03 (m, 2H), 7.38 (m, 3H), 7.04 (d, 2H), 5.00 (m, 2H), 4.53 (m, 1H), 3.62 (m, 2H), 2.22 (m, 1H), 1.89 (m, 4H).

Example 339

2-{4-[4-(2-Morpholin-4-yl-ethylcarbamoyl)-phenyl]-thiazol-2-ylcarbamoyl}-pyrrolidine-1-carboxylic acid benzyl ester (Compound 5339)

From 50 mg of 2-morpholin-4-yl-ethylamine following General Procedure 3A. MS: 564.2 (M+H$^+$); H$^1$ NMR (DMSO-d$_6$): δ(ppm) ((TFA salt) 12.58 (s, 1H), 9.50 (br s, 1H), 8.74 9s, 1H), 7.91 (m, 4H), 7.57 (br s, 2H), 7.10 (dd, 3H), 5.01 (m, 2H), 4.48 (m, 1H), 3.98 (m, 2H), 3.6-3.10 (m, 6H), 2.25 (m, 1H), 1.97 (m, 4H), 1.17 (m, 4H)

Example 340

Rac-trans-Cyclopentane-1,2-dicarboxylic acid 1-benzylamide 2-{[4-(4-cyclopropylcarbamoyl-phenyl)-thiazol-2-yl]-amide} (Compound 5340)

Rac-trans-2-[4-(4-Cyclopropylcarbamoyl-phenyl)-thiazol-2-ylcarbamoyl]cyclopentanecarboxylic acid.

Rac-trans-2-[4-(4-Cyclopropylcarbamoyl-phenyl)-thiazol-2-ylcarbamoyl]-cyclopentanecarboxylic acid methyl ester (100 mg) was dissolved in THF:MeOH:H20 (2:2:1, 5 mL) and treated with LiOH (10 eq. 45 mg) and stirred at room temperature for 15 hours. The mixture was neutralized with HOAc, and the solvents removed. The resulting mixture was redissolved in 5 ml of 90% DMF, 10% water with 0.1% TFA and purified by reverse phase HPLC to give the product. MS: 400.5 (M+H$^+$).

Rac-trans-Cyclopentane-1,2-dicarboxylic acid 1-benzylamide 2-{[4-(4-cyclopropylcarbamoyl-phenyl)-thiazol-2-yl]-amide} (Compound 5340)

Rac-frans -2-[4-(4-Cyclopropylcarbamoyl-phenyl)-thiazol-2-ylcarbamoyl]cyclopentanecarboxylic acid (15 mg) was dissolved in DMF (1 mL) and treated with HATU (1.1 eq. 19 mg) and DIEA (3 eq, 20 µL) and stirred for 15 minutes. Then benzyl amine (1.2 eq, 4 µL) was added and the mixture stirred at ambient temperature overnight. The reaction was cooled, filtered and the solvents removed. The resulting mixture was redissolved in 5 ml of 90% DMF, 10% water with .1% TFA and purified by reverse phase HPLC to give the product (24 mg). MS: 489.5 (M+H$^+$); H$^1$-NMR (DMSO-d$_6$): δ(ppm) 8.4 (m, 2H), 7.9-7.7 (m, 5H), 7.1 (m, 5H), 4.3 (m, 2H), 3.1 (m, 1H), 2.9 (m, 1H), 2.12-1.98 (m, 3H) 0.7-0.6 (m, 4H).

Example 341

2-{4-[4-(2-Carboxy-ethylcarbamoyl)-phenyl]-thiazol-2-ylcarbamoyl}-pyrrolidine-1-carboxylic acid benzyl ester (Compound 5341)

From 40 mg of 3-amino-propionic acid following General Procedure 3A. MS: 523.2 (M+H$^+$); H$^1$ NMR (DMSO-d$_6$): δ(ppm) 12.48 (s, 1H), 8.53 (t, 1H), 7.78 (m, 5H), 7.34 (br s, 2H), 7.10 (dd, 2H), 5.00 (m, 3H), 3.47 (m, 4H), 2.24 (m, 1H), 1.90 (m, 4H), 1.22 (m, 2H).

Example 342

(S)-Pyrrolidine-1,2-dicarboxylic acid 2-{[4-(4-cyclopropylcarbamoyl-phenyl)-thiazol-2-yl]amide} 1-phenylamide (Compound 5342)

A mixture of (S)-pyrrolidine-2-carboxylic acid [4-(4-cyclopropylcarbamoyl-phenyl)-thiazol-2-yl]-amide (General Procedure 31, 0.04 g, 0.09 mmol), TEA (0.007 mL), and benzylisocyanate in toluene (3 mL) was heated to 80° C. for 2 h. The mixture was concentrated in vacuo to give the crude product. Purification of the crude product by ISCO (MeOH/DCM) furnished the desired product. $^1$HNMR (DMSO-d$_6$) δ(ppm) 12.26 (s, 1H), 8.43-8.42 (d, 1H), 7.95-7.73 (m,5H), 7.29-7.17 (m, 5H), 6.94-6.91 (m, 1H), 4.52-4.49 (m, 1 H), 4.26-4.10 (m, 2H), 3.48 (m, 1H), 3.16-3.14 (d, 1H), 2.95-2.83 (m, 2H), 2.15-2.12 (m,1H), 1.97-1.92 (m, 3H),0.70-0.57 (m,4H); MS: 490.2 (M+H$^+$).

Example 343

2-{4-[4-(Piperidin-3-ylcarbamoyl)-phenyl]-thiazol-2-ylcarbamoyl}-pyrrolidine-1-carboxylic acid benzyl ester (Compound 5343)

3-(4-{2-[(1-Benzyloxycarbonyl-pyrrolidine-2-carbonyl)-amino]-thiazol-4-yl}-benzoylamino)-piperidine-1-carboxylic acid tert butyl ester (Compound 5336, Example 336, 100 mg, 0.16 mmol) was dissolved in 4 mL of 1:1 solution of CH$_2$Cl$_2$/TFA and stirred for 1.5 at room temperature. Reaction mixture was evaporated under reduced pressure to give pure desired product. MS: 534.2(M+H$^+$); H$^1$ NMR (MeOH-d$_4$): δ(ppm) (HCl salt)12.47 (s, 1H), 9.52 (s, 1H), 8.64 (s, 1H), 7.95 (m, 5H), 7.50 (br s, 2H), 7.08 (d, 2H), 5.03 (m, 2H), 4.49 (m, 1H), 4.12 (m, 1H), 3.68-2.96 (m, 6H), 2.28 (m, 1H), 1.90 (m, 8H).

Example 344

2-[(S)-1-Benzyloxycarbonyl-pyrrolidine-2-carbonyl)-amino]-4-(4-cyclopropylcarbamoyl-phenyl)-thiazole-5-carboxylic acid (Compound 5344)

A mixture of Compound 5362 (Example 362, 0.10 g, 0.18 mmol) and NaOH (1M, 2 mL, 2 mmol) in THF/MeOH/H$_2$O (2:1:2, 5 mL) was stirred at 50° C. overnight. The mixture was acidified with 1 N HCl and concentrated to give the desired product. $^1$HNMR (DMSO-d$_6$) δ(ppm) 12.78 (s, 1H), 8.49-8.48 (d, 1H), 7.83-7.49 (m, 7H), 7.34-7.29 (m, 2H), 7.16-7.10 (m, 2H), 5.08-4.90 (m, 2H), 4.49-4.47 (m, 1H), 3.55-3.44 (m, 1H), 2.87-2.82 (m, 1H), 2.25-2.24 (m, 1H), 1.90-1.87 (m, 3H), 0.71-0.59 (m, 4H); MS: 535.1 (M+H$^+$).

Example 345

2-{4-[4-(Pyridin-3-ylcarbamoyl)-phenyl]-thiazol-2-ylcarbamoyl}-pyrrolidine-1-carboxylic acid benzyl ester (Compound 5345)

From 50 mg of pyridine-2-ylamine following General Procedure 3A. MS: 528.1 (M+H$^+$); H$^1$ NMR (DMSO-d$_6$): δ(ppm) (HCl salt) 12.43 (d, 1H), 10.60 (s, 1H), 8.18 (m, 2H), 7.90 (d, 2H), 7.57 (m, 1H), 7.36 (s, 2H), 7.09 (m, 2H), 5.02 (m, 2H), 4.50 (m, 2H), 3.42 (m, 3H), 2.14 (m, 1H), 1.93 (m, 4H).

Example 346

Rac-trans -2-[4-(4-Cyclopropylcarbamoyl-phenyl)-thiazol-2-ylcarbamoyl]-cyclopentanecarboxylic acid methyl ester (Compound 5346).

Rac-trans-cyclopentane-1,2-dicarboxylic acid monomethyl ester (86 mg) was dissolved in DMF (5 mL) and treated with HATU (1.1 eq. 214 mg) and DIEA (3 eq, 267 µL) and stirred for 15 minutes. Then 4-(2-amino-thiazol-4-yl)-N-cyclopropyl-benzamide (1 eq, 129.5 mg) was added and the mixture stirred at ambient temperature overnight. The reaction was cooled, filtered and the solvents removed. The resulting mixture was redissolved in 5 ml of 90% DMF, 10% water with 0.1% TFA and purified by reverse phase HPLC to give the product. Yield 14 mg. MS: 414.5 (M+H$^+$); H$^1$-NMR (DMSO-d$_6$): δ(ppm) 12.4 (s, 1H), 8.4 (m, 2H), 7.9-7.7 (m, 5H), 3.6 (s, 3H), 3.2 (m, 2H), 2.8 (m, 1H), 2.0 (m, 2H), 1.7 (m, 4H) 0.7-0.6 (m, 4H).

Example 347

2-(4-Furan-2-yl-thiazol-2-ylcarbamoyl)-pyrrolidine-1-carboxylic acid benzyl ester (Compound 5347)

4-Furan-2-yl-thiazol-2-ylamine

4-Bromo-thiazol-2-ylamine (100 mg, 0.34 mmol) was combined with 57 mg (0.51 mmol) of 2-furan boronic acid. To this mixture was added 5 mL of MeOH, 1 mL of sat. NaHCO$_3$ (aq), and 0.8 mL of DMF. Reaction mixture was degassed and Pd[P(Ph)$_3$]$_4$ (25 mg) was added. Reaction mixture was heated at 70° C. for 7 hours. The reaction mixture was brought to room temperature and filtered. The filtrate was evaporated and purified using reverse phase HPLC.

2-(4-Furan-2-yl-thiazol-2-ylcarbamoyl)-pyrrolidine-1-carboxylic acid benzyl ester (Compound 5347)

Synthesized from 100 mg (0.6 mmol) of 4-furan-2-yl-thiazol-2-ylamine following General Procedure 3A. MS: 398.1 (M+H); H$^1$ NMR (DMSO-d$_6$): δ(ppm) MS: 398.7 (M+H$^+$); H$^1$ NMR (DMSO-d$_6$): δ(ppm) 8.08 (s, 1H), 7.33 (m, 7H), 6.65 (d, 1H), 5.03 (m, 2H), 4.50 (m, 1H), 3.58 (m, 2H), 2.24 (m, 1H), 1.89 (m, 4H).

Example 348

2-[4-(4-Cyclopropylcarbamoyl-phenyl)-thiazol-2-ylcarbamoyl]-pyrrolidine-1-carboxylic acid phenyl ester (Compound 5348)

From 47.0 g of phenyl chloroformate following General Procedure 3B. MS: 477.1(M+H$^+$); H$^1$ NMR (DMSO-d$_6$): δ(ppm) 12.58 (d, 1H), 8.40 (s, 1H), 7.82 (m, 4H), 7.21 (m, 5H), 4.64 (m, 1H), 3.45 (m, 4H), 2.42 (m, 1H), 2.36 (m, 1H), 2.01 (m, 4H), 0.60 (m, 4H).

Example 349

(R)-2-[4-(4-Cyclopropylcarbamoyl-phenyl)-thiazol-2-ylcarbamoyl]-pyrrolidine-1-carboxylic acid benzyl ester (Compound 5349)

From 2R-5-pyrrolidine-1,2-dicarboxylic acid 1-benzyl ester using General Procedure 3C. Yield 7.7 mg. MS: 491.3 (M+H). H$^1$-NMR (DMSO-d$_6$): δ(ppm) 8.4 (m, 1H), 7.9-7.7 (m, 5H), 7.3-7.1 (m, 5H), 5.2-5.0 (m, 2H), 4.5 (m, 1H), 3.5 (m, 2H), 2.8 (m, 1H), 2.2 (m, 2H), 1.9 (m, 3H), 0.7-0.5 (m, 4H).

Example 350

(S)-2-[4-(4-Cyclopropylcarbamoyl-phenyl)-thiazol-2-ylcarbamoyl]-thiazolidine-3-carboxylic acid benzyl ester (Compound 5350)

(S)-Thiazolidine-2-carboxylic acid [4-(4-cyclopropylcarbamoyl-phenyl)-thiazol-2-yl]-amide A solution of (S)-2-[4-(4-cyclopropylcarbamoyl-phenyl)-thiazol-2-ylcarbamoyl]-thiazolidine-3-carboxylic acid tert-butyl ester (341.6 mg, 0.72 mmol) in dichloromethane (3 mL) and trifluoroacetic acid (3 mL) was stirred at ambient temperature overnight. The reaction was filtered and purified by reverse phase HPLC to give the desired product.

(S)-2-[4-(4-Cyclopropylcarbamoyl-phenyl)-thiazol-2-ylcarbamoyl]-thiazolidine-3-carboxylic acid benzyl ester (Compound 5350)

A solution of (S)-thiazolidine-2-carboxylic acid [4-(4-cyclopropylcarbamoyl-phenyl)-thiazol-2-yl]-amide (50 mg, 0.13 mmol) in DMF (1 mL) was cooled to 0° C. DIEA (35 µL, 0.20 mmol) was added followed by benzyl chloroformate (30 µL, 0.21 mmol). The reaction was stirred at 0° C. and allowed to warm to ambient temperature over 2 hours. The reaction was filtered and purified by reverse phase HPLC to give the desired product. Yield 36.9 mg. MS: 509.1 (M+H$^+$); H$^1$ NMR (DMSO-d$_6$): δ(ppm) 0.55-0.74 (m, 4H), 2.80-2.91 (m, 1H), 3.10-3.27 (m, 2H), 3.65-3.75 (m, 1H), 3.90-4.04 (m, 1H), 4.94-5.17 (m, 2H), 5.51-5.55 (s, 1H), 7.06-7.41 (m, 5H), 7.79-7.98 (m, 5H), 8.41-8.48 (d, 1H), 12.50-12.60 (m, 1H).

Example 351

(S)-2-[4-(5-Cyclopropylcarbamoyl-furan-2-yl)-thiazol-2-ylcarbamoyl]-pyrrolidine-1-carboxylic acid benzyl ester (Compound 5351)

A mixture of 2-methyl furoate (4.0 mL, 37.4 mmol) and acetic anhydride (15 mL) was heated to 60° C., then BF$_3$.Et$_2$O (0.5 mL, 4.1 mmol) was added. The mixture was heated to reflux for 20 min., allowed to cool to room temperature, and then diluted with water. The resulting mixture was extracted with EtOAc (4×50 mL). The combined organic extract was washed with brine, dried (Na$_2$SO$_4$), and concentrated in vacuo to give the desired product 5-acetyl-furan-2-carboxylic acid methyl ester; MS: 169.1 (M+H$^+$).

Bromination of 5-acetyl-furan-2-carboxylic acid methyl ester (0.27 g, 1.61 mmol) with Br$_2$ (0.082 mL) in AcOH (6 mL) at room temperature gave 5-(2-bromo-acetyl)-furan-2-carboxylic acid methyl ester; MS: 246.1 (M+H$^+$).

5-(2-Bromo-acetyl)-furan-2-carboxylic acid methyl ester (0.39 g, 1.61 mmol) was treated with NaOAc (0.185 g, 2.25 mmol) and thiourea (0.12 g, 1.6 mmol) in EtOH to give 5-(2-Amino-thiazol-4-yl)-furan-2-carboxylic acid methyl ester; MS: 225.1 (M+H$^+$).

In a similar procedure as described for the synthesis of Compound 5312 (Example 312), 5-(2-amino-thiazol-4-yl)-furan-2-carboxylic acid methyl ester was treated with HATU (0.98 g, 2.38 mmol), DIEA (0.7 mL, 5.36 mmol), and (S)-Pyrrolidine-1,2-dicarboxylic acid 1-benzyl ester (0.61 g, 2.45 mmol) to furnish (S)-2-[4-(5-Methoxycarbonyl-furan-2-yl)-thiazol-2-ylcarbamoyl]-pyrrolidine-1-carboxylic acid benzyl ester; MS: 169.1 (M+H$^+$).

Hydrolysis of (S)-2-[4-(5-Methoxycarbonyl-furan-2-yl)-thiazol-2-ylcarbamoyl]-pyrrolidine-1-carboxylic acid benzyl ester (0.350 g, 0.77 mmol) with NaOH (1M, 2 mL, 2 mmol) gave (S)-2-[4-(5-Carboxy-furan-2-yl)-thiazol-2-ylcarbamoyl]-pyrrolidine-1-carboxylic acid benzyl ester; MS: 442.1 (M+H$^+$).

In a similar procedure as described for the synthesis of Compound 5352 (Example 352), treatment of (S)-2-[4-(5-Carboxy-furan-2-yl)-thiazol-2-ylcarbamoyl]-pyrrolidine-1-carboxylic acid benzyl ester with HATU (0.23 g, 0.6 mmol), DIEA (0.2 mL, 1.53 mmol), and cyclopropylamine (0.1 1 mL) furnished the desired product. $^1$HNMR (DMSO-d$_6$) δ(ppm) 12.59-12.57 (d, 1H), 8.42-8.39 (m, 1H), 7.64-7.62 (d, 1H), 7.36-7.30 (m, 2H), 7.14-7.10 (m, 3H), 6.73-6.70 (m, 1H), 5.10-4.87 (m, 2H), 4.51-4.43 (m, 2H), 3.52-3.36 (m, 2H), 2.80-2.77, (m, 2H), 2.27-2.24 (m, 1H), 1.94-1.83 (m, 3H), 0.73-0.58 (m, 4H); MS: 481.2 (M+H$^+$).

Example 352

(S)-2-[5-(4-Cyclopropylcarbamoyl-phenyl)-thiazol-2-ylcarbamoyl]-pyrrolidine-1-carboxylic acid benzyl ester (Compound 5352)

From (S)-2-[5-(4-carboxy-phenyl)-thiazol-2-ylcarbamoyl]-pyrrolidine-1-carboxylic acid benzyl ester (Compound 5353, Example 353, 0.04 g, 0.09 mmol), HATU (0.044 g, 0.12 mmol), and (0.03 mL, 0.36 mmol) of cyclopropylamine using General Procedure 3F. $^1$HNMR (DMSO-d$_6$) δ(ppm)12.44-12.42 (d, 1H), 8.43 (s, 1H), 7.99-7.65 (m, 5H), 7.35-7.10 (m, 4 H), 5.06-4.89 (m, 2H), 4.5-4.46 (m, 1H), 2.83 (s, 2H), 2.25 (m, 1H), 1.91 (m, 3H), 0.70-0.57, (m, 4H); MS: 491.1 (M+H$^+$).

Example 353

(S)-2-[5-(4-Carboxy-phenyl)-thiazol-2-ylcarbamoyl]-pyrrolidine-1-carboxylic acid benzyl ester (Compound 5353)

Following General procedure 3E, (S)-2-[5-(4-Methoxycarbonyl-phenyl)-thiazol-2-ylcarbamoyl]-pyrrolidine-1-carboxylic acid benzyl ester; MS: 465.1 (M+H$^+$ was obtained from 4-phenylboronic acid methyl ester (0. 13 g, 0.73 mmol). Then the title compounds was obtained from 0.19 g (0.4 mmol) of (S)-2-[5-(4-Methoxycarbonyl-phenyl)-thiazol-2-ylcarbamoyl]-pyrrolidine-1-carboxylic acid benzyl ester.

$^1$HNMR (DMSO-d6) δ(ppm)12.47 (s, 1H), 8.04-7.11 (m, 9H), 5.06-4.89 (m, 2H), 4.51-4.47 (m, 1H), 3.49-3.45 (m, 1H), 2.25 (m, 1H), 1.91 (m, 3H), 1.23-1.14 (m, 2H); MS: 452.1 (M+H$^+$).

Example 354

2-[4-(4-Cyclopentylsulfamoyl-phenyl)-thiazol-2-ylcarbamoyl]-pyrrolidine-1-carboxylic acid benzyl ester (Compound 5354)

4-(2-Bromo-acetyl)-N-cyclopentyl-benzenesulfonamide 4-(2-Bromo-acetyl)-benzenesulfonyl chloride (150 mg, 0.17 mmol) was dissolved in 4 mL of dry dichloromethane. To this solution at 0° C., was added triethylamine (0.03 mL, 0.2 mmol), followed by cyclopentylamine (0.2 mmol, 0.011 g). Reaction mixture was stirred at 0° C. for 15 minutes and then quenched with H$_2$O. The reaction mixture was extracted with H$_2$O. The organic phase was isolated, dried over MgSO4 and evaporated. It was used in the next step without any further purification.

4-(2-Amino-thiazol-4-yl)-N-cyclopentyl-benzenesulfonamide 4-(2-Bromo-acetyl)-N-cyclopentyl-benzenesulfonamide (150 mg, 0.43 mmol) was combined with thiourea (33 mg, 0.43 mmol) in 7 ml of dry EtOH. To this solution was added NaOAc (53 mg, 0.65 mmol). Reaction mixture was stirred at room temperature for 4 hours. Reaction mixture was evaporated to dryness and used in the next step without further purification.

2-[4-(4-Cyclopentylsulfamoyl-phenyl)-thiazol-2-ylcarbamoyl]-pyrrolidine-1-carboxylic acid benzyl ester (Compound 5354)

Synthesized from 4-(2-Amino-thiazol-4-yl)-N-cyclopentyl-benzenesulfonamide following General Procedure 3A. MS: 555.7 (M+H$^+$); H$^1$ NMR (MeOH-d$_4$): δ(ppm) 8.10 (dd, 2H), 7.90 (dd, 2H), 7.63 (d, 1H), 7.38 (m, 2H), 7.10 (m, 3H), 5.18 (m, 2H), 4.50 (m, 2H), 3.60 (m, 4H), 2.18 (m, 2H), 2.0-1.2 (m, 9H).

Example 355

(S)-2-[4-(5-Cyclopropylcarbamoyl-pyridin-2-yl)-thiazol-2-ylcarbamoyl]-pyrrolidine-1-carboxylic acid benzyl ester (Compound 5355)

To a solution of benzyl nicotinate (12.43 g, 58.0 mmol), H$_2$SO$_4$ (5.72 g, 146 mmol), and acetaldehyde (8.2 mL, 145 mmol) in degassed water (25 mL) at 0° C. were simultaneously added a solution of FeSO$_4$.7H$_2$O (40.3 g, 145 mmol) in degassed water (100 mL) and 70% t-BuOH in water (20 mL). The mixture was stirred for 20 min. then it was extracted with CHCl$_3$. The organic extract was washed with brine, dried (Na$_2$SO$_4$), and concentrated in vacuo to give the crude product. Purification by silica gel (EtOAc/hexanes) furnished 2.8 g of the desired product 6-Acetyl-nicotinic acid benzyl ester.

To a mixture of 6-acetyl-nicotinic acid benzyl ester (1.06 g, 4.15 mmol) in AcOH (12 mL) at 55° C. was added Br$_2$ (0.21 mL) dropwise. After stirring for 4 h., the reaction mixture was washed with Sat.NaHCO$_3$, water, brine, dried (MgSO$_4$), and concentrated in vacuo to give the crude product. Purification by reverse phase HPLC afforded the desired product 6-(2-Bromo-acetyl)-nicotinic acid benzyl ester.

A mixture of 6-(2-bromo-acetyl)-nicotinic acid benzyl ester (0.16 g, 0.48 mmol), thiourea (0.0.038 g), and NaOAc (0.051 g) in EtOH (6 mL) was stirred at room temperature overnight. The mixture was concentrated in vacuo to give the crude product 6-(2-Amino-thiazol-4-yl)-nicotinic acid benzyl ester.

A mixture of (S)-Pyrrolidine-1,2-dicarboxylic acid 1-benzyl ester (0.38 g, 1.52 mmol), HATU (0.58 g, 1.52 mmol)), and DIEA (0.4 mL, 3.0 mmol) in DMF (16 mL) was stirred at room temperature for 1 h. 6-(2-Amino-thiazol-4-yl)-nicotinic acid benzyl ester (0.32 g, 1.0 mmol) was added and the reaction mixture was heated to 50° C. for 48 h. The crude product was purified by reverse phase HPLC to furnish the desired product 6-{2-[((S)-1-Benzyloxycarbonyl-pyrrolidine-2-carbonyl)-amino]-thiazol-4-yl}-nicotinic acid benzyl ester.

Hydrolysis of 6-{2-[((S)-1-Benzyloxycarbonyl-pyrrolidine-2-carbonyl)-amino]-thiazol-4-yl}-nicotinic acid benzyl ester (0.075 g, 0.14 mmol) similar to the procedure described for the synthesis of Compound 5353 (Example 353), gave 6-{2-[((S)-1-Benzyloxycarbonyl-pyrrolidine-2-carbonyl)-amino]-thiazol-4-yl}-nicotinic acid.

A mixture of 6-{2-[((S)-1-Benzyloxycarbonyl-pyrrolidine-2-carbonyl)-amino]-thiazol-4-yl}-nicotinic acid (0.18 g, crude), HATU (0.07 g, 0.18 mmol)), and DIEA (0.1 mL, 0.77 mmol) in DMF (5 mL) was stirred at room temperature for 30 min. then cyclopropylamine (0.030 ml, 0.4 mmol) was added and the reaction mixture was stirred at room temperature overnight. Purification by reverse phase HPLC furnished the desired product. $^1$HNMR (DMSO-$d_6$) δ(ppm) 12.58-12.57 (d, 1H), 9.03 (s, 1H), 8.72-8.71 (d, 1H), 8.34-8.31 (m, 1H), 8.07-8.00 (m,2H), 7.44-7.38 (m, 2H), 7.22-7.12 (m, 2H), 5.17-4.95 (m, 2H), 4.61-4.55 (m, 1H), 3.59-3.52, (m, 2H), 2.95-2.90 (m,1H), 2.34-2.32 (m, 1H), 2.04-1.92 (m, 3H), 0.80-0.78 (m,4H); MS: 492.1 (M+H$^+$).

Example 356

2-{4-[4-(Piperidin-4-ylcarbamoyl)-phenyl]-thiazol-2-ylcarbamoyl}-pyrrolidine-1-carboxylic acid benzyl ester (Compound 5356)

4-(4-{2-[(1-Benzyloxycarbonyl-pyrrolidine-2-carbonyl)-amino]-thiazol-4-yl}-benzoylamino)-piperidine-1-carboxylic acid tert-butyl ester (Compound 5336 Example 336 100 mg, 0.16 mmol) was dissolved in 4 mL of 1:1 solution of CH$_2$Cl$_2$/TFA and stirred for 1.5 at room temperature. The reaction mixture was evaporated under reduced pressure to give pure desired product. MS: 534.2(M+H$^+$); H$^1$ NMR (MeOH-$d_4$): δ(ppm) (HCl salt) 7.99 (m, 4H), 7.28 (m, 3H), 7.12 (d, 1H), 7.00 (d, 2H), 5.02 (m, 2H), 4.56 (m, 2H), 4.19 (m, 1H), 3.69 (m, 1H), 3.55 (m, 4H), 3.17 (t, 2H), 2.16 (m, 1H), 2.11 (m, 4H), 1.92 (m, 4H).

Example 357

2-{4-[4-(4-Methyl-piperazine-1-carbonyl)-phenyl]-thiazol-2-ylcarbamoyl}-pyrrolidine-1-carboxylic acid benzyl ester (Compound 5357)

From 50 mg of 1-methyl-piperazine following General Procedure 3A. MS: 534.2 (M+H$^+$); H$^1$ NMR (DMSO-$d_6$): δ(ppm) 12.43 (br s, 1H), 10.01 (br s, 1H), 7.98 (br d, 2H), 7.78 (br d, 1H), 7.49 (d, 2H), 7.37 (br s, 2H), 7.13 (dd, 2H), 5.02 (m, 2H), 4.52 (m, 2H), 3.70-3.12 (m, 5H), 2.82 (s, 3H), 2.29 (m, 1H), 1.92 (m, 4H).

Example 358

1-(3-Phenyl-propionyl)-pyrrolidine-2-carboxylic acid [4-(4-cyclopropyl carbamoyl-phenyl)-thiazol-2-yl]-amide (Compound 5358)

From 50.6 mg of 3-Phenyl-propionyl chloride following General Procedure 3B. MS: 489.1(M+H$^+$); H$^1$ NMR (DMSO-$d_6$): δ(ppm) 12.36 (s, 1H), 8.42 (s, 1H), 7.90 (m, 5H), 7.10 (m, 4H), 4.57 (m, 1H), 3.55 (m, 1H), 2.09 (m, 2H), 2.82 (m, 2H), 2.11 (m, 1H), 1.90 (m, 4H), 1.17 (dd, 2H), 0.61 (m, 4H).

Example 359

(S)-1-Benzyl-pyrrolidine-2-carboxylic acid [4-(4-cyclopropylcarbamoyl-phenyl)-thiazol-2-yl]-amide (Compound 5359)

From 0.009 mL of benzaldehyde using General Procedure 3J. $^1$HNMR (DMSO-$d_6$) δ(ppm) 12.98 (s, 1H), 10.25 (s, 1H), 8.54-8.52 (d,1H), 8.01-7.91 (m, 5H), 7.58-7.42 (m, 5 H), 4.57-4.52 (m, 3H), 3.45 (m, 2H), 2.95-2.89 (m, 1H), 2.18-2.09 (m, 3H), 0.80-0.67 (m, 4H); MS: 447.1(M+H$^+$).

Example 360

2-(4-tert-butyl-thiazol-2-ylcabamoyl)-pyrrolidine-1-carboxylic acid benzyl ester (Compound 5360)

4-tert-Butyl-thiazol-2-ylamine

1-Bromo-3,3-dimethyl-butan-2-one (300 mg, 1.7 mmol) was dissolved in 10 mL of EtOH. To this solution was added thiourea (1.7 mmol, 129 mg) followed by NaOAc (3.4 mmol, 279 mg). This mixture was stirred at room temperature overnight. The reaction mixture was evaporated under reduced pressure and used without any further purification.

2-(4-tert-butyl-thiazol-2-ylcabamoyl)-pyrrolidine-1-carboxylic acid benzyl ester (Compound 5360)

From 300 mg (1.92 mmol) of 4-tert-butyl-thiazol-2-ylamine (IS2342-4) following General Procedure 3A. MS: 388.1(M+H$^-$); H$^1$ NMR (DMSO-$d_6$): δ(ppm) 7.37 (m, 2H), 7.10 (m, 3H), 6.83 (d, 1H), 5.02 (m, 2H), 4.47 (m, 1H). 3.80 (m, 2H), 2.27 (m, 1H), 2.01 (m, 4H), 1.15 (m, 9H).

Example 361

2-[4-(4-Cyclopropylcarbamoyl-phenyl)-thiazol-2-ylcarbamoyl]-pyrrolidine-1-carboxylic acid 4-fluoro-benzyl ester (Compound 5361)

From 400 mg of (4-fluoro-phenyl)-methanol following the procedure for Example 384. MS: 509.1 (M+H$^+$); H$^1$ NMR (DMSO-$d_6$): δ(ppm) 12.45 (s, 1H), 8.44 (s, 1H), 7.87 (m, 5H), 7.41 (s, 1H), 7.18 (D, 2H), 6.86 (t, 1H), 5.02 (m, 2H), 4.49 (m, 1H), 3.46 (m, 4H), 2.84 (m, 1H), 2.24 (m, 1H), 1.90 (m, 4H), 0.60 (m, 4H).

Example 362

2-[((S)-1-Benzyloxycarbonyl-pyrrolidine-2-carbonyl)-amino]-4-(4-cyclopropylcarbamoyl-phenyl)-thiazole-5-carboxylic acid methyl ester (Compound 5362)

A solution of 4,4,5,5,4',4',5',5'-octamethyl-[2,2']bi[[1,3,2]dioxaborolanyl] (3.9837 g, 15.67 mmol), 4-bromo-N-cyclopropyl-benzamide (1.2516 g, 5.21 mmol), potassium acetate (1.5353 g, 15.64 mmol), and Pd(PPh$_3$)$_2$Cl$_2$ (0.3677 g, 10.0 mol %) in DMSO (30 mL) was degassed and heated to 80° C. overnight in a sealed vial. The reaction was cooled, and distilled water and brine were added. The mixture was centrifuged, and the liquid was decanted. The resulting solid was purified by silica gel chromatography to give N-cyclopropyl-4-(4,4,5,5-tetramethyl-[1,3,2]dioxaborolan-2-yl)-benzamide.

To a suspension of 5-Bromo-thiazol-2-ylamine hydrochloride salt (12.0 g, 46.2 mmol) in THF (100 mL) was added TEA (8.4 mL, 60.3 mmol). The suspension was stirred and filtered. To this solution was added DMAP (0.39 g, 3.2 mmol) and the mixture was heated to reflux and (BOC)$_2$O (26.2 g, 120 mmol) was added. After refluxing for 2 h, the mixture was concentrated and then purified using silica gel chromatography to furnish (5-Bromo-thiazol-2-yl)-dicarbamic acid tert-butyl ester.

To a stirred mixture of (5-Bromo-thiazol-2-yl)-dicarbamic acid tert-butyl ester (1.0 g, 2.64 mmol) in THF (16 mL) at −78° C. was added LDA (2 M, 2.0 mL, 4 mmol) dropwise. After stirring for 20 min., dimethyldicarbonate (0.55 mL, 5.12 mmol) was added. The mixture was allowed to warm to room temperature and was quenched with water. The separated aqueous layer was extracted with EtOAc (4 ×40 mL). The combined organic extracts was washed with brine, dried (Na$_2$SO$_4$), and concentrated in vacuo to give 4-bromo-2-ditert-butoxycarbonylamino-thiazole-5-carboxylic acid methyl ester.

A mixture of 4-bromo-2-ditert-butoxycarbonylamino-thiazole-5-carboxylic acid methyl ester (0.42 g, 1.02 mmol), N-cyclopropyl-4-(4,4,5,5-tetramethyl-[1,3,2]dioxaborolan-2-yl)-benzamide (0.28 g, 0.97 mmol), Pd[P(Ph)$_3$]$_4$ (160 mg), and sat. NaHCO$_3$ (2 mL) in MeOH/DMF (1:1, 20 mL) was degassed and heated to reflux overnight. The resulting mixture was filtered, concentrated, and purified by reverse phase HPLC (20-100% of buffer B; buffer A: water containing 0.1% TFA; buffer B: MeCN containing 0.1 TFA). The combined fraction was evaporated to dryness to furnish 2-tert-Butoxycarbonylamino-4-(4-cyclopropylcarbamoyl-phenyl)-thiazole-5-carboxylic acid methyl ester; MS: 417.1 (M+H$^+$).

A mixture of 2-tert-Butoxycarbonylamino-4-(4-cyclopropylcarbamoyl-phenyl)-thiazole-5-carboxylic acid methyl ester (0.28 g, 6.71 mmol) and TFA (5 mL) in dichloromethane (5 mL) was stirred at room temperature for 2 h. The mixture was concentrated in vacuo to give 2-Amino-4-(4-cyclopropylcarbamoyl-phenyl)-thiazole-5-carboxylic acid methyl ester; MS: 417.1 (M+H$^+$).

In a similar procedure as described for the synthesis of Compound 5312 (Example 312), 2-amino-4-(4-cyclopropylcarbamoyl-phenyl)-thiazole-5-carboxylic acid methyl ester (0.098 g, 0.31 mmol) was treated with HATU (0.18 g, 0.46 mmol), DIEA (0.3 mL, 2.3 mmol), and (S)-pyrrolidine-1,2-dicarboxylic acid 1-benzyl ester (0.12 g, 0.46 mmol) to furnish the desired product. $^1$HNMR (DMSO-d$_6$) δ(ppm)12.90-12.88 (d, 1H), 8.89-8.85 (m, 1H), 8.51-8.50 (d, 1H), 7.86-7.72 (m, 4H), 7.37-7.33 (m, 2H), 7.15-7.09 (m, 2H), 5.09-4.87 (m, 2H), 4.51-4.49 (m, 1H), 3.74-3.72 (m, 3H), 3.53-3.47 (m, 1H), 2.88-2.84 (m, 1H), 2.45 (m, 1H), 1.91-1.87 (m, 3H), 0.71-0.59 (m, 4H); MS: 549.2 (M+H$^+$).

Example 363

(S)-2-[5-(3-Cyclopentylcarbamoyl-phenyl)-thiazol-2-ylcarbamoyl]-pyrrolidine-1-carboxylic acid benzyl ester (Compound 5363)

From 0.03 mL (0.26 mmol) of cyclopentylamine using General Procedure 3G. $^1$HNMR (DMSO-d$_6$) δ(ppm)12.42-12.40 (m, 1H), 8.39-8.36 (d, 1H), 7.80-7.09 (m, 9H), 5.07-4.89 (m, 2H), 4.50-4.47 (m, 1H), 4.25-4.23 (m, 1H), 3.53-3.36 (m, 2H), 2.28-2.25 (m, 1H), 1.90-1.54 (m, 10H), 1.23-1.14 (d,1H); MS: 519.2 (M+H$^+$).

Example 364

2-{4-[4-(Morpholine-4-carbonyl)-phenyl]-thiazol-2-ylcarbamoyl}-pyrrolidine-1-carboxylic acid benzyl ester (Compound 5364)

From 50 mg of morpholine following General Procedure 3A. MS: 521.7 (M+H$^+$); H$^1$ NMR (DMSO-d$_6$): δ(ppm) 12.42 (br s, 1H), 7.92 (m, 2H), 7.34-7.09 (m, 9H), 5.02 (m, 2H), 4.44 (m, 1H), 3.4-3.6 (s, 1H), 3.95 (m, 2H), 2.51 (m, 1H), 2.11 (m, 1H), 1.91 (m, 6H), 1.91 (m, 2H).

Example 365

3-(4-{2-[(1-Benzyloxycarbonyl-pyrrolidine-2-carbonyl)-amino]-thiazol-4-yl}-benzoylamino)-piperidine-1-carboxylic acid tert-butyl ester (Compound 5365)

2-[4-(2-carboxy-phenyl)-thiazol-2-ylcarbamoyl]-pyrrolidine-1-carboxylic acid benzyl ester (General Procedure 3A, 125 mg, 0.28 mmol) was dissolved in 4 mL of DMF. To this solution was added HATU (160.9 mg, 0.42 mmol) and DIEA (0.05 mL, 0.36 mmol). This solution was stirred at room temperature for 1 hour. To this solution was added 56.3 mg of 3-amino-piperidine-1-carboxylic acid-tert-butyl ester. Reaction mixture was stirred overnight at room temperature, and then purified using reverse phase HPLC. MS: 634.3 (M+H$^+$); H$^1$ NMR (DMSO-d$_6$): δ(ppm) 12.48 (s, 1H), 8.10 (m, 5H), 7.36 (br s, 2H), 7.08 (m, 3H), 5.01 (m, 2H), 4.43 (m, 2H), 3.80-3.50 (m, 4H), 2.81 (m, 2H), 2.23 (m, 2H), 1.93 (m, 5H), 1.29 (s, 9H).

Example 366

(S)-2-[4-(4-Cyclopropylcarbamoyl-phenyl)-thiazol-2-ylcarbamoyl]-5-oxo-pyrrolidine-1-carboxylic acid benzyl ester (Compound 5366)

From 2-S-5-oxo-pyrrolidine-1,2-dicarboxylic acid 1-benzyl ester using General Procedure 3C. Yield 18.6 mg. MS: 505.3 (M+H). H$^1$-NMR (DMSO-d$_6$): δ(ppm) 8.4 (m, 1H), 7.9-7.8 (m, 5H), 7.3-7.1 (m, 5H), 5.2-5.0 (m, 2H), 4.9 (m, 1H), 2.8 (m, 1H), 2.4 (m, 2H), 1.9 (m, 1H), 0.7-0.5 (m, 4H).

Example 367

(S)-1-Benzoyl-pyrrolidine-2-carboxylic acid [4-(4-cyclopropylcarbamoyl-phenyl)-thiazol-2-yl]amide (Compound 5367)

From 0.02 mL benzylchloride using General Procedure 3I. $^1$HNMR (DMSO-$d_6$) δ(ppm) 12.48 (s, 1H), 8.43-8.42 (d, 1H), 7.93-7.84 (m, 5H), 7.59-7.42 (m, 5H), 7.25 (s, 1H), 4.72-4.67 (m, 1H), 4.11-4.09 (m, 2H), 3.63-3.51 (m, 2H), 3.16-3.14 (m, 1H), 2.32-2.25 (m, 1H), 1.98-1.94 (m, 3H), 0.70-0.54 (m, 4H); MS: 461.1 (M+H$^+$).

Example 368

(S)-2-[5-(4-Cyclopentylcarbamoyl-phenyl)-thiazol-2-ylcarbamoyl]-pyrrolidine-1-carboxylic acid benzyl ester (Compound 5368)

From (S)-2-[5-(4-Carboxy-phenyl)-thiazol-2-ylcarbamoyl]-pyrrolidine-1-carboxylic acid benzyl ester (Compound 5353, example 353, 0.03 g, 0.07 mmol), HATU (0.033 g, 0.086 mmol), and (0.03 mL, 0.26 mmol) of cyclopentylamine using General Procedure 3F. $^1$HNMR (DMSO-$d_6$) δ(ppm) 12.42 (m, 0.7H), 8.30-8.27 (d, 1H), 7.80-7.11 (m, 10H), 5.06-4.89 (m, 2 H), 4.50 (m, 1H), 3.51-3.48 (m, 1H), 2.26 (m, 1H), 1.89-1.52 (m, 9H), 1.14 (s, 1H); MS: 519.2 (M+H$^+$).

Example 369

2-(4-{4-[(Cyclopropanecarbonyl-amino)-methyl]-phenyl}-thiazol-2-ylcarbamoyl)-pyrrolidine-1-carboxylic acid benzyl ester (Compound 5369)

2-[4-(4-Aminomethyl-phenyl)-thiazol-2-ylcarbamoyl]-pyrrolidine-1-carboxylic acid benzyl ester (Compound 5379, Example 379, 100 mg, 0.23 mmol) was dissolved in 5 mL of dry CH$_2$Cl$_2$. To this solution at 0° C. was added triethylamine (0.035 mL, 0.46 mmol) followed by cyclopropanecarbonyl chloride (48 mg, 0.46 mmol). The reaction mixture was stirred at 0° C. for 30 minutes and then quenched using H$_2$O. The organic phase was isolated and evaporated under reduced pressure to yield the crude product, which was then purified using reverse phase HPLC. MS: 505.2(M+H$^-$); H$^1$ NMR (DMSO-$d_6$): δ(ppm) 12.41 (s, 1H), 8.58 (s, 1H), 7.82 (d, 2H), 7.57 (d, 1H), 7.31 (dd, 4H), 7.10 (dd, 3H), 5.00 (m, 2H), 4.45 (m, 1H), 4.23 (d, 2H), 3.48 (m, 2H), 2.21 (m, 1H), 1.89 (m, 3H), 1.60 (m, 1H), 0.60 (d, 4H).

Example 370

2-{4-[4-(3-Methoxy-propylcarbamoyl)-phenyl]-thiazol-2-ylcarbamoyl]-pyrrolidine-1-carboxylic acid benzyl ester (Compound 5370)

From 13.7 mg of 3-methoxy-propylamine following General Procedure 3A. MS: 523.2 (M+H$^+$); H$^1$ NMR (DMSO-$d_6$): δ(ppm) 12.48 (s, 1H), 8.48 (s, 1H), 7.92 (m, 4H), 7.35 (m, 2H), 7.13 (d, 3H), 5.06 (m, 2H), 4.52 (m, 1H), 3.49 (m, 2H), 3.35 (s, 1H), 3.23 (s, 3H), 3.05 (m, 2H), 2.26 (m, 2H), 1.91-1.77 (m, 6H).

Example 371

1-(1-Phenyl-cyclopropanecarbonyl)-pyrrolidine-2-carboxylic acid [4-(4-cyclopropylcarbamoyl-phenyl)-thiazol-2-yl]-amide (Compound 5371)

From 55.7 mg of 1-phenyl-cyclopropane carbonyl chloride following General Procedure 3B. MS: 501.2(M+H$^+$); H$^1$ NMR (DMSO-$d_6$): δ(ppm) 12.24 (s, 1H), 8.41 (s, 1H), 7.90 (m, 4H), 7.22 (m, 5H), 4.58 (m, 1H), 3.21 (m, 1H), 2.82 (m, 1H), 2.10 (m, 1H), 1.88 (m, 4H), 1.22 (m, 5H), 0.58 (br d, 4H).

Example 372

2-{4-[4-(Pyridin-2-ylcarbamoyl)-phenyl]-thiazol-2-ylcarbamoyl}-pyrrolidine-1-carboxylic acid benzyl ester (Compound 5372)

From 50 mg of pyridine-2-ylamine following General Procedure 3A. MS: 528.2 (M+H$^+$); H$^1$ NMR (DMSO-$d_6$): δ(ppm) (HCl salt) 12.43 (d, 1H), 10.89 (s, 1H), 8.20 (s, 1H), 8.00 (m, 4H), 7.18 (m, 4H), 5.02 (m, 2H), 4.50 (m, 2H), 3.44 (m, 2H), 2.30 (m, 1H), 1.92 (m, 4H)

Example 373

2-[4-(4-Cyclopropylcarbamoyl-phenyl)-thiazol-2-ylcarbamoyl]-pyrrolidine-1-carboxylic acid methyl ester (Compound 5373)

From 26.5 mg of methyl chloroformate following General Procedure 3B. MS: 415.1 (M+H$^+$); H$^1$ NMR (DMSO-$d_6$): δ(ppm) 12.48 (d, 2H), 8.48 (d, 1H), 7.91 (m, 4H), 4.46 (m, 1H), 3.61 (s, 3H), 3.62 (m, 2H), 2.88 (m, 1H), 1.90 (m, 4H), 0.63 (m, 4H).

Example 374

2-[4-(4-{6-[5-(2-Oxo-hexahydro-thieno[3,4-d]imidazol-6-yl)-pentanoylamino]-phenyl)-thiazol-2-ylcarbamoyl]-pyrrolidine-1-carboxylic acid benzyl ester (Compound 5374)

6-[5-(2-Oxo-hexahydro-thieno[3,4-d]imidazol-6-yl)-pentanoylamino]-hexanoic acid (80 mg, 0.22 mmol) was combined with 0.1 ml of DIEA and 0.1 g of HATU in 3 ml of DMF. This solution was stirred at room temperature for 90 minutes. To this solution was added 94 mg (0.2 mmol) of 2-[4-(4-amino-phenyl)-thiazol-2-ylcarbamoyl]-pyrrolidine-1-carboxylic acid benzyl ester (Compound 5050, Example 50). Reaction mixture was stirred at room temperature overnight. It was diluted to 10 mL total volume with DMF and purified on reverse phase HPLC. MS: 762.3 (M+H$^+$); H$^1$ NMR (DMSO-$d_6$): δ(ppm) 12.40 (br d, 1H), 9.92 (s, 1H), 8.78 (m, 3H), 8.67 (m, 2H), 7.50 (m, 1H), 7.32 (d, 2H), 7.11 (dd, 2H), 6.39 (br s, 1H), 5.02 (m, 2H), 4.48 (m, 1H), 4.27 (m, 1H), 4.09 (m, 1H), 3.03 (m, 4H), 2.78(m, 1H), 2.50 (m, 2H), 2.29 (m, 4), 2.01 (m, 6H), 1.82-1.22 (m, 13H).

Example 375

(S)-2-[4-(4-Cyclopropylcarbamoyl-phenyl)-thiazol-2-ylcarbamoyl]-pyrrolidine-1-carboxylic acid tertbutyl ester (Compound 5375)

A mixture of (S)-pyrrolidine-1,2-dicarboxylic acid 1-tert-butyl ester (1.30 g, 6.04 mmol), HATU (2.31 g, 6.07 mmol)), and DIEA (1.2 mL, 9.18 mmol) in DMF (32 mL) was stirred at room temperature for 1 h. Then 4-(2-amino-thiazol-4-yl)-benzoic acid (0.89 g, 4.04 mmol) was added and the reaction mixture was stirred at room temperature overnight. The resulting mixture was purified by reverse phase HPLC to furnish the desired product (S)-2-[4-(4-carboxy-phenyl)-thiazol-2-ylcarbamoyl]-pyrrolidine-1-carboxylic acid tert-butyl ester; MS: 418.1 (M+H$^+$).

A mixture of (S)-2-[4-(4-carboxy-phenyl)-thiazol-2-ylcarbamoyl]-pyrrolidine-1-carboxylic acid tert-butyl ester (0.51 g, 1.22 mmol), HATU (0.47 g, 1.24 mmol)), and DIEA (0.2 mL, mmol) in DMF (10.0 mL) was stirred at room temperature for 1 h. Cyclopropyl amine (0.2 mL, 1.53 mmol) was added and the reaction mixture was stirred at room temperature overnight. The resulting mixture was purified by reverse phase HPLC to furnish the desired product. $^1$HNMR (DMSO-d$_6$) δ(ppm) 12.45-12.40 (m, 1H), 8.44-8.43 (d, 1H), 7.95-7.2 (m, 5H), 4.43-4.34 (m, 1H), 2.97-2.82 (m, 2H), 2.26-2.19 (m, 1H), 1.94-1.79 (m, 3H), 1.39-1.24 (m, 9H), 0.73-0.55 (m, 4H); MS: 457.2 (M+H$^+$).

Example 376

(2S,3S)-2-[4-(4-Cyclopropylcarbamoyl-phenyl)-thiazol-2-ylcarbamoyl]-3-hydroxy-pyrrolidine-1-carboxylic acid benzyl ester (Compound 5376)

(2S,3S)-3-Hydroxy-pyrrolidine-1,2-dicarboxylic acid 1-benzyl ester (2S,3S)-3-Hydroxy-pyrrolidine-2-carboxylic acid (254.5 mg, 1.9 mmol) was dissolved in DMF (15 mL) and distilled water (6 mL). The solution was cooled to 0° C., and DIEA (500 μL, 2.9 mmol) was added followed by benzyl chloroformate (410 μL, 2.9 mmol). The reaction was stirred at 0° C. and allowed to warm to ambient temperature overnight. The reaction was filtered and purified by reverse phase HPLC to give the desired product.

(2S,3S)-2-[4-(4-Cyclopropylcarbamoyl-phenyl)-thiazol-2-ylcarbamoyl]-3-hydroxy-pyrrolidine-1-carboxylic acid benzyl ester (Compound 5328)

(2S,3S)-3-Hydroxy-pyrrolidine-1,2-dicarboxylic acid 1-benzyl ester (41.9 mg, 1.6 mmol) and HATU (66.3 mg, 1.7 mmol) were dissolved in DMF (2 mL). DIEA (55 μL, 0.32 mmol) was then added, and the reaction was stirred at ambient temperature for 15 minutes. Then 4-(2-Amino-thiazol-4-yl)-N-cyclopropyl-benzamide trifluoroacetic acid salt (62.9 mg, 0.17 mmol) was added, and the reaction was stirred at ambient temperature overnight. The reaction was filtered and purified by reverse phase HPLC to give the desired product. Yield 11.8 mg. MS: 507.2 (M+H$^+$); H$^1$ NMR (DMSO-d$_6$): δ(ppm) 0.50-77 (m, 4H), 1.70-2.10 (m, 2H), 4.20-4.40 (m, 1H), 4.86-5.17 (m, 2H), 7.00-7.42 (m, 4H), 7.74-8.01 (m, 5H), 8.40-8.48 (m, 1H), 12.58-12.67 (m, 1H).

Example 377

2-(4-{4-[4-(2-Hydroxy-ethyl)-piperazine-1-carbonyl]-phenyl}-thiazol-2-ylcarbamoyl)-pyrrolidine-1-carboxylic acid benzyl ester (Compound 5377)

From 50 mg of 2-piperazin-1-yl-ethanol following General Procedure 3A. MS: 564.2 (M+H$^+$); H$^1$ NMR (DMSO-d6): δ(ppm) 12.48 (s, 1H), 9.98 (br s, 1H), 7.98 (d, 2H), 7.77 (d, 1H), 7.48 (d, 2H), 7.37 (s, 2H), 7.10 (dd, 1H), 5.01 (m, 2H), 4.54 (m, 1H), 3.8-3.1 (m, 12H), 2.25 (m, 1H), 1.90 (m, 4H).

Example 378

2-[4-(4-Cyclopropylsulfamoyl-phenyl)-thiazol-2-ylcarbamoyl]-pyrrolidine-1-carboxylic acid benzyl ester (Compound 5378)

Synthesized from 4-(2-bromo-acetyl)-N-cyclopropyl-benzenesulfonamide (150 mg, 0.57 mmol) following multi-step procedure for Example 354 (Compound 5354). MS: 527.1 (M+H$^+$); H$^1$ NMR (MeOH-d$_4$): δ(ppm) 8.18 (dd, 2H), 7.91 (dd, 2H), 8.03 (d, 1H), 7.28 (m, 2H), 7.11 (m, 2H), 5.09 (m, 2H), 3.48 (m, 1H), 2.76 (m, 2H), 2.98 (m, 3H), 1.29 (m, 1H), 0.51 (brs, 1H).

Example 379

2-[4-(4-Aminomethyl-phenyl)-thiazol-2-ylcarbamoyl]-pyrrolidine-1-carboxylic acid benzyl ester (Compound 5379)

2-[4-(4-Cyano-phenyl)-thiazol-2-ylcarbamoyl]-pyrrolidine-1-carboxylic acid benzyl ester (100 mg, 0.23 mmol) was suspended in 10 mL of dry EtOH. To this suspension was added NaBH$_4$ (12.8 mg, 0.46 mmol) followed by CoCl$_2$ (60 mg, 0.46 mmol). Reaction mixture was stirred at room temperature for 4 hours. Reaction mixture was filtered and filtrate concentrated under reduced pressure to yield crude product which was then purified using reverse phase HPLC. MS: 433.1 (M+H$^+$); H$^1$ NMR (MeOH-d$_4$): δ(ppm) 8.00 (d, 2H), 7.49 (m, 3H), 7.37 (m, 2H), 7.18 (d, 1H), 7.02 (m, 2H), 5.03 (m, 2H), 4.49 (m, 1H), 4.16 (s, 2H), 3.96 (m, 2H), 3.61 (m, 2H), 2.39 (m, 1H), 1.99 (m, 4H).

Example 380

(S)-2-{4-[4-(Cyclopentylmethyl-amino)-phenyl]-thiazol-2-ylcarbamoyl}-pyrrolidine-1-carboxylic acid benzylester (Compound 5380)

From 0.013 mL of cyclopentyl aldehyde using General Procedure 3D. $^1$HNMR (DMSO-d$_6$) δ(ppm)12.32-12.29 (s, 1H), 7.60-7.58 (d, 2H), 7.35-7.07 (m, 6H), 6.61-6.58 (d, 2H), 5.07-4.89 (m, 2H), 4.49 (m, 1H), 2.95-2.89 (m, 3H), 2.24-1.51 (m, 11H),1.25-1.26 (m, 5H); MS: 505.2 (M+H$^+$).

Example 381

2-[4-(3-Methyl-pyrazin-2-yl)-thiazol-2-ylcarbamoyl]-pyrrolidine-1-carboxylic acid benzyl ester (Compound 5381)

Synthesized from 2-bromo-1-(3-methyl-pyrazin-2-yl)-ethanone using the procedure for Example 360 (Compound 5360). MS: 424.1(M+H$^+$); H$^1$ NMR (DMSO-d$_6$): δ(ppm) 12.44 (s, 1H), 8.44 (d, 2H), 7.77 (d, 1H), 7.24 (m, 3H), 7.09 (dd, 2H), 5.01 (m, 2H), 4.50 (m, 1H), 3.43 (m, 1H), 2.79 (d, 3H), 2.27 (m, 1H), 1.84 (m, 4H).

Example 382

Rac-cis-Cyclopentane-1,2-dicarboxylic acid 1-benzylamide 2-{[4-(4-cyclopropylcarbamoyl-phenyl)-thiazol-2-yl]-amide} (Compound 5382)

Rac-cis -2-[4-(4-Cyclopropylcarbamoyl-phenyl)-thiazol-2-ylcarbamoyl]-cyclopentanecarboxylic acid methyl ester Rac-cis-cyclopentane-1,2-dicarboxylic acid monomethyl ester (172 mg) was dissolved in DMF (5 mL) and treated with HATU (1.1 eq. 470 mg) and DIEA (3 eq, 500 µL) and stirred for 15 minutes. Then 4-(2-amino-thiazol-4-yl)-N-cyclopropyl-benzamide (1 eq, 260 mg) was added and the mixture stirred at ambient temperature overnight. The reaction was cooled, filtered and the solvents removed. The resulting mixture was redissolved in 5 ml of 90% DMF, 10% water with 0.1% TFA and purified by reverse phase HPLC to give the product. MS: 414.5.

Rac-cis -2-[4-(4-Cyclopropylcarbamoyl-phenyl)-thiazol-2-ylcarbamoyl]cyclopentanecarboxylic acid Rac-cis-2-[4-(4-Cyclopropylcarbamoyl-phenyl)-thiazol-2-ylcarbamoyl]-cyclopentanecarboxylic acid methyl ester (100 mg) was dissolved in THF:MeOH:H2O (2:2:1, 5 mL) and treated with LiOH (10 eq. 45 mg) and stirred at room temperature for 15 hours. The mixture was neutralized with HOAc, and the solvents removed. The resulting mixture was redissolved in 5 ml of 90% DMF, 10% water with 0.1% TFA and purified by reverse phase HPLC to give the product. MS: 400.5 (M+H$^+$)

Rac-cis-Cyclopentane-1,2-dicarboxylic acid 1-benzylamide 2-{[4-(4-cyclopropylcarbamoyl-phenyl)-thiazol-2-yl]-amide} (Compound 5382)

Rac-cis-2-[4-(4-Cyclopropylcarbamoyl-phenyl)-thiazol-2-ylcarbamoyl]cyclopentanecarboxylic acid (15 mg) was dissolved in DMF (1 mL) and treated with HATU (1.1 eq. 19 mg) and DIEA (3 eq, 20 µL) and stirred for 15 minutes. Then benzyl amine (1.2 eq, 4 µL) was added and the mixture stirred at ambient temperature for 3 hours. The reaction was cooled, filtered and the solvents removed. The resulting mixture was redissolved in 5 ml of 90% DMF, 10% water with 0.1% TFA and purified by reverse phase HPLC to give the product (19 mg). MS: 489.5 (M+H$^+$); H$^1$-NMR (DMSO-d$_6$): δ(ppm) 12.2 (s, 1H), 8.4 (m, 2H), 7.9-7.7 (m, 5H), 7.1 (m, 5H), 4.2 (m, 2H), 3.2 (m, 1H), 3.05 (m, 1H), 2.8 (m, 1H), 2.0 (m, 1H), 1.7 (m, 3H) 0.7-0.6 (m, 4H).

Example 383

(S)-2-{4-[3-(Bis-cyclopropylmethyl-amino)-phenyl]-thiazol-2-ylcarbamoyl}-pyrrolidine-1-carboxylic acid benzyl ester (Compound 5383)

A mixture of (S)-2-[4-(3-Amino-phenyl)-thiazol-2-ylcarbamoyl]-pyrrolidine-1-carboxylic acid benzyl ester (Compound 5001, Example 1, 0.071 g, 0.17 mmol), glacial acetic acid (0.057 mL, 1.0 mmol), NaBH$_3$CN$_4$ (0.032 g, 0.5 mmol), and cyclopropyl aldehyde (0.030 mL, 0.4 mmol), in MeOH (4 mL) was stirred at room temperature overnight. The mixture was concentrated in vacuo to give the crude. Purification of the crude product by reverse phase HPLC (CH$_3$CN/H$_2$O) furnished the desired product. $^1$HNMR (DMSO-d$_6$) δ(ppm) 12.4 (s, 1H), 7.6-7.1 (m, 9H), 5.1-4.5 (m, 7.0H), 3.5-3.3 (m, 7H), 2.28-2.25 (m, 1H), 1.92-1.90 (m, 3H), 1.1-1.06 (m, 1H), 0.47-0.26 (m, 10H); (MS: 531.21 (M+H$^+$).

Example 384

2-[4-(4-Cyclopropylcarbamoyl-phenyl)-thiazol-2-ylcarbamoyl]-pyrrolidine-1-carboxylic acid pyridine-4-ylmethyl ester (Compound 5384)

Pyridine-4-yl-methanol (400 mg, 3.66 mmol) was dissolved in 12 mL of dry CH$_3$CN. To this solution was added disuccinimidyl carbonate (3.66 mmol, 940 mg) followed by triethylamine (11 mmol, 1.5 mL). This solution was stirred at room temperature for 2 hours and the evaporated. The residue was redissloved in 10 mL of CH$_2$Cl$_2$. To this solution was added 150 mg (0.42 mmol) of pyrrolidine-2-carboxylic acid [4-(4-cyclopropyl carbamoyl-phenyl)-thiazol-2-yl]-amide (General Procedure 3I), followed by triethylamine (5.5 mmol, 0.75 mL), and DMAP (30 mg). Reaction mixture was stirred at room temperature overnight. It was evaporated to dryness, redissolved in 10 mL of DMF and purified using reverse phase HPLC. MS: 492.1(M+H$^+$); H$^1$ NMR (DMSO-d$_6$): δ(ppm) 12.6 (d, 1H), 8.84 (d, 2H), 8.51 (s, 1H), 7.91 (m, 6H), 5.42 (m, 2H), 4.60 (m, 1H), 3.58 (m, 1H), 2.83 (m, 2H), 2.33 (m, 1H), 1.99 (m, 4H), 0.60 (dd, 4H).

Biological Examples

Example 1

Anti-Hepatitis C Activity

Compounds can exhibit anti-hepatitis C activity by inhibiting viral and host cell targets required in the replication cycle. A number of assays have been published to assess these activities. A general method that assesses the gross increase of HCV virus in culture is disclosed in U.S. Pat. No. 5,738,985 to Miles et al. In vitro assays have been reported in Ferrari et al. *J. of Vir.*, 73:1649-1654, 1999; Ishii et al., *Hepatology*, 29:1227-1235, 1999; Lohmann et al., *J. of Bio. Chem.*, 274: 10807-10815, 1999; and Yamashita et al., *J. of Bio. Chem.*, 273:15479-15486, 1998.

Replicon Assay

A cell line, ET (Huh-lucubineo-ET) was used for screening of compounds of the present invention for HCV RNA dependent RNA polymerase. The ET cell line was stably transfected with RNA transcripts harboring a I$_{389}$luc-ubi-neo/NS3-3'/ET; replicon with firefly luciferase-ubiquitin-neomycin phosphotransferase fusion protein and EMCV-IRES driven NS3-5B polyprotein containing the cell culture adaptive mutations (E1202G; T12801; K1846T) (Krieger at al, 2001 and unpublished). The ET cells were grown in DMEM, supplemented with 10% fetal calf serum, 2 mM Glutamine, Penicillin (100 IU/mL)/Streptomycin (100 µg/mL), 1× nonessential amino acids, and 250 µg/mL G418 ("Geneticin"). They were all available through Life Technologies (Bethesda, Md.). The cells were plated at 0.5-1.0× 10$^4$ cells/well in the 96 well plates and incubated for 24 hrs before adding nucleoside analogs. Then the compounds were added to the cells to achieve a final concentration of 5 or 50 µM. Luciferase activity were measured 48-72 hours later by adding a lysis buffer and the substrate (Catalog number Glo-lysis buffer E2661 and Bright-Glo luciferase system E2620 Promega, Madison, Wis.). Cells should not be too confluent during the assay. Percent inhibition of replication was plotted relative to no compound control. Under the same condition, cytotoxicity of the compounds was determined using cell proliferation reagent, WST-1(Roche, Germany). The compounds showing antiviral activities, but no significant cytotoxicities were chosen to determine $IC_{50}$ and $TC_{50}$. For these determinations, 10 concentrations of each compound were used. Concentrations for test compounds typically span a range of 500 fold. $IC_{50}$ and $TC_{50}$ values were calculated by fitting % inhibition at each concentration (I) to the following equation:

$$\% \text{ inhibition} = 100\%/[1+10^{(\log IC50 - \log (I))*b}]$$

where b is Hill's coefficient.

Preferably, when tested at 10 μM, the compounds of this invention will exhibit a % inhibition values of at least 25% and more preferably a % inhibition values of at least 50%.

Examples of % inhibition values at a test concentration of 10 μM according to the above equation are shown below.

| Compound No. | % inhibition at 10 uM |
| --- | --- |
| 5001 | 99.60 |
| 5002 | 94.65 |
| 5003 | 99.92 |
| 5004 | 99.93 |
| 5005 | 99.84 |
| 5006 | 99.94 |
| 5007 | 100.00 |
| 5008 | 62.99 |
| 5009 | 63.40 |
| 5010 | 6.41 |
| 5011 | 32.93 |
| 5012 | 1.01 |
| 5013 | 97.00 |
| 5014 | 66.60 |
| 5015 | 99.42 |
| 5016 | 100.00 |
| 5017 | 99.70 |
| 5018 | 99.97 |
| 5019 | 99.97 |
| 5020 | 58.20 |
| 5021 | 97.05 |
| 5022 | 56.05 |
| 5023 | 76.46 |
| 5024 | 11.00 |
| 5025 | 2.86 |
| 5026 | 100.00 |
| 5027 | 99.74 |
| 5028 | 98.88 |
| 5029 | 0.52 |
| 5031 | 2.85 |
| 5032 | 38.57 |
| 5033 | 2.51 |
| 5034 | 100.00 |
| 5035 | 100.00 |
| 5036 | 100.00 |
| 5037 | 100.00 |
| 5038 | 100.00 |
| 5039 | 99.60 |
| 5040 | 22.53 |
| 5041 | 75.98 |
| 5042 | 90.29 |
| 5043 | 3.61 |
| 5044 | 16.87 |
| 5045 | 6.85 |
| 5046 | 8.29 |
| 5047 | 37.66 |
| 5048 | 99.99 |
| 5049 | 95.63 |
| 5050 | 99.83 |
| 5051 | 3.42 |
| 5052 | 1.20 |
| 5053 | 4.55 |
| 5054 | 99.28 |
| 5055 | 99.33 |
| 5056 | 99.29 |
| 5058 | 18.60 |
| 5059 | 88.01 |
| 5060 | 98.39 |
| 5061 | 88.43 |
| 5062 | 94.72 |
| 5063 | 51.71 |
| 5064 | 18.05 |
| 5065 | 27.19 |
| 5066 | 5.72 |
| 5067 | 23.88 |
| 5068 | 13.51 |
| 5069 | 3.15 |
| 5089 | 100.00 |
| 5090 | 99.77 |
| 5091 | 100.00 |
| 5092 | 99.99 |
| 5093 | 99.95 |
| 5094 | 3.49 |
| 5096 | 99.98 |
| 5097 | 43.33 |
| 5098 | 97.16 |
| 5099 | 35.66 |
| 5100 | 99.07 |
| 5101 | 69.17 |
| 5102 | 9.80 |
| 5103 | 99.32 |
| 5104 | 97.31 |
| 5105 | 100.00 |
| 5106 | 46.32 |
| 5108 | 98.90 |
| 5109 | 100.00 |
| 5110 | 89.56 |
| 5111 | 40.00 |
| 5113 | 99.68 |
| 5114 | 25.00 |
| 5116 | 100.00 |
| 5117 | 99.78 |
| 5301 | 100.00 |
| 5302 | 100.00 |
| 5303 | 99.99 |
| 5305 | 76.35 |
| 5306 | 100.00 |
| 5307 | 100.00 |
| 5308 | 100.00 |
| 5309 | 99.45 |
| 5310 | 99.27 |
| 5311 | 99.72 |
| 5313 | 100.00 |
| 5314 | 100.00 |
| 5315 | 99.66 |
| 5316 | 3.19 |
| 5317 | 100.00 |
| 5319 | 67.41 |
| 5320 | 99.82 |
| 5321 | 91.27 |
| 5322 | 100.00 |
| 5323 | 81.45 |
| 5324 | 99.97 |
| 5325 | 86.90 |
| 5326 | 99.99 |
| 5327 | 100.00 |
| 5328 | 97.32 |
| 5329 | 97.03 |
| 5330 | 98.75 |
| 5331 | 42.98 |
| 5332 | 99.71 |
| 5334 | 99.94 |

-continued

| Compound No. | % inhibition at 10 uM |
|---|---|
| 5335 | 92.52 |
| 5336 | 96.32 |
| 5337 | 99.99 |
| 5338 | 75.20 |
| 5339 | 100.00 |
| 5340 | 100.00 |
| 5342 | 95.18 |
| 5343 | 100.00 |
| 5347 | 94.66 |
| 5349 | 28.57 |
| 5350 | 99.99 |
| 5351 | 22.34 |
| 5352 | 7.07 |
| 5353 | 50.18 |
| 5354 | 87.49 |
| 5355 | 99.94 |
| 5356 | 100.00 |
| 5358 | 84.84 |
| 5360 | 54.00 |
| 5361 | 98.36 |
| 5362 | 98.66 |
| 5363 | 1.64 |
| 5364 | 4.49 |
| 5365 | 99.89 |
| 5366 | 99.28 |
| 5367 | 97.27 |
| 5368 | 50.77 |
| 5369 | 98.33 |
| 5370 | 100.00 |
| 5371 | 99.99 |
| 5372 | 99.93 |
| 5373 | 81.51 |
| 5374 | 99.29 |
| 5375 | 98.73 |
| 5376 | 96.01 |
| 5377 | 5.71 |
| 5378 | 98.27 |
| 5379 | 25.00 |
| 5380 | 98.29 |
| 5382 | 99.99 |
| 5383 | 46.95 |
| 5384 | 99.66 |
| 5387 | 100.00 |

Formulation Examples

The following are representative pharmaceutical formulations containing a compound of the present invention.

Example 1

Tablet Formulation

The following ingredients are mixed intimately and pressed into single scored tablets.

| Ingredient | Quantity per tablet, mg |
|---|---|
| Compound of the invention | 400 |
| Cornstarch | 50 |
| Croscarmellose sodium | 25 |
| Lactose | 120 |
| Magnesium stearate | 5 |

Example 2

Capsule Formulation

The following ingredients are mixed intimately and loaded into a hard-shell gelatin capsule.

| Ingredient | Quantity per tablet, mg |
|---|---|
| Compound of the invention | 200 |
| Lactose, spray-dried | 148 |
| Magnesium stearate | 2 |

Example 3

Suspension Formulation

The following ingredients are mixed to form a suspension for oral administration (q.s.=sufficient amount).

| Ingredient | Amount |
|---|---|
| Compound of the invention | 1.0 g |
| Fumaric acid | 0.5 g |
| Sodium chloride | 2.0 g |
| Methyl paraben | 0.15 g |
| Propyl paraben | 0.05 g |
| Granulated sugar | 25.0 g |
| Sorbitol (70% solution) | 13.0 g |
| Veegum K (Vanderbilt Co.) | 1.0 g |
| flavoring | 0.035 mL |
| colorings | 0.5 mg |
| distilled water | q.s. to 100 mL |

Example 4

Injectable Formulation

The following ingredients are mixed to form an injectable formulation.

| Ingredient | Quantity per tablet, mg |
|---|---|
| Compound of the invention | 0.2 mg-20 mg |
| sodium acetate buffer solution, 0.4 M | 2.0 mL |
| HCl (1N) or NaOH (1N) | q.s. to suitable pH |
| water (distilled, sterile) | q.s. to 20 mL |

Example 5

Suppository Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| Ingredient | Quantity per tablet, mg |
|---|---|
| Compound of the invention | 500 mg |
| Witepsol ® H-15 | balance |

What is claimed is:

1. A compound having Formula (IIa) or a stereoisomer, tautomer, or a pharmaceutically acceptable salt thereof,

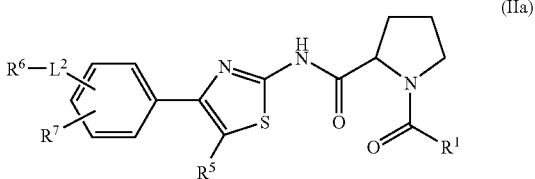

(IIa)

wherein:
L² is —(CH₂)ₙC(O)NH— or —(CH₂)ₙNHC(O)—;
n is 0, 1, 2, 3, or 4;
R⁶ is selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic;
R⁷ is selected from the group consisting of hydrogen, amino, substituted amino, halo, cyano, alkoxy, alkyl, substituted alkyl, nitro, substituted alkoxy, aryl, substituted aryl, substituted aryloxy, cycloalkyl, heterocyclic, substituted heterocyclic, hydroxyl, aminocarbonyl, substituted alkylthio, substituted sulfonyl, aminocarbonyl, aminocarbonylamino, and aminocarbonyloxy;
R⁵ is selected from the group consisting of hydrogen, halo, alkyl, and substituted alkyl;
R¹ is selected from the group consisting of amino, substituted amino, alkyl, arylalkyl, cycloalkyl, substituted cycloalkyl, aryl, substituted aryl, heteroaryl, substituted heteroaryl, alkoxy, aryloxy, arylalkoxy, —OR¹ᵃ, and —OCH₂R¹ᵃ; and
R¹ᵃ is selected from the group consisting of cycloalkyl, substituted cycloalkyl, heterocyclic, substituted heterocyclic, aryl, substituted aryl, heteroaryl, and substituted heteroaryl.

2. A compound of claim 1 wherein the pyrrolidine ring of Formula (IIa) has the S or R stereochemistry.

3. A compound of claim 1 wherein R⁶L² is attached to the meta or para position of the phenyl ring.

4. A compound of claim 1 wherein R⁵ is hydrogen.

5. A compound of claim 1 wherein R⁷ is hydrogen.

6. A compound of claim 1 wherein R⁶ is cycloalkyl, substituted cycloalkyl, cycloalkenyl, substituted cycloalkenyl, aryl, substituted aryl, heteroaryl, substituted heteroaryl, heterocyclic, or substituted heterocyclic.

7. A compound of claim 6 wherein R⁶ is selected from the group consisting of cyclopropyl, substituted cyclopropyl, cyclobutyl, substituted cyclobutyl, cyclopentyl, substituted cyclopentyl, cyclohexyl, substituted cyclohexyl, phenyl, substituted phenyl, morpholin-4-yl, morpholin-3-yl, morpholin-2-yl, pyridin-3-yl, substituted pyridin-3-yl, pyridin-4-yl, substituted pyridin-4-yl, pyrimidin-2-yl, substituted pyrimidin-2-yl, pyrimidin-4-yl, substituted pyrimidin-4-yl, pyrimidin-5-yl, and substituted pyrimidin-5-yl.

8. A compound of claim 1 wherein n is 0.

9. A compound of claim 8 wherein R¹ is selected from the group consisting of amino, substituted amino, alkyl, arylalkyl, cycloalkyl, substituted cycloalkyl, aryl, substituted aryl, heteroaryl, substituted heteroaryl, alkoxy, aryloxy, and arylalkoxy.

10. A compound of claim 1 wherein R¹ is —OCH₂R¹ᵃ.

11. A compound of claim 10 wherein R¹ᵃ is selected from the group consisting of cyclopropyl, substituted cyclopropyl, cyclobutyl, substituted cyclobutyl, cyclopentyl, substituted cyclopentyl, cyclohexyl, substituted cyclohexyl, phenyl, substituted phenyl, morpholin-4-yl, morpholin-3-yl, morpholin-2-yl, pyridin-3-yl, substituted pyridin-3-yl, pyridin-4-yl, substituted pyridin-4-yl, pyrimidin-2-yl, substituted pyrimidin-2-yl, pyrimidin-4-yl, substituted pyrimidin-4-yl, pyrimidin-5-yl, and substituted pyrimidin-5-yl.

12. A compound of claim 1 selected from the group consisting of
2-{4-[4-(Cyclopentanecarbonyl-amino)-phenyl]-thiazol-2-ylcarbamoyl}-pyrrolidine-1-carboxylic acid benzyl ester;
2-[4-(3-Acetylamino-phenyl)-thiazol-2-ylcarbamoyl]-pyrrolidine-1-carboxylic acid benzyl ester;
2-[4-(4-Propionylamino-phenyl)-thiazol-2-ylcarbamoyl]-pyrrolidine-1-carboxylic acid benzyl ester;
2-{4-[4-(Cyclopropanecarbonyl-amino)-phenyl]-thiazol-2-ylcarbamoyl}-pyrrolidine-1-carboxylic acid benzyl ester;
2-[4-(3-Benzoylamino-phenyl)-thiazol-2-ylcarbamoyl]-pyrrolidine-1-carboxylic acid benzyl ester;
2-{4-[3-(Cyclopentanecarbonyl-amino)-phenyl]-thiazol-2-ylcarbamoyl}-pyrrolidine-1-carboxylic acid benzyl ester;
2-{4-[4-(4-Chloro-benzoylamino)-phenyl]-thiazol-2-ylcarbamoyl}-pyrrolidine-1-carboxylic acid benzyl ester;
2-[4-(4-Benzoylamino-phenyl)-thiazol-2-ylcarbamoyl]-pyrrolidine-1-carboxylic acid benzyl ester;
2-{4-[3-(4-Chloro-benzoylamino)-phenyl]-thiazol-2-ylcarbamoyl}-pyrrolidine-1-carboxylic acid benzyl ester;
2-{4-[3-(Cyclopropanecarbonyl-amino)-phenyl]-thiazol-2-ylcarbamoyl}-pyrrolidine-1-carboxylic acid benzyl ester;
2-[4-(4-Acetylamino-phenyl)-thiazol-2-ylcarbamoyl]-pyrrolidine-1-carboxylic acid benzyl ester;
2-[4-(4-Pentanoylamino-phenyl)-thiazol-2-ylcarbamoyl]-pyrrolidine-1-carboxylic acid benzyl ester;
2-[4-(4-Ethylcarbamoyl-phenyl)-thiazol-2-ylcarbamoyl]-pyrrolidine-1-carboxylic acid benzyl ester;
2-(4-{4-[5-(2-Oxo-hexahydro-thieno[3,4-d]imidazol-4-yl)-pentanoylamino]-phenyl}-thiazol-2-ylcarbamoyl)-pyrrolidine-1-carboxylic acid benzyl ester;
2-[4-(4-Cyclopropylcarbamoyl-phenyl)-thiazol-2-ylcarbamoyl]-pyrrolidine-1-carboxylic acid benzyl ester;
2-[4-(4-Cyclopentylcarbamoyl-phenyl)-thiazol-2-ylcarbamoyl]-pyrrolidine-1-carboxylic acid benzyl ester;
2-[4-(4-Methylcarbamoyl-phenyl)-thiazol-2-ylcarbamoyl]-pyrrolidine-1-carboxylic acid benzyl ester;
2-[4-(3-Pentanoylamino-phenyl)-thiazol-2-ylcarbamoyl]-pyrrolidine-1-carboxylic acid benzyl ester;
2-[4-(4-Phenylcarbamoyl-phenyl)-thiazol-2-ylcarbamoyl]-pyrrolidine-1-carboxylic acid benzyl ester;
2-[4-(4-Isopropylcarbamoyl-phenyl)-thiazo-2-ylcarbamoyl]-pyrrolidine-1-carboxylic acid benzyl ester;
2-{4-[4-(Pyridin-4-ylcarbamoyl)-phenyl]-thiazol-2-ylcarbamoyl}-pyrrolidine-1-carboxylic acid benzyl ester;
2-[4-(4-Cyclohexylcarbamoyl-phenyl)-thiazol-2-ylcarbamoyl]-pyrrolidine-1-carboxylic acid benzyl ester;
2-{4-[4-(1,1-Dimethyl-2-morpholin-4-yl-ethylcarbamoyl)-phenyl]-thiazol-2-Ylcarbamoyl}-pyrrolidine-1-carboxylic acid benzyl ester;
2-{4-[4-(2-Piperidin-1-yl-ethylcarbamoyl)-phenyl]-thiazol-2-ylcarbamoyl}-pyrrolidine-1-carboxylic acid benzyl ester;

2-{4-[4-(3-Hydroxy-propylcarbamoyl)-phenyl]-thiazol-2-ylcarbamoyl}-pyrrolidine-1-carboxylic acid benzyl ester;
2-[4-(4-Cyclopropylcarbamoyl-phenyl)-thiazol-2-ylcarbamoyl]-pyrrolidine-1-carboxylic acid 2-isopropyl-5-methyl-cyclohexyl ester;
2-[4-(4-Cyclopropylcarbamoyl-phenyl)-thiazol-2-ylcarbamoyl]-pyrrolidine-1-carboxylic acid pyridin-3-ylmethyl ester;
1-(Pyridine-4-carbonyl)-pyrrolidine-2-carboxylic acid [4-(4-cyclopropylcarbamoyl-phenyl)-thiazol-2-yl]-amide;
2-{4-[4-(Pyrrolidin-3-ylcarbamoyl)-phenyl]-thiazol-2-ylcarbamoyl}-pyrrolidine-1-carboxylic acid benzyl ester;
2-{4-[4-(3-Morpholin-4-yl-propylcarbamoyl)-phenyl]-thiazol-2-ylcarbamoyl}-pyrrolidine-1-carboxylic acid benzyl ester;
1-Phenylacetyl-pyrrolidine-2-carboxylic acid [4-(4-cyclopropylcarbamoyl-phenyl)-thiazol-2-yl]-amide;
2-[4-(4-tert-Butylcarbamoyl-phenyl)-thiazol-2-ylcarbamoyl]-pyrrolidine-1-carboxylic acid benzyl ester;
1-(2-Phenoxy-acetyl)-pyrrolidine-2-carboxylic acid [4-(4-cyclopropylcarbamoyl-phenyl)-thiazol-2-yl]-amide;
Pyrrolidine-1,2-dicarboxylic acid 2-{[4-(4-cyclopropylcarbamoyl-phenyl)-thiazol-2-yl]-amide} 1-phenylamide;
4-(4-{2-[(1-Benzyloxycarbonyl-pyrrolidine-2-carbonyl)-amino]-thiazol-4-yl}-benzoylamino)-piperidine-1-carboxylic acid tert-butyl ester;
2-{4-[4-(Azetidin-3-ylcarbamoyl)-phenyl]-thiazol-2-ylcarbamoyl}-pyrrolidine-1-carboxylic acid benzyl ester;
2-{4-[4-(2-Morpholin-4-yl-ethylcarbamoyl)-phenyl]-thiazol-2-ylcarbamoyl}-pyrrolidine-1-carboxylic acid benzyl ester;
2-{4-[4-(2-Carboxy-ethylcarbamoyl)-phenyl]-thiazol-2-ylcarbamoyl}-pyrrolidine-1-carboxylic acid benzyl ester;
Pyrrolidine-1,2-dicarboxylic acid 1-benzylamide 2-{[4-(4-cyclopropylcarbamoyl-phenyl)-thiazol-2-yl]-amide};
2-{4-[4-(Piperidin-3-ylcarbamoyl)-phenyl]-thiazol-2-ylcarbamoyl}-pyrrolidine-1-carboxylic acid benzyl ester;
2-{4-[4-(Pyridin-3-ylcarbamoyl)-phenyl]-thiazol-2-ylcarbamoyl}-pyrrolidine-1-carboxylic acid benzyl ester;
2-[4-(4-Cyclopropylcarbamoyl-phenyl)-thiazol-2-ylcarbamoyl]-pyrrolidine-1-carboxylic acid phenyl ester;
2-[4-(4-Cyclopropylcarbamoyl-phenyl)-thiazol-2-ylcarbamoyl]-pyrrolidine-1-carboxylic acid benzyl ester;
2-{4-[4-(Piperidin-4-ylcarbamoyl)-phenyl]-thiazol-2-ylcarbamoyl}-pyrrolidine-1-carboxylic acid benzyl ester;
1-(3-Phenyl-propionyl)-pyrrolidine-2-carboxylic acid [4-(4-cyclopropylcarbamoyl-phenyl)-thiazol-2-yl]-amide;
2-[4-(4-Cyclopropylcarbamoyl-phenyl)-thiazol-2-ylcarbamoyl]-pyrrolidine-1-carboxylic acid 4-fluoro-benzyl ester;
3-(4-{2-[(1-Benzyloxycarbonyl-pyrrolidine-2-carbonyl)-amino]-thiazol-4-yl}-benzoylamino)-piperidine-1-carboxylic acid tert-butyl ester;
1-Benzoyl-pyrrolidine-2-carboxylic acid [4-(4-cyclopropylcarbamoyl-phenyl)-thiazol-2-yl]-amide;
2-(4-{4-[(Cyclopropanecarbonyl-amino)-methyl]-phenyl}-thiazol-2-ylcarbamoyl)-pyrrolidine-1-carboxylic acid benzyl ester;
2-{4-[4-(3-Methoxy-propylcarbamoyl)-phenyl]-thiazol-2-ylcarbamoyl}-pyrrolidine-1-carboxylic acid benzyl ester;
1-(1-Phenyl-cyclopropanecarbonyl)-pyrrolidine-2-carboxylic acid [4-(4-cyclopropylcarbamoyl-phenyl)-thiazol-2-yl]-amide;
2-{4-[4-(Pyridin-2-ylcarbamoyl)-phenyl]-thiazol-2-ylcarbamoyl}-pyrrolidine-1-carboxylic acid benzyl ester;
2-[4-(4-Cyclopropylcarbamoyl-phenyl)-thiazol-2-ylcarbamoyl]-pyrrolidine-1-carboxylic acid methyl ester;
2-[4-(4-{6-[5-(2-Oxo-hexahydro-thieno[3,4-d]imidazol-6-yl)-pentanoylamino]-Hexanoylamino}-phenyl)-thiazol-2-ylcarbamoyl]-pyrrolidine-1-carboxylic acid benzyl ester;
2-[4-(4-Cyclopropylcarbamoyl-phenyl)-thiazol-2-ylcarbamoyl]-pyrrolidine-1-carboxylic acid tert-butyl ester; and
2-[4-(4-Cyclopropylcarbamoyl-phenyl)-thiazol-2-ylcarbamoyl]-pyrrolidine-1-carboxylic acid pyridin-4-ylmethyl ester; or a stereoisomer, tautomer, or a pharmaceutically acceptable salt thereof.

13. A pharmaceutical composition comprising a pharmaceutically acceptable carrier and a therapeutically effective amount of the compound of claim 1.

* * * * *